United States Patent
Liu et al.

(10) Patent No.: US 8,871,908 B2
(45) Date of Patent: Oct. 28, 2014

(54) ANTIBODIES SPECIFIC FOR TROP-2 AND THEIR USES

(71) Applicant: Rinat Neuroscience Corp., South San Francisco, CA (US)

(72) Inventors: Shu-Hui Liu, Redwood City, CA (US); Wei-Hsien Ho, Belmont, CA (US); Pavel Strop, San Mateo, CA (US); Magdalena Grazyna Dorywalska, Redwood City, CA (US); Arvind Rajpal, San Francisco, CA (US); David Louis Shelton, Oakland, CA (US); Thomas-Toan Tran, San Jose, CA (US)

(73) Assignee: Rinat Neuroscience Corp., South San Francisco, CA (US)

( * ) Notice: Subject to any disclaimer, the term of this patent is extended or adjusted under 35 U.S.C. 154(b) by 0 days.

(21) Appl. No.: 13/670,730

(22) Filed: Nov. 7, 2012

(65) Prior Publication Data

US 2013/0122020 A1    May 16, 2013

Related U.S. Application Data

(60) Provisional application No. 61/559,015, filed on Nov. 11, 2011, provisional application No. 61/640,641, filed on Apr. 30, 2012, provisional application No. 61/717,288, filed on Oct. 23, 2012.

(51) Int. Cl.

| C07K 16/00 | (2006.01) |
|---|---|
| C12P 21/08 | (2006.01) |
| A61K 39/395 | (2006.01) |
| A61K 39/00 | (2006.01) |
| A61K 47/48 | (2006.01) |
| C07K 16/30 | (2006.01) |

(52) U.S. Cl.
CPC ......... *C07K 16/3076* (2013.01); *C07K 2317/92* (2013.01); *A61K 47/48569* (2013.01); *A61K 47/48561* (2013.01); *C07K 16/30* (2013.01); *A61K 2039/505* (2013.01)
USPC .................. 530/387.1; 530/387.3; 530/387.7; 530/388.1; 530/388.8; 530/388.85; 530/391.1; 530/391.7; 530/391.9; 424/130.1; 424/133.1; 424/138.1; 424/141.1; 424/155.1; 424/156.1; 424/178.1; 424/179.1; 424/180.1; 424/181.1; 424/182.1

(58) Field of Classification Search
None
See application file for complete search history.

(56) References Cited

U.S. PATENT DOCUMENTS

| 5,840,854 | A | 11/1998 | Hellstrom |
|---|---|---|---|
| 6,653,104 | B2 | 11/2003 | Goldenberg |
| 7,238,785 | B2 | 7/2007 | Govindan et al. |
| 7,420,040 | B2 | 9/2008 | Young |
| 7,420,041 | B2 | 9/2008 | Young |
| 7,517,964 | B2 | 4/2009 | Govindan et al. |
| 8,084,583 | B2 | 12/2011 | Govindan et al. |
| 8,574,575 | B2 | 11/2013 | Govindan et al. |
| 2003/0105000 | A1* | 6/2003 | Pero et al. ......................... 514/12 |
| 2008/0025977 | A1 | 1/2008 | Young et al. |
| 2008/0131363 | A1 | 6/2008 | Govindan et al. |
| 2008/0131428 | A1 | 6/2008 | Young et al. |
| 2008/0213267 | A1 | 9/2008 | Young et al. |
| 2012/0237518 | A1 | 9/2012 | Yamaguchi |
| 2013/0115208 | A1 | 5/2013 | Ho et al. |
| 2013/0129753 | A1 | 5/2013 | Doroski et al. |
| 2013/0230543 | A1 | 9/2013 | Pons et al. |

FOREIGN PATENT DOCUMENTS

| WO | WO 2007/095748 | 8/2007 |
|---|---|---|
| WO | WO 2008/144891 | 12/2008 |

OTHER PUBLICATIONS

Rudikoff et al. (PNAS, USA, 1982, 79: 1979-1983).*
Coleman et al. (Research in Immunology, 1994; 145(1): 33-36).*
Abaza et al. (Journal of Protein Chemistry, vol. 11, No. 5, 1992, pp. 433-444).*
Gussow et al. (1991, Methods in Enzymology 203:99-121).*
MacCallum et al. (J. Mol. Biol. (1996) 262, 732-745).*
Martin, A.C.R. (Antibodies: Abysis—new database, http://www.bioinf.org.uk/abs/ Oct. 14, 2013).*
Biacore® T100 (Biacore AB 2006).*
Cardillo, T., et al., "Humanized-Anti-Trop-2 IgG-SN-38 Conjugate for Effective Treatment of Diverse Epithelial Cancers: Preclinical Studies in Human Cancer Xenograft Models and Monkeys," Clinical Cancer Research, 2011, vol. 17:3157-3169.
International Search Report dated Feb. 7, 2013 for PCT application No. PCT/IB2012/056234, published on May 16, 2013 as WO 2013/068946.
Raji, R., et al., "Uterine and ovarian carcinosarcomas overexpressing Trop-2 are sensitive to hRS7, a humanized anti-Trop-2 antibody," Journal of Experimental & Clinical Cancer Research, 2011, vol. 30 (106):1-7.
Varughese, J., et al., "Cervical carcinomas overexpress human trophoblast cell-surface marker (Trop-2) and are highly sensitive to immunotherapy with hRS7, a humanized monoclonal anti-Trop-2 antibody," American Journal of Obstetrics & Gynecology, 2011, vol. 205:567.e1-7.
Written Opinion dated Feb. 7, 2013 for PCT application No. PCT/IB2012/056234, published on May 16, 2013 as WO 2013/068946.

* cited by examiner

*Primary Examiner* — Peter J Reddig
(74) *Attorney, Agent, or Firm* — Jenny J. Yeh

(57) ABSTRACT

The present invention provides antibodies that specifically bind to trophoblast cell-surface antigen-2 (Trop-2). The invention further provides antibody conjugates comprising such antibodies, antibody encoding nucleic acids, and methods of obtaining such antibodies. The invention further relates to therapeutic methods for use of these antibodies and Trop-2 antibody conjugates for the treatment of a condition associated with Trop-2 expression (e.g., cancer), such as colon, esophageal, gastric, head and neck, lung, ovarian, or pancreatic cancer.

26 Claims, 19 Drawing Sheets

| antibody treatment | Mean tumor volume (mm³) on day 43 | TGI (Tumor growth inhibition) |
|---|---|---|
| control IgG | 673.0 | 0% |
| 7E6 | 163.8 | 76% |
| 15E2 | 582.0 | 14% |
| 18B1 | 423.5 | 37% |

Figure 4

```
                  1                                                50
    hTrop1    (1) MA--------PRQVLAFGLLLAAATATFAAAQ ECVCENYKLAVNCFVNNN
    hTrop2    (1) MARGPGLAPPLRLPLLLVLAAVTGHTAAQDNCTCPTNKMTVCSPDGPG
 Consensus    (1)          PP  L    LLL  AA       AAQD C  C   KL V 51                                              100
    hTrop1   (44) RQCQGTSVGAQNTVICSKLAAKCLVMKAEMNGSKLGRAK--EGAIQNN
    hTrop2   (51) GRCQCRALGSGMAVDCSTLTSKCLLLKARMSAPKNARTLVRPSEHALVDN
 Consensus   (51)    CQC  ALGA   V CS L  AKCLLLKA M  K AR      P EAL  N 101                                             150
    hTrop1   (92) DGLYDPDCDESGLFKAQCNGTSTCWCVNTAGVRRTDK-DTEITCSERVR
    hTrop2  (101) DGLYDPDCDPEGRFKAQCNQESVCWCVNSVGVRRTDKGDLSLRCDELVR
 Consensus  (101) DGLYDPDCD  G FKAKQCN TS CWCVNS GVRRTDK D   I C E VR 151                                             200
    hTrop1  (141) TYWIIIELKHKAREKPYDSKSLRTALQKEITTRYQLDPKFITSILYENNV
    hTrop2  (151) THHIIDIRHNPTAGAFNHSDLDAELRPLFREKYRLHPKFVAAVHYEQPT
 Consensus  (151) TH  IIIDLKHK        F    L     L K   RY L PKFI AI YEN 201                                             250
    hTrop1  (191) TIDLVQNSSQKTQNLVDIADVAYYFEKDVKGESLFHSK-MDLTVNGEQ
    hTrop2  (201) IQLIIRQNSQKAAGDVDIGDAAYYFERDIRGESLFQGGGDLRVRCC-
 Consensus  (201) I  IDL QNSSQK    DVDIAD AYYFEKDIKGESLF K  LDL V GE 251                                             300
    hTrop1  (240) LDLDPGQTLIYYVDEKAPEFSMQGLKAGVIAVIVVVVIAVVAGIVVLVIS
    hTrop2  (250) -PLQVERTLIYYLDRIPPKFSMKRLTAGLIAVIVVVVIAVAGMAVLVI
 Consensus  (251)    L    TLIYYLDE  P FSM  L AGLIAVIVVVIALVAGI VLVIS 301                     325
    hTrop1  (290) RKKRMAKYEKAEIKEMGEMHRELNA
    hTrop2  (299) NKKKSGKYKKVEIKELGELRKEPSL
 Consensus  (301)  KKK  AKY K EIKELGEL KE
```

———————— Domain 1       ·················· Domain 2
— — — — Domain 3       ——— · · ——— Domain 4

Figure 5

```
                  1                                                  50
     hTrop2   (1) MARGPGLAPPPLRLPLLLLLVLAAVIGHTAAQDNCTCPTNKMTVCSPDGPG
     mTrop2   (1) MARGLDLAT------LLLLLLAMATRFCTAQSNCTCPTNKMTVCDTNGPG
Consensus   (51) MARG LAP      LLLLLLA T   AQ NCTCPTNKMTVC   GPG
                 51                                                 100
     hTrop2  (51) GRCQCRALGSGMAVDCSTLTSKCLLLKARMSAPKNARTLVRPSEHALVDN
     mTrop2  (45) GVCQCRATGSQVLVDCSTLTSKCLLLKARMSARSGRSLVMPSEIAILDN
Consensus   (51) G CQCRALGS M VDCSTLTSKCLLLKARMSA K ARSLV PSEHAILDN
                 101                                                150
     hTrop2 (101) DGLYDPDCDPEGRFKARQCNQTSVCWCVNSVGVRRTDKCDLSLRCDELVR
     mTrop2  (95) DGLYDPECDDKGRFKARQCNQTSVCWCVNSVGVRRTDKGDQSLRCDEVVR
Consensus  (101) DGLYDPDCD  GRFKARQCNQTSVCWCVNSVGVRRTDKGD SLRCDELVR
                 151                                                200
     hTrop2 (151) THHILIDLRHRPTAGAFNHSDLDAELRRLFRERYKLHPKFVAAVHYEQPT
     mTrop2 (145) THHILIELRHRPTDRAFNHSDLDSELRRLFQERYKLHESFLSAVHYEEPT
Consensus  (151) THHILIDLRHRPT  AFNHSDLDAELRRLF ERYKLHP FLAAVHYE PT
                 201                                                250
     hTrop2 (201) IQIELRQNTSQKAAGDVDIGDAAYYFERDIKGESLDLRVRGEP
     mTrop2 (195) IQIELRQNASQKGLRDVDIADAAYYFERDIKGISLFMGRRGLDVQVRGEP
Consensus  (201) IQIELRQN SQKA  DVDIADAAYYFERDIKGESLF GR GLDL VRGEP
                 251                                                300
     hTrop2 (251) LQVERTLIYYLDEIPPKFSMKRLTAGLIAVIVVTVVALVAGMAVLVITNR
     mTrop2 (245) LHVERTLIYYLDEKPPQFSMKRLTAGVTAVIAVSVAVVAGVVVLVYTKR
Consensus  (251) L VERTLIYYLDE PP FSMKRLTAGLIAVI VV VALVAGM VLVIT R
                 301               323
     hTrop2 (301) RKSGKYKKVEIKELGELRKEPSL
     mTrop2 (295) RKSGKYKKVEIKELGELRSFPSL
Consensus  (301) RKSGKYKKVEIKELGELR EPSL
```

———————— Domain 1      ·············· Domain 2
— — — — Domain 3       —··—··— Domain 4

Figure 6A

```
                    1                                              46
h7E6_VH      (1)   QVQLQESGPGLVKPSETLSLTCTVSGGSISSYGVHWIRQPPGKGLE
h7E6_VH_SVG  (1)   QVQLQESGPGLVKPSETLSLTCTVSGGSISSYGVHWIRQPPGKGLE
m7E6_VH      (1)   QVQLKESGPGLVAPSQSLSITCTVSGFSLTSYGVHWVRQPPGKGLE
Consensus    (1)   QVQLQESGPGLVKPSETLSLTCTVSGGSISSYGVHWIRQPPGKGLE
                    47                                             96
h7E6_VH      (47)  WIGVIWTGGSTDYNSALMSRVTISVDTSKNQFSLKLSSVTAADTAVYYCA
h7E6_VH_SVG  (47)  WIGVIWTSGVTDYNSALMGR  ISVDTSKNQFSLKLSSVTAADTAVYYCA
m7E6_VH      (47)  WLGVIWTGGSTDYNSALMSRLSINKDNSKSQVFLKMNSLQTDDTAMYYCA
Consensus    (47)  WIGVIWTGGSTDYNSALMSRVTISVDTSKNQFSLKLSSVTAADTAVYYCA
                    97                  119
h7E6_VH      (97)  RDGDYDRYTMDYWGQGTLVTVSS
h7E6_VH_SVG  (97)  RDGDYDRYTMDYWGQGTLVTVSS
m7E6_VH      (97)  RDGDYDRYTMDYWGQGTSVTVSS
Consensus    (97)  RDGDYDRYTMDYWGQGTLVTVSS
```

Figure 6B

```
                    1                                              46
h7E6_VL      (1)   DIVMTQSPDSLAVSLGERATINCRASKSVSTSGYSYMHWYQQKPGQ
h7E6_VL_L    (1)   DIVMTQSPDSLAVSLGERATINCRASKSVSTSLYSYMHWYQQKPGQ
h7E6_VL_N    (1)   DIVMTQSPDSLAVSLGERATINCRASKSVSTSNYSYMHWYQQKPGQ
m7E6_VL      (1)   DIVLTQSPASLAVSLGQRATISCRASKSVSTSGYSYMHWYQQKPGQ
Consensus    (1)   DIVMTQSPDSLAVSLGERATINCRASKSVSTSGYSYMHWYQQKPGQ
                    47                                             96
h7E6_VL      (47)  PPKLLIYLASNLESGVPDRFSGSGSGTDFTLTISSLQAEDVAVYYCQHSR
h7E6_VL_L    (47)  PPKLLIYLASNLESGVPDRFSGSGSGTDFTLTISSLQAEDVAVYYCQHSR
h7E6_VL_N    (47)  PPKLLIYLASNLESGVPDRFSGSGSGTDFTLTISSLQAEDVAVYYCQHSR
m7E6_VL      (47)  PPKLLIYLASNLESGVPARFSGSGSGTDFTLNIHPVEEEDAATYYCQHSR
Consensus    (47)  PPKLLIYLASNLESGVPDRFSGSGSGTDFTLTISSLQAEDVAVYYCQHSR
                    97           111
h7E6_VL      (97)  ELPYTFGQGTKLEIK
h7E6_VL_L    (97)  ELPYTFGQGTKLEIK
h7E6_VL_N    (97)  ELPYTFGQGTKLEIK
m7E6_VL      (97)  ELPYTFGGGTKLEIK
Consensus    (97)  ELPYTFGQGTKLEIK
```

Figure 7A

```
                    1                                                46
    h6G11_VH   (1)  QVQLVQSGAEVKKPGASVKVSCKASGYTFTSYWINWVRQAPGQGLE
h6G11_VH_FKG   (1)  QVQLVQSGAEVKKPGASVKVSCKASGYTFTSYWINWVRQAPGQGLE
    m6G11_VH   (1)  QVQLQQPGAELVRPGASVKLSCKASGYTFTSYWINWVKQRPGHGLE
   Consensus   (1)  QVQLVQSGAEVKKPGASVKVSCKASGYTFTSYWINWVRQAPGQGLE
                    47                                               96
    h6G11_VH  (47)  WMGNIYPSDSYSNYNQKFKDRVTMTRDTSTSTVYMELSSLRSEDTAVYYC
h6G11_VH_FKG  (47)  WMGNIFPSDSYSNYNKKFKDRVTMTRDTSTSTVYMELSSLRSEDTAVYYC
    m6G11_VH  (47)  WIGNIYPSDSYSNYNQKFKDKATLTVDKSSSTAYMQVSSPTSEDSAVYYC
   Consensus  (47)  WMGNIYPSDSYSNYNQKFKDRVTMTRDTSTSTVYMELSSLRSEDTAVYYC
                    97         115
    h6G11_VH  (97)  ARGSSFDYWGQGTLVTVSS
h6G11_VH_FKG  (97)  ARGSGFDYWGQGTLVTVSS
    m6G11_VH  (97)  TYGSSFDYWGQGTTVTVSS
   Consensus  (97)  ARGSSFDYWGQGTLVTVSS
```

Figure 7B

```
                    1                                                46
    h6G11_VL   (1)  EIVLTQSPATLSLSPGERATLSCRASQTIGTSIHWYQQKPGQAPRL
 h6G11_VL_SF   (1)  EIVLTQSPATLSLSPGERATLSCRASQTIGTSIHWYQQKPGQAPRL
    m6G11_VL   (1)  DILLTQSPAILSVSPGERVSFSCRASQTIGTSIHWYQQRTNGSPRL
   Consensus   (1)  EIVLTQSPATLSLSPGERATLSCRASQTIGTSIHWYQQKPGQAPRL
                    47                                               96
    h6G11_VL  (47)  LIYYASESISGIPARFSGSGSGTDFTLTISSLEPEDFAVYYCQQSNSWPF
 h6G11_VL_SF  (47)  LIYYASESISGIPARFSGSGSGTDFTLTISSLEPEDFAVYYCSQSFSWPF
    m6G11_VL  (47)  LIKYASESISGIPSRFSGSGSGTDFTLSINSVESEDIADYYCQQSNSWPF
   Consensus  (47)  LIYYASESISGIPARFSGSGSGTDFTLTISSLEPEDFAVYYCQQSNSWPF
                    97   107
    h6G11_VL  (97)  TFGQGTKLEIK
 h6G11_VL_SF  (97)  TFGQGTKLEIK
    m6G11_VL  (97)  TFGSGTKLEIK
   Consensus  (97)  TFGQGTKLEIK
```

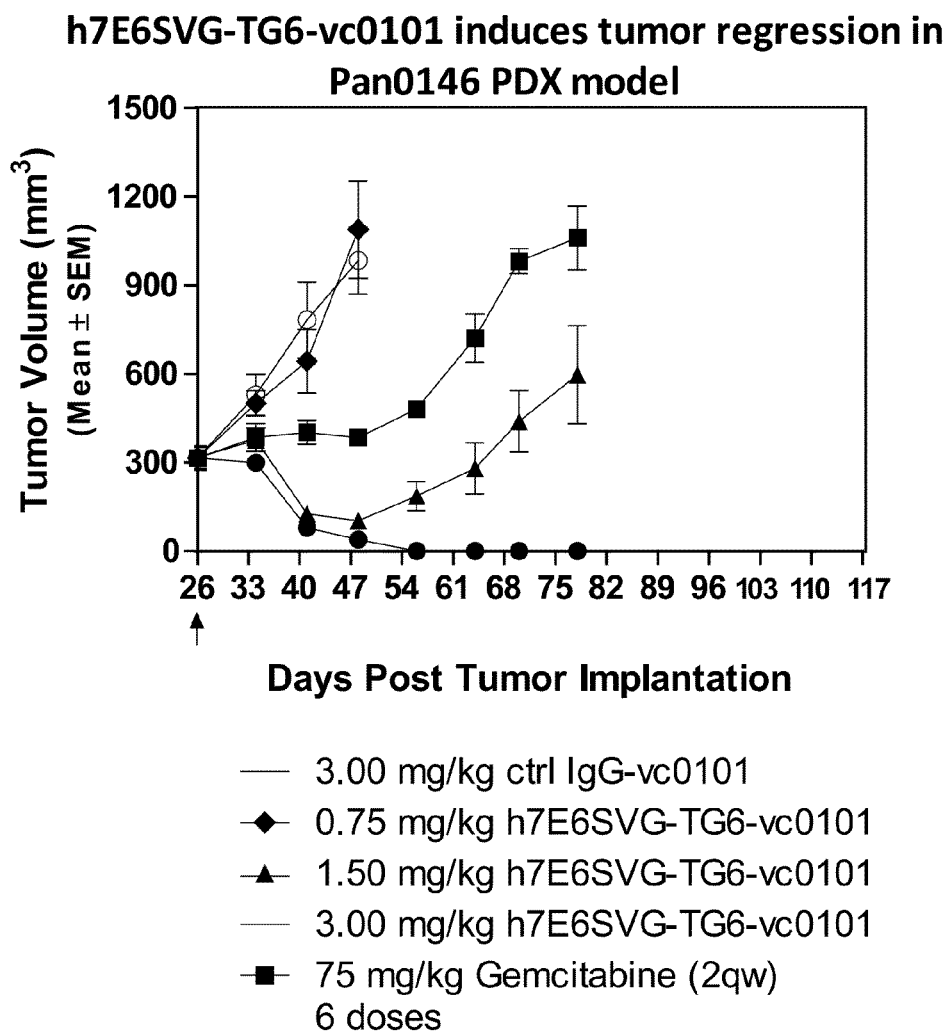

ANTIBODIES SPECIFIC FOR TROP-2 AND THEIR USES

RELATED APPLICATIONS

This application claims the benefits of U.S. Provisional Application No. 61/559,015 filed Nov. 11, 2011, U.S. Provisional Application No. 61/640,641 filed Apr. 30, 2012, and U.S. Provisional Application No. 61/717,288 filed Oct. 23, 2012 which are hereby incorporated by reference in their entireties.

REFERENCE TO SEQUENCE LISTING

This application is being filed electronically via EFS-Web and includes an electronically submitted sequence listing in .txt format. The .txt file contains a sequence listing entitled "PC71866A_SequenceListing_ST25.txt" created on Oct. 23, 2012 and having a size of 94.1 KB. The sequence listing contained in this .txt file is part of the specification and is incorporated herein by reference in its entirety.

FIELD

The present invention relates to antibodies, e.g., full length antibodies or antigen binding fragments thereof, that specifically bind to trophoblast cell-surface antigen (Trop-2). The invention further relates to antibody conjugates (e.g., antibody-drug-conjugates) comprising the Trop-2 antibodies, compositions comprising the Trop-2 antibodies, and methods of using the Trop-2 antibodies and their conjugates for treating conditions associated with Trop-2 expression (e.g., cancer).

BACKGROUND

Trophoblast cell-surface antigen (Trop-2), also referred to as M1S1, GA733-1 (gastric antigen 733-1), EGP-1 (epithelial glycoprotein-1), or TACSTD2 (tumor-associated calcium signal transducer), is a cell surface glycoprotein originally identified in human placental trophoblast and subsequently found to be highly expressed in most human carcinomas, but showed only restricted or limited expression in normal adult tissues. See, e.g., Varughese et al., Gynecologic Oncology, 122:171-177, 2011. Trop-2 is highly conserved among species. For example, human Trop-2 protein shares 79% identity with murine Trop-2 protein. See Cubas et al., Molecular Cancer, 9:253, 2010. Although the biological role of Trop-2 is still unclear, various studies have shown that overexpression of Trop-2 correlates with increased tumor aggressiveness, metastasis, and poor prognosis in various human carcinomas, such as colon cancer, ovarian cancer, and pancreatic cancer. See, e.g., Fang et al., Int. J. Colorectal Dis, 24:875-884, 2009; Bignotti et al., Eur. J. Cancer, 46:944-953, 2010; and Fong et al., Br J Cancer, 99:1290-1295, 2008. Studies have also shown that Trop-2 contributes to tumor pathogenesis at least in part by activating the ERK1/2 MAPK pathway which has important implications in cancer cell proliferation, migration, invasion, and survival. See Cubas et al., 2010, supra.

Overexpression of Trop-2 by epithelial tumor cells and its transmembrane location render Trop-2 an attractive target for cancer immunotherapy. Accordingly, a high affinity antibody to Trop-2, particularly to human Trop-2, would make a superior therapeutic agent for cancer treatment in human patients. Although various Trop-2 antibodies have been disclosed (see, e.g., U.S. Pat. No. 7,420,041 (antibody AR47A6.4.2), U.S. Pat. No. 5,840,854 (antibody BR110), U.S. Pat. No. 6,653,104 (antibody RS7), U.S. Pat. No. 7,517,964 (antibody RS7), US2012/0237518), it has been exceedingly difficult to identify monoclonal antibodies having high affinity, high specificity, and potent cytotoxic or tumor killing/inhibition/regression activity. There remains a need for antibodies and other immunotherapeutic agents (such as antibody-drug conjugates) directed against Trop-2 having improved efficacy and safety profile, and which are suitable for use with human patients.

SUMMARY

The invention disclosed herein is directed to antibodies and antibody conjugates (e.g., antibody-drug conjugates) that bind to Trop-2. In one aspect, the invention provides an antibody or antibody conjugate that specifically binds to domain 3 (e.g., amino acid residues 152-206) and domain 4 (e.g., amino acid residues 209-274) of human Trop-2 (SEQ ID NO:27) with a monovalent antibody binding affinity ($K_D$) of about 6.5 nM or less as measured by surface plasmon resonance.

In another aspect, the invention provides an isolated antibody, or an antigen binding fragment thereof, which specifically binds to Trop-2, wherein the antibody comprises a) a heavy chain variable (VH) region complementary determining regions comprising (i) a VH complementary determining region one (CDR1) comprising the sequence SYGVH (SEQ ID NO: 30), GGSISSY (SEQ ID NO: 36), or GGSISSYGVH (SEQ ID NO: 37); (ii) a VH CDR2 comprising the sequence VIWTX$_1$GX$_2$TDYNSALMX$_3$, wherein X$_1$ is G or S; X$_2$ is S or V; X$_3$ is S or G (SEQ ID NO: 49), or WTX$_1$GX$_2$ wherein X$_1$ is G or S, X$_2$ is S or V (SEQ ID NO: 50); and iii) a VH CDR3 comprising the sequence DGDYDRYTMDY (SEQ ID NO: 35); DYDRYTX$_1$DY, wherein X$_1$ is E or M (SEQ ID NO: 82); or DYDRYTX$_1$DY, wherein X$_1$ is any naturally occurring amino acid, e.g., A, R, N, D, C, Q, E, G, H, I, L, K, M, F, P, S, T, W, Y, or V (SEQ ID NO: 83) and/or b) a light chain variable region (VL) region complementary determining regions comprising (i) a VL CDR1 comprising the sequence RASKSVSTSX$_1$YSYMH, wherein X$_1$ is G, L, or N (SEQ ID NO: 63); (ii) a VL CDR2 comprising the sequence LASNLES (SEQ ID NO: 55); and (iii) a VL CDR3 comprising the sequence VLQHSRELPYT (SEQ ID NO: 56). In some embodiments, the antibody does not comprise a heavy chain variable region of the sequence QVQLKESG-PGLVAPSQSLSITCTVSGFSLTSYGVH-WVRQPPGKGLEWLGVIWTGGSTDY NSALMSRLS-INKDNSKSQVFLKMNSLQTDDTAMYYCARDGDYD-RYTMDYWGQGTSVTVSS (SEQ ID NO: 2) and a light chain variable region of the sequence DIVLTQSPASLAVS-LGQRATISCRASKSVSTSGYSYMHW-YQQKPGQPPKLLIYLASNLESG VPARFSGSGSGTD-FTLNIHPVEEEDAATYYCQHSRELPYTFGGGTKLEIK (SEQ ID NO: 1).

In another aspect, the invention provides an isolated antibody, or an antigen binding fragment thereof, which specifically binds to Trop-2, wherein the antibody comprises: a VH region comprising a VH CDR1, VH CDR2, and VH CDR3 of the VH sequence shown in SEQ ID NO: 5, 84, or 85; and/or a VL region comprising VL CDR1, VL CDR2, and VL CDR3 of the VL sequence shown in SEQ ID NO:3 or 6. In some embodiments, the VH region comprises (i) a VH CDR1 comprising the sequence SYGVH (SEQ ID NO: 30), GGSISSY (SEQ ID NO: 36), or GGSISSYGVH (SEQ ID NO: 37); (ii) a VH CDR2 comprising the sequence VIWTSGVTDYN-SALMG (SEQ ID NO: 38) or WTSGV (SEQ ID NO: 39); and (iii) a VH CDR3 comprising the sequence DGDYDRYT- MDY (SEQ ID NO: 35) or DYDRYTX$_1$DY, wherein X$_1$ is E or M (SEQ ID NO: 82). In some embodiments, the VL region comprises (i) a VL CDR1 comprising the sequence RASKS-VSTSGYSYMH (SEQ ID NO: 54) or RASKS-VSTSLYSYMH (SEQ ID NO: 57); (ii) a VL CDR2 comprising the sequence LASNLES (SEQ ID NO: 55); and (iii) a VL CDR3 comprising the sequence QHSRELPYT (SEQ ID NO: 56). In some embodiments, the antibody comprises (a) heavy chain CDRs comprising: (i) a CDR1 comprising the sequence SYGVH (SEQ ID NO: 30), GGSISSY (SEQ ID NO: 36), or GGSISSYGVH (SEQ ID NO: 37); (ii) a CDR2 comprising the sequence VIWTSGVTDYNSALMG (SEQ ID NO: 38) or WTSGV (SEQ ID NO: 39); and (iii) a CDR3 comprising the sequence DGDYDRYTMDY (SEQ ID NO: 35), DYDRYT-MDY (SEQ ID NO: 99), or DYDRYTEDY (SEQ ID NO: 100); and b) light chain CDRs comprising (i) a CDR1 comprising the sequence RASKSVSTSGYSYMH (SEQ ID NO: 54) or RASKSVSTSLYSYMH (SEQ ID NO: 57); (ii) a CDR2 comprising the sequence LASNLES (SEQ ID NO: 55); and (iii) a CDR3 comprising the sequence QHSRELPYT (SEQ ID NO: 56). In some embodiments, the VH region comprises the sequence shown in SEQ ID NO: 5, 84, or 85 or a variant with one or several conservative amino acid substitutions in residues that are not within a CDR and/or the VL region comprises the amino acid sequence shown in SEQ ID NO: 3, 6, or a variant thereof with one or several amino acid substitutions in amino acids that are not within a CDR. In some embodiments, the antibody comprises a light chain comprising the sequence shown in SEQ ID NO: 66 and/or a heavy chain comprising the sequence shown in SEQ ID NO: 65. In some embodiments, the antibody comprises a VH region produced by the expression vector with ATCC Accession No. PTA-12872. In some embodiments, the antibody comprises a VL region produced by the expression vector with ATCC Accession No. PTA-12871.

In another aspect, the invention provides an isolated antibody, or an antigen binding fragment thereof, which specifically binds to domain 1 (e.g., amino acid residues 31-71) of human Trop-2 (SEQ ID NO:27) with a binding affinity (K$_D$) of about 35 nM or less as measured by surface plasmon resonance.

In another aspect, the invention provides an isolated antibody, or an antigen binding fragment thereof, which specifically binds to Trop-2, wherein the antibody comprises a) a heavy chain variable (VH) region complementary determining regions comprising (i) a VH CDR1 comprising the sequence SYWIN (SEQ ID NO: 40), GYTFTSY (SEQ ID NO: 41), or GYTFTSYWIN (SEQ ID NO: 42); (ii) a VH CDR2 comprising the sequence NIX$_1$PSDSYSNYNX$_2$KFKD wherein X$_1$ is Y or F; X$_2$ is Q or K (SEQ ID NO: 51), or X$_1$PSDSY wherein X$_1$ is Y or F (SEQ ID NO:52); and iii) a VH CDR3 comprising the sequence GSX$_1$FDY wherein X$_1$ is S or G (SEQ ID NO: 53); and/or b) a VL region complementary determining regions comprising (i) a VL CDR1 comprising the sequence RASQTIGTSIH (SEQ ID NO: 59); (ii) a VL CDR2 comprising the sequence YASESIS (SEQ ID NO: 60); and (iii) a VL CDR3 comprising the sequence X$_1$QSX$_2$SWPFT wherein X$_1$ is Q or S; X$_2$ is N or F (SEQ ID NO: 64).

In another aspect, the invention provides an isolated antibody, or an antigen binding fragment thereof, which specifically binds to Trop-2, wherein the antibody comprises: a VH region comprising a VH CDR1, VH CDR2, and VH CDR3 of the VH sequence shown in SEQ ID NO: 13; and/or a VL region comprising VL CDR1, VL CDR2, and VL CDR3 of the VL sequence shown in SEQ ID NO: 12. In some embodiments, the VH region comprises (i) a VH CDR1 comprising the sequence SYWIN (SEQ ID NO: 40), GYTFTSY (SEQ ID NO: 41), or GYTFTSYWIN (SEQ ID NO: 42); (ii) a VH CDR2 comprising the sequence NIFPSDSYSNYNKKFKD (SEQ ID NO: 46) or FPSDSY (SEQ ID NO: 47); and (iii) a VH CDR3 comprising the sequence GSGFDY (SEQ ID NO: 48). In some embodiments, the VL region comprises (i) a VL CDR1 comprising the sequence RASQTIGTSIH (SEQ ID NO: 59); (ii) a VL CDR2 comprising the sequence YASESIS (SEQ ID NO: 60); and (iii) a VL CDR3 comprising the sequence SQSFSWPFT (SEQ ID NO: 62). In some embodiments, the antibody comprises (a) heavy chain CDRs comprising: (i) a CDR1 comprising the sequence SYWIN (SEQ ID NO: 40), GYTFTSY (SEQ ID NO: 41), or GYTFTSYWIN (SEQ ID NO: 42); (ii) a CDR2 comprising the sequence NIFPSDSYSNYNKKFKD (SEQ ID NO: 46) or FPSDSY (SEQ ID NO: 47); and (iii) a VH CDR3 comprising the sequence GSGFDY (SEQ ID NO: 48); and b) light chain CDRs comprising: (i) a CDR1 comprising the sequence RASQTIGTSIH (SEQ ID NO: 59); (ii) a CDR2 comprising the sequence YASESIS (SEQ ID NO: 60); and (iii) a CDR3 comprising the sequence SQSFSWPFT (SEQ ID NO: 62). In some embodiments, the VH region comprises the sequence shown in SEQ ID NO: 13 or a variant with one or several conservative amino acid substitutions in residues that are not within a CDR and/or the VL region comprises the amino acid sequence shown in SEQ ID NO: 12 or a variant thereof with one or several amino acid substitutions in amino acids that are not within a CDR. In some embodiments, the antibody comprises a light chain comprising the sequence shown in SEQ ID NO: 68 and a heavy chain comprising the sequence shown in SEQ ID NO: 67.

In some embodiments, the antibody can be a human antibody, a humanized antibody, or a chimeric antibody. In some embodiments, the antibody is a monoclonal antibody.

In some embodiments, the antibody comprises a constant region. In some embodiments, the antibody is of the human IgG1, IgG2 or IgG2Δa, IgG3, or IgG4 subclass. In some embodiments, the antibody comprises a glycosylated constant region. In some embodiments, the antibody comprises a constant region having increased binding affinity to one or more human Fc gamma receptor(s).

In another aspect, the invention provides an isolated antibody which specifically binds to Trop-2 and competes with the antibodies as described herein (e.g., m7E6, h7E6_SVG, h7E6_SVG4, h7E6_SVG19, h7E6_SVG6, h7E6_SVG20, h7E6_SVG22, h7E6_SVG28, h7E6_SVG30, h7E6_SVGL, h7E6_SVGL1, h7E6_SVGL2, h7E6_SVGL3, h7E6_SVGL4, h7E6_SVGL5, h7E6_SVGN, m6G11, h6G11, or h6G11_FKG_SF). In some embodiments, the antibody competes with h7E6_SVG and has a monovalent antibody binding affinity (K$_D$) of about 6.5 nM or less as measured by surface plasmon resonance.

In another aspect, the invention provides a conjugate of the antibody or the antigen binding fragment as described herein, wherein the antibody or the antigen binding fragment is conjugated to an agent, wherein the agent is selected from the group consisting of a cytotoxic agent, an immunomodulating agent, an imaging agent, a therapeutic protein, a biopolymer, and an oligonucleotide. In some embodiments, the agent is a cytotoxic agent (e.g., monomethyl auristatin D (MMAD) or other auristatins).

In another aspect, the invention provides an isolated antibody comprising an acyl donor glutamine-containing tag engineered at a specific site of the antibody. In some embodiments, the tag comprises amino acid glutamine (Q) or an amino acid sequence GGLLQGG (SEQ ID NO:78), LLQGA (SEQ ID NO:79), GGLLQGA (SEQ ID NO:81), LLQ, or LLQX$_1$X$_2$X$_3$X$_4$X$_5$, wherein X$_1$ is G or P, wherein X$_2$ is A, G, P, or absent, wherein X$_3$ is A, G, K, P, or absent, wherein X$_4$ is G, K, or absent, and wherein X$_5$ is K or absent (SEQ ID NO: 88). In some embodiments, the Trop-2 antibody or the conjugate as described herein comprises an acyl donor glutamine-containing tag engineered at a specific site, such as G, GGLLQGG (SEQ ID NO:78), LLQGA (SEQ ID NO:79), GGLLQGA (SEQ ID NO:81), LLQ, or LLQX$_1$X$_2$X$_3$X$_4$X$_5$, wherein X$_1$ is G or P, wherein X$_2$ is A, G, P, or absent, wherein X$_3$ is A, G, K, P, or absent, wherein X$_4$ is G, K, or absent, and wherein X$_5$ is K or absent (SEQ ID NO: 88).

In one variation, the invention provides an isolated antibody comprising an acyl donor glutamine-containing tag and an amino acid modification at position 222, 340, or 370 of the antibody (Kabat numbering scheme), wherein the modification is an amino acid deletion, insertion, substitution, mutation, or any combination thereof. In some embodiments, the Trop-2 antibody or the conjugate as described herein comprises the acyl donor glutamine-containing tag (e.g., Q, GGLLQGG (SEQ ID NO:78), LLQGA (SEQ ID NO:79), GGLLQGA (SEQ ID NO:81), LLQ, or LLQX$_1$X$_2$X$_3$X$_4$X$_5$, wherein X$_1$ is G or P, wherein X$_2$ is A, G, P, or absent, wherein X$_3$ is A, G, K, P, or absent, wherein X$_4$ is G, K, or absent, and wherein X$_5$ is K or absent (SEQ ID NO: 88)) engineered at a specific site (e.g., at a carboxyl terminus of the heavy or light chain or at an another site) of the Trop-2 antibody and an amino acid modification at position 222, 340, or 370 of the antibody (Kabat numbering scheme). In some embodiments, the amino acid modification is a substitution from lysine to arginine.

In another aspect, the invention provides a conjugate of the antibody or the antigen binding fragment as described herein, wherein the conjugate comprises the formula: antibody-(acyl donor glutamine-containing tag)-(linker)-(cytotoxic agent), wherein the acyl donor glutamine-containing tag is engineered at a specific site of the antibody or the antigen binding fragment (e.g., at a carboxyl terminus of the heavy or light chain or at an another site), wherein the tag is conjugated to a linker (e.g., a linker containing one or more reactive amines (e.g., primary amine NH$_2$)), and wherein the linker is conjugated to a cytotoxic agent (e.g., MMAD or other auristatins).

In some embodiments, the conjugate is selected from the group consisting of 1) antibody-LLQGA-(acetyl-lysine-valine-citrulline-p-aminobenzyloxycarbonyl)-0101, wherein acetyl-lysine-valine-citrulline-p-aminobenzyloxycarbonyl is AcLys-VC-PABC, and wherein 0101 is 2-methylalanyl-N-[(3R,4S,5S)-3-methoxy-1-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-5-methyl-1-oxoheptan-4-yl]-N-methyl-L-valinamide; 2) antibody-LLQGA-AcLys-VC-PABC-MMAD; 3) antibody-LLQX$_1$X$_2$X$_3$X$_4$X$_5$ (SEQ ID NO: 88)-AcLys-VC-PABC-0101; 4) antibody-LLQX$_1$X$_2$X$_3$X$_4$X$_5$ (SEQ ID NO: 88)-AcLys-VC-PABC-MMAD; 5) antibody-GGLLQGG (SEQ ID NO: 78)-AcLys-VC-PABC-0101; and 6) antibody-GGLLQGG (SEQ ID NO: 78)-AcLys-VC-PABC-MMAD. In some embodiments, the conjugate comprises an amino acid substitution from lysine to arginine at position 222. In some embodiments, the conjugate comprises an amino acid lysine (K) deletion at the C-terminus of the heavy chain of the antibody.

In another aspect, the invention provides a conjugate of the antibody or the antigen binding fragment as described herein, the conjugate comprises amino acid substitutions at positions N297Q and K222R, a linker comprising amino-PEG6-propionyl, and a cytotoxic agent (e.g., MMAD or other auristatins).

In another aspect, the invention provides a pharmaceutical composition comprising a therapeutically effective amount of the Trop-2 antibody or the conjugate as described herein and a pharmaceutically acceptable carrier.

In another aspect, the invention provides an isolated polynucleotide comprising a nucleotide sequence encoding the Trop-2 antibody as described herein. In some embodiments, provided is a vector comprising the polynucleotide.

In another aspect, the invention provides an isolated host cell that recombinantly produces the Trop-2 antibody as described herein.

In another aspect, the invention provides a method for treating a condition associated with Trop-2 expression in a subject comprising administering to the subject in need thereof an effective amount of the pharmaceutical composition as described herein. In some embodiments, the condition is a cancer. In some embodiments, the cancer is selected from the group consisting of bladder, breast, cervical, choriocarcinoma, colon, esophageal, gastric, glioblastoma, head and neck, kidney, lung, oral, ovarian, pancreatic, prostate cancer, and skin cancer.

In another aspect, the invention provides a method of inhibiting tumor growth or progression in a subject who has a Trop-2 expressing tumor, comprising administering to the subject in need thereof an effective amount of the pharmaceutical composition as described herein.

In another aspect, the invention provides a method of inhibiting metastasis of Trop-2 expressing cancer cells in a subject, comprising administering to the subject in need thereof an effective amount of the pharmaceutical composition as described herein.

In another aspect, the invention provides a method of inducing tumor regression in a subject who has a Trop-2 expressing tumor, comprising administering to the subject in need thereof an effective amount of the pharmaceutical composition as described herein.

In some embodiments, the antibody or the conjugate as described herein can be administered parenterally in an individual. In some embodiments, the individual is a human.

In some embodiments, the antibody described herein does not comprise a heavy chain variable region of the sequence QVQLKESGPGLVAPSQSLSITCTVSGFSLTSYGVHWVRQPPGKGLEWLGVIWTGGSTDYNSALMSRLSINKDNSKSQVFLKMNSLQTDDTAMYYCARDGDYDRYTMDYWGQGTSVTVSS (SEQ ID NO: 2) and a light chain variable region of the sequence DIVLTQSPASLAVSLGQRATISCRASKSVSTSGYSYMHWYQQKPGQPPKLLIYLASNLESGVPARFSGSGSGTDFTLNIHPVEEEDAATYYCQHSRELPYTFGGGTKLEIK (SEQ ID NO: 1).

BRIEF DESCRIPTION OF THE FIGURES/DRAWINGS

Figure 3:
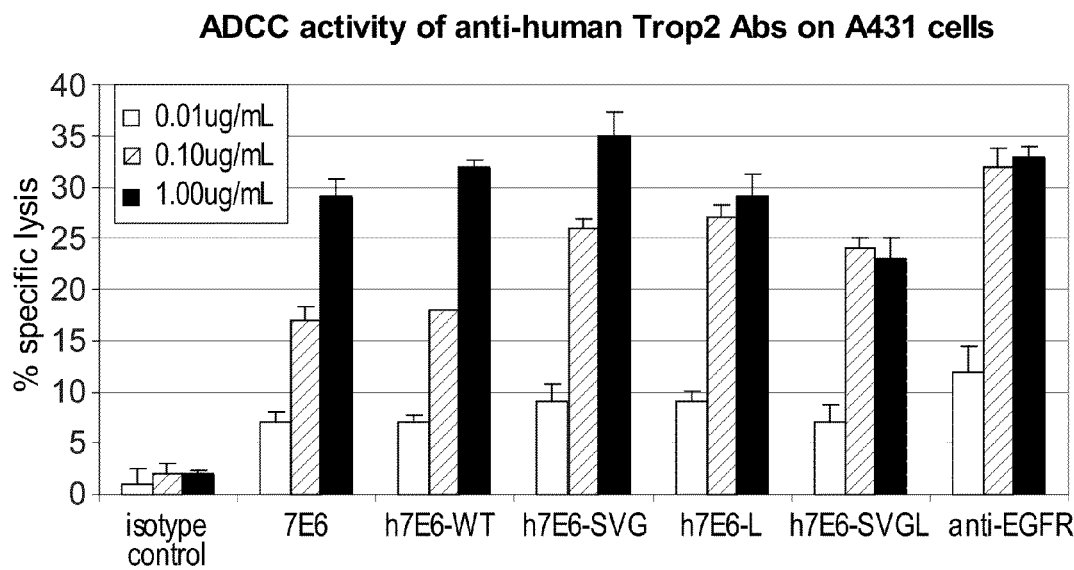

FIG. 3 depicts the ADCC activity of chimeric and humanized Trop-2 7E6 antibodies in A431 cells. 7E6 corresponds to the chimeric Trop-2 7E6 antibody (e.g., antibody comprising SEQ ID NOs: 2 and 3), h7E6-WT corresponds to an antibody comprising SEQ ID NOs: 4 and 3, h7E6-SVG corresponds to an antibody comprising SEQ ID NOs: 5 and 3, h7E6-L corresponds to an antibody comprising SEQ ID NOs: 4 and 6, h7E6-SVGL corresponds to an antibody comprising SEQ ID NOs: 5 and 6, and anti-EGFR (Epidermal Growth Factor Receptor) corresponds to a positive control antibody.

FIG. 4 depicts the amino acid sequence alignment between human Trop-1 (SEQ ID NO: 29) and human Trop-2 (SEQ ID NO: 27), and the consensus sequence (SEQ ID NO: 69).

FIG. 5 depicts the amino acid sequence alignment between human Trop-2 (SEQ ID NO: 27) and mouse Trop-2 (SEQ ID NO: 28), and the consensus sequence (SEQ ID NO: 70).

FIG. 6A depicts the amino acid sequence alignment of the heavy chain variable regions of Trop-2 antibodies h7E6 (SEQ ID NO: 4), h7E6_SVG (SEQ ID NO: 5), and m7E6 (SEQ ID NO: 2), and their consensus sequence (SEQ ID NO: 71).

FIG. 6B depicts the amino acid sequence alignment of the light chain variable regions of Trop-2 antibodies h7E6_VL (SEQ ID NO: 3), h7E6_VL_L (SEQ ID NO: 6), h7E6_VL_N (SEQ ID NO: 7), and m7E6_VL (SEQ ID NO: 1), and their consensus sequence (SEQ ID NO: 72).

FIG. 7A depicts the amino acid sequence alignment of the heavy chain variable regions of Trop-2 antibodies h6G11 (SEQ ID NO: 11), h6G11_FKG_SF (SEQ ID NO: 13), and m6G11 (SEQ ID NO: 9), and their consensus sequence (SEQ ID NO: 73).

FIG. 7B depicts the amino acid sequence alignment of the light chain variable regions of Trop-2 antibodies h6G11 (SEQ ID NO: 10), h6G11_FKG_SF (SEQ ID NO: 12), and m6G11 (SEQ ID NO: 8), and their consensus sequence (SEQ ID NO: 74).

Figure 8:
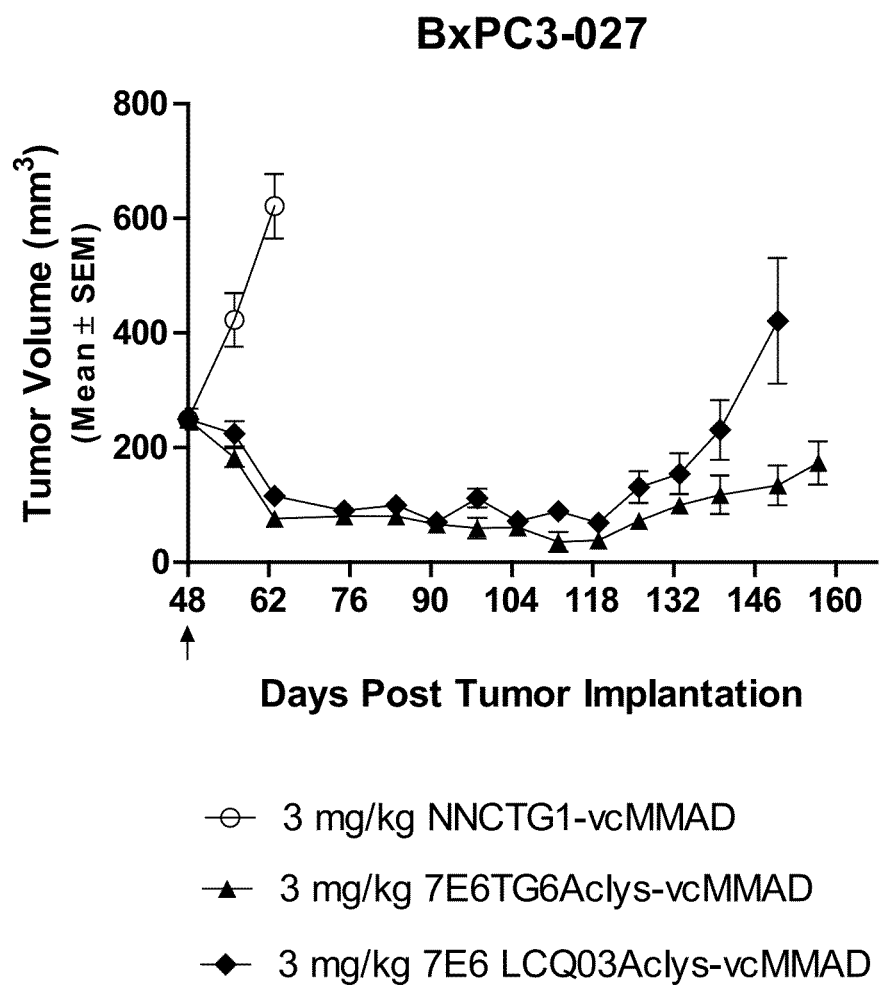

FIG. 8 depicts that chimeric (7E6) Trop-2 antibody conjugated to AcLys-vc-PABC-MMAD induced long term tumor regression in BxPC3 Xenograft model. AcLys-vc-PABC-MMAD corresponds to Acetyl-Lysine-Valine-Citrulline-p-aminobenzyloxycarbonyl-Monomethyl Auristatin D. LCQ03 and TG6 correspond to glutamine-containing transglutaminase tags SEQ ID NOs:78 and 79, respectively. NNC-TG1-vcMMAD represents control antibody conjugated to glutamine-containing transglutaminase tag (SEQ ID NO: 75) and vcMMAD.

Figure 9A:
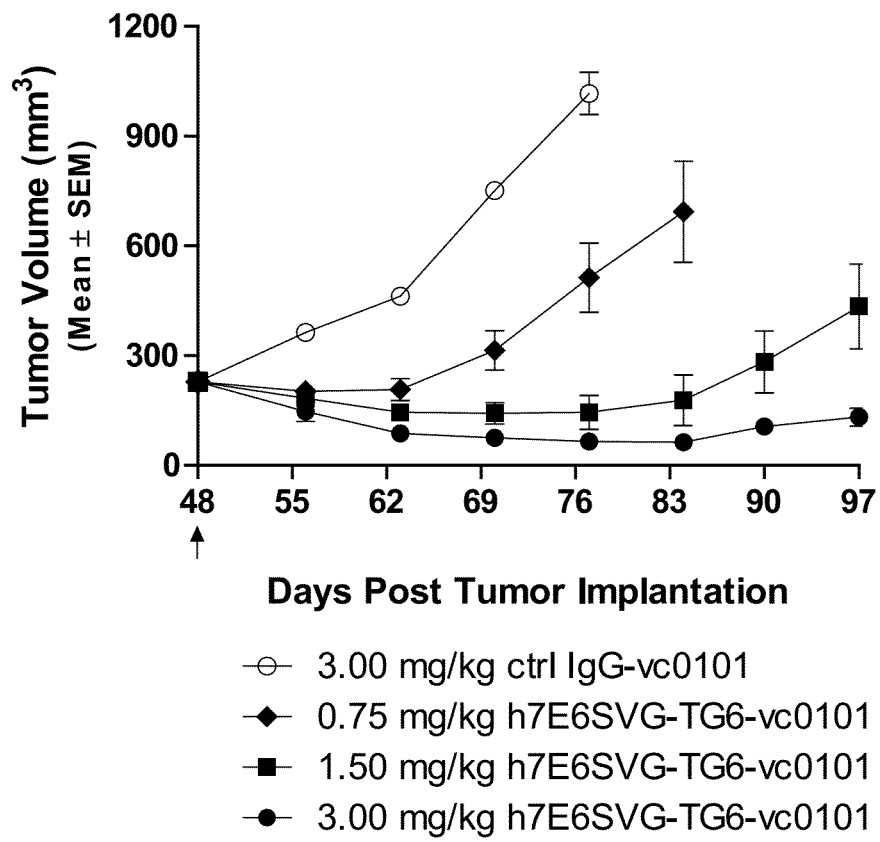

FIG. 9A depicts that humanized (h7E6SVG) Trop-2 antibody conjugated to vc0101 induced tumor regression in pancreatic tumor BxPC3 xenograft model. Vc0101 corresponds to AcLys-vc-PABC-0101 (Acetyl-Lysine-valine-citrulline-p-aminobenzyloxycarbonyl-(2-methylalanyl-N-[(3R,4S,5S)-3-methoxy-1-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-5-methyl-1-oxoheptan-4-yl]-N-methyl-L-valinamide). TG6 corresponds to glutamine-containing transglutaminase tag SEQ ID NO:79.

Figure 9B:
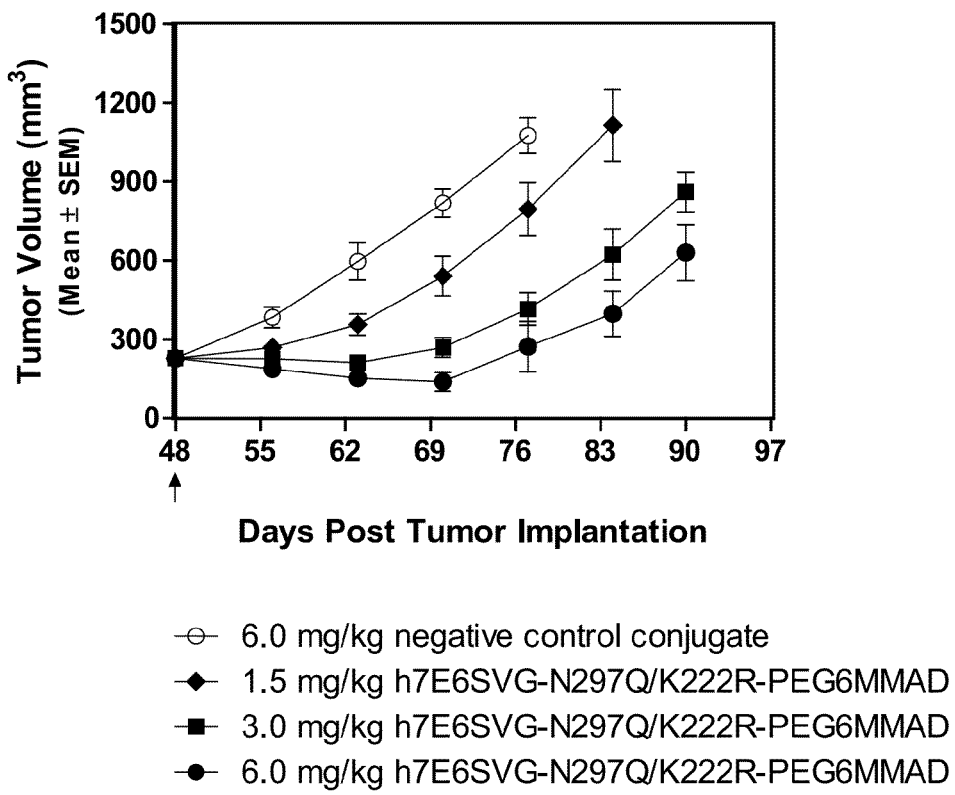

FIG. 9B depicts that humanized (h7E6SVG) Trop-2 antibody having amino acid substitutions at positions 297 and 222 and conjugated to PEG6-MMAD induced tumor regression in pancreatic tumor BxPC3 xenograft model. PEG6-MMAD corresponds to (Propylene Glycol)$_6$-propionyl-MMAD.

Figure 9C:
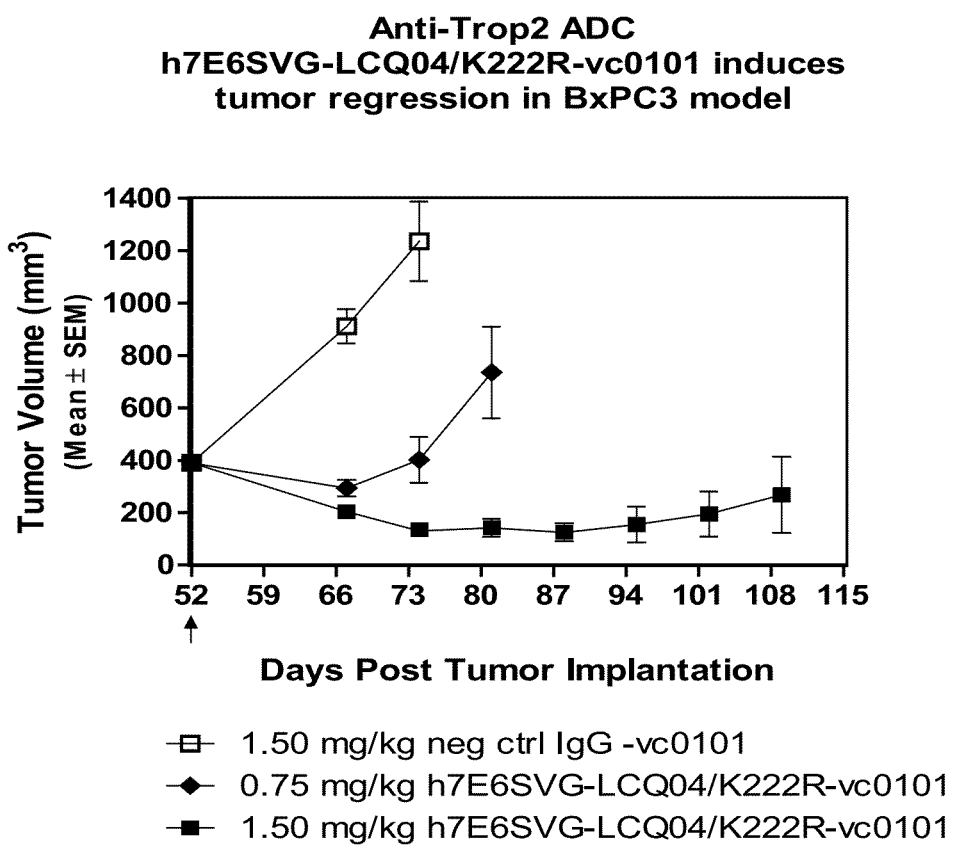

FIG. 9C depicts that humanized (h7E6SVG) Trop-2 antibody having amino acid substitution at position 222 and conjugated to vc0101 induced tumor regression in pancreatic tumor BxPC3 xenograft model. LCQ04 corresponds to glutamine-containing transglutaminase tag SEQ ID NO: 79. vc0101 corresponds to AcLys-vc-PABC-0101.

Figure 10:
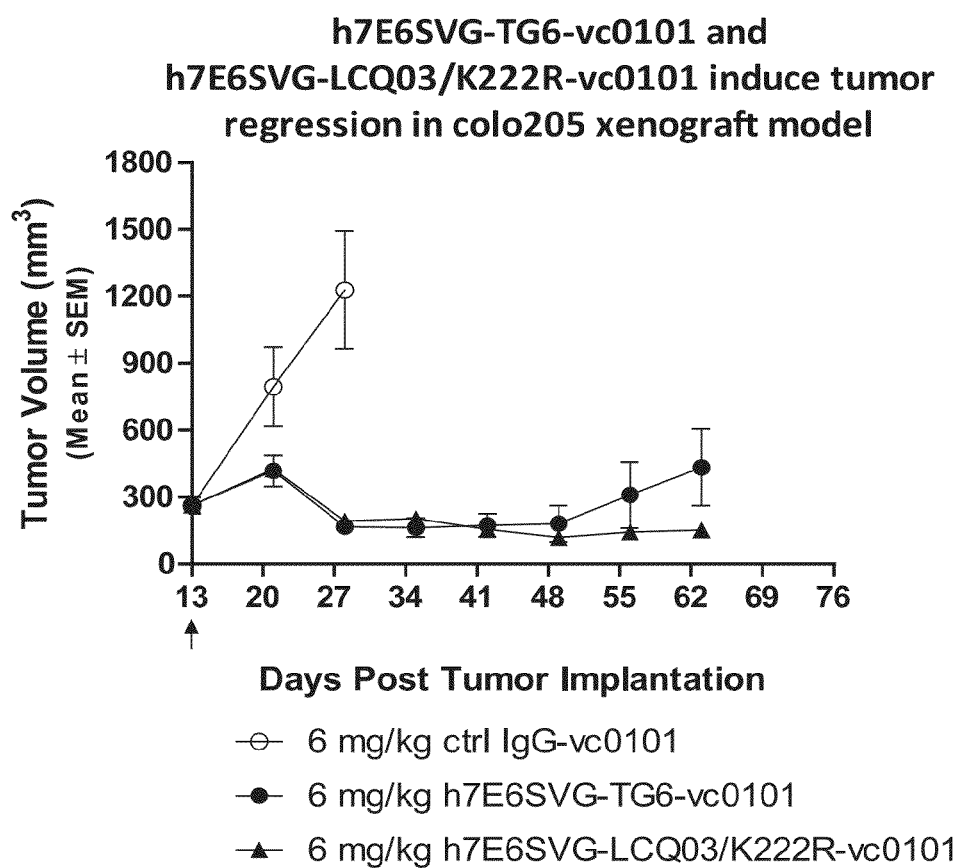

FIG. 10 depicts that humanized (h7E6SVG) Trop-2 antibody conjugated to vc0101 induced tumor regression in colorectal tumor Colo205 xenograft model. TG6 and LCQ03 correspond to glutamine-containing transglutaminase tags SEQ ID NOs: 79 and 78, respectively.

Figure 11:
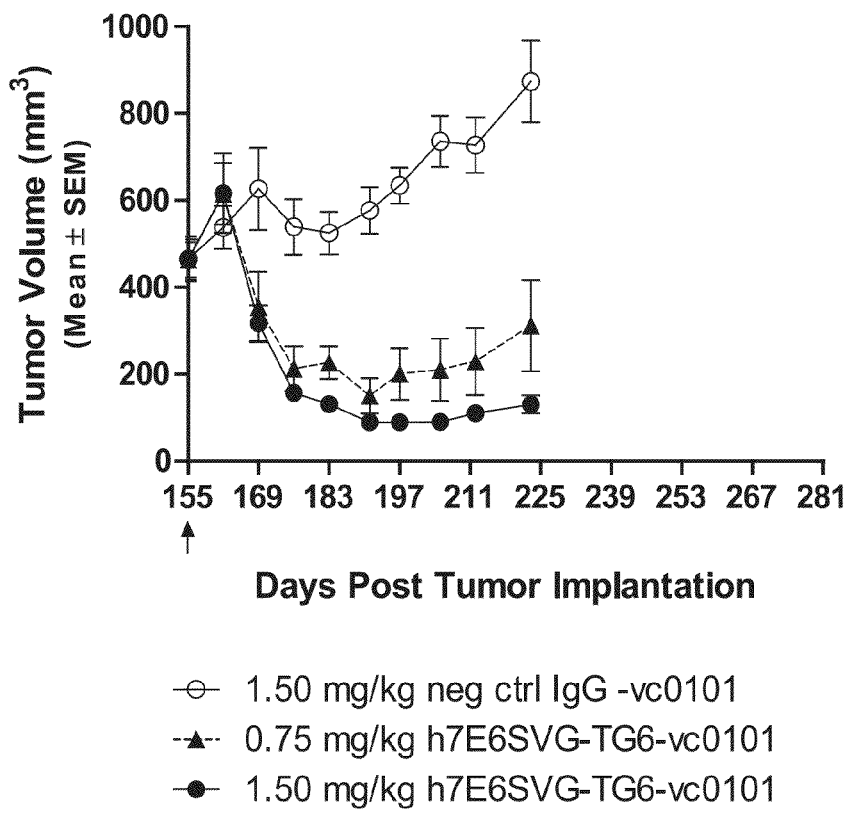

FIG. 11 depicts that humanized (h7E6SVG) Trop-2 antibody conjugated to vc0101 induced tumor regression in Ovarian PDX Ova196756 xenograft model. TG6 corresponds to glutamine-containing transglutaminase tag SEQ ID NO: 79.

Figure 12B:
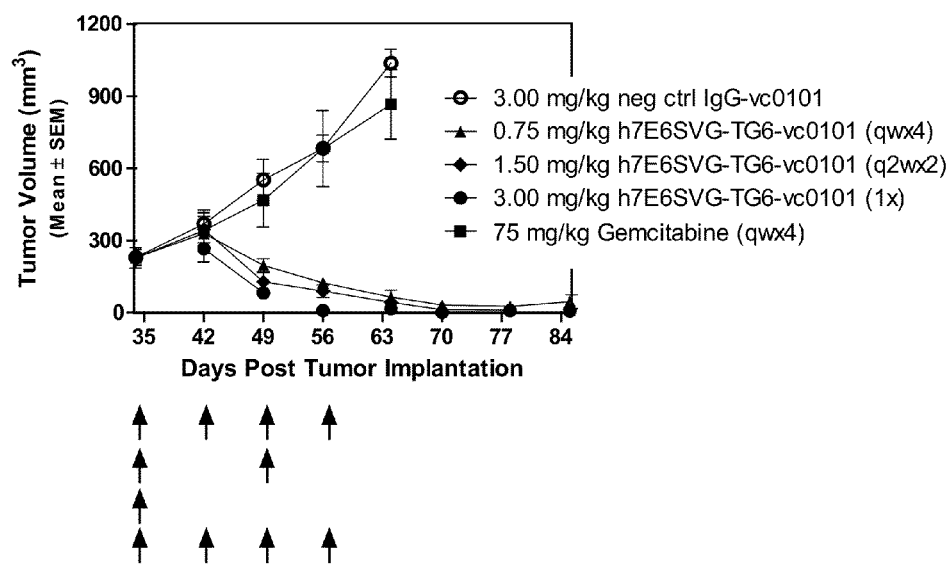

FIG. 12A shows that humanized (h7E6SVG) Trop-2 antibody conjugated to vc0101 has superior efficacy than gemcitabine to induce tumor regression in Pan0146 pancreatic PDX model. TG6 corresponds to glutamine-containing transglutaminase tag SEQ ID NO: 79 (same as in FIG. 12B).

FIG. 12B shows that continuous dosing of humanized (h7E6SVG) Trop-2 antibody conjugated to vc0101 resulted in sustained tumor regression in pancreatic PDX Pan0146 xenograft model.

Figure 13:
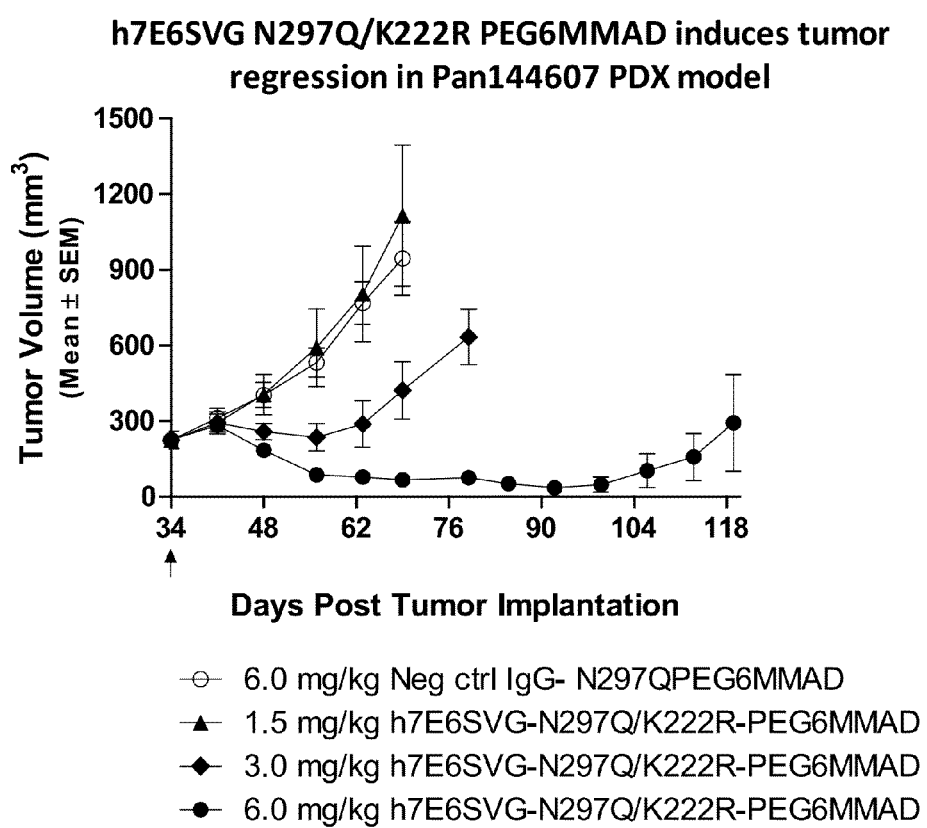

FIG. 13 shows that that a single dose of the humanized anti-Trop2 antibody conjugated with PEG6-MMAD induced tumor regression in pancreatic Pan144607 PDX model.

Figure 14:
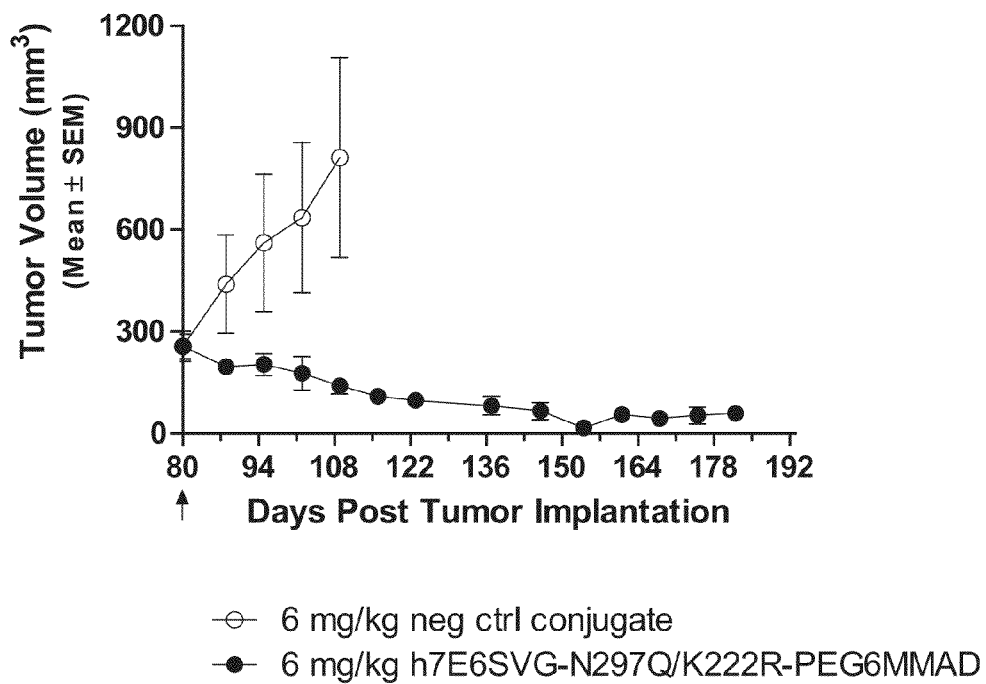

FIG. 14 shows that a single dose of the humanized anti-Trop2 antibody conjugated with PEG6-MMAD induced tumor regression in pancreatic Pan0135 PDX model.

DETAILED DESCRIPTION

The invention disclosed herein provides antibodies and antibody conjugates (e.g., antibody-drug conjugates) that specifically bind to Trop-2 (e.g., human Trop-2). The invention also provides polynucleotides encoding these antibodies, compositions comprising these antibodies, and methods of making and using these antibodies. The invention also provides methods for treating a condition associated with Trop-2 expression in a subject, such as cancer (e.g., colon, gastric, head and neck, lung, ovarian, and pancreatic cancer).

General Techniques

The practice of the present invention will employ, unless otherwise indicated, conventional techniques of molecular biology (including recombinant techniques), microbiology, cell biology, biochemistry and immunology, which are within the skill of the art. Such techniques are explained fully in the literature, such as, Molecular Cloning: A Laboratory Manual, second edition (Sambrook et al., 1989) Cold Spring Harbor Press; Oligonucleotide Synthesis (M. J. Gait, ed., 1984); Methods in Molecular Biology, Humana Press; Cell Biology: A Laboratory Notebook (J. E. Cellis, ed., 1998) Academic Press; Animal Cell Culture (R. I. Freshney, ed., 1987); Introduction to Cell and Tissue Culture (J. P. Mather and P. E. Roberts, 1998) Plenum Press; Cell and Tissue Culture: Laboratory Procedures (A. Doyle, J. B. Griffiths, and D. G. Newell, eds., 1993-1998) J. Wiley and Sons; Methods in Enzymology (Academic Press, Inc.); Handbook of Experimental Immunology (D. M. Weir and C. C. Blackwell, eds.); Gene Transfer Vectors for Mammalian Cells (J. M. Miller and M. P. Calos, eds., 1987); Current Protocols in Molecular Biology (F. M. Ausubel et al., eds., 1987); PCR: The Polymerase Chain Reaction, (Mullis et al., eds., 1994); Current Protocols in Immunology (J. E. Coligan et al., eds., 1991); Short Protocols in Molecular Biology (Wiley and Sons, 1999); Immunobiology (C. A. Janeway and P. Travers, 1997); Antibodies (P. Finch, 1997); Antibodies: a practical approach (D. Catty., ed., IRL Press, 1988-1989); Monoclonal antibodies: a practical approach (P. Shepherd and C. Dean, eds., Oxford University Press, 2000); Using antibodies: a laboratory manual (E. Harlow and D. Lane (Cold Spring Harbor Laboratory Press, 1999); The Antibodies (M. Zanetti and J. D. Capra, eds., Harwood Academic Publishers, 1995).

DEFINITIONS

An "antibody" is an immunoglobulin molecule capable of specific binding to a target, such as a carbohydrate, polynucleotide, lipid, polypeptide, etc., through at least one antigen recognition site, located in the variable region of the immunoglobulin molecule. As used herein, the term encompasses not only intact polyclonal or monoclonal antibodies, but also fragments thereof (such as Fab, Fab', F(ab')$_2$, Fv), single chain (ScFv) and domain antibodies (including, for example, shark and camelid antibodies), and fusion proteins comprising an antibody, and any other modified configuration of the immunoglobulin molecule that comprises an antigen recognition site. An antibody includes an antibody of any class, such as IgG, IgA, or IgM (or sub-class thereof), and the antibody need not be of any particular class. Depending on the antibody amino acid sequence of the constant region of its heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA1 and IgA2. The heavy-chain constant regions that correspond to the different classes of immunoglobulins are called alpha, delta, epsilon, gamma, and mu, respectively. The subunit structures and three-dimensional configurations of different classes of immunoglobulins are well known.

The term "antigen binding fragment" or "antigen binding portion" of an antibody, as used herein, refers to one or more fragments of an intact antibody that retain the ability to specifically bind to a given antigen (e.g., Trop-2). Antigen binding functions of an antibody can be performed by fragments of an intact antibody. Examples of binding fragments encompassed within the term "antigen binding fragment" of an antibody include Fab; Fab'; F(ab')$_2$; an Fd fragment consisting of the VH and CH1 domains; an Fv fragment consisting of the VL and VH domains of a single arm of an antibody; a single domain antibody (dAb) fragment (Ward et al., Nature 341:544-546, 1989), and an isolated complementarity determining region (CDR).

An antibody, an antibody conjugate, or a polypeptide that "preferentially binds" or "specifically binds" (used interchangeably herein) to a target (e.g., Trop-2 protein) is a term well understood in the art, and methods to determine such specific or preferential binding are also well known in the art. A molecule is said to exhibit "specific binding" or "preferential binding" if it reacts or associates more frequently, more rapidly, with greater duration and/or with greater affinity with a particular cell or substance than it does with alternative cells or substances. An antibody "specifically binds" or "preferentially binds" to a target if it binds with greater affinity, avidity, more readily, and/or with greater duration than it binds to other substances. For example, an antibody that specifically or preferentially binds to a Trop-2 epitope is an antibody that binds this epitope with greater affinity, avidity, more readily, and/or with greater duration than it binds to other Trop-2 epitopes or non-Trop-2 epitopes. It is also understood that by reading this definition, for example, an antibody (or moiety or epitope) that specifically or preferentially binds to a first target may or may not specifically or preferentially bind to a second target. As such, "specific binding" or "preferential binding" does not necessarily require (although it can include) exclusive binding. Generally, but not necessarily, reference to binding means preferential binding.

A "variable region" of an antibody refers to the variable region of the antibody light chain or the variable region of the antibody heavy chain, either alone or in combination. As known in the art, the variable regions of the heavy and light chain each consist of four framework regions (FR) connected by three complementarity determining regions (CDRs) also known as hypervariable regions. The CDRs in each chain are held together in close proximity by the FRs and, with the CDRs from the other chain, contribute to the formation of the antigen binding site of antibodies. There are at least two techniques for determining CDRs: (1) an approach based on cross-species sequence variability (i.e., Kabat et al. Sequences of Proteins of Immunological Interest, (5th ed., 1991, National Institutes of Health, Bethesda Md.)); and (2) an approach based on crystallographic studies of antigen-antibody complexes (Al-lazikani et al., 1997, J. Molec. Biol. 273:927-948). As used herein, a CDR may refer to CDRs defined by either approach or by a combination of both approaches.

A "CDR" of a variable domain are amino acid residues within the variable region that are identified in accordance with the definitions of the Kabat, Chothia, the accumulation of both Kabat and Chothia, AbM, contact, and/or conformational definitions or any method of CDR determination well known in the art. Antibody CDRs may be identified as the hypervariable regions originally defined by Kabat et al. See, e.g., Kabat et al., 1992, Sequences of Proteins of Immunological Interest, 5th ed., Public Health Service, NIH, Washington D.C. The positions of the CDRs may also be identified as the structural loop structures originally described by Chothia and others. See, e.g., Chothia et al., Nature 342:877-883, 1989. Other approaches to CDR identification include the "AbM definition," which is a compromise between Kabat and Chothia and is derived using Oxford Molecular's AbM antibody modeling software (now Accelrys®), or the "contact definition" of CDRs based on observed antigen contacts, set forth in MacCallum et al., J. Mol. Biol., 262:732-745, 1996. In another approach, referred to herein as the "conformational definition" of CDRs, the positions of the CDRs may be identified as the residues that make enthalpic contributions to antigen binding. See, e.g., Makabe et al., Journal of Biological Chemistry, 283:1156-1166, 2008. Still other CDR boundary definitions may not strictly follow one of the above approaches, but will nonetheless overlap with at least a portion of the Kabat CDRs, although they may be shortened or lengthened in light of prediction or experimental findings that particular residues or groups of residues or even entire CDRs do not significantly impact antigen binding. As used herein, a CDR may refer to CDRs defined by any approach known in the art, including combinations of approaches. The methods used herein may utilize CDRs defined according to any of these approaches. For any given embodiment containing more than one CDR, the CDRs may be defined in accordance with any of Kabat, Chothia, extended, AbM, contact, and/or conformational definitions.

As used herein, "monoclonal antibody" refers to an antibody obtained from a population of substantially homogeneous antibodies, i.e., the individual antibodies comprising the population are identical except for possible naturally-occurring mutations that may be present in minor amounts. Monoclonal antibodies are highly specific, being directed against a single antigenic site. Furthermore, in contrast to polyclonal antibody preparations, which typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler and Milstein, Nature 256:495, 1975, or may be made by recombinant DNA methods such as described in U.S. Pat. No. 4,816,567. The monoclonal antibodies may also be isolated from phage libraries generated using the techniques described in McCafferty et al., Nature 348:552-554, 1990, for example.

As used herein, "humanized" antibody refers to forms of non-human (e.g. murine) antibodies that are chimeric immunoglobulins, immunoglobulin chains, or fragments thereof (such as Fv, Fab, Fab', F(ab')$_2$ or other antigen binding subsequences of antibodies) that contain minimal sequence derived from non-human immunoglobulin. Preferably, humanized antibodies are human immunoglobulins (recipient antibody) in which residues from a complementary determining region (CDR) of the recipient are replaced by residues from a CDR of a non-human species (donor antibody) such as mouse, rat, or rabbit having the desired specificity, affinity, and capacity. In some instances, Fv framework region (FR) residues of the human immunoglobulin are replaced by corresponding non-human residues. Furthermore, the humanized antibody may comprise residues that are found neither in the recipient antibody nor in the imported CDR or framework sequences, but are included to further refine and optimize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region or domain (Fc), typically that of a human immunoglobulin. Preferred are antibodies having Fc regions modified as described in WO 99/58572. Other forms of humanized antibodies have one or more CDRs (CDR L1, CDR L2, CDR L3, CDR H1, CDR H2, or CDR H3) which are altered with respect to the original antibody, which are also termed one or more CDRs "derived from" one or more CDRs from the original antibody.

As used herein, "human antibody" means an antibody having an amino acid sequence corresponding to that of an antibody produced by a human and/or which has been made using any of the techniques for making human antibodies known to those skilled in the art or disclosed herein. This definition of a human antibody includes antibodies comprising at least one human heavy chain polypeptide or at least one human light chain polypeptide. One such example is an antibody comprising murine light chain and human heavy chain polypeptides. Human antibodies can be produced using various techniques known in the art. In one embodiment, the human antibody is selected from a phage library, where that phage library expresses human antibodies (Vaughan et al., Nature Biotechnology, 14:309-314, 1996; Sheets et al., Proc. Natl. Acad. Sci. (USA) 95:6157-6162, 1998; Hoogenboom and Winter, J. Mol. Biol., 227:381, 1991; Marks et al., J. Mol. Biol., 222: 581, 1991). Human antibodies can also be made by immunization of animals into which human immunoglobulin loci have been transgenically introduced in place of the endogenous loci, e.g., mice in which the endogenous immunoglobulin genes have been partially or completely inactivated. This approach is described in U.S. Pat. Nos. 5,545,807; 5,545, 806; 5,569,825; 5,625,126; 5,633,425; and 5,661,016. Alternatively, the human antibody may be prepared by immortalizing human B lymphocytes that produce an antibody directed against a target antigen (such B lymphocytes may be recovered from an individual or from single cell cloning of the cDNA, or may have been immunized in vitro). See, e.g., Cole et al. Monoclonal Antibodies and Cancer Therapy, Alan R. Liss, p. 77, 1985; Boerner et al., J. Immunol., 147 (1):86-95, 1991; and U.S. Pat. No. 5,750,373.

The term "chimeric antibody" is intended to refer to antibodies in which the variable region sequences are derived from one species and the constant region sequences are derived from another species, such as an antibody in which the variable region sequences are derived from a mouse antibody and the constant region sequences are derived from a human antibody.

The terms "polypeptide", "oligopeptide", "peptide" and "protein" are used interchangeably herein to refer to chains of amino acids of any length, preferably, relatively short (e.g., 10-100 amino acids). The chain may be linear or branched, it may comprise modified amino acids, and/or may be interrupted by non-amino acids. The terms also encompass an amino acid chain that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art. It is understood that the polypeptides can occur as single chains or associated chains.

A "monovalent antibody" comprises one antigen binding site per molecule (e.g., IgG or Fab). In some instances, a monovalent antibody can have more than one antigen binding sites, but the binding sites are from different antigens.

A "bivalent antibody" comprises two antigen binding sites per molecule (e.g., IgG). In some instances, the two binding sites have the same antigen specificities. However, bivalent antibodies may be bispecific.

A "bispecific," "dual-specific" or "bifunctional" antibody is a hybrid antibody having two different antigen binding sites. The two antigen binding sites of a bispecific antibody bind to two different epitopes, which may reside on the same or different protein targets.

Antibodies of the invention can be produced using techniques well known in the art, e.g., recombinant technologies, phage display technologies, synthetic technologies or combinations of such technologies or other technologies readily known in the art (see, for example, Jayasena, S. D., Clin. Chem., 45: 1628-50, 1999 and Fellouse, F. A., et al, J. Mol. Biol., 373(4):924-40, 2007).

As known in the art, "polynucleotide," or "nucleic acid," as used interchangeably herein, refer to chains of nucleotides of any length, and include DNA and RNA. The nucleotides can be deoxyribonucleotides, ribonucleotides, modified nucleotides or bases, and/or their analogs, or any substrate that can be incorporated into a chain by DNA or RNA polymerase. A polynucleotide may comprise modified nucleotides, such as methylated nucleotides and their analogs. If present, modification to the nucleotide structure may be imparted before or after assembly of the chain. The sequence of nucleotides may be interrupted by non-nucleotide components. A polynucleotide may be further modified after polymerization, such as by conjugation with a labeling component. Other types of modifications include, for example, "caps", substitution of one or more of the naturally occurring nucleotides with an analog, internucleotide modifications such as, for example, those with uncharged linkages (e.g., methyl phosphonates, phosphotriesters, phosphoamidates, carbamates, etc.) and with charged linkages (e.g., phosphorothioates, phosphorodithioates, etc.), those containing pendant moieties, such as, for example, proteins (e.g., nucleases, toxins, antibodies, signal peptides, poly-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid supports. The 5' and 3' terminal OH can be phosphorylated or substituted with amines or organic capping group moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-O-methyl-, 2'-O-allyl, 2'-fluoro- or 2'-azido-ribose, carbocyclic sugar analogs, alpha- or beta-anomeric sugars, epimeric sugars such as arabinose, xyloses or lyxoses, pyranose sugars, furanose sugars, sedoheptuloses, acyclic analogs and abasic nucleoside analogs such as methyl riboside. One or more phosphodiester linkages may be replaced by alternative linking groups. These alternative linking groups include, but are not limited to, embodiments wherein phosphate is replaced by P(O)S("thioate"), P(S)S ("dithioate"), (O)NR$_2$ ("amidate"), P(O)R, P(O)OR', CO or CH$_2$ ("formacetal"), in which each R or R' is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need be identical. The preceding description applies to all polynucleotides referred to herein, including RNA and DNA.

As known in the art a "constant region" of an antibody refers to the constant region of the antibody light chain or the constant region of the antibody heavy chain, either alone or in combination.

As used herein, "substantially pure" refers to material which is at least 50% pure (i.e., free from contaminants), more preferably, at least 90% pure, more preferably, at least 95% pure, yet more preferably, at least 98% pure, and most preferably, at least 99% pure.

A "host cell" includes an individual cell or cell culture that can be or has been a recipient for vector(s) for incorporation of polynucleotide inserts. Host cells include progeny of a single host cell, and the progeny may not necessarily be completely identical (in morphology or in genomic DNA complement) to the original parent cell due to natural, accidental, or deliberate mutation. A host cell includes cells transfected in vivo with a polynucleotide(s) of this invention.

As known in the art, the term "Fc region" is used to define a C-terminal region of an immunoglobulin heavy chain. The "Fc region" may be a native sequence Fc region or a variant Fc region. Although the boundaries of the Fc region of an immunoglobulin heavy chain might vary, the human IgG heavy chain Fc region is usually defined to stretch from an amino acid residue at position Cys226, or from Pro230, to the carboxyl-terminus thereof. The numbering of the residues in the Fc region is that of the EU index as in Kabat. Kabat et al., Sequences of Proteins of Immunological Interest, 5th Ed. Public Health Service, National Institutes of Health, Bethesda, Md., 1991. The Fc region of an immunoglobulin generally comprises two constant regions, CH2 and CH3.

As used in the art, "Fc receptor" and "FcR" describe a receptor that binds to the Fc region of an antibody. The preferred FcR is a native sequence human FcR. Moreover, a preferred FcR is one which binds an IgG antibody (a gamma receptor) and includes receptors of the FcγRI, FcγRII, and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. FcRs are reviewed in Ravetch and Kinet, Ann. Rev. Immunol., 9:457-92, 1991; Capel et al., Immunomethods, 4:25-34, 1994; and de Haas et al., J. Lab. Clin. Med., 126: 330-41, 1995. "FcR" also includes the neonatal receptor, FcRn, which is responsible for the transfer of maternal IgGs to the fetus (Guyer et al., J. Immunol., 117:587, 1976; and Kim et al., J. Immunol., 24:249, 1994).

The term "compete", as used herein with regard to an antibody, means that a first antibody, or an antigen binding fragment (or portion) thereof, binds to an epitope in a manner sufficiently similar to the binding of a second antibody, or an antigen binding portion thereof, such that the result of binding of the first antibody with its cognate epitope is detectably decreased in the presence of the second antibody compared to the binding of the first antibody in the absence of the second antibody. The alternative, where the binding of the second antibody to its epitope is also detectably decreased in the presence of the first antibody, can, but need not be the case. That is, a first antibody can inhibit the binding of a second antibody to its epitope without that second antibody inhibiting the binding of the first antibody to its respective epitope. However, where each antibody detectably inhibits the binding of the other antibody with its cognate epitope or ligand, whether to the same, greater, or lesser extent, the antibodies are said to "cross-compete" with each other for binding of their respective epitope(s). Both competing and cross-competing antibodies are encompassed by the present invention. Regardless of the mechanism by which such competition or cross-competition occurs (e.g., steric hindrance, conformational change, or binding to a common epitope, or portion thereof), the skilled artisan would appreciate, based upon the teachings provided herein, that such competing and/or cross-competing antibodies are encompassed and can be useful for the methods disclosed herein.

A "functional Fc region" possesses at least one effector function of a native sequence Fc region. Exemplary "effector functions" include C1q binding; complement dependent cytotoxicity; Fc receptor binding; antibody-dependent cell-mediated cytotoxicity; phagocytosis; down-regulation of cell surface receptors (e.g. B cell receptor), etc. Such effector functions generally require the Fc region to be combined with a binding domain (e.g. an antibody variable domain) and can be assessed using various assays known in the art for evaluating such antibody effector functions.

A "native sequence Fc region" comprises an amino acid sequence identical to the amino acid sequence of an Fc region found in nature. A "variant Fc region" comprises an amino acid sequence which differs from that of a native sequence Fc region by virtue of at least one amino acid modification, yet retains at least one effector function of the native sequence Fc region. In some embodiments, the variant Fc region has at least one amino acid substitution compared to a native sequence Fc region or to the Fc region of a parent polypeptide, e.g. from about one to about ten amino acid substitutions, and preferably, from about one to about five amino acid substitutions in a native sequence Fc region or in the Fc region of the parent polypeptide. The variant Fc region herein will preferably possess at least about 80% sequence identity with a native sequence Fc region and/or with an Fc region of a parent polypeptide, and most preferably, at least about 90% sequence identity therewith, more preferably, at least about 95%, at least about 96%, at least about 97%, at least about 98%, at least about 99% sequence identity therewith.

The term "effector function" refers to the biological activities attributable to the Fc region of an antibody. Examples of antibody effector functions include, but are not limited to, antibody-dependent cell-mediated cytotoxicity (ADCC), Fc receptor binding, complement dependent cytotoxicity (CDC), phagocytosis, C1q binding, and down regulation of cell surface receptors (e.g., B cell receptor; BCR). See, e.g., U.S. Pat. No. 6,737,056. Such effector functions generally require the Fc region to be combined with a binding domain (e.g., an antibody variable domain) and can be assessed using various assays known in the art for evaluating such antibody effector functions. An exemplary measurement of effector function is through Fcγ3 and/or C1q binding.

As used herein "antibody-dependent cell-mediated cytotoxicity" or "ADCC" refers to a cell-mediated reaction in which nonspecific cytotoxic cells that express Fc receptors (FcRs) (e.g. natural killer (NK) cells, neutrophils, and macrophages) recognize bound antibody on a target cell and subsequently cause lysis of the target cell. ADCC activity of a molecule of interest can be assessed using an in vitro ADCC assay, such as that described in U.S. Pat. No. 5,500,362 or 5,821,337. Useful effector cells for such assays include peripheral blood mononuclear cells (PBMC) and NK cells. Alternatively, or additionally, ADCC activity of the molecule of interest may be assessed in vivo, e.g., in an animal model such as that disclosed in Clynes et al., 1998, *PNAS (USA)*, 95:652-656.

"Complement dependent cytotoxicity" or "CDC" refers to the lysing of a target in the presence of complement. The complement activation pathway is initiated by the binding of the first component of the complement system (C1q) to a molecule (e.g. an antibody) complexed with a cognate antigen. To assess complement activation, a CDC assay, e.g. as described in Gazzano-Santoro et al., *J. Immunol. Methods*, 202: 163 (1996), may be performed.

As used herein, "treatment" is an approach for obtaining beneficial or desired clinical results. For purposes of this invention, beneficial or desired clinical results include, but are not limited to, one or more of the following: reducing the proliferation of (or destroying) neoplastic or cancerous cells, inhibiting metastasis of neoplastic cells, shrinking or decreasing the size of Trop-2 expressing tumor, remission of a Trop-2 associated disease (e.g., cancer), decreasing symptoms resulting from a Trop-2 associated disease (e.g., cancer), increasing the quality of life of those suffering from a Trop-2 associated disease (e.g., cancer), decreasing the dose of other medications required to treat a Trop-2 associated disease (e.g., cancer), delaying the progression of a Trop-2 associated disease (e.g, cancer), curing a Trop-2 associated disease (e.g, cancer), and/or prolong survival of patients having a Trop-2 associated disease (e.g., cancer).

"Ameliorating" means a lessening or improvement of one or more symptoms as compared to not administering a Trop-2 antibody or a Trop-2 antibody conjugate. "Ameliorating" also includes shortening or reduction in duration of a symptom.

As used herein, an "effective dosage" or "effective amount" of drug, compound, or pharmaceutical composition is an amount sufficient to effect any one or more beneficial or desired results. For prophylactic use, beneficial or desired results include eliminating or reducing the risk, lessening the severity, or delaying the outset of the disease, including biochemical, histological and/or behavioral symptoms of the disease, its complications and intermediate pathological phenotypes presenting during development of the disease. For therapeutic use, beneficial or desired results include clinical results such as reducing incidence or amelioration of one or more symptoms of various Trop-2 associated diseases or conditions (such as gastric, head and neck, lung, ovarian, and pancreatic cancers), decreasing the dose of other medications required to treat the disease, enhancing the effect of another medication, and/or delaying the progression of the Trop-2 associated disease of patients. An effective dosage can be administered in one or more administrations. For purposes of this invention, an effective dosage of drug, compound, or pharmaceutical composition is an amount sufficient to accomplish prophylactic or therapeutic treatment either directly or indirectly. As is understood in the clinical context, an effective dosage of a drug, compound, or pharmaceutical composition may or may not be achieved in conjunction with another drug, compound, or pharmaceutical composition. Thus, an "effective dosage" may be considered in the context of administering one or more therapeutic agents, and a single agent may be considered to be given in an effective amount if, in conjunction with one or more other agents, a desirable result may be or is achieved.

An "individual" or a "subject" is a mammal, more preferably, a human. Mammals also include, but are not limited to, farm animals, sport animals, pets, primates, horses, dogs, cats, mice and rats.

As used herein, "vector" means a construct, which is capable of delivering, and, preferably, expressing, one or more gene(s) or sequence(s) of interest in a host cell. Examples of vectors include, but are not limited to, viral vectors, naked DNA or RNA expression vectors, plasmid, cosmid or phage vectors, DNA or RNA expression vectors associated with cationic condensing agents, DNA or RNA expression vectors encapsulated in liposomes, and certain eukaryotic cells, such as producer cells.

As used herein, "expression control sequence" means a nucleic acid sequence that directs transcription of a nucleic acid. An expression control sequence can be a promoter, such as a constitutive or an inducible promoter, or an enhancer. The expression control sequence is operably linked to the nucleic acid sequence to be transcribed.

As used herein, "pharmaceutically acceptable carrier" or "pharmaceutical acceptable excipient" includes any material which, when combined with an active ingredient, allows the ingredient to retain biological activity and is non-reactive with the subject's immune system. Examples include, but are not limited to, any of the standard pharmaceutical carriers such as a phosphate buffered saline solution, water, emulsions such as oil/water emulsion, and various types of wetting agents. Preferred diluents for aerosol or parenteral administration are phosphate buffered saline (PBS) or normal (0.9%) saline. Compositions comprising such carriers are formulated by well known conventional methods (see, for example, Remington's Pharmaceutical Sciences, 18th edition, A. Gennaro, ed., Mack Publishing Co., Easton, Pa., 1990; and Remington, The Science and Practice of Pharmacy 21st Ed. Mack Publishing, 2005).

The term "acyl donor glutamine-containing tag" or "glutamine tag" as used herein refers to a polypeptide or a protein containing one or more Gln residue(s) that acts as a transglutaminase amine acceptor. See, e.g., WO2012059882.

The term "$k_{on}$", as used herein, refers to the rate constant for association of an antibody to an antigen. Specifically, the rate constants ($k_{on}$ and $k_{off}$) and equilibrium dissociation constants are measured using Fab antibody fragments (i.e. monovalent) and Trop-2 proteins (e.g., Trop-2-Fc fusion protein).

The term "$k_{off}$", as used herein, refers to the rate constant for dissociation of an antibody from the antibody/antigen complex.

The term "$K_D$", as used herein, refers to the equilibrium dissociation constant of an antibody-antigen interaction.

Reference to "about" a value or parameter herein includes (and describes) embodiments that are directed to that value or parameter per se. For example, description referring to "about X" includes description of "X." Numeric ranges are inclusive of the numbers defining the range.

It is understood that wherever embodiments are described herein with the language "comprising," otherwise analogous embodiments described in terms of "consisting of" and/or "consisting essentially of" are also provided.

Where aspects or embodiments of the invention are described in terms of a Markush group or other grouping of alternatives, the present invention encompasses not only the entire group listed as a whole, but each member of the group individually and all possible subgroups of the main group, but also the main group absent one or more of the group members. The present invention also envisages the explicit exclusion of one or more of any of the group members in the claimed invention.

Unless otherwise defined, all technical and scientific terms used herein have the same meaning as commonly understood by one of ordinary skill in the art to which this invention belongs. In case of conflict, the present specification, including definitions, will control. Throughout this specification and claims, the word "comprise," or variations such as "comprises" or "comprising" will be understood to imply the inclusion of a stated integer or group of integers but not the exclusion of any other integer or group of integers. Unless otherwise required by context, singular terms shall include pluralities and plural terms shall include the singular.

Exemplary methods and materials are described herein, although methods and materials similar or equivalent to those described herein can also be used in the practice or testing of the present invention. The materials, methods, and examples are illustrative only and not intended to be limiting.

Trop-2 Antibodies and Methods of Making Thereof

The present invention provides an antibody that binds to Trop-2. In one aspect, the invention provides an isolated antibody, or an antigen binding fragment thereof, which specifically binds to domain 3 (e.g., amino acid residues 153-206) and domain 4 (e.g., amino acid residues 209-273) of human Trop-2 (e.g., SEQ ID NO:27) with a monovalent antibody binding affinity ($K_D$) of 6.5 nM or less as measured by surface plasmon resonance. In another aspect, the invention provides an isolated antibody, or an antigen binding fragment thereof, which specifically binds to domain 1 (e.g., amino acid residues 27-70) of human Trop-2 (e.g., SEQ ID NO:27) with a binding affinity ($K_D$) of about 35 nM or less as measured by surface plasmon resonance.

The antibodies and antibody conjugates of the invention are characterized by any one or more of the following characteristics: (a) bind to Trop-2; (b) decrease or downregulate the protein expression of Trop-2; (c) treat, prevent, ameliorate one or more symptoms of a condition associated with Trop-2 expression in a subject (e.g., cancer, such as gastric, head and neck, lung, ovarian, or pancreatic cancer); (d) inhibit tumor growth or progression in a subject (who has a Trop-2 expressing tumor); (e) inhibit metastasis of Trop-2 expressing cancer cells in a subject (who has one or more Trop-2 expressing cancer cells); (f) induce regression (e.g., long-term regression) of a Trop-2 expressing tumor; (g) exert cytotoxic activity in Trop-2 expressing cells; (h) deactivate or down-regulate the ERK1/2 MAPK pathway; and (i) block Trop-2 interaction with other yet to be identified factors.

The antibodies useful in the present invention can encompass monoclonal antibodies, polyclonal antibodies, antibody fragments (e.g., Fab, Fab', F(ab')2, Fv, Fc, etc.), chimeric antibodies, bispecific antibodies, heteroconjugate antibodies, single chain (ScFv), mutants thereof, fusion proteins comprising an antibody portion (e.g., a domain antibody), humanized antibodies, and any other modified configuration of the immunoglobulin molecule that comprises an antigen recognition site of the required specificity, including glycosylation variants of antibodies, amino acid sequence variants of antibodies, and covalently modified antibodies. The antibodies may be murine, rat, human, or any other origin (including chimeric or humanized antibodies).

In some embodiments, the Trop-2 antibody as described herein is a monoclonal antibody. For example, the Trop-2 antibody is a humanized monoclonal antibody or a chimeric monoclonal antibody.

In some embodiments, the antibody comprises a modified constant region, such as, for example without limitation, a constant region that has increased potential for provoking an immune response. For example, the constant region may be modified to have increased affinity to an Fc gamma receptor such as, e.g., FcγRI, FcγRIIA, or FcγIII.

In some embodiments, the antibody comprises a modified constant region, such as a constant region that is immunologically inert, that is, having a reduced potential for provoking an immune response. In some embodiments, the constant region is modified as described in Eur. J. Immunol., 29:2613-2624, 1999; PCT Application No. PCT/GB99/01441; and/or UK Patent Application No. 98099518. The Fc can be human IgG1, human IgG2, human IgG3, or human IgG4. The Fc can be human IgG2 containing the mutation A330P331 to S330S331 (IgG2Δa), in which the amino acid residues are numbered with reference to the wild type IgG2 sequence. Eur. J. Immunol., 29:2613-2624, 1999. In some embodiments, the antibody comprises a constant region of $IgG_4$ comprising the following mutations (Armour et al., Molecular Immunology 40 585-593, 2003): E233F234L235 to P233V234A235 (IgG4Δc), in which the numbering is with reference to wild type IgG4. In yet another embodiment, the Fc is human IgG4 E233F234L235 to P233V234A235 with deletion G236 (IgG4Δb). In another embodiment, the Fc is any human IgG4 Fc (IgG4, IgG4Δb or IgG4Δc) containing hinge stabilizing mutation S228 to P228 (Aalberse et al., Immunology 105, 9-19, 2002). In another embodiment, the Fc can be aglycosylated Fc.

In some embodiments, the constant region is aglycosylated by mutating the oligosaccharide attachment residue (such as Asn297) and/or flanking residues that are part of the glycosylation recognition sequence in the constant region. In some embodiments, the constant region is aglycosylated for N-linked glycosylation enzymatically. The constant region may be aglycosylated for N-linked glycosylation enzymatically or by expression in a glycosylation deficient host cell.

One way of determining binding affinity of antibodies to Trop-2 is by measuring binding affinity of monofunctional Fab fragments of the antibody. To obtain monofunctional Fab fragments, an antibody (for example, IgG) can be cleaved with papain or expressed recombinantly. The affinity of a Trop-2 Fab fragment of an antibody can be determined by surface plasmon resonance (Biacore™3000™ surface plasmon resonance (SPR) system, Biacore™, INC, Piscataway N.J.) equipped with pre-immobilized streptavidin sensor chips (SA) or anti-mouse Fc or anti-human Fc using HBS-EP running buffer (0.01M HEPES, pH 7.4, 0.15 NaCl, 3 mM EDTA, 0.005% v/v Surfactant P20). Biotinylated or Fc fusion human Trop-2 can be diluted into HBS-EP buffer to a concentration of less than 0.5 μg/mL and injected across the individual chip channels using variable contact times, to achieve two ranges of antigen density, either 50-200 response units (RU) for detailed kinetic studies or 800-1,000 RU for screening assays. Regeneration studies have shown that 25 mM NaOH in 25% v/v ethanol effectively removes the bound Fab while keeping the activity of Trop-2 on the chip for over 200 injections. Typically, serial dilutions (spanning concentrations of 0.1-10× estimated $K_D$) of purified Fab samples are injected for 1 min at 100 μL/minute and dissociation times of up to 2 hours are allowed. The concentrations of the Fab proteins are determined by ELISA and/or SDS-PAGE electrophoresis using a Fab of known concentration (as determined by amino acid analysis) as a standard. Kinetic association rates ($k_{on}$) and dissociation rates ($k_{off}$) are obtained simultaneously by fitting the data globally to a 1:1 Langmuir binding model (Karlsson, R. Roos, H. Fagerstam, L. Petersson, B. (1994). Methods Enzymology 6. 99-110) using the BIAevaluation program. Equilibrium dissociation constant ($K_D$) values are calculated as $k_{off}/k_{on}$. This protocol is suitable for use in determining binding affinity of an antibody to any Trop-2, including human Trop-2, Trop-2 of another mammal (such as mouse Trop-2, rat Trop-2, or primate Trop-2), as well as different forms of Trop-2 (e.g., glycosylated Trop-2). Binding affinity of an antibody is generally measured at 25° C., but can also be measured at 37° C.

The Trop-2 antibodies as described herein may be made by any method known in the art. For the production of hybridoma cell lines, the route and schedule of immunization of the host animal are generally in keeping with established and conventional techniques for antibody stimulation and production, as further described herein. General techniques for production of human and mouse antibodies are known in the art and/or are described herein.

It is contemplated that any mammalian subject including humans or antibody producing cells therefrom can be manipulated to serve as the basis for production of mammalian, including human and hybridoma cell lines. Typically, the host animal is inoculated intraperitoneally, intramuscularly, orally, subcutaneously, intraplantar, and/or intradermally with an amount of immunogen, including as described herein.

Hybridomas can be prepared from the lymphocytes and immortalized myeloma cells using the general somatic cell hybridization technique of Kohler, B. and Milstein, C., Nature 256:495-497, 1975 or as modified by Buck, D. W., et al., In Vitro, 18:377-381, 1982. Available myeloma lines, including but not limited to X63-Ag8.653 and those from the Salk Institute, Cell Distribution Center, San Diego, Calif., USA, may be used in the hybridization. Generally, the technique involves fusing myeloma cells and lymphoid cells using a fusogen such as polyethylene glycol, or by electrical means well known to those skilled in the art. After the fusion, the cells are separated from the fusion medium and grown in a selective growth medium, such as hypoxanthine-aminopterin-thymidine (HAT) medium, to eliminate unhybridized parent cells. Any of the media described herein, supplemented with or without serum, can be used for culturing hybridomas that secrete monoclonal antibodies. As another alternative to the cell fusion technique, EBV immortalized B cells may be used to produce the Trop-2 monoclonal antibodies of the subject invention. The hybridomas are expanded and subcloned, if desired, and supernatants are assayed for anti-immunogen activity by conventional immunoassay procedures (e.g., radioimmunoassay, enzyme immunoassay, or fluorescence immunoassay).

Hybridomas that may be used as source of antibodies encompass all derivatives, progeny cells of the parent hybridomas that produce monoclonal antibodies specific for Trop-2, or a portion thereof.

Hybridomas that produce such antibodies may be grown in vitro or in vivo using known procedures. The monoclonal antibodies may be isolated from the culture media or body fluids, by conventional immunoglobulin purification procedures such as ammonium sulfate precipitation, gel electrophoresis, dialysis, chromatography, and ultrafiltration, if desired. Undesired activity, if present, can be removed, for example, by running the preparation over adsorbents made of the immunogen attached to a solid phase and eluting or releasing the desired antibodies off the immunogen. Immunization of a host animal with a human Trop-2, or a fragment containing the target amino acid sequence conjugated to a protein that is immunogenic in the species to be immunized, e.g., keyhole limpet hemocyanin, serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic anhydride, $SOCl_2$, or $R^1N=C=NR$, where R and $R^1$ are different alkyl groups, can yield a population of antibodies (e.g., monoclonal antibodies).

If desired, the Trop-2 antibody (monoclonal or polyclonal) of interest may be sequenced and the polynucleotide sequence may then be cloned into a vector for expression or propagation. The sequence encoding the antibody of interest may be maintained in vector in a host cell and the host cell can then be expanded and frozen for future use. Production of recombinant monoclonal antibodies in cell culture can be carried out through cloning of antibody genes from B cells by means known in the art. See, e.g. Tiller et al., J. Immunol. Methods 329, 112, 2008; U.S. Pat. No. 7,314,622.

In an alternative, the polynucleotide sequence may be used for genetic manipulation to "humanize" the antibody or to improve the affinity, or other characteristics of the antibody. For example, the constant region may be engineered to more nearly resemble human constant regions to avoid immune response if the antibody is used in clinical trials and treatments in humans. It may be desirable to genetically manipulate the antibody sequence to obtain greater affinity to Trop-2 and greater efficacy in inhibiting Trop-2.

There are four general steps to humanize a monoclonal antibody. These are: (1) determining the nucleotide and predicted amino acid sequence of the starting antibody light and heavy variable domains (2) designing the humanized antibody, i.e., deciding which antibody framework region to use during the humanizing process (3) the actual humanizing methodologies/techniques and (4) the transfection and expression of the humanized antibody. See, for example, U.S. Pat. Nos. 4,816,567; 5,807,715; 5,866,692; 6,331,415; 5,530,101; 5,693,761; 5,693,762; 5,585,089; and 6,180,370.

A number of "humanized" antibody molecules comprising an antigen binding site derived from a non-human immunoglobulin have been described, including chimeric antibodies having rodent or modified rodent V regions and their associated CDRs fused to human constant regions. See, for example, Winter et al. Nature 349:293-299, 1991, Lobuglio et al. Proc. Nat. Acad. Sci. USA 86:4220-4224, 1989, Shaw et al. J Immunol. 138:4534-4538, 1987, and Brown et al. Cancer Res. 47:3577-3583, 1987. Other references describe rodent CDRs grafted into a human supporting framework region (FR) prior to fusion with an appropriate human antibody constant region. See, for example, Riechmann et al. Nature 332:323-327, 1988, Verhoeyen et al. Science 239:1534-1536, 1988, and Jones et al. Nature 321:522-525, 1986. Another reference describes rodent CDRs supported by recombinantly engineered rodent framework regions. See, for example, European Patent Publication No. 0519596. These "humanized" molecules are designed to minimize unwanted immunological response toward rodent anti-human antibody molecules which limits the duration and effectiveness of therapeutic applications of those moieties in human recipients. For example, the antibody constant region can be engineered such that it is immunologically inert (e.g., does not trigger complement lysis). See, e.g. PCT Publication No. PCT/GB99/01441; UK Patent Application No. 9809951.8. Other methods of humanizing antibodies that may also be utilized are disclosed by Daugherty et al., Nucl. Acids Res. 19:2471-2476, 1991, and in U.S. Pat. Nos. 6,180,377; 6,054, 297; 5,997,867; 5,866,692; 6,210,671; and 6,350,861; and in PCT Publication No. WO 01/27160.

The general principles related to humanized antibodies discussed above are also applicable to customizing antibodies for use, for example, in dogs, cats, primate, equines and bovines. Further, one or more aspects of humanizing an antibody described herein may be combined, e.g., CDR grafting, framework mutation and CDR mutation.

In one variation, fully human antibodies may be obtained by using commercially available mice that have been engineered to express specific human immunoglobulin proteins. Transgenic animals that are designed to produce a more desirable (e.g., fully human antibodies) or more robust immune response may also be used for generation of humanized or human antibodies. Examples of such technology are Xenomouse™ from Abgenix, Inc. (Fremont, Calif.) and HuMAb-Mouse® and TC Mouse™ from Medarex, Inc. (Princeton, N.J.).

In an alternative, antibodies may be made recombinantly and expressed using any method known in the art. In another alternative, antibodies may be made recombinantly by phage display technology. See, for example, U.S. Pat. Nos. 5,565, 332; 5,580,717; 5,733,743; and 6,265,150; and Winter et al., Annu. Rev. Immunol. 12:433-455, 1994. Alternatively, the phage display technology (McCafferty et al., Nature 348: 552-553, 1990) can be used to produce human antibodies and antibody fragments in vitro, from immunoglobulin variable (V) domain gene repertoires from unimmunized donors. According to this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B cell. Phage display can be performed in a variety of formats; for review see, e.g., Johnson, Kevin S, and Chiswell, David J., Current Opinion in Structural Biology 3:564-571, 1993. Several sources of V-gene segments can be used for phage display. Clackson et al., Nature 352:624-628, 1991, isolated a diverse array of anti-oxazolone antibodies from a small random combinatorial library of V genes derived from the spleens of immunized mice. A repertoire of V genes from unimmunized human donors can be constructed and antibodies to a diverse array of antigens (including self-antigens) can be isolated essentially following the techniques described by Mark et al., J. Mol. Biol. 222:581-597, 1991, or Griffith et al., EMBO J. 12:725-734, 1993. In a natural immune response, antibody genes accumulate mutations at a high rate (somatic hypermutation). Some of the changes introduced will confer higher affinity, and B cells displaying high-affinity surface immunoglobulin are preferentially replicated and differentiated during subsequent antigen challenge. This natural process can be mimicked by employing the technique known as "chain shuffling." (Marks et al., Bio/Technol. 10:779-783, 1992). In this method, the affinity of "primary" human antibodies obtained by phage display can be improved by sequentially replacing the heavy and light chain V region genes with repertoires of naturally occurring variants (repertoires) of V domain genes obtained from unimmunized donors. This technique allows the production of antibodies and antibody fragments with affinities in the pM-nM range. A strategy for making very large phage antibody repertoires (also known as "the mother-of-all libraries") has been described by Waterhouse et al., Nucl. Acids Res. 21:2265-2266, 1993. Gene shuffling can also be used to derive human antibodies from rodent antibodies, where the human antibody has similar affinities and specificities to the starting rodent antibody. According to this method, which is also referred to as "epitope imprinting", the heavy or light chain V domain gene of rodent antibodies obtained by phage display technique is replaced with a repertoire of human V domain genes, creating rodent-human chimeras. Selection on antigen results in isolation of human variable regions capable of restoring a functional antigen binding site, i.e., the epitope governs (imprints) the choice of partner. When the process is repeated in order to replace the remaining rodent V domain, a human antibody is obtained (see PCT Publication No. WO 93/06213). Unlike traditional humanization of rodent antibodies by CDR grafting, this technique provides completely human antibodies, which have no framework or CDR residues of rodent origin.

Antibodies may be made recombinantly by first isolating the antibodies and antibody producing cells from host animals, obtaining the gene sequence, and using the gene sequence to express the antibody recombinantly in host cells (e.g., CHO cells). Another method which may be employed is to express the antibody sequence in plants (e.g., tobacco) or transgenic milk. Methods for expressing antibodies recombinantly in plants or milk have been disclosed. See, for example, Peeters, et al. Vaccine 19:2756, 2001; Lonberg, N. and D. Huszar Int. Rev. Immunol 13:65, 1995; and Pollock, et al., J Immunol Methods 231:147, 1999. Methods for making derivatives of antibodies, e.g., humanized, single chain, etc. are known in the art.

Immunoassays and flow cytometry sorting techniques such as fluorescence activated cell sorting (FACS) can also be employed to isolate antibodies that are specific for Trop-2.

The antibodies as described herein can be bound to many different carriers. Carriers can be active and/or inert. Examples of well-known carriers include polypropylene, polystyrene, polyethylene, dextran, nylon, amylases, glass, natural and modified celluloses, polyacrylamides, agaroses, and magnetite. The nature of the carrier can be either soluble or insoluble for purposes of the invention. Those skilled in the art will know of other suitable carriers for binding antibodies, or will be able to ascertain such, using routine experimentation. In some embodiments, the carrier comprises a moiety that targets the myocardium.

DNA encoding the monoclonal antibodies is readily isolated and sequenced using conventional procedures (e.g., by using oligonucleotide probes that are capable of binding specifically to genes encoding the heavy and light chains of the monoclonal antibodies). The hybridoma cells serve as a preferred source of such DNA. Once isolated, the DNA may be placed into expression vectors (such as expression vectors disclosed in PCT Publication No. WO 87/04462), which are then transfected into host cells such as E. coli cells, simian COS cells, Chinese hamster ovary (CHO) cells, or myeloma cells that do not otherwise produce immunoglobulin protein, to obtain the synthesis of monoclonal antibodies in the recombinant host cells. See, e.g., PCT Publication No. WO 87/04462. The DNA also may be modified, for example, by substituting the coding sequence for human heavy and light chain constant regions in place of the homologous murine sequences, Morrison et al., Proc. Nat. Acad. Sci. 81:6851, 1984, or by covalently joining to the immunoglobulin coding sequence all or part of the coding sequence for a non-immunoglobulin polypeptide. In that manner, "chimeric" or "hybrid" antibodies are prepared that have the binding specificity of a Trop-2 monoclonal antibody herein.

The Trop-2 antibodies as described herein can be identified or characterized using methods known in the art, whereby reduction of Trop-2 expression levels is detected and/or measured. In some embodiments, a Trop-2 antibody is identified by incubating a candidate agent with Trop-2 and monitoring binding and/or attendant reduction of Trop-2 expression levels. The binding assay may be performed with purified Trop-2 polypeptide(s), or with cells naturally expressing, or transfected to express, Trop-2 polypeptide(s). In one embodiment, the binding assay is a competitive binding assay, where the ability of a candidate antibody to compete with a known Trop-2 antibody for Trop-2 binding is evaluated. The assay may be performed in various formats, including the ELISA format.

Following initial identification, the activity of a candidate Trop-2 antibody can be further confirmed and refined by bioassays, known to test the targeted biological activities. Alternatively, bioassays can be used to screen candidates directly. Some of the methods for identifying and characterizing Trop-2 antibodies are described in detail in the Examples.

Trop-2 antibodies may be characterized using methods well known in the art. For example, one method is to identify the epitope to which it binds, or "epitope mapping." There are many methods known in the art for mapping and characterizing the location of epitopes on proteins, including solving the crystal structure of an antibody-antigen complex, competition assays, gene fragment expression assays, and synthetic peptide-based assays, as described, for example, in Chapter 11 of Harlow and Lane, Using Antibodies, a Laboratory Manual, Cold Spring Harbor Laboratory Press, Cold Spring Harbor, N.Y., 1999. In an additional example, epitope mapping can be used to determine the sequence to which a Trop-2 antibody binds. Epitope mapping is commercially available from various sources, for example, Pepscan Systems (Edelhertweg 15, 8219 P H Lelystad, The Netherlands). The epitope can be a linear epitope, i.e., contained in a single stretch of amino acids, or a conformational epitope formed by a three-dimensional interaction of amino acids that may not necessarily be contained in a single stretch. Peptides of varying lengths (e.g., at least 4-6 amino acids long) can be isolated or synthesized (e.g., recombinantly) and used for binding assays with a Trop-2 antibody. In another example, the epitope to which the Trop-2 antibody binds can be determined in a systematic screening by using overlapping peptides derived from the Trop-2 sequence and determining binding by the Trop-2 antibody. According to the gene fragment expression assays, the open reading frame encoding Trop-2 is fragmented either randomly or by specific genetic constructions and the reactivity of the expressed fragments of Trop-2 with the antibody to be tested is determined. The gene fragments may, for example, be produced by PCR and then transcribed and translated into protein in vitro, in the presence of radioactive amino acids. The binding of the antibody to the radioactively labeled Trop-2 fragments is then determined by immunoprecipitation and gel electrophoresis. Certain epitopes can also be identified by using large libraries of random peptide sequences displayed on the surface of phage particles (phage libraries). Alternatively, a defined library of overlapping peptide fragments can be tested for binding to the test antibody in simple binding assays. In an additional example, mutagenesis of an antigen binding domain, domain swapping experiments and alanine scanning mutagenesis can be performed to identify residues required, sufficient, and/or necessary for epitope binding. For example, domain swapping experiments can be performed using a mutant Trop-2 in which various fragments of the Trop-2 protein have been replaced (swapped) with sequences from Trop-2 from another species (e.g., mouse), or a closely related, but antigenically distinct protein (e.g., Trop-1). By assessing binding of the antibody to the mutant Trop-2, the importance of the particular Trop-2 fragment to antibody binding can be assessed.

Yet another method which can be used to characterize a Trop-2 antibody is to use competition assays with other antibodies known to bind to the same antigen, i.e., various fragments on Trop-2, to determine if the Trop-2 antibody binds to the same epitope as other antibodies. Competition assays are well known to those of skill in the art.

An expression vector can be used to direct expression of a Trop-2 antibody. One skilled in the art is familiar with administration of expression vectors to obtain expression of an exogenous protein in vivo. See, e.g., U.S. Pat. Nos. 6,436,908; 6,413,942; and 6,376,471. Administration of expression vectors includes local or systemic administration, including injection, oral administration, particle gun or catheterized administration, and topical administration. In another embodiment, the expression vector is administered directly to the sympathetic trunk or ganglion, or into a coronary artery, atrium, ventrical, or pericardium.

Targeted delivery of therapeutic compositions containing an expression vector, or subgenomic polynucleotides can also be used. Receptor-mediated DNA delivery techniques are described in, for example, Findeis et al., Trends Biotechnol., 1993, 11:202; Chiou et al., Gene Therapeutics: Methods And Applications Of Direct Gene Transfer, J. A. Wolff, ed., 1994; Wu et al., J. Biol. Chem., 263:621, 1988; Wu et al., J. Biol. Chem., 269:542, 1994; Zenke et al., Proc. Natl. Acad. Sci. USA, 87:3655, 1990; and Wu et al., J. Biol. Chem., 266:338, 1991. Therapeutic compositions containing a polynucleotide are administered in a range of about 100 ng to about 200 mg of DNA for local administration in a gene therapy protocol. Concentration ranges of about 500 ng to about 50 mg, about 1 µg to about 2 mg, about 5 µg to about 500 µg, and about 20 µg to about 100 µg of DNA can also be used during a gene therapy protocol. The therapeutic polynucleotides and polypeptides can be delivered using gene delivery vehicles. The gene delivery vehicle can be of viral or non-viral origin (see generally, Jolly, Cancer Gene Therapy, 1:51, 1994; Kimura, Human Gene Therapy, 5:845, 1994; Connelly, Human Gene Therapy, 1995, 1:185; and Kaplitt, Nature Genetics, 6:148, 1994). Expression of such coding sequences can be induced using endogenous mammalian or heterologous promoters. Expression of the coding sequence can be either constitutive or regulated.

Viral-based vectors for delivery of a desired polynucleotide and expression in a desired cell are well known in the art.

Exemplary viral-based vehicles include, but are not limited to, recombinant retroviruses (see, e.g., PCT Publication Nos. WO 90/07936; WO 94/03622; WO 93/25698; WO 93/25234; WO 93/11230; WO 93/10218; WO 91/02805; U.S. Pat. Nos. 5,219,740 and 4,777,127; GB Pat. No. 2,200,651; and EP Pat. No. 0 345 242), alphavirus-based vectors (e.g., Sindbis virus vectors, Semliki forest virus (ATCC VR-67; ATCC VR-1247), Ross River virus (ATCC VR-373; ATCC VR-1246) and Venezuelan equine encephalitis virus (ATCC VR-923; ATCC VR-1250; ATCC VR 1249; ATCC VR-532)), and adeno-associated virus (AAV) vectors (see, e.g., PCT Publication Nos. WO 94/12649, WO 93/03769; WO 93/19191; WO 94/28938; WO 95/11984 and WO 95/00655). Administration of DNA linked to killed adenovirus as described in Curiel, Hum. Gene Ther., 1992, 3:147 can also be employed.

Non-viral delivery vehicles and methods can also be employed, including, but not limited to, polycationic condensed DNA linked or unlinked to killed adenovirus alone (see, e.g., Curiel, Hum. Gene Ther., 3:147, 1992); ligand-linked DNA (see, e.g., Wu, J. Biol. Chem., 264:16985, 1989); eukaryotic cell delivery vehicles cells (see, e.g., U.S. Pat. No. 5,814,482; PCT Publication Nos. WO 95/07994; WO 96/17072; WO 95/30763; and WO 97/42338) and nucleic charge neutralization or fusion with cell membranes. Naked DNA can also be employed. Exemplary naked DNA introduction methods are described in PCT Publication No. WO 90/11092 and U.S. Pat. No. 5,580,859. Liposomes that can act as gene delivery vehicles are described in U.S. Pat. No. 5,422,120; PCT Publication Nos. WO 95/13796; WO 94/23697; WO 91/14445; and EP 0524968. Additional approaches are described in Philip, Mol. Cell Biol., 14:2411, 1994 and in Woffendin, Proc. Natl. Acad. Sci., 91:1581, 1994.

In some embodiments, the invention encompasses compositions, including pharmaceutical compositions, comprising antibodies described herein or made by the methods and having the characteristics described herein. As used herein, compositions comprise one or more antibodies that bind to Trop-2, and/or one or more polynucleotides comprising sequences encoding one or more these antibodies. These compositions may further comprise suitable excipients, such as pharmaceutically acceptable excipients including buffers, which are well known in the art.

Accordingly, the invention provides any of the following, or compositions (including pharmaceutical compositions) comprising any of the following: (a) an antibody having a partial light chain sequence of a)
(SEQ ID NO: 1)
DIVLTQSPASLAVSLGQRATISCRASKSVSTSGYSYMHWYQQKPGQP
PKLLIYLASNLESGVPARFSGSGSGTDFTLNIHPVEEEDAATYYCQH
SRELPYTFGGGTKLEIK, (SEQ ID NO: 3)
DIVMTQSPDSLAVSLGERATINCRASKSVSTSGYSYMHWYQQKPGQP
PKLLIYLASNLESGVPDRFSGSGSGTDFTLTISSLQAEDVAVYYCQH
SRELPYTFGQGTKLEIK, (SEQ ID NO: 6)
DIVMTQSPDSLAVSLGERATINCRASKSVSTSLYSYMHWYQQKPGQP
PKLLIYLASNLESGVPDRFSGSGSGTDFTLTISSLQAEDVAVYYCQH
SRELPYTFGQGTKLEIK, (SEQ ID NO: 7)
DIVMTQSPDSLAVSLGERATINCRASKSVSTSNYSYMHWYQQKPGQP
PKLLIYLASNLESGVPDRFSGSGSGTDFTLTISSLQAEDVAVYYCQH
SRELPYTFGQGTKLEIK, (SEQ ID NO: 8)
DILLTQSPAILSVSPGERVSFSCRASQTIGTSIHWYQQRTNGSPRLL
IKYASESISGIPSRFSGSGSGTDFTLSINSVESEDIADYYCQQSNSW
PFTFGSGTKLEIK, (SEQ ID NO: 10)
GVHSEIVLTQSPATLSLSPGERATLSCRASQTIGTSIHWYQQKPGQA
PRLLIYYASESISGIPARFSGSGSGTDFTLTISSLEPEDFAVYYCQQ
SNSWPFTFGQGTKLEIK, or (SEQ ID NO: 12)
EIVLTQSPATLSLSPGERATLSCRASQTIGTSIHWYQQKPGQAPRLL
IYYASESISGIPARFSGSGSGTDFTLTISSLEPEDFAVYYCSQSFSW
PFTFGQGTKLEIK and/or (b) an antibody having a partial heavy chain sequence of (SEQ ID NO: 2)
QVQLKESGPGLVAPSQSLSITCTVSGFSLTSYGVHWVRQPPGKGLEW
LGVIWTGGSTDYNSALMSRLSINKDNSKSQVFLKMNSLQTDDTAMYY
CARDGDYDRYTMDYWGQGTSVTVSS, (SEQ ID NO: 4)
QVQLQESGPGLVKPSETLSLTCTVSGGSISSYGVHWIRQPPGKGLEW
IGVIWTGGSTDYNSALMSRVTISVDTSKNQFSLKLSSVTAADTAVYY
CARDGDYDRYTMDYWGQGTLVTVSS, (SEQ ID NO: 5)
QVQLQESGPGLVKPSETLSLTCTVSGGSISSYGVHWIRQPPGKGLEW
IGVIWTSGVTDYNSALMGRVTISVDTSKNQFSLKLSSVTAADTAVYY
CARDGDYDRYTMDYWGQGTLVTVSS, (SEQ ID NO: 9)
QVQLQQPGAELVRPGASVKLSCKASGYTFTSYWINWVKQRPGHGLEW
IGNIYPSDSYSNYNQKFKDKATLTVDKSSSTAYMQVSSPTSEDSAVY
YCTYGSSFDYWGQGTTVTVSS, (SEQ ID NO: 11)
QVQLVQSGAEVKKPGASVKVSCKASGYTFTSYWINWVRQAPGQGLEW
MGNIYPSDSYSNYNQKFKDRVTMTRDTSTSTVYMELSSLRSEDTAVY
YCARGSSFDYWGQGTLVTVSS,
or (SEQ ID NO: 13)
QVQLVQSGAEVKKPGASVKVSCKASGYTFTSYWINWVRQAPGQGLEW
MGNIFPSDSYSNYNKKFKDRVTMTRDTSTSTVYMELSSLRSEDTAVY
YCARGSGFDYWGQGTLVTVSS.

TABLE 1

| mAb | Light Chain | Heavy Chain |
| --- | --- | --- |
| m7E6 | DIVLTQSPASLAVSLGQRATISCRASKSVSTSGYSYMHWYQQKPGQPPKLLIYLASNLESGVPARFSGSGSGTDFTLNIHPVEEEDAATYYCQHSRELPYTFGGGTKLEIK (SEQ ID NO: 1) | QVQLKESGPGLVAPSQSLSITCTVSGFSLTSYGVHWVRQPPGKGLEWLGVIWTGGSTDYNSALMSRLSINKDNSKSQVFLKMNSLQTDDTAMYYCARDGDYDRYTMDYWGQGTSVTVSS (SEQ ID NO: 2) |

TABLE 1-continued

| mAb | Light Chain | Heavy Chain |
|---|---|---|
| h7E6 | DIVMTQSPDSLAVSLGERATINCRASKS VSTSGYSYMHWYQQKPGQPPKLLIYLAS NLESGVPDRFSGSGSGTDFTLTISSLQA EDVAVYYCQHSRELPYTFGQGTKLEIK (SEQ ID NO: 3) | QVQLQESGPGLVKPSETLSLTCTVSGGSI SSYGVHWIRQPPGKGLEWIGVIWTGGSTD YNSALMSRVTISVDTSKNQFSLKLSSVTA ADTAVYYCARDGDYDRYTMDYWGQGTLVT VSS (SEQ ID NO: 4) |
| h7E6_SVG | DIVMTQSPDSLAVSLGERATINCRASKS VSTSGYSYMHWYQQKPGQPPKLLIYLAS NLESGVPDRFSGSGSGTDFTLTISSLQA EDVAVYYCQHSRELPYTFGQGTKLEIK (SEQ ID NO: 3) | QVQLQESGPGLVKPSETLSLTCTVSGGSI SSYGVHWIRQPPGKGLEWIGVIWTSGVTD YNSALMGRVTISVDTSKNQFSLKLSSVTA ADTAVYYCARDGDYDRYTMDYWGQGTLVT VSS (SEQ ID NO: 5) |
| h7E6_SVG1 | DIVMTQSPDSLAVSLGERATINCRASKS VSTSGYSYMHWYQQKPGQPPKLLIYLAS NLESGVPDRFSGSGSGTDFTLTISSLQA EDVAVYYCQHSRELPYTFGQGTKLEIK (SEQ ID NO: 3) | QVQLQESGPGLVKPSETLSLTCTVSGGSI SSYGVHWIRQPPGKGLEWIGVIWTSGVTD YNSALMGRVTISVDTSKNQFSLKLSSVTA ADTAVYYCA$X_1X_2$DYDRYTX$_3$DYRWGQGT LVTVSS wherein $X_1$, $X_2$, and $X_3$ are any naturally occurring amino acids (SEQ ID NO: 84) |
| h7E6_SVG2 | DIVMTQSPDSLAVSLGERATINCRASKS VSTSGYSYMHWYQQKPGQPPKLLIYLAS NLESGVPDRFSGSGSGTDFTLTISSLQA EDVAVYYCQHSRELPYTFGQGTKLEIK (SEQ ID NO: 3) | QVQLQESGPGLVKPSETLSLTCTVSGGSI SSYGVHWIRQPPGKGLEWIGVIWTSGVTD YNSALMGRVTISVDTSKNQFSLKLSSVTA ADTAVYYCAR$X_1X_2$DYDRYTX$_3$DYWGQGT LVTVSS wherein $X_1$ and $X_2$ are any naturally occurring amino acids; $X_3$ is E or M (SEQ ID NO: 85) |
| H7E6_SVGL | DIVMTQSPDSLAVSLGERATINCRASKS VSTSLYSYMHWYQQKPGQPPKLLIYLAS NLESGVPDRFSGSGSGTDFTLTISSLQA EDVAVYYCQHSRELPYTFGQGTKLEIK (SEQ ID NO: 6) | QVQLQESGPGLVKPSETLSLTCTVSGGSI SSYGVHWIRQPPGKGLEWIGVIWTSGVTD YNSALMGRVTISVDTSKNQFSLKLSSVTA ADTAVYYCARDGDYDRYTMDYWGQGTLVT VSS (SEQ ID NO: 5) |
| h7E6_SVGN | DIVMTQSPDSLAVSLGERATINCRASKS VSTSNYSYMHWYQQKPGQPPKLLIYLAS NLESGVPDRFSGSGSGTDFTLTISSLQA EDVAVYYCQHSRELPYTFGQGTKLEIK (SEQ ID NO: 7) | QVQLQESGPGLVKPSETLSLTCTVSGGSI SSYGVHWIRQPPGKGLEWIGVIWTSGVTD YNSALMGRVTISVDTSKNQFSLKLSSVTA ADTAVYYCARDGDYDRYTMDYWGQGTLVT VSS (SEQ ID NO: 5) |
| m6G11 | DILLTQSPAILSVSPGERVSFSCRASQT IGTSIHWYQQRTNGSPRLLIKYASESIS GIPSRTSGSGSGTDFTLSINSVESEDIA DYYCQQSNSWPFTFGSGTKLEIK (SEQ ID NO: 8) | QVQLQQPGAELVRPGASVKLSCKASGYTF TSYWINWVKQRPGHGLEWIGNIYPSDSYS NYNQKFKDKATLTVDKSSTAYMQVSSPT SEDSAVYYCTGSSFDYWGQGTTVTVSS (SEQ ID NO: 9) |
| h6G11 | EIVLTQSPATLSLSPGERATLSCRASQT IGTSIHWYQQKPGQAPRLLIYYASESIS GIPARFSGSGSGTDFTLTISSLEPEDFA VYYCQQSNSWPFTFGQGTKLEIK (SEQ ID NO: 10) | QVQLVQSGAEVKKPGASVKVSCKASGYTF TSYWINWVRQAPGQGLEWMGNIYPSDSYS NYNQKFKDRVTMTRDTSTSTVYMELSSLR SEDTAVYYCARGSSFDYWGQGTLVTVSS (SEQ ID NO: 11) |
| H6G11_FKG_SF | EIVLTQSPATLSLSPGERATLSCRASQT IGTSIHWYQQKPGQAPRLLIYYASESIS GIPARFSGSGSGTDFTLTISSLEPEDFA VYYCSQSFSWPFTFGQGTKLEIK (SEQ ID NO: 12) | QVQLVQSGAEVKKPGASVKVSCKASGYTF TSYWINWVRQAPGQGLEWMGNIFPSDSYS NYNKKFKDRVTMTRDTSTSTVYMELSSLR SEDTAVYYCARGSSFDYWGQGTLVTVSS (SEQ ID NO: 13) |

In Table 1, the underlined sequences are CDR sequences according to Kabat and in bold according to Chothia.

The invention also provides CDR portions of antibodies to Trop-2 (including Chothia, Kabat CDRs, and CDR contact regions). Determination of CDR regions is well within the skill of the art. It is understood that in some embodiments, CDRs can be a combination of the Kabat and Chothia CDR (also termed "combined CRs" or "extended CDRs"). In some embodiments, the CDRs are the Kabat CDRs. In other embodiments, the CDRs are the Chothia CDRs. In other words, in embodiments with more than one CDR, the CDRs may be any of Kabat, Chothia, combination CDRs, or combinations thereof. Table 2 provides examples of CDR sequences provided herein.

TABLE 2

| mAb | CDRH1 | CDRH2 | CDRH3 |
|---|---|---|---|
| | | Heavy Chain | |
| m7E6 | SYGVH (Kabat); (SEQ ID NO: 30) GFSLTSY (Chothia); (SEQ ID NO: 31) GFSLTSYGVH (extended) (SEQ ID NO: 32) | VIWTGGSTDHNSALMS (Kabat) (SEQ ID NO: 33) WTGGS (Chothia) (SEQ ID NO: 34) | DGDYDRYTMDY (SEQ ID NO: 35) |
| h7E6 | SYGVH (Kabat); (SEQ ID NO: 30) GGSISSY (Chothia); GGSISSYGVH (extended) (SEQ ID NO: 37) | VIWTGGSTDYNSALMS (Kabat) (SEQ ID NO: 33) WTGGS (Chothia) (SEQ ID NO: 34) | DGDYDRYTMDY (SEQ ID NO: 35) |
| h7E6_SVG | SYGVH (Kabat); (SEQ ID NO: 30) GGSISSY (Chothia); (SEQ ID NO: 36) GGSISSYGVH (extended) (SEQ ID NO: 37) | VIWTSGVTDYNSALMG (Kabat) (SEQ ID NO: 38) WTSGV (Chothia) (SEQ ID NO: 39) | DGDYDRYTMDY (SEQ ID NO: 35) |
| h7E6_SVG1 | SYGVH (Kabat); (SEQ ID NO: 30) GGSISSY (Chothia); (SEQ ID NO: 36) GGSISSYGVH (extended) (SEQ ID NO: 37) | VIWTSGVTDYNSALMG (Kabat) (SEQ ID NO: 38) WTSGV (Chothia) (SEQ ID NO: 39) | $X_1X_2$DYDRYT$X_3$DY wherein $X_1$, $X_2$, and $X_3$ are any naturally occurring amino acids (SEQ ID NO: 86) |
| h7E6_SVG2 | SYGVH (Kabat); (SEQ ID NO: 30) GGSISSY (Chothia); (SEQ ID NO: 36) GGSISSYGVH (extended) (SEQ ID NO: 37) | VIWTSGVTDYNSALMG (Kabat) (SEQ ID NO: 38) WTSGV (Chothia) (SEQ ID NO: 39) | $X_1X_2$DYDRYT$X_3$DY wherein $X_1$ and $X_2$, are any naturally occurring amino acids; wherein $X_3$ is E or M (SEQ ID NO: 87) |
| h7E6_SVG3 | SYGVH (Kabat); (SEQ ID NO: 30) GGSISSY (Chothia); (SEQ ID NO: 36) GGSISSYGVH (extended) (SEQ ID NO: 37) | VIWTSGVTDYNSALMG (Kabat) (SEQ ID NO: 38) WTSGV (Chothia) (SEQ ID NO: 39) | DYDRYT$X_1$DY wherein $X_1$ is any naturally occurring amino acid; (SEQ ID NO: 83) |
| h7E6_SVG4 | SYGVH (Kabat); (SEQ ID NO: 30) GGSISSY (Chothia); (SEQ ID NO: 36) GGSISSYGVH (extended) (SEQ ID NO: 37) | VIWTSGVTDYNSALMG (Kabat) (SEQ ID NO: 38) WTSVG (Chothia) (SEQ ID NO: 39) | DYDRYT$X_1$DY wherein $X_1$ is E or M (SEQ ID NO: 82) |
| h7E6_SGV5 | SYGVH (Kabat); (SEQ ID NO: 30) GGSISSY (Chothia); (SEQ ID NO: 36) GGSISSYGVH (extended) (SEQ ID NO: 37) | VIWTSGVTDYNSALMG (Kabat) (SEQ ID NO: 38) WTSGV (Chothia) (SEQ ID NO: 39) | LGDYDRYTMDY (SEQ ID NO: 103) |
| h7E6_SVG6 | SYGVH (Kabat); (SEQ ID NO: 30) GGSISSY (Chothia); (SEQ ID NO: 36) GGSISSYGVH (extended) (SEQ ID NO: 37) | VIWTSGVTDYNSALMG (Kabat) (SEQ ID NO: 38) WTSGV (Chothia) (SEQ ID NO: 39) | YGDYDRYTMDY (SEQ ID NO: 104) |
| h7E6_SVG7 | SYGVH (Kabat); (SEQ ID NO: 30) GGSISSY (Chothia); GGSISSYGVH (extended) (SEQ ID NO: 37) | VIWTSGVTDYNSALMG (Kabat) (SEQ ID NO: 38) WTSGV (Chothia) (SEQ ID NO: 39) | FGDYDRYTMDY (SEQ ID NO: 105) |
| h7E6_SVG8 | SYGVH (Kabat); (SEQ ID NO: 30) GGSISSY (Chothia); (SEQ ID NO: 36) GGSISSYGVH (extended) (SEQ ID NO: 37) | VIWTSGVTDYNSALMG (Kabat) (SEQ ID NO: 38) WTSGV (Chothia) (SEQ ID NO: 39) | HGDYDRYTMDY (SEQ ID NO: 106) |

TABLE 2-continued

| mAb | CDRH1 | CDRH2 | CDRH3 |
|---|---|---|---|
| h7E6_SVG9 | SYGVH (Kabat); (SEQ ID NO: 30) GGSISSY (Chothia); (SEQ ID NO: 36) GGSISSYGVH (extended) (SEQ ID NO: 37) | VIWTSGVTDYNSALMG (Kabat) (SEQ ID NO: 38) WTSGV (Chothia) (SEQ ID NO: 39) | AGDYDRYTMDY (SEQ ID NO: 107) |
| h7E6_SVG10 | SYGVH (Kabat); (SEQ ID NO: 30) GGSISSY (Chothia); (SEQ ID NO: 36) GGSISSYGVH (extended) (SEQ ID NO: 37) | VIWTSGVTDYNSALMG (Kabat) (SEQ ID NO: 38) WTSGV (Chothia) (SEQ ID NO: 39) | TGDYDRYTMDY (SEQ ID NO: 108) |
| h7E6_SVG11 | SYGVH (Kabat); (SEQ ID NO: 30) GGSISSY (Chothia); (SEQ ID NO: 36) GGSISSYGVH (extended) (SEQ ID NO: 37) | VIWTSGVTDYNSALMG (Kabat) (SEQ ID NO: 38) WTSGV (Chothia) (SEQ ID NO: 39) | SGDYDRYTMDY (SEQ ID NO: 109) |
| h7E6_SVG12 | SYGVH (Kabat); (SEQ ID NO: 30) GGSISSY (Chothia); (SEQ ID NO: 36) GGSISSYGVH (extended) (SEQ ID NO: 37) | VIWTSGVTDYNSALMG (Kabat) (SEQ ID NO: 38) WTSGV (Chothia) (SEQ ID NO: 39) | IGDYDRYTMDY (SEQ ID NO: 110) |
| h7E6_SVG13 | SYGVH (Kabat); (SEQ ID NO: 30) GGSISSY (Chothia); (SEQ ID NO: 36) GGSISSYGVH (extended) (SEQ ID NO: 37) | VIWTSGVTDYNSALMG (Kabat) (SEQ ID NO: 38) WTSGV (Chothia) (SEQ ID NO: 39) | RGDYDRYTMDY (SEQ ID NO: 111) |
| h7E6_SVG14 | SYGVH (Kabat); (SEQ ID NO: 30) GGSISSY (Chothia); (SEQ ID NO: 36) GGSISSYGVH (extended) (SEQ ID NO: 37) | VIWTSGVTDYNSALMG (Kabat) (SEQ ID NO: 38) WTSGV (Chothia) (SEQ ID NO: 39) | VGDYDRYTMDY (SEQ ID NO: 112) |
| h7E6_SVG15 | SYGVH (Kabat); (SEQ ID NO: 30) GGSISSY (Chothia); (SEQ ID NO: 36) GGSISSYGVH (extended) (SEQ ID NO: 37) | VIWTSGVTDYNSALMG (Kabat) (SEQ ID NO: 38) WTSGV (Chothia) (SEQ ID NO: 39) | WGDYDRYTMDY (SEQ ID NO: 113) |
| h7E6_SVG16 | SYGVH (Kabat); (SEQ ID NO: 30) GGSISSY (Chothia); (SEQ ID NO: 36) GGSISSYGVH (extended) (SEQ ID NO: 37) | VIWTSGVTDYNSALMG (Kabat) (SEQ ID NO: 38) WTSGV (Chothia) (SEQ ID NO: 39) | QGDYDRYTMDY (SEQ ID NO: 114) |
| h7E6_SVG17 | SYGVH (Kabat); (SEQ ID NO: 30) GGSISSY (Chothia); (SEQ ID NO: 36) GGSISSYGVH (extended) (SEQ ID NO: 37) | VIWTSGVTDYNSALMG (Kabat) (SEQ ID NO: 38) WTSGV (Chothia) (SEQ ID NO: 39) | GGDYDRYTMDY (SEQ ID NO: 115) |
| h7E6_SVG18 | SYGVH (Kabat); (SEQ ID NO: 30) GGSISSY (Chothia); (SEQ ID NO: 36) GGSISSYGVH (extended) (SEQ ID NO: 37) | VIWTSGVTDYNSALMG (Kabat) (SEQ ID NO: 38) WTSGV (Chothia) (SEQ ID NO: 39) | KGDYDRYTMDY (SEQ ID NO: 116) |
| h7E6_SVG19 | SYGVH (Kabat); (SEQ ID NO: 30) GGSISSY (Chothia); (SEQ ID NO: 36) GGSISSYGVH (extended) (SEQ ID NO: 37) | VIWTSGVTDYNSALMG (Kabat) (SEQ ID NO: 38) WTSGV (Chothia) (SEQ ID NO: 39) | DSDYDRYTMDY (SEQ ID NO: 117) |

TABLE 2-continued

| mAb | CDRH1 | CDRH2 | CDRH3 |
|---|---|---|---|
| h7E6_SVG20 | SYGVH (Kabat); (SEQ ID NO: 30) GGSISSY (Chothia); (SEQ ID NO: 36) GGSISSYGVH (extended) (SEQ ID NO: 37) | VIWTSGVTDYNSALMG (Kabat) (SEQ ID NO: 38) WTSGV (Chothia) (SEQ ID NO: 39) | DKDYDRYTMDY (SEQ ID NO: 118) |
| h7E6_SVG21 | SYGVH (Kabat); (SEQ ID NO: 30) GGSISSY (Chothia); (SEQ ID NO: 36) GGSISSYGVH (extended) (SEQ ID NO: 37) | VIWTSGVTDYNSALMG (Kabat) (SEQ ID NO: 38) WTSGV (Chothia) (SEQ ID NO: 39) | DHDYDRYTMDY (SEQ ID NO: 119) |
| h7E6_SVG22 | SYGVH (Kabat); (SEQ ID NO: 30) GGSISSY (Chothia); (SEQ ID NO: 36) GGSISSYGVH (extended) (SEQ ID NO: 37) | VIWTSGVTDYNSALMG (Kabat) (SEQ ID NO: 38) WTSGV (Chothia) (SEQ ID NO: 39) | DADYDRYTMDY (SEQ ID NO: 120) |
| h7E6_SVG23 | SYGVH (Kabat); (SEQ ID NO: 30) GGSISSY (Chothia); (SEQ ID NO: 36) GGSISSYGVH (extended) (SEQ ID NO: 37) | VIWTSGVTDYNSALMG (Kabat) (SEQ ID NO: 38) WTSGV (Chothia) (SEQ ID NO: 39) | DFDYDRYTMDY (SEQ ID NO: 121) |
| h7E6_SVG24 | SYGVH (Kabat); (SEQ ID NO: 30) GGSISSY (Chothia); (SEQ ID NO: 36) GGSISSYGVH (extended) (SEQ ID NO: 37) | VIWTSGVTDYNSALMG (Kabat) (SEQ ID NO: 38) WTSGV (Chothia) (SEQ ID NO: 39) | DTDYDRYTMDY (SEQ ID NO: 122) |
| h7E6_SVG25 | SYGVH (Kabat); (SEQ ID NO: 30) GGSISSY (Chothia); (SEQ ID NO: 36) GGSISSYGVH (extended) (SEQ ID NO: 37) | VIWTSGVTDYNSALMG (Kabat) (SEQ ID NO: 38) WTSGV (Chothia) (SEQ ID NO: 39) | DRDYDRYTMDY (SEQ ID NO: 123) |
| h7E6_SVG26 | SYGVH (Kabat); (SEQ ID NO: 30) GGSISSY (Chothia); (SEQ ID NO: 36) GGSISSYGVH (extended) (SEQ ID NO: 37) | VIWTSGVTDYNSALMG (Kabat) (SEQ ID NO: 38) WTSGV (Chothia) (SEQ ID NO: 39) | DVDYDRYTMDY (SEQ ID NO: 124) |
| h7E6_SVG27 | SYGVH (Kabat); (SEQ ID NO: 30) GGSISSY (Chothia); (SEQ ID NO: 36) GGSISSYGVH (extended) (SEQ ID NO: 37) | VIWTSGVTDYNSALMG (Kabat) (SEQ ID NO: 38) WTSGV (Chothia) (SEQ ID NO: 39) | DQDYDRYTMDY (SEQ ID NO: 125) |
| h7E6_SVG28 | SYGVH (Kabat); (SEQ ID NO: 30) GGSISSY (Chothia); (SEQ ID NO: 36) GGSISSYGVH (extended) (SEQ ID NO: 37) | VIWTSGVTDYNSALMG (Kabat) (SEQ ID NO: 38) WTSGV (Chothia) (SEQ ID NO: 39) | DLDYDRYTMDY (SEQ ID NO: 126) |
| h7E6_SVG29 | SYGVH (Kabat); (SEQ ID NO: 30) GGSISSY (Chothia); (SEQ ID NO: 36) GGSISSYGVH (extended) (SEQ ID NO: 37) | VIWTSGVTDYNSALMG (Kabat) (SEQ ID NO: 38) WTSGV (Chothia) (SEQ ID NO: 39) | DYDYDRYTMDY (SEQ ID NO: 127) |
| h7E6_SVG30 | SYGVH (Kabat); (SEQ ID NO: 30) GGSISSY (Chothia); (SEQ ID NO: 36) GGSISSYGVH (extended) (SEQ ID NO: 37) | VIWTSGVTDYNSALMG (Kabat) (SEQ ID NO: 38) WTSGV (Chothia) (SEQ ID NO: 39) | DEDYDRYTMDY (SEQ ID NO: 128) |

TABLE 2-continued

| mAb | CDRH1 | CDRH2 | CDRH3 |
| --- | --- | --- | --- |
| h7E6_SVG31 | SYGVH (Kabat); (SEQ ID NO: 30) GGSISSY (Chothia); (SEQ ID NO: 36) GGSISSYGVH (extended) (SEQ ID NO: 37) | VIWTSGVTDYNSALMG (Kabat) (SEQ ID NO: 38) WTSGV (Chothia) (SEQ ID NO: 39) | DNDYDRYTMDY (SEQ ID NO: 129) |
| h7E6_SVG32 | SYGVH (Kabat); (SEQ ID NO: 30) GGSISSY (Chothia); (SEQ ID NO: 36) GGSISSYGVH (extended) (SEQ ID NO: 37) | VIWTSGVTDYNSALMG (Kabat) (SEQ ID NO: 38) WTSGV (Chothia) (SEQ ID NO: 39) | DWDRYDRYTMDY (SEQ ID NO: 130) |
| h7E6_SVGL | SYGVH (Kabat); (SEQ ID NO: 30) GGSISSY (Chothia); (SEQ ID NO: 36) GGSISSYGVH (extended) (SEQ ID NO: 37) | VIWTSGVTDYNSALMG (Kabat) (SEQ ID NO: 38) WTSGV (Chothia) (SEQ ID NO: 39) | DGDYDRYTMDY (SEQ ID NO: 35) |
| h7E6_SVGL1 | SYGVH (Kabat); (SEQ ID NO: 30) GGSISSY (Chothia); (SEQ ID NO: 36) GGSISSYGVH (extended) (SEQ ID NO: 37) | VIWTSGVTDYNSALMG (Kabat) (SEQ ID NO: 38) WTSGV (Chothia) (SEQ ID NO: 39) | DSDYDRYTMDY (SEQ ID NO: 117) |
| h7E6_SVGL2 | SYGVH (Kabat); (SEQ ID NO: 30) GGSISSY (Chothia); (SEQ ID NO: 36) GGSISSYGVH (extended) (SEQ ID NO: 37) | VIWTSGVTDYNSALMG (Kabat) (SEQ ID NO: 38) WTSGV (Chothia) (SEQ ID NO: 39) | DKDYDRYTMDY (SEQ ID NO: 118) |
| h7E6_SVGL3 | SYGVH (Kabat); (SEQ ID NO: 30) GGSISSY (Chothia); (SEQ ID NO: 36) GGSISSYGVH (extended) (SEQ ID NO: 37) | VIWTSGVTDYNSALMG (Kabat) (SEQ ID NO: 38) WTSGV (Chothia) (SEQ ID NO: 39) | DADYDRYTMDY (SEQ ID NO: 120) |
| h7E6_SVGL4 | SYGVH (Kabat); (SEQ ID NO: 30) GGSISSY (Chothia); (SEQ ID NO: 36) GGSISSYGVH (extended) (SEQ ID NO: 37) | VIWTSGVTDYNSALMG (Kabat) (SEQ ID NO: 38) WTSGV (Chothia) (SEQ ID NO: 39) | DLDYDRYTMDY (SEQ ID NO: 126) |
| h7E6_SVGL5 | SYGVH (Kabat); (SEQ ID NO: 30) GGSISSY (Chothia); (SEQ ID NO: 36) GGSISSYGVH (extended) (SEQ ID NO: 37) | VIWTSGVTDYNSALMG (Kabat) (SEQ ID NO: 38) WTSGV (Chothia) (SEQ ID NO: 39) | DEDYDRYTMDY (SEQ ID NO: 128) |
| h7E6_SVGN | SYGVH (Kabat); (SEQ ID NO: 30) GGSISSY (Chothia); (SEQ ID NO: 36) GGSISSYGVH (extended) (SEQ ID NO: 37) | VIWTSGVTDYNSALMG (Kabat) (SEQ ID NO: 38) WTSGV (Chothia) (SEQ ID NO: 39) | DGDYDRYTMDY (SEQ ID NO: 35) |
| h7E6 Heavy Chain Consensus | $GX_1SX_2X_3SY$ wherein $X_1$ is F or G; $X_2$ is L or I; $X_3$ is T or S (Chothia); (SEQ ID NO: 76) $GX_1SX_2X_3SYGVH$ wherein $X_1$ is F or G; $X_2$ is L or I; $X_3$ is T or S (SEQ ID NO: 77) | $VISTX_1GX_2TDYNASLMX_3$ wherein $X_1$, $X_2$, and $X_3$ is G or S; $X_2$ is S or V; $X_3$ is S or G (Kabat) (SEQ ID NO: 49) $WTX_1GX_2$ wherein $X_1$ is G or S; $X_2$ is S or V (Chothia) (SEQ ID NO: 50) | $X_1X_2DYDRYTX_3DY$ wherein $X_1$, $X_2$, and $X_3$ are any naturally occurring amino acids (SEQ ID NO: 86) $X_1X_2DYDRYTX_3DY$ wherein $X_1$ and $X_2$, are any naturally occurring amino acids; wherein $X_3$ is E or M (SEQ ID NO: 87) $DYDRYTX_1DY$ wherein $X_1$ is any naturally occurring amino acid; |

TABLE 2-continued

| mAb | CDRH1 | CDRH2 | CDRH3 |
|---|---|---|---|
| | | | (SEQ ID NO: 83)<br>DYDRYTX$_1$DY<br>wherein X$_1$ is E or M<br>(SEQ ID NO: 82) |
| m6G11 | SYWIN (Kabat);<br>(SEQ ID NO: 40)<br>GYTFTSY (Chothia);<br>(SEQ ID NO: 41)<br>GYTFTSYWIN (extended)<br>(SEQ ID NO: 42) | NIYPSDSYSNYNQKFKD (Kabat)<br>(SEQ ID NO: 43)<br>YPSDSY (Chothia)<br>(SEQ ID NO: 44) | GSSFDY<br>(SEQ ID NO: 45) |
| h6G11 | SYWIN (Kabat);<br>(SEQ ID NO: 40)<br>GYTFTSY (Chothia);<br>(SEQ ID NO: 41)<br>GYTFTSYWIN (extended)<br>(SEQ ID NO: 42) | NIYPSDSYSNYNQKFKD (Kabat)<br>(SEQ ID NO: 43)<br>YPSDSY (Chothia)<br>(SEQ ID NO: 44) | GSSFDY<br>(SEQ ID NO: 45) |
| h6G11_FKG_SF | SYWIN (Kabat);<br>(SEQ ID NO: 40)<br>GYTFTSY (Chothia);<br>(SEQ ID NO: 41)<br>GYTFTSYWIN (extended)<br>(SEQ ID NO: 42) | NIFPSDSYSNYNKKFKD (Kabat)<br>(SEQ ID NO: 46)<br>FPSDSY (Chothia)<br>(SEQ ID NO: 47) | GSGFDY<br>(SEQ ID NO: 48) |
| h6G11<br>Heavy<br>Chain<br>consensus | | NIX$_1$PSDSYSNYNX2KFKD<br>wherein X$_1$ is Y or F;<br>X$_2$ is Q or K (Kabat)<br>(SEQ ID NO: 51)<br>X$_1$PSDSY<br>wherein X$_1$ is Y or F<br>(Chothia)<br>(SEQ ID NO: 52) | GSX$_1$FDY<br>wherein X$_1$ is S or G<br>(SEQ ID NO: 53) |
| Light Chain | | | |
| m7E6 | RASKSVSTSGYSYMH<br>(SEQ ID NO: 54) | LASNLES<br>(SEQ ID NO: 55) | QHSRELPYT<br>(SEQ ID NO: 56) |
| h7E6 | RASKSVSTSGYSYMH<br>(SEQ ID NO: 54) | LASNLES<br>(SEQ ID NO: 55) | QHSRELPYT<br>(SEQ ID NO: 56) |
| h7E6_SVG<br>(including<br>h7E6_SVG1<br>through<br>h&E6_SVG32 | RASKSVSTSGYSYMH<br>(SEQ ID NO: 54) | LASNLES<br>(SEQ ID NO: 55) | QHSRELPYT<br>(SEQ ID NO: 56) |
| h7E6_SVGL<br>(including<br>h7E6_SCGL1<br>through<br>h7E6_SVGL5 | RASKSVSTSLYSYMH<br>(SEQ ID NO: 57) | LASNLES<br>(SEQ ID NO: 55) | QHSRELPYT<br>(SEQ ID NO: 56) |
| h7E6_SVGN | RASKSVSTSNYSYMH<br>(SEQ ID NO: 58) | LASNLES<br>(SEQ ID NO: 55) | QHSRELPYT<br>(SEQ ID NO: 56) |
| h7E6<br>Light<br>Chain<br>Consensus | RASKSVSTSX$_1$YSYM<br>H wherein X$_1$ is G, L,<br>or N<br>(SEQ ID NO: 63) | | |
| m6G11 | RASQTIGTSIH<br>(SEQ ID NO: 59) | YASESIS<br>(SEQ ID NO: 60) | QQSNSWPFT<br>(SEQ ID NO: 61) |
| h6G11 | RASQTIGTSIH<br>(SEQ ID NO: 59) | YASESIS<br>(SEQ ID NO: 60) | QQSNSWPFT<br>(SEQ ID NO: 61) |
| h6G11_FKG_SF | RASQTIGTSIH<br>(SEQ ID NO: 59) | YASESIS<br>(SEQ ID NO: 60) | SQSFSWPFT<br>(SEQ ID NO: 62) |
| h6G11<br>Light<br>Chain<br>consensus | | | X$_1$QSX$_2$SWPFT<br>wherein X$_1$ is Q or S;<br>X$_2$ is N or F<br>(SEQ ID NO: 64) |

In some embodiments, the present invention provides an antibody that binds to Trop-2 and competes with the antibody as described herein, such as m7E6, h7E6, h7E6_SVG, h7E6_SVG1, h7E6_SVG2, h7E6_SVG3, h7E6_SVG4, h7E6_SVG5, h7E6_SVG6, h7E6_SVG7, h7E6_SVG8, h7E6_SVG9, h7E6_SVG10, h7E6_SVG11, h7E6_SVG12, h7E6_SVG13, h7E6_SVG14, h7E6_SVG15, h7E6_SVG16, h7E6_SVG17, h7E6_SVG18, h7E6_SVG19, h7E6_SVG20, h7E6_SVG21, h7E6_SVG22, h7E6_SVG23, h7E6_SVG24, h7E6_SVG25, h7E6_SVG26, h7E6_SVG27, h7E6_SVG28, h7E6_SVG29, h7E6_SVG30, h7E6_SVG31, h7E6_SVG32, h7E6_SVGL, h7E6_SVGL1, h7E6_SVGL2, h7E6_SVGL3, h7E6_SVGL4, h7E6_SVGL5, h7E6_SVGN, m6G11, h6G11, or h6G11_FKG_SF. In some embodiments, the antibody competes the binding of Trop-2 with antibody h7E6_SVG, h7E6_SVG4, h7E6_SVG19, h7E6_SVG20, h7E6_SVG22, h7E6_SVG28, h7E6_SVG30, h7E6_SVGL, h7E6_SVGL1, h7E6_SVGL2, h7E6_SVGL3, h7E6_SVGL4, h7E6_SVGL5, h7E6_SVGN, or h6G11_FKG_SF. In some embodiments, the antibody competes the binding of Trop-2 with antibody h7E6_SVG and has a monovalent antibody binding affinity ($K_D$) of about any of or less than about any of 6.5 nM, 6.0 nM, 5.5 nM, 5.0 nM, 4.5 nM, 4.0 nM, 3.5 nM, 3.0 nM, 2.5 nM, 2.0 nM, 1.5 nM, 1.0 nM, 0.5 nM, or 0.25 nM as measured by surface plasmon resonance. In some embodiments, the antibody competes with the binding of Trop-2 with antibody h7E6 and has a monovalent antibody binding affinity ($K_D$) of about any of or less than about any of 30 nM, 25 nM, 22 nM, 20 nM, 15 nM, or 10 nM. In some embodiments, the competing antibody does not comprise a heavy chain variable region of the sequence QVQLKESGPGLVAPSQSLSITCTVSGFSLTSYGVHWVRQPPGKGLEWLGVIWTGGSTDYNSALMSRLSINKDNSKSQVFLKMNSLQTDDTAMYYCARDGDYDRYTMDYWGQGTSVTVSS (SEQ ID NO: 2) and a light chain variable region of the sequence DIVLTQSPASLAVSLGQRATISCRASKSVSTSGYSYMHWYQQKPGQPPKLLIYLASNLESGVPARFSGSGSGTDFTLNIH-PVEEEDAATYYCQHSRELPYTFGGGTKLEIK (SEQ ID NO: 1). In some embodiments, the competing antibody is not antibody AR47A6.4.2, AR52A301.5, AR36A36.11.1, BR110 or RS7.

In some embodiments, the present invention provides an antibody or an antigen binding fragment, which specifically bind to Trop-2, wherein the antibody comprises a VH region comprising a sequence shown in SEQ ID NO: 5, 84, or 85; and/or a VL region comprising a sequence shown in SEQ ID NO: 3. In some embodiments, the antibody comprises a light chain comprising the sequence DIVMTQSPDSLAVSLGER-ATINCRASKSVSTSGYSYMHWYQQK-PGQPPKLLIYLASNLES GVPDRFSGSGSGTDFTLTISS-LQAEDVAVYYCQHSRELPYTFGQGTKLEIKRTVAAPSVFI FPPSDEQLKSGTASWCLLNN-FYPREAKVQWKVDNALQSGNSQESVTE-QDSKDSTYSLS STLTLSKADYEKHKVY-ACEVTHQGLSSPVTKSFNRGEC (SEQ ID NO: 66) and a heavy chain comprising the sequence QVQLQESG-PGLVKPSETLSLTCTVSGGSISSYGVH-WIRQPPGKGLEWIGVIWTSGVTDYN SALMGRVTIS-VDTSKNQFSLKLSSVTAADTAVYYCARDGDYDRYT-MDYWGQGTLVTVSS ASTKGPSVFPLAPSSKSTSGG-TAALGCLVKDYFPEPVTVSWNSGALTS-GVHTFPAVLQSS GLYSLSSWTVPSSSLGTQTYICNVN-HKPSNTKVDKKVEPKSCDKTHTCPPCPAPELLGG PSVFLFPPKPKDTLMISRTPEVTCWVD-VSHEDPEVKFNWYVDGVEVHNAKTKPREEQYN STYRVVSVLTVLHQDWLNGKEYKCK-VSNKALPAPIEKTISKAKGQPREPQVYTLPPSREE MTKNQVSLTCLVKGFYPSDIA-VEWESNGQPENNYKTTPPVLDSDGSFF-LYSKLTVDKSRW QQGNVFSCSVMHEALHNHYTQK-SLSLSPGK (SEQ ID NO: 65). In some embodiments, the antibody comprises a light chain comprising the sequence SEQ ID NO: 66 and a heavy chain comprising the sequence SEQ ID NO: 101 or 102.

In some embodiments, the present invention provides an antibody or an antigen binding fragment, which specifically bind to Trop-2, wherein the antibody comprises a VH region comprising a sequence shown in SEQ ID NO: 13; and/or a VL region comprising a sequence shown in SEQ ID NO: 12. In some embodiments, the antibody comprises a light chain comprising the sequence EIVLTQSPATLSLSPGER-ATLSCRASQTIGTSIHWYQQK-PGQAPRLLIYYASESISGIPARFS GSGSGTD-FTLTISSLEPEDFAVYYCSQSFSWPFTFGQGTKLEIK-RTVAAPSVFIFPPSDEQL KSGTASWCLLNN-FYPREAKVQWKVDNALQSGNSQESVTE-QDSKDSTYSLSSTLTLSKA DYEKHKVY-ACEVTHQGLSSPVTKSFNRGEC (SEQ ID NO: 68) and a heavy chain comprising the sequence QVQLVQSGAE-VKKPGASVKVSCKASGYTFTSYWIN-WVRQAPGQGLEWMGNIFPSDSYS NYNKKFKDRVT-MTRDTSTSTVYMELSSLRSEDTAVYYCARGSGFDY-WGQGTLVTVSSAS TKGPSVFPLAPSSKSTSGGTAAL-GCLVKDYFPEPVTVSWNSGALTSGVHTFPAVLQSSGL YSLSSVVTVPSSSLGTQTYICNVNH-KPSNTKVDKKVEPKSCDKTHTCPPCPAPELLGGPS VFLFPPKPKDTLMISRTPEVTCVVVD-VSHEDPEVKFNWYVDGVEVHNAKTKPREEQYNST YRVVSVLTVLHQDWLNGKEYKCK-VSNKALPAPIEKTISKAKGQPREPQVYTLPPSREEMT KNQVSLTCLVKGFYPSDIA-VEWESNGQPENNYKTTPPVLDSDGSFF-LYSKLTVDKSRWQ QGNVFSCSVMHEALHNHYTQK-SLSLSPGK (SEQ ID NO: 67).

In some embodiments, the invention also provides CDR portions of antibodies to Trop-2 antibodies based on CDR contact regions. CDR contact regions are regions of an antibody that imbue specificity to the antibody for an antigen. In general, CDR contact regions include the residue positions in the CDRs and Vernier zones which are constrained in order to maintain proper loop structure for the antibody to bind a specific antigen. See, e.g., Makabe et al., J. Biol. Chem., 283:1156-1166, 2007. Determination of CDR contact regions is well within the skill of the art.

The binding affinity ($K_D$) of the Trop-2 antibody as described herein to Trop-2 (such as human Trop-2) can be about 0.002 to about 200 nM. In some embodiments, the binding affinity is any of about 200 nM, about 100 nM, about 50 nM, about 45 nM, about 40 nM, about 35 nM, about 30 nM, about 25 nM, about 20 nM, about 15 nM, about 10 nM, about 8 nM, about 7.5 nM, about 7 nM, about 6.5 nM, about 6 nM, about 5.5 nM, about 5 nM, about 4 nM, about 3 nM, about 2 nM, about 1 nM, about 500 pM, about 100 pM, about 60 pM, about 50 pM, about 20 pM, about 15 pM, about 10 pM, about 5 pM, or about 2 pM. In some embodiments, the binding affinity is less than any of about 250 nM, about 200 nM, about 100 nM, about 50 nM, about 30 nM, about 20 nM, about 10 nM, about 7.5 nM, about 7 nM, about 6.5 nM, about 6 nM, about 5 nM, about 4.5 nM, about 4 nM, about 3.5 nM, about 3 nM, about 2.5 nM, about 2 nM, about 1.5 nM, about 1 nM, about 500 pM, about 100 pM, about 50 pM, about 20 pM, about 10 pM, about 5 pM, or about 2 pM.

In some embodiments, the binding affinity (e.g., monovalent antibody binding) of the antibodies as described herein is about 35 nM or less as measured by surface plasmon resonance. In some embodiments, the binding affinity (e.g., monovalent antibody binding) of the antibodies as described herein is about 6.5 nM or less as measured by surface plasmon resonance.

The invention also provides methods of making any of these antibodies. The antibodies of this invention can be made by procedures known in the art. The polypeptides can be produced by proteolytic or other degradation of the antibodies, by recombinant methods (i.e., single or fusion polypeptides) as described above or by chemical synthesis. Polypeptides of the antibodies, especially shorter polypeptides up to about 50 amino acids, are conveniently made by chemical synthesis. Methods of chemical synthesis are known in the art and are commercially available. For example, an antibody could be produced by an automated polypeptide synthesizer employing the solid phase method. See also, U.S. Pat. Nos. 5,807,715; 4,816,567; and 6,331,415.

In another alternative, the antibodies can be made recombinantly using procedures that are well known in the art. In one embodiment, a polynucleotide comprises a sequence encoding the heavy chain and/or the light chain variable regions of antibody m7E6, h7E6, h7E6_SVG, h7E6_SVG1, h7E6_SVG2, h7E6_SVG3, h7E6_SVG4, h7E6_SVG5, h7E6_SVG6, h7E6_SVG7, h7E6_SVG8, h7E6_SVG9, h7E6_SVG10, h7E6_SVG11, h7E6_SVG12, h7E6_SVG13, h7E6_SVG14, h7E6_SVG15, h7E6_SVG16, h7E6_SVG17, h7E6_SVG18, h7E6_SVG19, h7E6_SVG20, h7E6_SVG21, h7E6_SVG22, h7E6_SVG23, h7E6_SVG24, h7E6_SVG25, h7E6_SVG26, h7E6_SVG27, h7E6_SVG28, h7E6_SVG29, h7E6_SVG30, h7E6_SVG31, h7E6_SVG32, h7E6_SVGL, h7E6_SVGL1, h7E6_SVGL2, h7E6_SVGL3, h7E6_SVGL4, h7E6_SVGL5, h7E6_SVGN, m6G11, h6G11, or h6G11_FKG_SF. The sequence encoding the antibody of interest may be maintained in a vector in a host cell and the host cell can then be expanded and frozen for future use. Vectors (including expression vectors) and host cells are further described herein.

The invention also encompasses scFv of antibodies of this invention. Single chain variable region fragments are made by linking light and/or heavy chain variable regions by using a short linking peptide (Bird et al., Science 242:423-426, 1988). An example of a linking peptide is (GGGGS)$_3$ (SEQ ID NO: 80), which bridges approximately 3.5 nm between the carboxy terminus of one variable region and the amino terminus of the other variable region. Linkers of other sequences have been designed and used (Bird et al., 1988, supra). Linkers should be short, flexible polypeptides and preferably comprised of less than about 20 amino acid residues. Linkers can in turn be modified for additional functions, such as attachment of drugs or attachment to solid supports. The single chain variants can be produced either recombinantly or synthetically. For synthetic production of scFv, an automated synthesizer can be used. For recombinant production of scFv, a suitable plasmid containing polynucleotide that encodes the scFv can be introduced into a suitable host cell, either eukaryotic, such as yeast, plant, insect or mammalian cells, or prokaryotic, such as E. coli. Polynucleotides encoding the scFv of interest can be made by routine manipulations such as ligation of polynucleotides. The resultant scFv can be isolated using standard protein purification techniques known in the art.

Other forms of single chain antibodies, such as diabodies or minibodies are also encompassed. Diabodies are bivalent, bispecific antibodies in which heavy chain variable (VH) and light chain variable (VL) domains are expressed on a single polypeptide chain, but using a linker that is too short to allow for pairing between the two domains on the same chain, thereby forcing the domains to pair with complementary domains of another chain and creating two antigen binding sites (see e.g., Holliger, P., et al., Proc. Natl. Acad Sci. USA 90:6444-6448, 1993; Poljak, R. J., et al., Structure 2:1121-1123, 1994). Minibody includes the VL and VH domains of a native antibody fused to the hinge region and CH3 domain of the immunoglobulin molecule. See, e.g., U.S. Pat. No. 5,837,821.

For example, bispecific antibodies, monoclonal antibodies that have binding specificities for at least two different antigens, can be prepared using the antibodies disclosed herein. Methods for making bispecific antibodies are known in the art (see, e.g., Suresh et al., Methods in Enzymology 121:210, 1986). Traditionally, the recombinant production of bispecific antibodies was based on the coexpression of two immunoglobulin heavy chain-light chain pairs, with the two heavy chains having different specificities (Millstein and Cuello, Nature 305, 537-539, 1983).

According to one approach to making bispecific antibodies, antibody variable domains with the desired binding specificities (antibody-antigen combining sites) are fused to immunoglobulin constant region sequences. The fusion preferably is with an immunoglobulin heavy chain constant region, comprising at least part of the hinge, CH2 and CH3 regions. It is preferred to have the first heavy chain constant region (CH1), containing the site necessary for light chain binding, present in at least one of the fusions. DNAs encoding the immunoglobulin heavy chain fusions and, if desired, the immunoglobulin light chain, are inserted into separate expression vectors, and are cotransfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

In one approach, the bispecific antibodies are composed of a hybrid immunoglobulin heavy chain with a first binding specificity in one arm, and a hybrid immunoglobulin heavy chain-light chain pair (providing a second binding specificity) in the other arm. This asymmetric structure, with an immunoglobulin light chain in only one half of the bispecific molecule, facilitates the separation of the desired bispecific compound from unwanted immunoglobulin chain combinations. This approach is described in PCT Publication No. WO 94/04690.

In another approach, the bispecific antibodies are composed of amino acid modification in the first hinge region in one arm, and the substituted/replaced amino acid in the first hinge region has an opposite charge to the corresponding amino acid in the second hinge region in another arm. This approach is described in International Patent Application No. PCT/US2011/036419 (WO2011/143545).

In another approach, the bispecific antibodies can be generated using a glutamine-containing peptide tag engineered to the antibody directed to an epitope (e.g., Trop-2) in one arm and another peptide tag (e.g., a Lys-containing peptide tag or a reactive endogenous Lys) engineered to a second antibody directed to a second epitope in another arm in the presence of transglutaminase. This approach is described in International Patent Application No. PCT/IB2011/054899 (WO2012/059882).

Heteroconjugate antibodies, comprising two covalently joined antibodies, are also within the scope of the invention. Such antibodies have been used to target immune system cells to unwanted cells (U.S. Pat. No. 4,676,980), and for treatment of HIV infection (PCT Publication Nos. WO 91/00360 and WO 92/200373; EP 03089). Heteroconjugate antibodies may be made using any convenient cross-linking methods. Suitable cross-linking agents and techniques are well known in the art, and are described in U.S. Pat. No. 4,676,980.

Chimeric or hybrid antibodies also may be prepared in vitro using known methods of synthetic protein chemistry, including those involving cross-linking agents. For example, immunotoxins may be constructed using a disulfide exchange reaction or by forming a thioether bond. Examples of suitable reagents for this purpose include iminothiolate and methyl-4-mercaptobutyrimidate.

In the recombinant humanized antibodies, the Fcγ portion can be modified to avoid interaction with Fcγ receptor and the complement and immune systems. The techniques for preparation of such antibodies are described in WO 99/58572. For example, the constant region may be engineered to more resemble human constant regions to avoid immune response if the antibody is used in clinical trials and treatments in humans. See, for example, U.S. Pat. Nos. 5,997,867 and 5,866,692.

The invention encompasses modifications to the antibodies and polypeptides of the invention variants shown in Table 1, including functionally equivalent antibodies which do not significantly affect their properties and variants which have enhanced or decreased activity and/or affinity. For example, the amino acid sequence may be mutated to obtain an antibody with the desired binding affinity to Trop-2. Modification of polypeptides is routine practice in the art and need not be described in detail herein. Examples of modified polypeptides include polypeptides with conservative substitutions of amino acid residues, one or more deletions or additions of amino acids which do not significantly deleteriously change the functional activity, or which mature (enhance) the affinity of the polypeptide for its ligand, or use of chemical analogs.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue or the antibody fused to an epitope tag. Other insertional variants of the antibody molecule include the fusion to the N- or C-terminus of the antibody of an enzyme or a polypeptide which increases the half-life of the antibody in the blood circulation.

Substitution variants have at least one amino acid residue in the antibody molecule removed and a different residue inserted in its place. The sites of greatest interest for substitutional mutagenesis include the hypervariable regions, but FR alterations are also contemplated. Conservative substitutions are shown in Table 3 under the heading of "conservative substitutions." If such substitutions result in a change in biological activity, then more substantial changes, denominated "exemplary substitutions" in Table 3, or as further described below in reference to amino acid classes, may be introduced and the products screened.

TABLE 3

Amino Acid Substitutions

| Original Residue (naturally occurring amino acid) | Conservative Substitutions | Exemplary Substitutions |
|---|---|---|
| Ala (A) | Val | Val; Leu; Ile |
| Arg (R) | Lys | Lys; Gln; Asn |
| Asn (N) | Gln | Gln; His; Asp, Lys; Arg |
| Asp (D) | Glu | Glu; Asn |
| Cys (C) | Ser | Ser; Ala |
| Gln (Q) | Asn | Asn; Glu |
| Glu (E) | Asp | Asp; Gln |
| Gly (G) | Ala | Ala |
| His (H) | Arg | Asn; Gln; Lys; Arg |
| Ile (I) | Leu | Leu; Val; Met; Ala; Phe; Norleucine |
| Leu (L) | Ile | Norleucine; Ile; Val; Met; Ala; Phe |
| Lys (K) | Arg | Arg; Gln; Asn |
| Met (M) | Leu | Leu; Phe; Ile |
| Phe (F) | Tyr | Leu; Val; Ile; Ala; Tyr |
| Pro (P) | Ala | Ala |
| Ser (S) | Thr | Thr |
| Thr (T) | Ser | Ser |
| Trp (W) | Tyr | Tyr; Phe |
| Tyr (Y) | Phe | Trp; Phe; Thr; Ser |
| Val (V) | Leu | Ile; Leu; Met; Phe; Ala; Norleucine |

Substantial modifications in the biological properties of the antibody are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring amino acid residues are divided into groups based on common side-chain properties:

(1) Non-polar: Norleucine, Met, Ala, Val, Leu, Ile;
(2) Polar without charge: Cys, Ser, Thr, Asn, Gln;
(3) Acidic (negatively charged): Asp, Glu;
(4) Basic (positively charged): Lys, Arg;
(5) Residues that influence chain orientation: Gly, Pro; and
(6) Aromatic: Trp, Tyr, Phe, His.

Non-conservative substitutions are made by exchanging a member of one of these classes for another class.

Any cysteine residue not involved in maintaining the proper conformation of the antibody also may be substituted, generally with serine, to improve the oxidative stability of the molecule and prevent aberrant cross-linking. Conversely, cysteine bond(s) may be added to the antibody to improve its stability, particularly where the antibody is an antibody fragment such as an Fv fragment.

Amino acid modifications can range from changing or modifying one or more amino acids to complete redesign of a region, such as the variable region. Changes in the variable region can alter binding affinity and/or specificity. In some embodiments, no more than one to five conservative amino acid substitutions are made within a CDR domain. In other embodiments, no more than one to three conservative amino acid substitutions are made within a CDR domain. In still other embodiments, the CDR domain is CDR H3 and/or CDR L3.

Modifications also include glycosylated and nonglycosylated polypeptides, as well as polypeptides with other post-translational modifications, such as, for example, glycosylation with different sugars, acetylation, and phosphorylation. Antibodies are glycosylated at conserved positions in their constant regions (Jefferis and Lund, Chem. Immunol. 65:111-128, 1997; Wright and Morrison, TibTECH 15:26-32, 1997). The oligosaccharide side chains of the immunoglobulins affect the protein's function (Boyd et al., Mol. Immunol. 32:1311-1318, 1996; Wittwe and Howard, Biochem. 29:4175-4180, 1990) and the intramolecular interaction between portions of the glycoprotein, which can affect the conformation and presented three-dimensional surface of the glycoprotein (Jefferis and Lund, supra; Wyss and Wagner, Current Opin. Biotech. 7:409-416, 1996). Oligosaccharides may also serve to target a given glycoprotein to certain molecules based upon specific recognition structures. Glycosylation of antibodies has also been reported to affect antibody-dependent cellular cytotoxicity (ADCC). In particular, CHO cells with tetracycline-regulated expression of β(1,4)-N-acetylglucosaminyltransferase III (GnTIII), a glycosyltransferase catalyzing formation of bisecting GlcNAc, was reported to have improved ADCC activity (Umana et al., Mature Biotech. 17:176-180, 1999).

Glycosylation of antibodies is typically either N-linked or O-linked. N-linked refers to the attachment of the carbohydrate moiety to the side chain of an asparagine residue. The tripeptide sequences asparagine-X-serine, asparagine-X-threonine, and asparagine-X-cysteine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-acetylgalactosamine, galactose, or xylose to a hydroxyamino acid, most commonly serine or threonine, although 5-hydroxyproline or 5-hydroxylysine may also be used.

Addition of glycosylation sites to the antibody is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody (for O-linked glycosylation sites).

The glycosylation pattern of antibodies may also be altered without altering the underlying nucleotide sequence. Glycosylation largely depends on the host cell used to express the antibody. Since the cell type used for expression of recombinant glycoproteins, e.g. antibodies, as potential therapeutics is rarely the native cell, variations in the glycosylation pattern of the antibodies can be expected (see, e.g. Hse et al., J. Biol. Chem. 272:9062-9070, 1997).

In addition to the choice of host cells, factors that affect glycosylation during recombinant production of antibodies include growth mode, media formulation, culture density, oxygenation, pH, purification schemes and the like. Various methods have been proposed to alter the glycosylation pattern achieved in a particular host organism including introducing or overexpressing certain enzymes involved in oligosaccharide production (U.S. Pat. Nos. 5,047,335; 5,510,261 and 5,278,299). Glycosylation, or certain types of glycosylation, can be enzymatically removed from the glycoprotein, for example, using endoglycosidase H (Endo H), N-glycosidase F, endoglycosidase F1, endoglycosidase F2, endoglycosidase F3. In addition, the recombinant host cell can be genetically engineered to be defective in processing certain types of polysaccharides. These and similar techniques are well known in the art.

Other methods of modification include using coupling techniques known in the art, including, but not limited to, enzymatic means, oxidative substitution and chelation. Modifications can be used, for example, for attachment of labels for immunoassay. Modified polypeptides are made using established procedures in the art and can be screened using standard assays known in the art, some of which are described below and in the Examples.

In some embodiments of the invention, the antibody comprises a modified constant region, such as a constant region that has increased affinity to a human Fc gamma receptor, is immunologically inert or partially inert, e.g., does not trigger complement mediated lysis, does not stimulate antibody-dependent cell mediated cytotoxicity (ADCC), or does not activate macrophages; or has reduced activities (compared to the unmodified antibody) in any one or more of the following: triggering complement mediated lysis, stimulating antibody-dependent cell mediated cytotoxicity (ADCC), or activating microglia. Different modifications of the constant region may be used to achieve optimal level and/or combination of effector functions. See, for example, Morgan et al., Immunology 86:319-324, 1995; Lund et al., J. Immunology 157:4963-9 157:4963-4969, 1996; Idusogie et al., J. Immunology 164: 4178-4184, 2000; Tao et al., J. Immunology 143: 2595-2601, 1989; and Jefferis et al., Immunological Reviews 163:59-76, 1998. In some embodiments, the constant region is modified as described in Eur. J. Immunol., 1999, 29:2613-2624; PCT Application No. PCT/GB99/01441; and/or UK Patent Application No. 9809951.8. In other embodiments, the antibody comprises a human heavy chain IgG2 constant region comprising the following mutations: A330P331 to S330S331 (amino acid numbering with reference to the wild type IgG2 sequence). Eur. J. Immunol., 1999, 29:2613-2624. In still other embodiments, the constant region is aglycosylated for N-linked glycosylation. In some embodiments, the constant region is aglycosylated for N-linked glycosylation by mutating the glycosylated amino acid residue or flanking residues that are part of the N-glycosylation recognition sequence in the constant region. For example, N-glycosylation site N297 may be mutated to A, Q, K, or H. See, Tao et al., J. Immunology 143: 2595-2601, 1989; and Jefferis et al., Immunological Reviews 163:59-76, 1998. In some embodiments, the constant region is aglycosylated for N-linked glycosylation. The constant region may be aglycosylated for N-linked glycosylation enzymatically (such as removing carbohydrate by enzyme PNGase), or by expression in a glycosylation deficient host cell.

Other antibody modifications include antibodies that have been modified as described in PCT Publication No. WO 99/58572. These antibodies comprise, in addition to a binding domain directed at the target molecule, an effector domain having an amino acid sequence substantially homologous to all or part of a constant region of a human immunoglobulin heavy chain. These antibodies are capable of binding the target molecule without triggering significant complement dependent lysis, or cell-mediated destruction of the target. In some embodiments, the effector domain is capable of specifically binding FcRn and/or FcγRIIb. These are typically based on chimeric domains derived from two or more human immunoglobulin heavy chain $C_H2$ domains. Antibodies modified in this manner are particularly suitable for use in chronic antibody therapy, to avoid inflammatory and other adverse reactions to conventional antibody therapy.

The invention includes affinity matured embodiments. For example, affinity matured antibodies can be produced by procedures known in the art (Marks et al., Bio/Technology, 10:779-783, 1992; Barbas et al., Proc Nat. Acad. Sci, USA 91:3809-3813, 1994; Schier et al., Gene, 169:147-155, 1995; Yelton et al., J. Immunol., 155:1994-2004, 1995; Jackson et al., J. Immunol., 154(7):3310-9, 1995, Hawkins et al., J. Mol. Biol., 226:889-896, 1992; and PCT Publication No. WO2004/058184).

The following methods may be used for adjusting the affinity of an antibody and for characterizing a CDR. One way of characterizing a CDR of an antibody and/or altering (such as improving) the binding affinity of a polypeptide, such as an antibody, termed "library scanning mutagenesis". Generally, library scanning mutagenesis works as follows. One or more amino acid positions in the CDR are replaced with two or more (such as 3, 4, 5, 6, 7, 8, 9, 10, 11, 12, 13, 14, 15, 16, 17, 18, 19, or 20) amino acids using art recognized methods. This generates small libraries of clones (in some embodiments, one for every amino acid position that is analyzed), each with a complexity of two or more members (if two or more amino acids are substituted at every position). Generally, the library also includes a clone comprising the native (unsubstituted) amino acid. A small number of clones, e.g., about 20-80 clones (depending on the complexity of the library), from each library are screened for binding affinity to the target polypeptide (or other binding target), and candidates with increased, the same, decreased, or no binding are identified. Methods for determining binding affinity are well-known in the art. Binding affinity may be determined using Biacore™ surface plasmon resonance analysis, which detects differences in binding affinity of about 2-fold or greater. Biacore™ is particularly useful when the starting antibody already binds with a relatively high affinity, for example a $K_D$ of about 10 nM or lower. Screening using Biacore™ surface plasmon resonance is described in the Examples, herein.

Binding affinity may be determined using Kinexa Biocensor, scintillation proximity assays, ELISA, ORIGEN immunoassay (IGEN), fluorescence quenching, fluorescence transfer, and/or yeast display. Binding affinity may also be screened using a suitable bioassay.

In some embodiments, every amino acid position in a CDR is replaced (in some embodiments, one at a time) with all 20 natural amino acids using art recognized mutagenesis methods (some of which are described herein). This generates small libraries of clones (in some embodiments, one for every amino acid position that is analyzed), each with a complexity of 20 members (if all 20 amino acids are substituted at every position).

In some embodiments, the library to be screened comprises substitutions in two or more positions, which may be in the same CDR or in two or more CDRs. Thus, the library may comprise substitutions in two or more positions in one CDR. The library may comprise substitution in two or more positions in two or more CDRs. The library may comprise substitution in 3, 4, 5, or more positions, said positions found in two, three, four, five or six CDRs. The substitution may be prepared using low redundancy codons. See, e.g., Table 2 of Balint et al., Gene 137(1):109-18, 1993.

The CDR may be CDRH3 and/or CDRL3. The CDR may be one or more of CDRL1, CDRL2, CDRL3, CDRH1, CDRH2, and/or CDRH3. The CDR may be a Kabat CDR, a Chothia CDR, or an extended CDR.

Candidates with improved binding may be sequenced, thereby identifying a CDR substitution mutant which results in improved affinity (also termed an "improved" substitution). Candidates that bind may also be sequenced, thereby identifying a CDR substitution which retains binding.

Multiple rounds of screening may be conducted. For example, candidates (each comprising an amino acid substitution at one or more position of one or more CDR) with improved binding are also useful for the design of a second library containing at least the original and substituted amino acid at each improved CDR position (i.e., amino acid position in the CDR at which a substitution mutant showed improved binding). Preparation, and screening or selection of this library is discussed further below.

Library scanning mutagenesis also provides a means for characterizing a CDR, in so far as the frequency of clones with improved binding, the same binding, decreased binding or no binding also provide information relating to the importance of each amino acid position for the stability of the antibody-antigen complex. For example, if a position of the CDR retains binding when changed to all 20 amino acids, that position is identified as a position that is unlikely to be required for antigen binding. Conversely, if a position of CDR retains binding in only a small percentage of substitutions, that position is identified as a position that is important to CDR function. Thus, the library scanning mutagenesis methods generate information regarding positions in the CDRs that can be changed to many different amino acids (including all 20 amino acids), and positions in the CDRs which cannot be changed or which can only be changed to a few amino acids.

Candidates with improved affinity may be combined in a second library, which includes the improved amino acid, the original amino acid at that position, and may further include additional substitutions at that position, depending on the complexity of the library that is desired, or permitted using the desired screening or selection method. In addition, if desired, adjacent amino acid position can be randomized to at least two or more amino acids. Randomization of adjacent amino acids may permit additional conformational flexibility in the mutant CDR, which may in turn, permit or facilitate the introduction of a larger number of improving mutations. The library may also comprise substitution at positions that did not show improved affinity in the first round of screening.

The second library is screened or selected for library members with improved and/or altered binding affinity using any method known in the art, including screening using Biacore™ surface plasmon resonance analysis, and selection using any method known in the art for selection, including phage display, yeast display, and ribosome display.

The invention also encompasses fusion proteins comprising one or more fragments or regions from the antibodies of this invention. In one embodiment, a fusion polypeptide is provided that comprises at least 10 contiguous amino acids of the variable light chain region shown in SEQ ID NOs: 1, 3, 6, 7, 8, 10, and 12 and/or at least 10 amino acids of the variable heavy chain region shown in SEQ ID NOs: 2, 4, 5, 9, 11, and 13. In other embodiments, a fusion polypeptide is provided that comprises at least about 10, at least about 15, at least about 20, at least about 25, or at least about 30 contiguous amino acids of the variable light chain region and/or at least about 10, at least about 15, at least about 20, at least about 25, or at least about 30 contiguous amino acids of the variable heavy chain region. In another embodiment, the fusion polypeptide comprises a light chain variable region and/or a heavy chain variable region, as shown in any of the sequence pairs selected from among SEQ ID NOs: 1 and 2, 3 and 4, 3 and 5, 6 and 5, 7 and 5, 8 and 9, 10 and 11, and 12 and 13. In another embodiment, the fusion polypeptide comprises one or more CDR(s). In still other embodiments, the fusion polypeptide comprises CDR H3 (VH CDR3) and/or CDR L3 (VL CDR3). For purposes of this invention, a fusion protein contains one or more antibodies and another amino acid sequence to which it is not attached in the native molecule, for example, a heterologous sequence or a homologous sequence from another region. Exemplary heterologous sequences include, but are not limited to a "tag" such as a FLAG tag or a 6H is tag. Tags are well known in the art.

A fusion polypeptide can be created by methods known in the art, for example, synthetically or recombinantly. Typically, the fusion proteins of this invention are made by preparing an expressing a polynucleotide encoding them using recombinant methods described herein, although they may also be prepared by other means known in the art, including, for example, chemical synthesis.

This invention also provides compositions comprising antibodies conjugated (for example, linked) to an agent that facilitate coupling to a solid support (such as biotin or avidin). For simplicity, reference will be made generally to antibodies with the understanding that these methods apply to any of the Trop-2 antibody embodiments described herein. Conjugation generally refers to linking these components as described herein. The linking (which is generally fixing these components in proximate association at least for administration) can be achieved in any number of ways. For example, a direct reaction between an agent and an antibody is possible when each possesses a substituent capable of reacting with the other. For example, a nucleophilic group, such as an amino or sulfhydryl group, on one may be capable of reacting with a carbonyl-containing group, such as an anhydride or an acid halide, or with an alkyl group containing a good leaving group (e.g., a halide) on the other.

The invention also provides isolated polynucleotides encoding the antibodies of the invention, and vectors and host cells comprising the polynucleotide.

Accordingly, the invention provides polynucleotides (or compositions, including pharmaceutical compositions), comprising polynucleotides encoding any of the following: the m7E6, h7E6, h7E6_SVG, h7E6_SVG1, h7E6_SVG2, h7E6_SVG3, h7E6_SVG4, h7E6_SVG5, h7E6_SVG6, h7E6_SVG7, h7E6_SVG8, h7E6_SVG9, h7E6_SVG10, h7E6_SVG11, h7E6_SVG12, h7E6_SVG13, h7E6_SVG14, h7E6_SVG15, h7E6_SVG16, h7E6_SVG17, h7E6_SVG18, h7E6_SVG19, h7E6_SVG20, h7E6_SVG21, h7E6_SVG22, h7E6_SVG23, h7E6_SVG24, h7E6_SVG25, h7E6_SVG26, h7E6_SVG27, h7E6_SVG28, h7E6_SVG29, h7E6_SVG30, h7E6_SVG31, h7E6_SVG32, h7E6_SVGL, h7E6_SVGL1, h7E6_SVGL2, h7E6_SVGL3, h7E6_SVGL4, h7E6_SVGL5, h7E6_SVGN, m6G11, h6G11, h6G11_FKG_SF, or any fragment or part thereof having the ability to bind Trop-2.

In another aspect, the invention provides polynucleotides encoding any of the antibodies (including antibody fragments) and polypeptides described herein, such as antibodies and polypeptides having impaired effector function. Polynucleotides can be made and expressed by procedures known in the art.

In another aspect, the invention provides compositions (such as a pharmaceutical compositions) comprising any of the polynucleotides of the invention. In some embodiments, the composition comprises an expression vector comprising a polynucleotide encoding any of the antibodies described herein. In still other embodiments, the composition comprises either or both of the polynucleotides shown in SEQ ID NO: 15 and SEQ ID NO: 14 below:

m7E6 heavy chain variable region
(SEQ ID NO: 15)
CAGGTCCAACTGCAGGAATCAGGTCCAGGCCTGGTGAAACCGTCTGA
AACCCTGAGCCTGACATGCACCGTGAGCGGTGGTAGTATTAGCTCTT
ACGGCGTCCATTGGATCCGTCAACCGCCTGGTAAAGGTCTGGAATGG
ATTGGCGTGATCTGGACCGGTGGTAGCACCGACTATAACAGCGCACT
GATGAGCCGCGTGACCATCTCGGTAGACACGTCGAAAAACCAGTTCA
GCCTGAAACTGAGCAGCGTGACCGCCGCGGATACCGCTGTTTATTAC
TGCGCACGCGACGGGATTATGATCGCTACACCATGGATTATTGGGG
CCAGGGTACCCTGGTCACCGTCTCCTCA m7E6 light chain variable region
(SEQ ID NO: 14)
GACATTGTGCTGACACAGTCTCCTGCTTCCTTAGCTGTATCTCTGGG
GCAGAGGGCCACCATCTCATGCAGGGCCAGCAAAAGTGTCAGTACAT
CTGGCTATAGTTATATGCACTGGTACCAACAGAAACCAGGACAGCCA
CCCAAACTCCTCATCTATCTTGCATCCAACCTAGAATCTGGGGTCCC
TGCCAGGTTCAGTGGCAGTGGGTCTGGGACAGACTTCACCCTCAACA
TCCATCCTGTGGAGGAGGAGGATGCTGCAACCTATTACTGTCAGCAC
AGTAGGGAGCTTCCGTACACGTTCGGAGGGGGGACCAAGCTGGAGAT
CAAA In other embodiments, the composition comprises either or both of the polynucleotides shown in SEQ ID NO: 17 and SEQ ID NO: 16 below:

h7E6 heavy chain variable region
(SEQ ID NO: 17)
CAGGTCCAACTGCAGGAATCAGGTCCAGGCCTGGTGAAACCGTCTGA
AACCCTGAGCCTGACATGCACCGTGAGCGGTGGTAGTATTAGCTCTT
ACGGCGTCCATTGGATCCGTCAACCGCCTGGTAAAGGTCTGGAATGG
ATTGGCGTGATCTGGACCGGTGGTAGCACCGACTATAACAGCGCACT
GATGAGCCGCGTGACCATCTCGGTAGACACGTCGAAAAACCAGTTCA
GCCTGAAACTGAGCAGCGTGACCGCCGCGGATACCGCTGTTTATTAC
TGCGCACGCGACGGGATTATGATCGCTACACCATGGATTATTGGGG
CCAGGGTACCCTGGTCACCGTCTCCTCA h7E6 light chain variable region
(SEQ ID NO: 16)
GATATCGTAATGACCCAATCTCCGGATTCGCTGGCGGTATCACTGGG
CGAACGTGCCACGATTAACTGCCGTGCAAGCAAATCAGTGTCGACCT
CCGGCTACAGCTATATGCACTGGTATCAACAGAAACCGGGCCAGCCG
CCGAAACTGCTGATCTATCTGGCTAGCAACCTGGAGAGCGGTGTGCC
TGATCGCTTTAGTGGCTCCGGTAGCGGTACCGATTTCACGCTGACCA
TCAGCTCCCTGCAGGCAGAAGACGTGGCCGTGTATTATTGTCAGCAC
AGCCGTGAGCTGCCGTATACTTTTGGCCAGGGGACAAAACTGGAAAT
CAAA In still other embodiments, the composition comprises either or both of the polynucleotides shown in SEQ ID NO: 18 and SEQ ID NO: 16 below:

h7E6_SVG heavy chain variable region
(SEQ ID NO: 18)
CAGGTCCAACTGCAGGAATCAGGTCCAGGCCTGGTGAAACCGTCTGA
AACCCTGAGCCTGACATGCACCGTGAGCGGTGGTAGTATTAGCTCTT
ACGCGTCCATTGGATCCGTCAACCGCCTGGTAAAGGTCTGGAATGGA
TTGGCGTGATCTGGACCAGTGGTGTGACCGACTATAACAGCGCACTG
ATGGGCCGCGTGACCATCTCGGTAGACACGTCGAAAAACCAGTTCAG
CCTGAAACTGAGCAGCGTGACCGCCGCGGATACCGCTGTTTATTACT
GCGCACGCGACGGGATTATGATCGCTACACCATGGATTATTGGGGC
CAGGGTACCCTGGTCACCGTCTCCTCA h7E6_SVG light chain variable region
(SEQ ID NO: 16)
GATATCGTAATGACCCAATCTCCGGATTCGCTGGCGGTATCACTGGG
CGAACGTGCCACGATTAACTGCCGTGCAAGCAAATCAGTGTCGACCT
CCGGCTACAGCTATATGCACTGGTATCAACAGAAACCGGGCCAGCCG
CCGAAACTGCTGATCTATCTGGCTAGCAACCTGGAGAGCGGTGTGCC
TGATCGCTTTAGTGGCTCCGGTAGCGGTACCGATTTCACGCTGACCA
TCAGCTCCCTGCAGGCAGAAGACGTGGCCGTGTATTATTGTCAGCAC
AGCCGTGAGCTGCCGTATACTTTTGGCCAGGGGACAAAACTGGAAAT
CAAA In other embodiments, the composition comprises either or both of the polynucleotides shown in SEQ ID NO: 18 and SEQ ID NO: 19 below:

h7E6_SVGL heavy chain variable region
(SEQ ID NO: 18)
CAGGTCCAACTGCAGGAATCAGGTCCAGGCCTGGTGAAACCGTCTGA
AACCCTGAGCCTGACATGCACCGTGAGCGGTGGTAGTATTAGCTCTT
ACGCGTCCATTGGATCCGTCAACCGCCTGGTAAAGGTCTGGAATGGA
TTGGCGTGATCTGGACCAGTGGTGTGACCGACTATAACAGCGCACTG
ATGGGCCGCGTGACCATCTCGGTAGACACGTCGAAAAACCAGTTCAG
CCTGAAACTGAGCAGCGTGACCGCCGCGGATACCGCTGTTTATTACT
GCGCACGCGACGGGGATTATGATCGCTACACCATGGATTATTGGGGC
CAGGGTACCCTGGTCACCGTCTCCTCA h7E6_SVGL light chain variable region
(SEQ ID NO: 19)
GATATCGTAATGACCCAATCTCCGGATTCGCTGGCGGTATCACTGGG
CGAACGTGCCACGATTAACTGCCGTGCAAGCAAATCAGTGTCGACCT
CCTTGTACAGCTATATGCACTGGTATCAACAGAAACCGGGCCAGCCG
CCGAAACTGCTGATCTATCTGGCTAGCAACCTGGAGAGCGGTGTGCC
TGATCGCTTTAGTGGCTCCGGTAGCGGTACCGATTTCACGCTGACCA
TCAGCTCCCTGCAGGCAGAAGACGTGGCCGTGTATTATTGTCAGCAC
AGCCGTGAGCTGCCGTATACTTTTGGCCAGGGGACAAAACTGGAAAT
CAAA(SEQ ID NO: 19).

In still other embodiments, the composition comprises either or both of the polynucleotides shown in SEQ ID NO: 18 and SEQ ID NO: 20 below:

h7E6_SVGN heavy chain variable region
(SEQ ID NO: 18)
CAGGTCCAACTGCAGGAATCAGGTCCAGGCCTGGTGAAACCGTCTGA
AACCCTGAGCCTGACATGCACCGTGAGCGGTGGTAGTATTAGCTCTT
ACGCGTCCATTGGATCCGTCAACCGCCTGGTAAAGGTCTGGAATGGA
TTGGCGTGATCTGGACCAGTGGTGTGACCGACTATAACAGCGCACTG
ATGGGCCGCGTGACCATCTCGGTAGACACGTCGAAAAACCAGTTCAG
CCTGAAACTGAGCAGCGTGACCGCCGCGGATACCGCTGTTTATTACT
GCGCACGCGACGGGGATTATGATCGCTACACCATGGATTATTGGGGC
CAGGGTACCCTGGTCACCGTCTCCTCA h7E6_SVGN light chain variable region
(SEQ ID NO: 20)
GATATCGTAATGACCCAATCTCCGGATTCGCTGGCGGTATCACTGGG
CGAACGTGCCACGATTAACTGCCGTGCAAGCAAATCAGTGTCGACCT
CCAATTACAGCTATATGCACTGGTATCAACAGAAACCGGGCCAGCCG
CCGAAACTGCTGATCTATCTGGCTAGCAACCTGGAGAGCGGTGTGCC
TGATCGCTTTAGTGGCTCCGGTAGCGGTACCGATTTCACGCTGACCA
TCAGCTCCCTGCAGGCAGAAGACGTGGCCGTGTATTATTGTCAGCAC
AGCCGTGAGCTGCCGTATACTTTTGGCCAGGGGACAAAACTGGAAAT
CAAA In other embodiments, the composition comprises either or both of the polynucleotides shown in SEQ ID NO: 25 and SEQ ID NO: 20 below:

h6G11_FKG_SF heavy chain variable region
(SEQ ID NO: 25)
CAGGTGCAGTTGGTTCAGAGCGGCGCGGAAGTCAAGAAACCCGGCGC
CTCCGTGAAAGTGAGCTGCAAAGCGAGCGGCTACACCTTCACCAGTT
ATTGGATTAACTGGGTGCGCCAGGCCCCAGGCCAGGGCTGGAGTGG
ATGGGAAACATCTTCCCATCTGACTCTTACAGCAACTATAATAAGAA
ATTTAAGGATCGCGTAACAATGACCCGTGACACCAGCACCAGCACTG
TTTACATGGAGCTGAGTTCTCTGCGTTCTGAAGATACCGCCGTGTAC
TACTGCGCACGCGGTTCCGGGTTCGATTACTGGGGCCAGGGGACCCT
GGTCACCGTCTCCTCA h6G11_FKG_SF light chain variable region
(SEQ ID NO: 26)
GAGATCGTGCTGACCCAAAGTCCAGCCACCCTTTCCCTGTCTCCAGG
CGAACGCGCAACCCTGAGCTGCCGCGCTTCTCAGACCATTGGTACCT
CCATTCATTGGTATCAGCAGAAGCCCGGCCAAGCCCCGCGTCTGCTG
ATCTATTACGCCTCAGAAAGTATTTCAGGCATCCCCGCTCGCTTCTC
CGGCTCCGGCAGCGGAACCGACTTCACACTTACAATCTCTAGTTTGG
AGCCAGAAGACTTCGCCGTTTACTACTGTTCGCAGTCTTTTAGCTGG
CCATTTACCTTTGGCCAGGGCACGAAGCTGGAAATCAAG In other embodiments, the composition comprises either or both of the polynucleotides shown in SEQ ID NO: 22 and SEQ ID NO: 21 below:

m6G11 heavy chain variable region
(SEQ ID NO: 22)
CAGGTCCAACTGCAGCAGCCTGGGGCTGAGCTGGTGAGGCCTGGGGCT
TCAGTGAAGCTGTCCTGCAAGGCTTCTGGCTACACCTTCACCAGCTAC
TGGATAAACTGGGTGAAGCAGAGGCCTGGACATGGCCTTGAGTGGATC
GGAAATATTTATCCTTCTGATAGTTATTCTAACTACAATCAAAAGTTC
AAGGACAAGGCCACATTGACTGTAGACAAATCCTCCAGCACAGCCTAC
ATGCAGGTCAGCAGCCCGACATCTGAGGACTCTGCGGTCTATTACTGT
ACGTACGGTAGTAGCTTTGACTACTGGGGCCAAGGCACCACGGTCACC
GTCTCCTCA m6G11 light chain variable region
(SEQ ID NO: 21)
GACATCTTGCTGACTCAGTCTCCAGCCATCCTGTCTGTGAGTCCAGGA
GAAAGAGTCAGTTTCTCCTGCAGGGCCAGTCAGACCATTGGCACAAGC
ATACACTGGTATCAGCAAAGAACAAATGGTTCTCCAAGGCTTCTCATA
AAGTATGCTTCTGAGTCTATCTCTGGGATCCCTTCCAGGTTTAGTGGC
AGTGGATCAGGGACAGATTTTACTCTTAGCATCAACAGTGTGGAGTCT
GAAGATATTGCAGATTATTACTGTCAACAAAGTAATAGCTGGCCATTC
ACGTTCGGCTCGGGGACCAAGCTGGAAATAAAA In other embodiments, the composition comprises either or both of the polynucleotides shown in SEQ ID NO: 24 and SEQ ID NO: 23 below:

h6G11 heavy chain variable region
(SEQ ID NO: 24)
CAGGTGCAGTTGGTTCAGAGCGGCGCGGAAGTCAAGAAACCCGGCGCC
TCCGTGAAAGTGAGCTGCAAAGCGAGCGGCTACACCTTCACCAGTTAT
TGGATTAACTGGGTGCGCCAGGCCCCAGGCCAGGGGCTGGAGTGGATG
GGAAACATCTACCCCATCTGACTCTTACAGCAACTATAATCAGAAATTT
AAGGATCGCGTAACAATGACCCGTGACACCAGCACCAGCACTGTTTAC
ATGGAGCTGAGTTCTCTGCGTTCTGAAGATACCGCCGTGTACTACTGC
GCACGCGGTTCCAGTTTCGATTACTGGGGCCAGGGGACCCTGGTCACC
GTCTCCTCA h6G11 light chain variable region
(SEQ ID NO: 23)
GAGATCGTGCTGACCCAAAGTCCAGCCACCCTTTCCCTGTCTCCAGGC
GAACGCGCAACCCTGAGCTGCCGCGCTTCTCAGACCATTGGTACCTCC
ATTCATTGGTATCAGCAGAAGCCCGGCCAAGCCCCGCGTCTGCTGATC
TATTACGCCTCAGAAAGTATTTCAGGCATCCCCGCTCGCTTCTCCGGC
TCCGGCAGCGGAACCGACTTCACACTTACAATCTCTAGTTTGGAGCCA
GAAGACTTCGCCGTTTACTACTGTCAGCAGTCTAACAGCTGGCCATTT
ACCTTTGGCCAGGGCACGAAGCTGGAAATCAAG Expression vectors, and administration of polynucleotide compositions are further described herein.

In another aspect, the invention provides a method of making any of the polynucleotides described herein.

Polynucleotides complementary to any such sequences are also encompassed by the present invention. Polynucleotides may be single-stranded (coding or antisense) or double-stranded, and may be DNA (genomic, cDNA or synthetic) or RNA molecules. RNA molecules include HnRNA molecules, which contain introns and correspond to a DNA molecule in a one-to-one manner, and mRNA molecules, which do not contain introns. Additional coding or non-coding sequences may, but need not, be present within a polynucleotide of the present invention, and a polynucleotide may, but need not, be linked to other molecules and/or support materials.

Polynucleotides may comprise a native sequence (i.e., an endogenous sequence that encodes an antibody or a portion thereof) or may comprise a variant of such a sequence. Polynucleotide variants contain one or more substitutions, additions, deletions and/or insertions such that the immunoreactivity of the encoded polypeptide is not diminished, relative to a native immunoreactive molecule. The effect on the immunoreactivity of the encoded polypeptide may generally be assessed as described herein. Variants preferably exhibit at least about 70% identity, more preferably, at least about 80% identity, yet more preferably, at least about 90% identity, and most preferably, at least about 95% identity to a polynucleotide sequence that encodes a native antibody or a portion thereof.

Two polynucleotide or polypeptide sequences are said to be "identical" if the sequence of nucleotides or amino acids in the two sequences is the same when aligned for maximum correspondence as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, or 40 to about 50, in which a sequence may be compared to a reference sequence of the same number of contiguous positions after the two sequences are optimally aligned.

Optimal alignment of sequences for comparison may be conducted using the Megalign program in the Lasergene suite of bioinformatics software (DNASTAR, Inc., Madison, Wis.), using default parameters. This program embodies several alignment schemes described in the following references: Dayhoff, M. O., 1978, A model of evolutionary change in proteins—Matrices for detecting distant relationships. In Dayhoff, M. O. (ed.) Atlas of Protein Sequence and Structure, National Biomedical Research Foundation, Washington DC Vol. 5, Suppl. 3, pp. 345-358; Hein J., 1990, Unified Approach to Alignment and Phylogenes pp. 626-645 Methods in Enzymology vol. 183, Academic Press, Inc., San Diego, Calif.; Higgins, D. G. and Sharp, P. M., 1989, CABIOS 5:151-153; Myers, E. W. and Muller W., 1988, CABIOS 4:11-17; Robinson, E. D., 1971, Comb. Theor. 11:105; Santou, N., Nes, M., 1987, Mol. Biol. Evol. 4:406-425; Sneath, P. H. A. and Sokal, R. R., 1973, Numerical Taxonomy the Principles and Practice of Numerical Taxonomy, Freeman Press, San Francisco, Calif.; Wilbur, W. J. and Lipman, D. J., 1983, Proc. Natl. Acad. Sci. USA 80:726-730.

Preferably, the "percentage of sequence identity" is determined by comparing two optimally aligned sequences over a window of comparison of at least 20 positions, wherein the portion of the polynucleotide or polypeptide sequence in the comparison window may comprise additions or deletions (i.e., gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical nucleic acid bases or amino acid residue occurs in both sequences to yield the number of matched positions, dividing the number of matched positions by the total number of positions in the reference sequence (i.e. the window size) and multiplying the results by 100 to yield the percentage of sequence identity.

Variants may also, or alternatively, be substantially homologous to a native gene, or a portion or complement thereof. Such polynucleotide variants are capable of hybridizing under moderately stringent conditions to a naturally occurring DNA sequence encoding a native antibody (or a complementary sequence).

Suitable "moderately stringent conditions" include prewashing in a solution of 5×SSC, 0.5% SDS, 1.0 mM EDTA (pH 8.0); hybridizing at 50° C.-65° C., 5×SSC, overnight; followed by washing twice at 65° C. for 20 minutes with each of 2×, 0.5× and 0.2×SSC containing 0.1% SDS.

As used herein, "highly stringent conditions" or "high stringency conditions" are those that: (1) employ low ionic strength and high temperature for washing, for example 0.015 M sodium chloride/0.0015 M sodium citrate/0.1% sodium dodecyl sulfate at 50° C.; (2) employ during hybridization a denaturing agent, such as formamide, for example, 50% (v/v) formamide with 0.1% bovine serum albumin/0.1% Ficoll/ 0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 µg/ml), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C. The skilled artisan will recognize how to adjust the temperature, ionic strength, etc. as necessary to accommodate factors such as probe length and the like.

It will be appreciated by those of ordinary skill in the art that, as a result of the degeneracy of the genetic code, there are many nucleotide sequences that encode a polypeptide as described herein. Some of these polynucleotides bear minimal homology to the nucleotide sequence of any native gene. Nonetheless, polynucleotides that vary due to differences in codon usage are specifically contemplated by the present invention. Further, alleles of the genes comprising the polynucleotide sequences provided herein are within the scope of the present invention. Alleles are endogenous genes that are altered as a result of one or more mutations, such as deletions, additions and/or substitutions of nucleotides. The resulting mRNA and protein may, but need not, have an altered structure or function. Alleles may be identified using standard techniques (such as hybridization, amplification and/or database sequence comparison).

The polynucleotides of this invention can be obtained using chemical synthesis, recombinant methods, or PCR. Methods of chemical polynucleotide synthesis are well known in the art and need not be described in detail herein. One of skill in the art can use the sequences provided herein and a commercial DNA synthesizer to produce a desired DNA sequence.

For preparing polynucleotides using recombinant methods, a polynucleotide comprising a desired sequence can be inserted into a suitable vector, and the vector in turn can be introduced into a suitable host cell for replication and amplification, as further discussed herein. Polynucleotides may be inserted into host cells by any means known in the art. Cells are transformed by introducing an exogenous polynucleotide by direct uptake, endocytosis, transfection, F-mating or electroporation. Once introduced, the exogenous polynucleotide can be maintained within the cell as a non-integrated vector (such as a plasmid) or integrated into the host cell genome. The polynucleotide so amplified can be isolated from the host cell by methods well known within the art. See, e.g., Sambrook et al., 1989.

Alternatively, PCR allows reproduction of DNA sequences. PCR technology is well known in the art and is described in U.S. Pat. Nos. 4,683,195, 4,800,159, 4,754,065 and 4,683,202, as well as PCR: The Polymerase Chain Reaction, Mullis et al. eds., Birkauswer Press, Boston, 1994.

RNA can be obtained by using the isolated DNA in an appropriate vector and inserting it into a suitable host cell. When the cell replicates and the DNA is transcribed into RNA, the RNA can then be isolated using methods well known to those of skill in the art, as set forth in Sambrook et al., 1989, supra, for example.

Suitable cloning vectors may be constructed according to standard techniques, or may be selected from a large number of cloning vectors available in the art. While the cloning vector selected may vary according to the host cell intended to be used, useful cloning vectors will generally have the ability to self-replicate, may possess a single target for a particular restriction endonuclease, and/or may carry genes for a marker that can be used in selecting clones containing the vector. Suitable examples include plasmids and bacterial viruses, e.g., pUC18, pUC19, Bluescript (e.g., pBS SK+) and its derivatives, mp18, mp19, pBR322, pMB9, ColE1, pCR1, RP4, phage DNAs, and shuttle vectors such as pSA3 and pAT28. These and many other cloning vectors are available from commercial vendors such as BioRad, Strategene, and Invitrogen.

Expression vectors generally are replicable polynucleotide constructs that contain a polynucleotide according to the invention. It is implied that an expression vector must be replicable in the host cells either as episomes or as an integral part of the chromosomal DNA. Suitable expression vectors include but are not limited to plasmids, viral vectors, including adenoviruses, adeno-associated viruses, retroviruses, cosmids, and expression vector(s) disclosed in PCT Publication No. WO 87/04462. Vector components may generally include, but are not limited to, one or more of the following: a signal sequence; an origin of replication; one or more marker genes; suitable transcriptional controlling elements (such as promoters, enhancers and terminator). For expression (i.e., translation), one or more translational controlling elements are also usually required, such as ribosome binding sites, translation initiation sites, and stop codons.

The vectors containing the polynucleotides of interest can be introduced into the host cell by any of a number of appropriate means, including electroporation, transfection employing calcium chloride, rubidium chloride, calcium phosphate, DEAE-dextran, or other substances; microprojectile bombardment; lipofection; and infection (e.g., where the vector is an infectious agent such as vaccinia virus). The choice of introducing vectors or polynucleotides will often depend on features of the host cell.

The invention also provides host cells comprising any of the polynucleotides described herein. Any host cells capable of over-expressing heterologous DNAs can be used for the purpose of isolating the genes encoding the antibody, polypeptide or protein of interest. Non-limiting examples of mammalian host cells include but not limited to COS, HeLa, and CHO cells. See also PCT Publication No. WO 87/04462. Suitable non-mammalian host cells include prokaryotes (such as *E. coli* or *B. subtillis*) and yeast (such as *S. cerevisae, S. pombe*; or *K. lactis*). Preferably, the host cells express the cDNAs at a level of about 5 fold higher, more preferably, 10 fold higher, even more preferably, 20 fold higher than that of the corresponding endogenous antibody or protein of interest, if present, in the host cells. Screening the host cells for a specific binding to Trop-2 or an Trop-2 domain (e.g., domains 1-4) is effected by an immunoassay or FACS. A cell overexpressing the antibody or protein of interest can be identified.

Trop-2 Antibody Conjugates

The present invention also provides a conjugate (or immunoconjugate) of the Trop-2 antibody as described herein, or of the antigen binding fragment thereof, wherein the antibody or the antigen binding fragment is conjugated to an agent (e.g., a cytotoxic agent) for targeted immunotherapy (e.g., antibody-drug conjugates) either directly or indirectly via a linker. For example, a cytotoxic agent can be linked or conjugated to the Trop-2 antibody or the antigen binding fragment thereof as described herein for targeted local delivery of the cytotoxic agent moiety to tumors (e.g., Trop-2 expressing tumor).

Methods for conjugating cytotoxic agent or other therapeutic agents to antibodies have been described in various publications. For example, chemical modification can be made in the antibodies either through lysine side chain amines or through cysteine sulfhydryl groups activated by reducing interchain disulfide bonds for the conjugation reaction to occur. See, e.g., Tanaka et al., FEBS Letters 579:2092-2096, 2005, and Gentle et al., Bioconjugate Chem. 15:658-663, 2004. Reactive cysteine residues engineered at specific sites of antibodies for specific drug conjugation with defined stoichiometry have also been described. See, e.g., Junutula et al., Nature Biotechnology, 26:925-932, 2008. Conjugation using an acyl donor glutamine-containing tag or an endogenous glutamine made reactive (i.e., the ability to form a covalent bond as an acyl donor) by polypeptide engineering in the presence of transglutaminase and an amine (e.g., a cytotoxic agent comprising or attached to a reactive amine) is also described in International Patent Application Serial No. PCT/IB2011/054899 (WO2012/059882).

In some embodiments, the Trop-2 antibody or the conjugate as described herein comprises an acyl donor glutamine-containing tag engineered at a specific site of the antibody (e.g., a carboxyl terminus, an amino terminus, or at another site in the Trop-2 antibody). In some embodiments, the tag comprises an amino acid glutamine (Q) or an amino acid sequence GGLLQGG (SEQ ID NO:78), LLQGA (SEQ ID NO:79), GGLLQGA (SEQ ID NO:81), LLQ, LLQGPGK (SEQ ID NO: 90), LLQGPG (SEQ ID NO: 91), LLQGPA (SEQ ID NO: 92), LLQGP (SEQ ID NO: 93), LLQP (SEQ ID NO: 94), LLQPGK (SEQ ID NO: 95), LLQGAPGK (SEQ ID NO: 96), LLQGAPG (SEQ ID NO: 97), LLQGAP (SEQ ID NO: 98), LLQX$_1$X$_2$X$_3$X$_4$X$_5$, wherein X$_1$ is G or P, wherein X$_2$ is A, G, P, or absent, wherein X$_3$ is A, G, K, P, or absent, wherein X$_4$ is K, G or absent, and wherein X$_5$ is K or absent (SEQ ID NO: 88), or LLQX$_1$X$_2$X$_3$X$_4$X$_5$, wherein X$_1$ is any naturally occurring amino acid and wherein X$_2$, X$_3$, X$_4$, and X$_5$ are any naturally occurring amino acids or absent (SEQ ID NO: 89). In some embodiments, the Trop-2 antibody or the conjugate as described herein comprises an acyl donor glutamine-containing tag engineered at a specific site of the antibody, wherein the tag comprises an amino acid sequence GGLLQGG (SEQ ID NO:78) engineered at the light chain carboxyl terminus of the Trop-2 antibody. In some embodiments, the Trop-2 antibody or the conjugate as described herein comprises an acyl donor glutamine-containing tag engineered at a specific site of the antibody, wherein the tag comprises an amino acid sequence GGLLQGA (SEQ ID NO:81) engineered at the light chain carboxyl terminus of the Trop-2 antibody. In other embodiments, the Trop-2 antibody or the conjugate as described herein comprises an acyl donor glutamine-containing tag engineered at a specific site of the antibody, wherein the tag comprises an amino acid sequence LLQGA (SEQ ID NO:79) engineered at the heavy chain carboxyl terminus of the Trop-2 antibody and wherein the lysine residue at the heavy chain carboxyl terminus is deleted. In other embodiments, the Trop-2 antibody or the conjugate as described herein comprises an acyl donor glutamine-containing tag engineered at a specific site of the antibody, wherein the tag comprises an amino acid sequence LLQ engineered at the heavy chain carboxyl terminus of the Trop-2 antibody and wherein the lysine residue at the heavy chain carboxyl terminus is deleted. In some embodiments, the Trop-2 antibody or the conjugate as described herein comprises an amino acid substitution from asparagine (N) to glutamine (Q) at position 297 of the Trop-2 antibody.

Also provided is an isolated antibody comprising an acyl donor glutamine-containing tag and an amino acid modification at position 222, 340, or 370 of the antibody (Kabat numbering scheme), wherein the modification is an amino acid deletion, insertion, substitution, mutation, or any combination thereof. Accordingly, in some embodiments, provided is the Trop-2 antibody or the conjugate as described herein comprising the acyl donor glutamine-containing tag (e.g., Q, GGLLQGG (SEQ ID NO:78), LLQGA (SEQ ID NO:79), GGLLQGA (SEQ ID NO:81), LLQ, LLQGPGK (SEQ ID NO: 90), LLQGPG (SEQ ID NO: 91), LLQGPA (SEQ ID NO: 92), LLQGP (SEQ ID NO: 93), LLQP (SEQ ID NO: 94), LLQPGK (SEQ ID NO: 95), LLQGAPGK (SEQ ID NO: 96), LLQPGK (SEQ ID NO: 97), LLQGAP (SEQ ID NO: 98), LLQX$_1$X$_2$X$_3$X$_4$X$_5$, wherein X$_1$ is G or P, wherein X$_2$ is A, G, P, or absent, wherein X$_3$ is A, G, K, P, or absent, wherein X$_4$ is K, G or absent, and wherein X$_5$ is K or absent (SEQ ID NO: 88), or LLQX$_1$X$_2$X$_3$X$_4$X$_5$, wherein X$_1$ is any naturally occurring amino acid and wherein X$_2$, X$_3$, X$_4$, and X$_5$ are any naturally occurring amino acids or absent (SEQ ID NO: 89) conjugated at a specific site (e.g., at a carboxyl terminus of the heavy or light chain or at another site) of the Trop-2 antibody and an amino acid modification at position 222, 340, or 370 of the antibody (Kabat numbering scheme). In some embodiments, the amino acid modification is a substitution from lysine to arginine (e.g., K222R, K340R, or K370R). In some embodiments, the Trop-2 antibody or the conjugate as described herein comprises an acyl donor glutamine-containing tag comprising the sequence GGLLQGG (SEQ ID NO:78) engineered at the C-terminus of the Trop-2 antibody light chain and an amino acid substitution from lysine to arginine at position 222 of the antibody (Kabat numbering scheme). In some embodiments, the Trop-2 antibody or the conjugate as described herein comprises an acyl donor glutamine-containing tag comprising the sequence GGLLQGA (SEQ ID NO:81) engineered at the C-terminus of the Trop-2 antibody light chain and an amino acid substitution from lysine to arginine at position 222 of the antibody (Kabat numbering scheme). In some embodiments, the Trop-2 antibody or the conjugate as described herein comprises an acyl donor glutamine-containing tag comprising the sequence LLQGA (SEQ ID NO:79) engineered at the C-terminus of the Trop-2 antibody heavy chain and an amino acid substitution from lysine to arginine at position 222 of the antibody (Kabat numbering scheme), wherein the lysine residue at the heavy chain carboxyl terminus is deleted. In some embodiments, the Trop-2 antibody or the conjugate as described herein comprises an acyl donor glutamine-containing tag comprising the sequence LLQ engineered at the C-terminus of the Trop-2 antibody heavy chain and an amino acid substitution from lysine to arginine at position 222 of the antibody (Kabat numbering scheme), wherein the lysine residue at the heavy chain carboxyl terminus is deleted. In some embodiments, the Trop-2 antibody or the conjugate as described herein comprises an acyl donor glutamine-containing tag comprising a glutamine engineered at position 297 of the Trop-2 antibody and an amino acid substitution from lysine to arginine at position 222 of the antibody (Kabat numbering scheme).

The agents that can be conjugated to the Trop-2 antibodies or the antigen binding fragments of the present invention include, but are not limited to, cytotoxic agents, immunomodulating agents, imaging agents, therapeutic proteins, biopolymers, or oligonucleotides.

Examples of a cytotoxic agent include, but are not limited to, an anthracycline, an auristatin, a dolastatin, CC-1065, a duocarmycin, an enediyne, a geldanamycin, a maytansine, a puromycin, a taxane, a vinca alkaloid, SN-38, tubulysin, hemiasterlin, and stereoisomers, isosteres, analogs or derivatives thereof.

The anthracyclines are derived from bacteria *Streptomyces* and have been used to treat a wide range of cancers, such as leukemias, lymphomas, breast, uterine, ovarian, and lung cancers. Exemplary anthracyclines include, but are not limited to, daunorubicin, doxorubicin (i.e., adriamycin), epirubicin, idarubicin, valrubicin, and mitoxantrone.

Dolastatins and their peptidic analogs and derivatives, auristatins, are highly potent antimitotic agents that have been shown to have anticancer and antifungal activity. See, e.g., U.S. Pat. No. 5,663,149 and Pettit et al., *Antimicrob. Agents Chemother.* 42:2961-2965, 1998. Exemplary dolastatins and auristatins include, but are not limited to, dolastatin 10, auristatin E, auristatin EB (AEB), auristatin EFP (AEFP), MMAD (Monomethyl Auristatin D or monomethyl dolastatin 10), MMAF (Monomethyl Auristatin F or N-methylvaline-valine-dolaisoleuine-dolaproine-phenylalanine), MMAE (Monomethyl Auristatin E or N-methylvaline-valine-dolaisoleuine-dolaproine-norephedrine), 5-benzoylvaleric acid-AE ester (AEVB), and other novel auristatins (such as the ones described in U.S. Application No. 61/561,255 and 61/676,423). In some embodiments, the auristatin is 0101 (2-methylalanyl-N-[(3R,4S,5S)-3-methoxy-1-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-5-methyl-1-oxoheptan-4-yl]-N-methyl-L-valinamide) having the following structure:

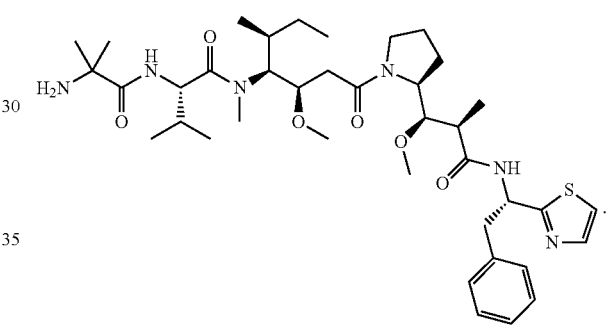

Duocarmycin and CC-1065 are DNA alkylating agents with cytotoxic potency. See Boger and Johnson, *PNAS* 92:3642-3649, 1995. Exemplary dolastatins and auristatins include, but are not limited to, (+)-docarmycin A and (+)-duocarmycin SA, and (+)-CC-1065.

Enediynes are a class of anti-tumor bacterial products characterized by either nine- and ten-membered rings or the presence of a cyclic system of conjugated triple-double-triple bonds. Exemplary enediynes include, but are not limited to, calicheamicin, esperamicin, and dynemicin.

Geldanamycins are benzoquinone ansamycin antibiotic that bind to Hsp90 (Heat Shock Protein 90) and have been used antitumor drugs. Exemplary geldanamycins include, but are not limited to, 17-AAG (17-N-Allylamino-17-Demethoxygeldanamycin) and 17-DMAG (17-Dimethylaminoethylamino-17-demethoxygeldanamycin).

Maytansines or their derivatives maytansinoids inhibit cell proliferation by inhibiting the microtubules formation during mitosis through inhibition of polymerization of tubulin. See Remillard et al., Science 189:1002-1005, 1975. Exemplary maytansines and maytansinoids include, but are not limited to, mertansine (DM1) and its derivatives as well as ansamitocin.

Taxanes are diterpenes that act as anti-tubulin agents or mitotic inhibitors. Exemplary taxanes include, but are not limited to, paclitaxel (e.g., TAXOL®) and docetaxel (TAXOTERE®).

Vinca alkyloids are also anti-tubulin agents. Exemplary vinca alkyloids include, but are not limited to, vincristine, vinblastine, vindesine, and vinorelbine.

In some embodiments, the agent is an immunomodulating agent. Examples of an immunomodulating agent include, but are not limited to, gancyclovier, etanercept, tacrolimus, sirolimus, voclosporin, cyclosporine, rapamycin, cyclophosphamide, azathioprine, mycophenolgate mofetil, methotrextate, glucocorticoid and its analogs, cytokines, stem cell growth factors, lymphotoxins, tumor necrosis factor (TNF), hematopoietic factors, interleukins (e.g., interleukin-1 (IL-1), IL-2, IL-3, IL-6, IL-10, IL-12, IL-18, and IL-21), colony stimulating factors (e.g., granulocyte-colony stimulating factor (G-CSF) and granulocyte macrophage-colony stimulating factor (GM-CSF)), interferons (e.g., interferons-α, -β and -γ), the stem cell growth factor designated "S 1 factor," erythropoietin and thrombopoietin, or a combination thereof.

In some embodiments, the agent is an imaging agent (e.g., a fluorophore or a PET (Positron Emission Tomography) label, SPECT (Single-Photon Emission Computed Tomography) label, or MRI (Magnetic Resonance Imaging) label.

Examples of fluorophores include, but are not limited to, fluorescein isothiocyanate (FITC) (e.g., 5-FITC), fluorescein amidite (FAM) (e.g., 5-FAM), eosin, carboxyfluorescein, erythrosine, Alexa Fluor® (e.g., Alexa 350, 405, 430, 488, 500, 514, 532, 546, 555, 568, 594, 610, 633, 647, 660, 680, 700, or 750), carboxytetramethylrhodamine (TAMRA) (e.g., 5,-TAMRA), tetramethylrhodamine (TMR), and sulforhodamine (SR) (e.g., SR101).

In some embodiments, therapeutic or diagnostic radioisotopes or other labels (e.g., PET or SPECT labels) can be incorporated in the agent for conjugation to the Trop-2 antibodies or the antigen binding fragments as described herein. Examples of a radioisotope or other labels include, but are not limited to, $^{3}H$, $^{11}C$, $^{13}N$, $^{14}C$, $^{15}N$, $^{15}O$, $^{35}S$, $^{18}F$, $^{32}P$, $^{33}P$, $^{47}Sc$, $^{51}Cr$, $^{57}Co$, $^{58}Co$, $^{59}Fe$, $^{62}Cu$, $^{64}Cu$, $^{67}Cu$, $^{67}Ga$, $^{68}Ga$, $^{75}Se$, $^{76}Br$, $^{77}Br$, $^{86}Y$, $^{89}Zr$, $^{90}Y$, $^{94}Tc$, $^{95}Ru$, $^{97}Ru$, $^{99}Tc$, $^{103}Ru$, $^{105}Rh$, $^{105}Ru$, $^{107}Hg$, $^{109}Pd$, $^{111}Ag$, $^{111}In$, $^{113}In$, $^{121}Te$, $^{122}Te$, $^{123}I$, $^{124}I$, $^{125}I$, $^{125}Te$, $^{126}I$, $^{131}I$, $^{131}In$, $^{133}I$, $^{142}Pr$, $^{143}Pr$, $^{153}Pb$, $^{153}Sm$, $^{161}Tb$, $^{165}Tm$, $^{166}Dy$, $^{166}H$, $^{167}Tm$, $^{168}Tm$, $^{169}Yb$, $^{171}Lu$, $^{186}Re$, $^{188}Re$, $^{189}Re$, $^{197}Pt$, $^{198}Au$, $^{199}Au$, $^{201}Tl$, $^{203}Hg$, $^{211}At$, $^{212}Bi$, $^{212}Pb$, $^{213}Bi$, $^{223}Ra$, $^{224}Ac$, and $^{225}Ac$.

In some embodiments, the agent is a therapeutic protein including, but is not limited to, a toxin, a hormone, an enzyme, and a growth factor.

Examples of a toxin protein (or polypeptide) include, but are not limited to, dipththeria (e.g., diphtheria A chain), *Pseudomonas* exotoxin and endotoxin, ricin (e.g., ricin A chain), abrin (e.g., abrin A chain), modeccin (e.g., modeccin A chain), alpha-sarcin, *Aleurites fordii* proteins, dianthin proteins, ribonuclease (RNase), DNase I, Staphylococcal enterotoxin-A, pokeweed antiviral protein, gelonin, diphtherin toxin, *Phytolaca americana* proteins (PAPI, PAPII, and PAP-S), *momordica charantia* inhibitor, curcin, crotin, sapaonaria officinalis inhibitor, mitogellin, restrictocin, phenomycin, enomycin, tricothecenes, inhibitor cystine knot (ICK) peptides (e.g., ceratotoxins), and conotoxin (e.g., KIIIA or SmIIIa).

In some embodiments, the agent is a biocompatible polymer. The Trop-2 antibodies or the antigen binding fragments as described herein can be conjugated to the biocompatible polymer to increase serum half-life and bioactivity, and/or to extend in vivo half-lives. Examples of biocompatible polymers include water-soluble polymer, such as polyethylene glycol (PEG) or its derivatives thereof and zwitterion-containing biocompatible polymers (e.g., a phosphorylcholine containing polymer).

In some embodiments, the agent is an oligonucleotide, such as anti-sense oligonucleotides.

In another aspect, the invention provides a conjugate of the antibody or the antigen binding fragment as described herein, wherein the conjugate comprises the formula: antibody-(acyl donor glutamine-containing tag)-(linker)-(cytotoxic agent), wherein the acyl donor glutamine-containing tag is engineered at a specific site of the antibody or the antigen binding fragment (e.g., at a carboxyl terminus of the heavy or light chain or at an another site), wherein the tag is conjugated to a linker (e.g., a linker containing one or more reactive amines (e.g., primary amine $NH_2$)), and wherein the linker is conjugated to a cytotoxic agent (e.g., MMAD or other auristatins such as 0101).

Examples of a linker containing one or more reactive amines include, but are not limited to, acetyl-lysine-valine-citrulline-p-aminobenzyloxycarbonyl (AcLys-VC-PABC) or amino PEG6-propionyl. See, e.g. WO2012/059882.

In some embodiments, the acyl donor glutamine-containing tag comprises GGLLQGG (SEQ ID NO:78), LLQGA (SEQ ID NO:79), GGLLQGA (SEQ ID NO:81), LLQ, LLQGPGK (SEQ ID NO: 90), LLQGPG (SEQ ID NO: 91), LLQGPA (SEQ ID NO: 92), LLQGP (SEQ ID NO: 93), LLQP (SEQ ID NO: 94), LLQPGK (SEQ ID NO: 95), LLQ-GAPGK (SEQ ID NO: 96), LLQGAPG (SEQ ID NO: 97), LLQGAP (SEQ ID NO: 98), $LLQX_1X_2X_3X_4X_5$, wherein $X_1$ is G or P, wherein $X_2$ is A, G, P, or absent, wherein $X_3$ is A, G, K, P, or absent, wherein $X_4$ is K, G or absent, and wherein $X_5$ is K or absent (SEQ ID NO: 88), or $LLQX_1X_2X_3X_4X_5$, wherein $X_1$ is any naturally occurring amino acid and wherein $X_2, X_3, X_4,$ and $X_5$ are any naturally occurring amino acids or absent (SEQ ID NO: 89).

In some embodiments, the conjugate is 1) antibody-LLQGA (SEQ ID NO: 79)-AcLys-VC-PABC-0101; 2) antibody-LLQGA (SEQ ID NO: 79)-AcLys-VC-PABC-MMAD; 3) antibody-$LLQX_1X_2X_3X_4X_5$ (SEQ ID NO: 88)-AcLys-VC-PABC-0101; 4) antibody-$LLQX_1X_2X_3X_4X_5$ (SEQ ID NO: 88)-AcLys-VC-PABC-MMAD; 5) antibody-GGLLQGG (SEQ ID NO: 78)-AcLys-VC-PABC-0101; and 6) antibody-GGLLQGG (SEQ ID NO: 78)-AcLys-VC-PABC-MMAD. In some embodiments, the acyl donor glutamine-containing tag comprising, e.g., LLQ, SEQ ID NO: 79, 90, 91, 92, 93, 94, 95, 96, 97, or 98, is engineered at the C-terminus of the heavy chain of the antibody, wherein the lysine residue at the C-terminus is deleted. In other embodiments, the acyl donor glutamine-containing tag (e.g., GGLLQGG (SEQ ID NO: 78)) is engineered at the C-terminus of the light chain of the antibody. Examples of the antibody include, but are not limited to, h7E6_SVG, h7E6_SVG1, h7E6_SVG2, h7E6_SVG3, and h7E6_SVG4, h7E6_SVG5, h7E6_SVG6, h7E6_SVG7, h7E6_SVG8, h7E6_SVG9, h7E6_SVG10, h7E6_SVG11, h7E6_SVG12, h7E6_SVG13, h7E6_SVG14, h7E6_SVG15, h7E6_SVG16, h7E6_SVG17, h7E6_SVG18, h7E6_SVG19, h7E6_SVG20, h7E6_SVG21, h7E6_SVG22, h7E6_SVG23, h7E6_SVG24, h7E6_SVG25, h7E6_SVG26, h7E6_SVG27, h7E6_SVG28, h7E6_SVG29, h7E6_SVG30, h7E6_SVG31, h7E6_SVG32, h7E6_SVGL, h7E6_SVGL1, h7E6_SVGL2, h7E6_SVGL3, h7E6_SVGL4, h7E6_SVGL5, h7E6SVGN, h6G11, or h6G11_FKG_SF.

In one variation, the conjugate further comprises an amino acid substitution from lysine to arginine at position 222. Accordingly, for example, the conjugate is 1) antibody-GGLLQGG (SEQ ID NO: 78)-AcLys-VC-PABC-MMAD and comprises K222R; 2) antibody-GGLLQGG (SEQ ID NO: 78)-AcLys-VC-PABC-0101 and comprises K222R; 3) antibody-LLQGA (SEQ ID NO: 79)-AcLys-VC-PABC-0101 and comprises K222R; 4) antibody-LLQGA (SEQ ID NO: 79)-AcLys-VC-PABC-MMAD and comprises K222R; and 5) antibody-LLQX$_1$X$_2$X$_3$X$_4$X$_5$ (SEQ ID NO: 88)-AcLys-VC-PABC-MMAD and comprises K222R. In some embodiments, the acyl donor glutamine-containing tag comprising, e.g., LLQ, SEQ ID NO: 79, 90, 91, 92, 93, 94, 95, 96, 97, or 98, is engineered at the C-terminus of the heavy chain of the antibody, wherein the lysine residue at the C-terminus is deleted. In other embodiments, the acyl donor glutamine-containing tag (e.g., GGLLQGG (SEQ ID NO: 78)) is engineered at the C-terminus of the light chain of the antibody. Examples of the antibody include, but are not limited to, h7E6_SVG, h7E6_SVG1, h7E6_SVG2, h7E6_SVG3, and h7E6_SVG4, h7E6_SVG5, h7E6_SVG6, h7E6_SVG7, h7E6_SVG8, h7E6_SVG9, h7E6_SVG10, h7E6_SVG11, h7E6_SVG12, h7E6_SVG13, h7E6_SVG14, h7E6_SVG15, h7E6_SVG16, h7E6_SVG17, h7E6_SVG18, h7E6_SVG19, h7E6_SVG20, h7E6_SVG21, h7E6_SVG22, h7E6_SVG23, h7E6_SVG24, h7E6_SVG25, h7E6_SVG26, h7E6_SVG27, h7E6_SVG28, h7E6_SVG29, h7E6_SVG30, h7E6_SVG31, h7E6_SVG32, h7E6_SVGL, h7E6_SVGL1, h7E6_SVGL2, h7E6_SVGL3, h7E6_SVGL4, h7E6_SVGL5, h6G11, or h6G11_FKG_SF.

In another aspect, the invention provides a conjugate of the antibody or the antigen binding fragment as described herein, the conjugate comprises amino acid substitutions at positions N297Q and K222R, a linker comprising amino-PEG6-propionyl, and a cytotoxic agent (e.g., MMAD or other auristatins). For example, the conjugate is h7E6_SVG, h7E6_SVG1, h7E6_SVG2, h7E6_SVG3, h7E6_SVG4, h7E6_SVG5, h7E6_SVG6, h7E6_SVG7, h7E6_SVG8, h7E6_SVG9, h7E6_SVG10, h7E6_SVG11, h7E6_SVG12, h7E6_SVG13, h7E6_SVG14, h7E6_SVG15, h7E6_SVG16, h7E6_SVG17, h7E6_SVG18, h7E6_SVG19, h7E6_SVG20, h7E6_SVG21, h7E6_SVG22, h7E6_SVG23, h7E6_SVG24, h7E6_SVG25, h7E6_SVG26, h7E6_SVG27, h7E6_SVG28, h7E6_SVG29, h7E6_SVG30, h7E6_SVG31, h7E6_SVG32, h7E6_SVGL, h7E6_SVGL1, h7E6_SVGL2, h7E6_SVGL3, h7E6_SVGL4, h7E6_SVGL5, h6G11, or h6G11_FKG_SF conjugating to amino-PEG6-propionyl and MMAD or h7E6_SVG, h7E6_SVG1, h7E6_SVG2, h7E6_SVG3, h7E6_SVG4, h7E6_SVG5, h7E6_SVG6, h7E6_SVG7, h7E6_SVG8, h7E6_SVG9, h7E6_SVG10, h7E6_SVG11, h7E6_SVG12, h7E6_SVG13, h7E6_SVG14, h7E6_SVG15, h7E6_SVG16, h7E6_SVG17, h7E6_SVG18, h7E6_SVG19, h7E6_SVG20, h7E6_SVG21, h7E6_SVG22, h7E6_SVG23, h7E6_SVG24, h7E6_SVG25, h7E6_SVG26, h7E6_SVG27, h7E6_SVG28, h7E6_SVG29, h7E6_SVG30, h7E6_SVG31, h7E6_SVG32, h7E6_SVGL, h7E6_SVGL1, h7E6_SVGL2, h7E6_SVGL3, h7E6_SVGL4, h7E6_SVGL5, h6G11, or h6G11_FKG_SF conjugating to amino-PEG6-propionyl and 0101.

Methods of Using the Trop-2 Antibodies and the Antibody Conjugates Thereof

The antibodies and the antibody conjugates of the present invention are useful in various applications including, but are not limited to, therapeutic treatment methods and diagnostic treatment methods.

In one aspect, the invention provides a method for treating a condition associated with Trop-2 expression in a subject. In some embodiments, the method of treating a condition associated with Trop-2 expression in a subject comprises administering to the subject in need thereof an effective amount of a composition (e.g., pharmaceutical composition) comprising the Trop-2 antibodies or the Trop-2 antibody conjugates as described herein. The conditions associated with Trop-2 expression include, but are not limited to, abnormal Trop-2 expression, altered or aberrant Trop-2 expression, Trop-2 overexpression, and a proliferative disorder (e.g., cancer).

Accordingly, in some embodiments, provided is a method of treating a cancer in a subject comprising administering to the subject in need thereof an effective amount of a composition comprising the Trop-2 antibodies or the Trop-2 antibody conjugates as described herein. As used herein, cancers include, but are not limited to bladder, breast, cervical, choriocarcinoma, colon, esophageal, gastric, glioblastoma, head and neck, kidney, lung, oral, ovarian, pancreatic, prostate, and skin cancer. In some embodiments, provided is a method of inhibiting tumor growth or progression in a subject who has a Trop-2 expressing tumor, comprising administering to the subject in need thereof an effective amount of a composition comprising the Trop-2 antibodies or the Trop-2 antibody conjugates as described herein. In other embodiments, provided is a method of inhibiting metastasis of Trop-2 expressing cancer cells in a subject, comprising administering to the subject in need thereof an effective amount of a composition comprising the Trop-2 antibodies or the Trop-2 antibody conjugates as described herein. In other embodiments, provided is a method of inducing regression of a Trop-2 expressing tumor regression in a subject, comprising administering to the subject in need thereof an effective amount of a composition comprising the Trop-2 antibodies or the Trop-2 antibody conjugates as described herein.

In another aspect, provided is a method of detecting, diagnosing, and/or monitoring a condition associated with Trop-2 expression. For example, the Trop-2 antibodies as described herein can be labeled with a detectable moiety such as an imaging agent and an enzyme-substrate label. The antibodies as described herein can also be used for in vivo diagnostic assays, such as in vivo imaging (e.g., PET or SPECT), or a staining reagent.

In some embodiments, the methods described herein further comprise a step of treating a subject with an additional form of therapy. In some embodiments, the additional form of therapy is an additional anti-cancer therapy including, but not limited to, chemotherapy, radiation, surgery, hormone therapy, and/or additional immunotherapy.

In some embodiments, the additional form of therapy comprises administering one or more therapeutic agent in addition to the Trop-2 antibodies or the Trop-2 antibody conjugates as described herein. The therapeutic agents include, but are not limited to, a second antibody (e.g., an anti-VEGF antibody, an anti-HER2 antibody, anti-CD25 antibody, and/or an anti-CD20 antibody), an angiogenesis inhibitor, a cytotoxic agent, an anti-inflammatory agent (e.g., paclitaxel, docetaxel, cisplatin, doxorubicin, prednisone, mitomycin, progesterone, tamoxifen, or fluorouracil)

The Trop-2 antibody or the Trop-2 antibody conjugates can be administered to an individual via any suitable route. It should be understood by persons skilled in the art that the examples described herein are not intended to be limiting but to be illustrative of the techniques available. Accordingly, in some embodiments, the Trop-2 antibody or the Trop-2 antibody conjugate is administered to an individual in accord with known methods, such as intravenous administration, e.g., as a bolus or by continuous infusion over a period of time, by intramuscular, intraperitoneal, intracerebrospinal, intracranial, transdermal, subcutaneous, intra-articular, sublingually, intrasynovial, via insufflation, intrathecal, oral, inhalation or topical routes. Administration can be systemic, e.g., intravenous administration, or localized. Commercially available nebulizers for liquid formulations, including jet nebulizers and ultrasonic nebulizers are useful for administration. Liquid formulations can be directly nebulized and lyophilized powder can be nebulized after reconstitution. Alternatively, the Trop-2 antibody or the Trop-2 antibody conjugate can be aerosolized using a fluorocarbon formulation and a metered dose inhaler, or inhaled as a lyophilized and milled powder.

In one embodiment, the Trop-2 antibody or the Trop-2 antibody conjugate is administered via site-specific or targeted local delivery techniques. Examples of site-specific or targeted local delivery techniques include various implantable depot sources of the Trop antibody or the Trop-2 antibody conjugate or local delivery catheters, such as infusion catheters, indwelling catheters, or needle catheters, synthetic grafts, adventitial wraps, shunts and stents or other implantable devices, site specific carriers, direct injection, or direct application. See, e.g., PCT Publication No. WO 00/53211 and U.S. Pat. No. 5,981,568.

Various formulations of the Trop-2 antibody or the Trop-2 antibody conjugate may be used for administration. In some embodiments, the Trop-2 antibody or the Trop-2 antibody conjugate may be administered neat. In some embodiments, of the Trop-2 antibody (or the Trop-2 antibody conjugate) and a pharmaceutically acceptable excipient may be in various formulations. Pharmaceutically acceptable excipients are known in the art, and are relatively inert substances that facilitate administration of a pharmacologically effective substance. For example, an excipient can give form or consistency, or act as a diluent. Suitable excipients include but are not limited to stabilizing agents, wetting and emulsifying agents, salts for varying osmolarity, encapsulating agents, buffers, and skin penetration enhancers. Excipients as well as formulations for parenteral and nonparenteral drug delivery are set forth in Remington, The Science and Practice of Pharmacy 20th Ed. Mack Publishing, 2000.

In some embodiments, these agents are formulated for administration by injection (e.g., intraperitoneally, intravenously, subcutaneously, intramuscularly, etc.). Accordingly, these agents can be combined with pharmaceutically acceptable vehicles such as saline, Ringer's solution, dextrose solution, and the like. The particular dosage regimen, i.e., dose, timing and repetition, will depend on the particular individual and that individual's medical history.

Trop-2 antibodies or the Trop-2 antibody conjugates as described herein can be administered using any suitable method, including by injection (e.g., intraperitoneally, intravenously, subcutaneously, intramuscularly, etc.). The Trop-2 antibody or the Trop-2 antibody conjugate can also be administered via inhalation, as described herein. Generally, for administration of a Trop-2 antibody and a Trop-2 antibody conjugate, an initial candidate dosage can be about 2 mg/kg. For the purpose of the present invention, a typical daily dosage might range from about any of 3 μg/kg to 30 μg/kg to 300 μg/kg to 3 mg/kg, to 30 mg/kg, to 100 mg/kg or more, depending on the factors mentioned above. For example, dosage of about 1 mg/kg, about 2.5 mg/kg, about 5 mg/kg, about 10 mg/kg, and about 25 mg/kg may be used. For repeated administrations over several days or longer, depending on the condition, the treatment is sustained until a desired suppression of symptoms occurs or until sufficient therapeutic levels are achieved, for example, to inhibit or delay tumor growth/progression or metastasis of cancer cells. An exemplary dosing regimen comprises administering an initial dose of about 2 mg/kg, followed by a weekly maintenance dose of about 1 mg/kg of the Trop-2 antibody or Trop-2 antibody conjugate, or followed by a maintenance dose of about 1 mg/kg every other week. Other exemplary dosing regimen comprises administering increasing doses (e.g., initial dose of 1 mg/kg and gradual increase to one or more higher doses every week or longer time period). Other dosage regimens may also be useful, depending on the pattern of pharmacokinetic decay that the practitioner wishes to achieve. For example, in some embodiments, dosing from one to four times a week is contemplated. In other embodiments dosing once a month or once every other month or every three months is contemplated. The progress of this therapy is easily monitored by conventional techniques and assays. The dosing regimen (including the Trop-2 antibody or the Trop-2 antibody conjugate used) can vary over time.

For the purpose of the present invention, the appropriate dosage of a Trop-2 antibody or a Trop-2 antibody conjugate will depend on the Trop-2 antibody or the Trop-2 antibody conjugate (or compositions thereof) employed, the type and severity of symptoms to be treated, whether the agent is administered for therapeutic purposes, previous therapy, the patient's clinical history and response to the agent, the patient's clearance rate for the administered agent, and the discretion of the attending physician. Typically the clinician will administer a Trop-2 antibody or a Trop-2 antibody conjugate until a dosage is reached that achieves the desired result. Dose and/or frequency can vary over course of treatment. Empirical considerations, such as the half-life, generally will contribute to the determination of the dosage. For example, antibodies that are compatible with the human immune system, such as humanized antibodies or fully human antibodies, may be used to prolong half-life of the antibody and to prevent the antibody being attacked by the host's immune system. Frequency of administration may be determined and adjusted over the course of therapy, and is generally, but not necessarily, based on treatment and/or suppression and/or amelioration and/or delay of symptoms, e.g., tumor growth inhibition or delay, etc. Alternatively, sustained continuous release formulations of Trop-2 antibodies or Trop-2 antibody conjugates may be appropriate. Various formulations and devices for achieving sustained release are known in the art.

In one embodiment, dosages for a Trop-2 antibody or a trop-2 antibody conjugate may be determined empirically in individuals who have been given one or more administration(s) of the Trop-2 antibody or its Trop-2 antibody conjugate. Individuals are given incremental dosages of a Trop-2 antibody or a Trop-2 antagonist. To assess efficacy, an indicator of the disease can be followed.

Administration of an Trop-2 antibody or an Trop-2 antibody conjugate in accordance with the method in the present invention can be continuous or intermittent, depending, for example, upon the recipient's physiological condition, whether the purpose of the administration is therapeutic or prophylactic, and other factors known to skilled practitioners. The administration of a Trop-2 antibody or a Trop-2 antibody conjugate may be essentially continuous over a preselected period of time or may be in a series of spaced doses.

In some embodiments, more than one Trop-2 antibody or Trop-2 antibody conjugate may be present. At least one, at least two, at least three, at least four, at least five different or more Trop-2 antibody or Trop-2 antibody conjugate can be present. Generally, those Trop-2 antibodies or Trop-2 antibody conjugates may have complementary activities that do not adversely affect each other. For example, one or more of the following Trop-2 antibody may be used: a first Trop-2 antibody directed to one epitope on Trop-2 and a second Trop-2 antibody directed to a different epitope on Trop-2.

Therapeutic formulations of the Trop-2 antibody or the Trop-2 antibody conjugate used in accordance with the present invention are prepared for storage by mixing an antibody having the desired degree of purity with optional pharmaceutically acceptable carriers, excipients or stabilizers (Remington, The Science and Practice of Pharmacy 21st Ed. Mack Publishing, 2005), in the form of lyophilized formulations or aqueous solutions. Acceptable carriers, excipients, or stabilizers are nontoxic to recipients at the dosages and concentrations employed, and may comprise buffers such as phosphate, citrate, and other organic acids; salts such as sodium chloride; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens, such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG).

Liposomes containing the Trop-2 antibody or the Trop-2 antibody conjugate are prepared by methods known in the art, such as described in Epstein, et al., Proc. Natl. Acad. Sci. USA 82:3688, 1985; Hwang, et al., Proc. Natl. Acad. Sci. USA 77:4030, 1980; and U.S. Pat. Nos. 4,485,045 and 4,544,545. Liposomes with enhanced circulation time are disclosed in U.S. Pat. No. 5,013,556. Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter.

The active ingredients may also be entrapped in microcapsules prepared, for example, by coacervation techniques or by interfacial polymerization, for example, hydroxymethylcellulose or gelatin-microcapsules and poly-(methylmethacrylate) microcapsules, respectively, in colloidal drug delivery systems (for example, liposomes, albumin microspheres, microemulsions, nano-particles and nanocapsules) or in macroemulsions. Such techniques are disclosed in Remington, The Science and Practice of Pharmacy 21st Ed. Mack Publishing, 2005.

Sustained-release preparations may be prepared. Suitable examples of sustained-release preparations include semipermeable matrices of solid hydrophobic polymers containing the antibody, which matrices are in the form of shaped articles, e.g. films, or microcapsules. Examples of sustained-release matrices include polyesters, hydrogels (for example, poly(2-hydroxyethyl-methacrylate), or 'poly(vinylalcohol)), polylactides (U.S. Pat. No. 3,773,919), copolymers of L-glutamic acid and 7 ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), sucrose acetate isobutyrate, and poly-D-(−)-3-hydroxybutyric acid.

The formulations to be used for in vivo administration must be sterile. This is readily accomplished by, for example, filtration through sterile filtration membranes. Therapeutic Trop-2 antibody or Trop-2 antibody conjugate compositions are generally placed into a container having a sterile access port, for example, an intravenous solution bag or vial having a stopper pierceable by a hypodermic injection needle.

The compositions according to the present invention may be in unit dosage forms such as tablets, pills, capsules, powders, granules, solutions or suspensions, or suppositories, for oral, parenteral or rectal administration, or administration by inhalation or insufflation.

For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer that serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate. Suitable surface-active agents include, in particular, non-ionic agents, such as polyoxyethylenesorbitans (e.g. Tween™ 20, 40, 60, 80 or 85) and other sorbitans (e.g. Span™ 20, 40, 60, 80 or 85). Compositions with a surface-active agent will conveniently comprise between 0.05 and 5% surface-active agent, and can be between 0.1 and 2.5%. It will be appreciated that other ingredients may be added, for example mannitol or other pharmaceutically acceptable vehicles, if necessary.

Suitable emulsions may be prepared using commercially available fat emulsions, such as Intralipid™, Liposyn™, Infonutrol™, Lipofundin™ and Lipiphysan™. The active ingredient may be either dissolved in a pre-mixed emulsion composition or alternatively it may be dissolved in an oil (e.g. soybean oil, safflower oil, cottonseed oil, sesame oil, corn oil or almond oil) and an emulsion formed upon mixing with a phospholipid (e.g. egg phospholipids, soybean phospholipids or soybean lecithin) and water. It will be appreciated that other ingredients may be added, for example glycerol or glucose, to adjust the tonicity of the emulsion. Suitable emulsions will typically contain up to 20% oil, for example, between 5 and 20%. The fat emulsion can comprise fat droplets between 0.1 and 1.0 µm, particularly 0.1 and 0.5 µm, and have a pH in the range of 5.5 to 8.0.

The emulsion compositions can be those prepared by mixing a Trop-2 antibody or a Trop-2 antibody conjugate with Intralipid™ or the components thereof (soybean oil, egg phospholipids, glycerol and water).

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as set out above. In some embodiments, the compositions are administered by the oral or nasal respiratory route for local or systemic effect. Compositions in preferably sterile pharmaceutically acceptable solvents may be nebulised by use of gases. Nebulised solutions may be breathed directly from the nebulising device or the nebulising device may be attached to a face mask, tent or intermittent positive pressure breathing machine. Solution, suspension or powder compositions may be administered, preferably orally or nasally, from devices which deliver the formulation in an appropriate manner.

Compositions

The compositions used in the methods of the invention comprise an effective amount of a Trop-2 antibody or a Trop-2 antibody conjugate as described herein. Examples of such compositions, as well as how to formulate, are also described in an earlier section and below. In some embodiments, the composition comprises one or more Trop-2 antibodies or Trop-2 antibody conjugates. For example, Trop-2 antibody recognizes human Trop-2. In some embodiments, the Trop-2 antibody is a human antibody, a humanized antibody, or a chimeric antibody. In some embodiments, the Trop-2 antibody comprises a constant region that is capable of triggering a desired immune response, such as antibody-mediated lysis or ADCC. In other embodiments, the Trop-2 antibody comprises a constant region that does not trigger an unwanted or undesirable immune response, such as antibody-mediated lysis or ADCC. In other embodiments, the Trop-2 antibody comprises one or more CDR(s) of the antibody (such as one, two, three, four, five, or, in some embodiments, all six CDRs).

It is understood that the compositions can comprise more than one Trop-2 antibody or Trop-2 antibody conjugate (e.g., a mixture of Trop-2 antibodies that recognize different epitopes of Trop-2). Other exemplary compositions comprise more than one Trop-2 antibody or Trop-2 antibody conjugate that recognize the same epitope(s), or different species of Trop-2 antibodies or Trop-2 antibody conjugate that bind to different epitopes of Trop-2 (e.g., human Trop-2).

The composition used in the present invention can further comprise pharmaceutically acceptable carriers, excipients, or stabilizers (Remington: The Science and practice of Pharmacy 21st Ed., 2005, Lippincott Williams and Wilkins, Ed. K. E. Hoover), in the form of lyophilized formulations or aqueous solutions. Acceptable carriers, excipients, or stabilizers are nontoxic to recipients at the dosages and concentrations, and may comprise buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrans; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG). Pharmaceutically acceptable excipients are further described herein.

Kits

The invention also provides kits for use in the instant methods. Kits of the invention include one or more containers comprising the Trop-2 antibody or the Trop-2 antibody conjugate as described herein and instructions for use in accordance with any of the methods of the invention described herein. Generally, these instructions comprise a description of administration of the Trop-2 antibody or the Trop-2 antibody conjugate for the above described therapeutic treatments.

The instructions relating to the use of the Trop-2 antibodies or the Trop-2 antibody conjugates as described herein generally include information as to dosage, dosing schedule, and route of administration for the intended treatment. The containers may be unit doses, bulk packages (e.g., multi-dose packages) or sub-unit doses. Instructions supplied in the kits of the invention are typically written instructions on a label or package insert (e.g., a paper sheet included in the kit), but machine-readable instructions (e.g., instructions carried on a magnetic or optical storage disk) are also acceptable.

The kits of this invention are in suitable packaging. Suitable packaging includes, but is not limited to, vials, bottles, jars, flexible packaging (e.g., sealed Mylar or plastic bags), and the like. Also contemplated are packages for use in combination with a specific device, such as an inhaler, nasal administration device (e.g., an atomizer) or an infusion device such as a minipump. A kit may have a sterile access port (for example the container may be an intravenous solution bag or a vial having a stopper pierceable by a hypodermic injection needle). The container may also have a sterile access port (for example the container may be an intravenous solution bag or a vial having a stopper pierceable by a hypodermic injection needle). At least one active agent in the composition is a Trop-2 antibody. The container may further comprise a second pharmaceutically active agent.

Kits may optionally provide additional components such as buffers and interpretive information. Normally, the kit comprises a container and a label or package insert(s) on or associated with the container.

Mutations and Modifications

To express the Trop-2 antibodies of the present invention, DNA fragments encoding VH and VL regions can first be obtained using any of the methods described above. Various modifications, e.g. mutations, substitutions, deletions, and/or additions can also be introduced into the DNA sequences using standard methods known to those of skill in the art. For example, mutagenesis can be carried out using standard methods, such as PCR-mediated mutagenesis, in which the mutated nucleotides are incorporated into the PCR primers such that the PCR product contains the desired mutations or site-directed mutagenesis.

One type of substitution, for example, that may be made is to change one or more cysteines in the antibody, which may be chemically reactive, to another residue, such as, without limitation, alanine or serine. For example, there can be a substitution of a non-canonical cysteine. The substitution can be made in a CDR or framework region of a variable domain or in the constant region of an antibody. In some embodiments, the cysteine is canonical.

The antibodies may also be modified, e.g. in the variable domains of the heavy and/or light chains, e.g., to alter a binding property of the antibody. For example, a mutation may be made in one or more of the CDR regions to increase or decrease the $K_D$ of the antibody for Trop-2, to increase or decrease $k_{off}$, or to alter the binding specificity of the antibody. Techniques in site-directed mutagenesis are well-known in the art. See, e.g., Sambrook et al. and Ausubel et al., supra.

A modification or mutation may also be made in a framework region or constant region to increase the half-life of an Trop-2 antibody. See, e.g., PCT Publication No. WO 00/09560. A mutation in a framework region or constant region can also be made to alter the immunogenicity of the antibody, to provide a site for covalent or non-covalent binding to another molecule, or to alter such properties as complement fixation, FcR binding and antibody-dependent cell-mediated cytotoxicity. According to the invention, a single antibody may have mutations in any one or more of the CDRs or framework regions of the variable domain or in the constant region.

In a process known as "germlining", certain amino acids in the VH and VL sequences can be mutated to match those found naturally in germline VH and $V_L$ sequences. In particular, the amino acid sequences of the framework regions in the $V_H$ and VL sequences can be mutated to match the germline sequences to reduce the risk of immunogenicity when the antibody is administered. Germline DNA sequences for human VH and VL genes are known in the art (see e.g., the "Vbase" human germline sequence database; see also Kabat, E. A., et al., 1991, Sequences of Proteins of Immunological Interest, Fifth Edition, U.S. Department of Health and Human Services, NIH Publication No. 91-3242; Tomlinson et al., J. Mol. Biol. 227:776-798, 1992; and Cox et al., Eur. J. Immunol. 24:827-836, 1994.

Another type of amino acid substitution that may be made is to remove potential proteolytic sites in the antibody. Such sites may occur in a CDR or framework region of a variable domain or in the constant region of an antibody. Substitution of cysteine residues and removal of proteolytic sites may decrease the risk of heterogeneity in the antibody product and thus increase its homogeneity. Another type of amino acid substitution is to eliminate asparagine-glycine pairs, which form potential deamidation sites, by altering one or both of the residues. In another example, the C-terminal lysine of the heavy chain of an Trop-2 antibody of the invention can be cleaved. In various embodiments of the invention, the heavy and light chains of the Trop-2 antibodies may optionally include a signal sequence.

Once DNA fragments encoding the VH and VL segments of the present invention are obtained, these DNA fragments can be further manipulated by standard recombinant DNA techniques, for example to convert the variable region genes to full-length antibody chain genes, to Fab fragment genes, or to a scFv gene. In these manipulations, a VL- or VH-encoding DNA fragment is operatively linked to another DNA fragment encoding another protein, such as an antibody constant region or a flexible linker. The term "operatively linked", as used in this context, is intended to mean that the two DNA fragments are joined such that the amino acid sequences encoded by the two DNA fragments remain in-frame.

The isolated DNA encoding the VH region can be converted to a full-length heavy chain gene by operatively linking the VH-encoding DNA to another DNA molecule encoding heavy chain constant regions (CH1, CH2 and CH3). The sequences of human heavy chain constant region genes are known in the art (see e.g., Kabat, E. A., et al., 1991, Sequences of Proteins of Immunological Interest, Fifth Edition, U.S. Department of Health and Human Services, NIH Publication No. 91-3242) and DNA fragments encompassing these regions can be obtained by standard PCR amplification. The heavy chain constant region can be an IgG1, IgG2, IgG3, IgG4, IgA, IgE, IgM or IgD constant region, but most preferably is an IgG1 or IgG2 constant region. The IgG constant region sequence can be any of the various alleles or allotypes known to occur among different individuals, such as Gm(1), Gm(2), Gm(3), and Gm(17). These allotypes represent naturally occurring amino acid substitution in the IgG1 constant regions. For a Fab fragment heavy chain gene, the $V_H$-encoding DNA can be operatively linked to another DNA molecule encoding only the heavy chain CH1 constant region. The CH1 heavy chain constant region may be derived from any of the heavy chain genes.

The isolated DNA encoding the VL region can be converted to a full-length light chain gene (as well as a Fab light chain gene) by operatively linking the VL-encoding DNA to another DNA molecule encoding the light chain constant region, CL. The sequences of human light chain constant region genes are known in the art (see e.g., Kabat, E. A., et al., 1991, Sequences of Proteins of Immunological Interest, Fifth Edition, U.S. Department of Health and Human Services, NIH Publication No. 91-3242) and DNA fragments encompassing these regions can be obtained by standard PCR amplification. The light chain constant region can be a kappa or lambda constant region. The kappa constant region may be any of the various alleles known to occur among different individuals, such as Inv(1), Inv(2), and Inv(3). The lambda constant region may be derived from any of the three lambda genes.

To create a scFv gene, the VH- and VL-encoding DNA fragments are operatively linked to another fragment encoding a flexible linker, e.g., encoding the amino acid sequence $(Gly_4\text{-}Ser)_3$, (SEQ ID NO: 80) such that the VH and VL sequences can be expressed as a contiguous single-chain protein, with the VL and VH regions joined by the flexible linker (See e.g., Bird et al., 1988, Science 242:423-426; Huston et al., 1988, Proc. Natl. Acad. Sci. USA 85:5879-5883; McCafferty et al., 1990, Nature 348:552-554. The single chain antibody may be monovalent, if only a single VH and VL are used, bivalent, if two VH and VL are used, or polyvalent, if more than two VH and VL are used. Bispecific or polyvalent antibodies may be generated that bind specifically to Trop-2 and to another molecule.

In another embodiment, a fusion antibody or immunoadhesin may be made that comprises all or a portion of an Trop-2 antibody of the invention linked to another polypeptide. In another embodiment, only the variable domains of the Trop-2 antibody are linked to the polypeptide. In another embodiment, the VH domain of an Trop-2 antibody is linked to a first polypeptide, while the VL domain of an Trop-2 antibody is linked to a second polypeptide that associates with the first polypeptide in a manner such that the VH and VL domains can interact with one another to form an antigen binding site. In another preferred embodiment, the VH domain is separated from the VL domain by a linker such that the VH and VL domains can interact with one another. The VH-linker-VL antibody is then linked to the polypeptide of interest. In addition, fusion antibodies can be created in which two (or more) single-chain antibodies are linked to one another. This is useful if one wants to create a divalent or polyvalent antibody on a single polypeptide chain, or if one wants to create a bispecific antibody.

In other embodiments, other modified antibodies may be prepared using Trop-2 antibody encoding nucleic acid molecules. For instance, "Kappa bodies" (Ill et al., Protein Eng. 10:949-57, 1997), "Minibodies" (Martin et al., EMBO J., 13:5303-9, 1994), "Diabodies" (Holliger et al., Proc. Natl. Acad. Sci. USA 90:6444-6448, 1993), or "Janusins" (Traunecker et al., EMBO J. 10:3655-3659, 1991 and Traunecker et al., Int. J. Cancer (Suppl.) 7:51-52, 1992) may be prepared using standard molecular biological techniques following the teachings of the specification.

Bispecific antibodies or antigen binding fragments can be produced by a variety of methods including fusion of hybridomas or linking of Fab' fragments. See, e.g., Songsivilai & Lachmann, Clin. Exp. Immunol. 79:315-321, 1990, Kostelny et al., J. Immunol. 148:1547-1553, 1992. In addition, bispecific antibodies may be formed as "diabodies" or "Janusins." In some embodiments, the bispecific antibody binds to two different epitopes of Trop-2. In some embodiments, the modified antibodies described above are prepared using one or more of the variable domains or CDR regions from the Trop-2 antibodies provided herein.

Representative materials of the present invention were deposited in the American Type Culture Collection (ATCC) at 10801 University Boulevard, Manassas, Va., 20108, United States of America, on Apr. 26, 2012. Vector having ATCC Accession No. PTA-12872 is a polynucleotide encoding a humanized Trop-2 antibody heavy chain variable region deposited under the name pCR4-TOPO-h7E6SVGHv, and vector having ATCC Accession No. PTA-12871 is a polynucleotide encoding a humanized Trop-2 antibody light chain variable region under the name pCR4-TOPO-h7E6SVGLv. The deposits were made under the provisions of the Budapest Treaty on the International Recognition of the Deposit of Microorganisms for the Purpose of Patent Procedure and Regulations thereunder (Budapest Treaty). This assures maintenance of a viable culture of the deposit for 30 years from the date of deposit. The deposit will be made available by ATCC under the terms of the Budapest Treaty, and subject to an agreement between Pfizer, Inc. and ATCC, which assures permanent and unrestricted availability of the progeny of the culture of the deposit to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 U.S.C. Section 122 and the Commissioner's rules pursuant thereto (including 37 C.F.R. Section 1.14 with particular reference to 886 OG 638).

The assignee of the present application has agreed that if a culture of the materials on deposit should die or be lost or destroyed when cultivated under suitable conditions, the materials will be promptly replaced on notification with another of the same. Availability of the deposited material is not to be construed as a license to practice the invention in contravention of the rights granted under the authority of any government in accordance with its patent laws.

The following examples are offered for illustrative purposes only, and are not intended to limit the scope of the present invention in any way. Indeed, various modifications of the invention in addition to those shown and described herein will become apparent to those skilled in the art from the foregoing description and fall within the scope of the appended claims.

EXAMPLES

Example 1

Antibody Binding Affinity Determination for Recombinant Anti-Trop-2 Mouse Antibodies The affinities of anti-Trop-2 mouse antibodies generated from hybridomas were measured on a surface plasmon resonance Biacore™ 2000 or 3000 biosensor equipped with a research-grade CM5 sensor chip (Biacore™ AB, Uppsala, Sweden—now GE Healthcare). Anti-mouse IgG was first amine coupled to the CM5 sensor surface. Various anti-Trop-2 mouse IgGs were then captured by anti-mouse IgG. Monomeric Trop-2 extracellular domain prepared from papain digestion of Trop-2-Fc fusion protein was then injected as the analyte at 3 fold dilution series. Affinity of anti-Trop-2 mouse antibodies ranges from 7.5 to 31.8 nM. Table 4.

TABLE 4

| Antibody | ka(1/Ms) | kd(1/s) | KD(nM) to huTrop-2 |
|---|---|---|---|
| 3E9 | 1.83E+05 | 2.38E−03 | 13.0 |
| 6G11 | 2.70E+05 | 8.60E−03 | 31.8 |
| 7E6 | 1.60E+05 | 1.19E−03 | 7.5 |
| 15E2 | 1.61E+05 | 4.07E−03 | 25.3 |
| 18B1 | 4.37E+05 | 1.04E−02 | 23.8 |

Example 2

Domain Mapping of Recombinant Anti-Trop-2 Mouse Antibodies

Domain mapping was done by swapping the Trop-2 extracellular domains with either Trop-1 (EpCAM) or mouse Trop-2 equivalent regions. See FIGS. 4-5. Anti-Trop-2 antibodies 3E9, 6G11, 7E6, and 18B1 (expressed as recombinant mouse IgG2a) do not bind either human Trop-1 or mouse Trop-2 while 15E2 binds mouse Trop-2 but not human Trop-1. These hybrid proteins were expressed as human Fc fusion proteins in 293F cells. Binding of anti-Trop-2 antibodies to these domain hybrids were determined by Biacore. Recognition of certain human Trop-2 domains by anti-Trop-2 antibodies were defined when domain swapping results in loss or reduction in binding. Anti-Trop-2 antibody clones 3E9, 7E6, and 15E2 bind to domains 3 and 4 while clones 6G11 and 18B1 bind to domain 1. Table 5. Definition of different domains of Trop-2 can be found, e.g., in Chong et al., J. Biol. Chem. 276(8):5804-13, 2001.

TABLE 5

| | Binding of anti-Trop-2 antibodies to different Trop-2 domains | | | |
|---|---|---|---|---|
| | domain replacement | domain 1 | domain 2 | domain 3 | domain 4 |
| 3E9 | hTrop1 | − | − | + | + |
| | mTrop-2 | − | − | +/− | + |
| 6G11 | hTrop1 | + | − | − | − |
| | mTrop-2 | + | − | − | − |
| 7E6 | hTrop1 | − | − | + | + |
| | mTrop-2 | − | − | − | + |
| 15E2 | hTrop1 | − | − | + | +/− |
| | mTrop-2 | − | − | +/− | − |
| 18B1 | hTrop1 | + | − | − | − |
| | mTrop-2 | + | − | − | − |

+ indicates domain replacement results in loss of binding
+/− indicates domain replacement results in decrease of binding
− indicates domain replacement does not affect binding Example 3

In Vivo Efficacy Studies with Colo205 Xenograft Model

Figure 1:
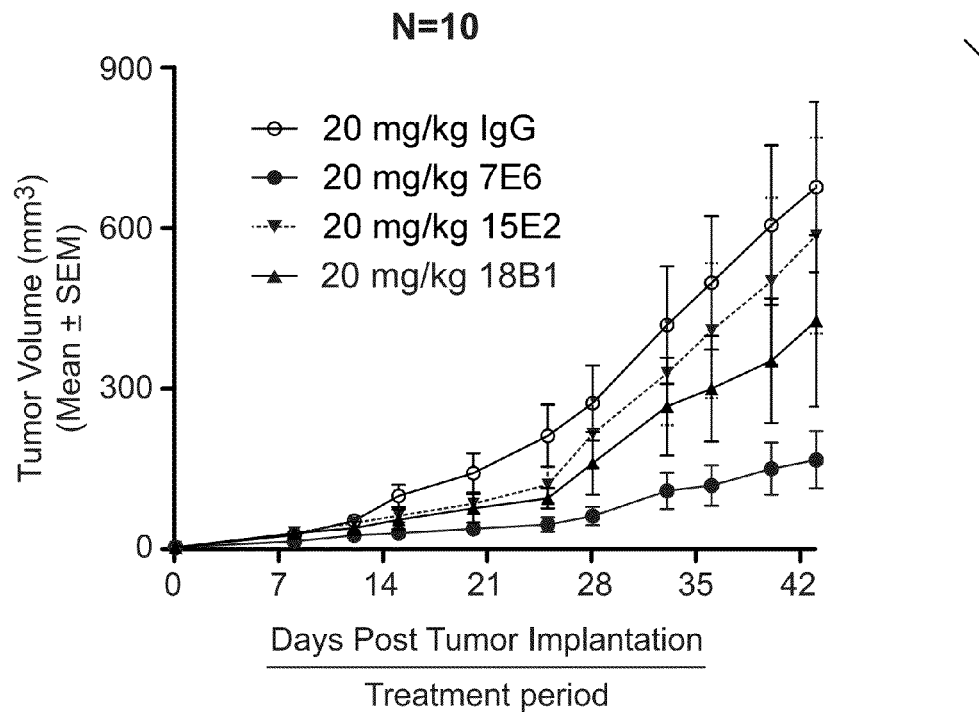
FIG. 1 depicts in vivo efficacy studies of various Trop-2 mouse antibodies (7E6, 15E2, and 18B1) in target-expressing Colo205 xenograft model.

In vivo efficacy studies of Anti-Trop-2 mouse IgGs were performed with target-expressing colo205 xenograft model. One million colo205 colon cancer cells were implanted subcutaneously into 5-8 weeks old nu/nu mice (day 0). Animals were randomized by body weight the next day (day 1) into different treatment cohorts (control IgG, 7E6, 15E2, or 18B1 group; n=10/group). 20 mg/kg of anti-Trop-2 antibodies from different treatment cohorts and control mIgG were administered through bolus tail vein injection three times a week for total 12 doses. All experimental animals were monitored for body weight changes daily. Tumor volume was measured twice a week by a caliper device and calculated with the following formula: Tumor volume=(length×width$^2$)/2. Studies were terminated before tumor volumes reached 2000 mm$^3$. TGI (% tumor growth inhibition) was determined as [1−tumor sizes (treatment group)/tumor size (control group)]×100. Table 6 and FIG. 1 show that anti-Trop-2 antibodies 7E6, 15E2, and 18B1 inhibit Colo205 xenograft tumor growth in vivo.

TABLE 6

| antibody treatment | Mean tumor volume (mm3) on day 43 | TGI (Tumor growth inhibition) |
| --- | --- | --- |
| control IgG | 673.0 | 0% |
| 7E6 | 163.8 | 76% |
| 15E2 | 582.0 | 14% |
| 18B1 | 423.5 | 37% |

Example 4

In Vivo Efficacy Studies with A431 Xenograft Model a) Inhibition of A431 Xenograft Tumor Growth by Anti-Trop-2 Antibodies 7E6, 15E2, and 18B1

Figure 2A:
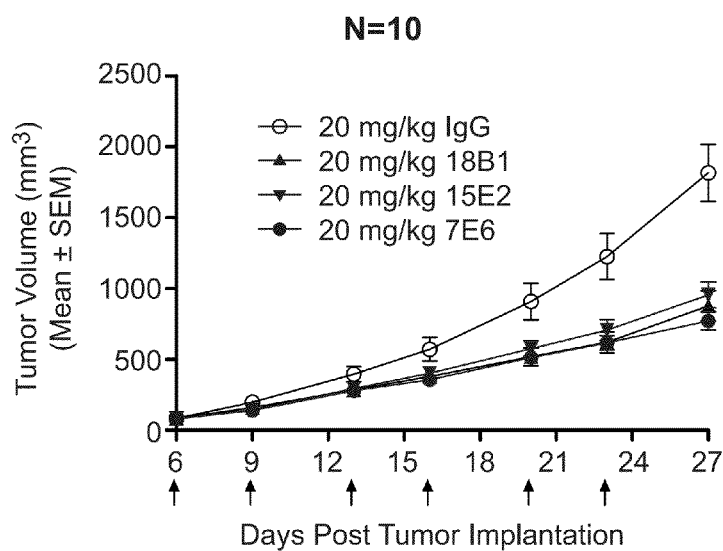
FIG. 2A depicts in vivo efficacy studies of various Trop-2 mouse antibodies (7E6, 15E2, and 18B1) in target-expressing A431 xenograft model.

In vivo efficacy studies of anti-Trop-2 mouse IgGs were performed with target-expressing A431 xenograft model. Two million A431 epidermoid cancer cells were implanted subcutaneously into 5-8 weeks old nu/nu mice until the tumor sizes reached around 100 mm$^3$. Animals were randomized by tumor sizes and dosing was done through bolus tail vein injection. Anti-Trop-2 antibodies were expressed as recombinant mouse IgG2a antibodies from 293F transient expression. 20 mg/kg of anti-Trop-2 antibodies (18B1, 15E2, and 7E6 recombinant mIgG2a) or control IgG were administered through bolus tail vein injection twice a week for total 6 doses. Tumor volume was measured twice a week by a caliper device and calculated with the following formula: Tumor volume=(length×width$^2$)/2. Studies were terminated before tumor volumes reached 2000 mm$^3$. TGI (% tumor growth inhibition) was determined as [1−tumor sizes (treatment group)/tumor size (control group)]×100. Table 7A and FIG. 2A show that anti-Trop 2 antibodies 7E6, 15E2, and 18B1 inhibit A431 xenograft tumor growth in vivo.

TABLE 7A

Figure 2B:
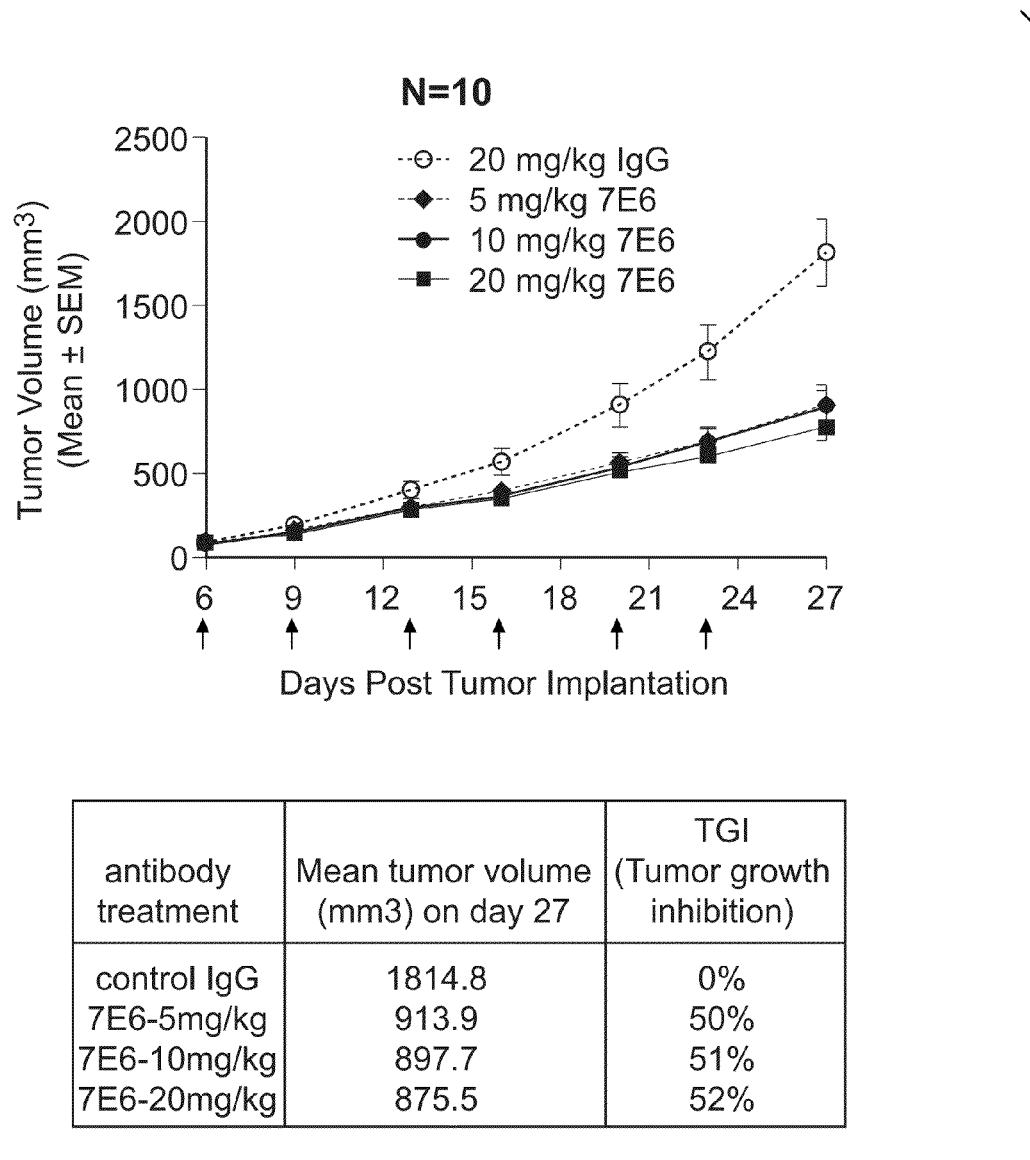
FIG. 2B depicts inhibition of A431 Xenograft tumor growth by Trop-2 antibody 7E6 in a dose-response study.

| antibody treatment | Mean tumor volume (mm3) on day 27 | TGI (Tumor growth inhibition) |
| --- | --- | --- |
| control IgG | 1814.8 | 0% |
| 7E6 | 770.7 | 58% |
| 15E2 | 953.6 | 47% |
| 18B1 | 875.5 | 52% | b) Inhibition of A431 Xenograft Tumor Growth by Anti-Trop-2 Antibody 7E6 in Dose-Response Study Using the same xenograft model as described in Example 4a above, various doses of anti-Trop-2 7E6 antibody (5, 10, and 20 mg/kg) or 20 mg/kg control IgG were administered through bolus tail vein injection twice a week for total 6 doses. Table 7B and FIG. 2B show inhibition of A431 xenograft tumor growth in vivo by various doses of 7E6.

TABLE 7B

| antibody treatment | Mean tumor volume (mm3) on day 27 | TGI (Tumor growth inhibition) |
| --- | --- | --- |
| control IgG | 1814.8 | 0% |
| 7E6-5 mg/kg | 913.9 | 50% |
| 7E6-10 mg/kg | 897.7 | 51% |
| 7E6-20 mg/kg | 875.5 | 52% | c) Inhibition of A431 Xenograft Tumor Growth by Anti-Trop-2 Antibodies 6G11, 7E6, and 18B1

Figure 2C:
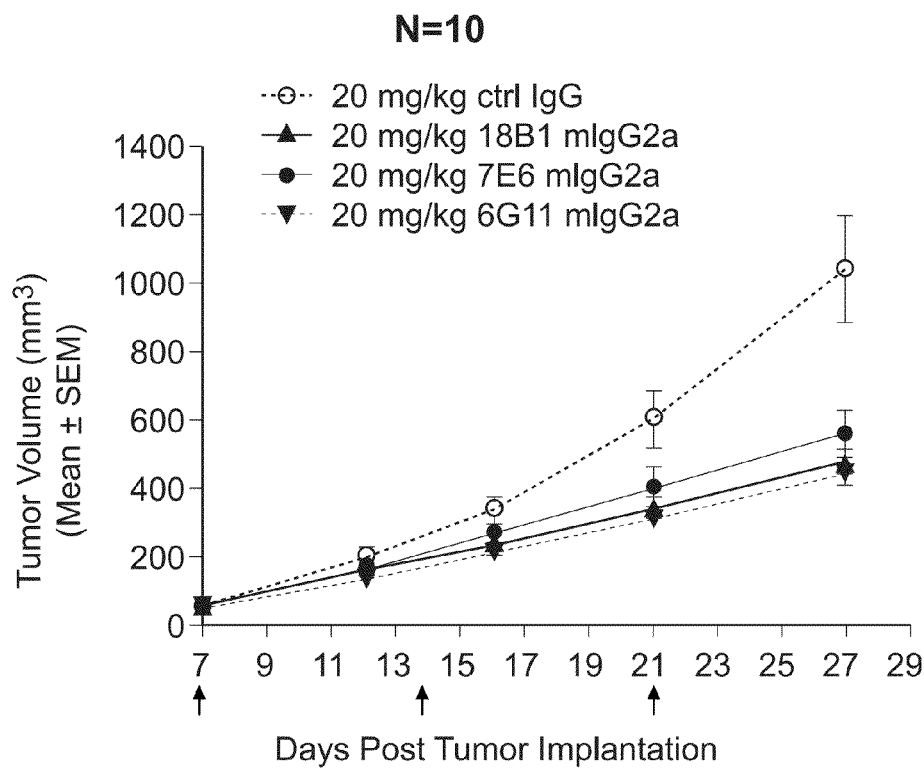
FIG. 2C depicts inhibition of A431 Xenograft tumor growth by Trop-2 antibodies 6G11, 7E6, and 18B1 in A431 xenograft model.

Similarly, 20 mg/kg of anti-Trop-2 antibodies (6G11, 7E6, and 18B1 and control IgG), all expressed recombinantly as mIgG2s, were administered through bolus tail vein injection once a week for a total of 3 doses in A431 xenograft model as described in Example 4a). Table 7C and FIG. 2C show that anti-Trop 2 antibodies 6G11, 7E6, and 18B1 inhibit A431 xenograft tumor growth in vivo.

TABLE 7C

| antibody treatment | Mean tumor volume (mm3) on day 27 | TGI (Tumor growth inhibition) |
| --- | --- | --- |
| control IgG | 1044.0 | 0% |
| 6G11 | 444.8 | 57% |
| 7E6 | 561.0 | 46% |
| 18B1 | 477.6 | 54% |

Example 5

Antibody Binding Affinity Determination for Humanized Anti-Trop-2 Antibodies—7E6

The affinities of chimeric and humanized anti-Trop-2 7E6 antibodies were measured on a surface plasmon resonance Biacore™ T200 biosensor equipped with a research-grade CM4 sensor chip (Biacore™ AB, Uppsala, Sweden—now GE Healthcare). The human Trop-2-hFc or cynomolgus monkey Trop-2-hFc proteins were captured on the CM5 EDA chip 37 sensor surface coupled with anti-human Fc. Chimeric and humanized 7E6 recombinant Fab fragments were injected as 3 fold dilution series. Tables 8A and 8B show affinity measurement of humanized anti-Trop-2 7E6 antibodies to human Trop-2 protein and cynomolgus monkey, respectively.

TABLE 8A

| Antibody | ka(1/Ms) | kd(1/s) | KD(nM) to huTrop-2 |
| --- | --- | --- | --- |
| mouse7E6 | 1.66E+05 | 1.34E−03 | 8.08 |
| h7E6-WT | 1.39E+05 | 2.94E−03 | 21.10 |
| h7E6_SVG | 9.76E+04 | 4.35E−04 | 4.46 |
| h7E6_L | 1.30E+05 | 1.50E−04 | 1.15 |
| h7E6_SVGL | 1.31E+05 | 3.27E−05 | 0.25 |

TABLE 8B

| Antibody | ka(1/Ms) | kd(1/s) | KD(nM) to cynoTrop-2 |
| --- | --- | --- | --- |
| mouse7E6 | 1.45E+05 | 2.40E−03 | 16.50 |
| h7E6-WT | 1.44E+05 | 6.35E−03 | 44.00 |

TABLE 8B-continued

| Antibody | ka(1/Ms) | kd(1/s) | KD(nM) to cynoTrop-2 |
|---|---|---|---|
| h7E6_SVG | 2.65E+05 | 1.89E-03 | 7.00 |
| h7E6_L | 1.26E+05 | 3.35E-04 | 2.66 |
| h7E6_SVGL | 1.30E+05 | 7.42E-05 | 0.57 |

Example 6

Antibody Binding Affinity Determination for Humanized Anti-Trop-2 Antibodies—6G11

The affinities of humanized 6G11 antibodies were measured on a surface plasmon resonance Biacore™ 2000 biosensor equipped with a research-grade CM5 sensor chip (Biacore™ AB, Uppsala, Sweden—now GE Healthcare). Human Trop-2-mFc protein was captured on the CM5 chip coupled with anti-mouse Fc. Human 6G11_WT or Human 6G11_FKG_SF chimeric Fab fragments were injected as 3 fold dilution series. Table 9 shows affinity measurement of humanized anti-Trop-2 6G11 antibodies to human Trop-2 protein.

TABLE 9

| Antibody | ka(1/Ms) | kd(1/s) | KD(nM) to huTrop-2 |
|---|---|---|---|
| h6G11_WT | 3.60E+05 | 9.60E-03 | 27.0 |
| h6G11_FKG_SF | 6.40E+05 | 3.80E-04 | 0.6 |

Example 7

Flow Cytometry of Mouse and Humanized Anti-Trop-2 Antibodies on Trop-2 Positive and Negative Tumor Cells a) 7E6

Binding of mouse chimeric and humanized anti-Trop-2 7E6 antibodies (expressed in human IgG1 subtype) were assessed on Trop-2 expressing (A431 and Colo205) and non-expressing (SW620) cells by flow cytometry. For A431 cell staining, 200,000 cells were incubated with 0.5 ug antibody in 100 uL binding buffer (PBS (Phosphate Buffered Saline)+0.5% BSA (Bovine Serum Albumin)), followed by incubation with Dylight488-conjugated goat anti-human (Fab')-2-specific secondary antibody from Jackson immunoresearch Laboratories (West Grove, Pa.). For Colo205 and SW620 cells, 300,000 cells were used with 1 ug of primary antibody, followed by AlexaFluor 647 anti-human (Fab')-2-specific secondary antibody from Jackson immunoresearch Laboratories (West Grove, Pa.). Table 10 shows at least about 93% binding on Trop-2 positive tumor cells by mouse 7E6 and humanized 7E6 antibodies.

TABLE 10

| Antibody | A431 (Trop-2+++) | | Colo205 (Trop-2+) | | SW620 (Trop-2−) | |
|---|---|---|---|---|---|---|
| | MFI | % positive | MFI | % positive | MFI | % positive |
| 2nd Ab only | 1049 | 3.4 | 183 | 3.9 | 154 | 2.0 |
| mouse 7E6 | 103000 | 94.0 | 2258 | 99.0 | 149 | 2.2 |

TABLE 10-continued

| Antibody | A431 (Trop-2+++) | | Colo205 (Trop-2+) | | SW620 (Trop-2−) | |
|---|---|---|---|---|---|---|
| | MFI | % positive | MFI | % positive | MFI | % positive |
| h7E6_WT | 102000 | 94.8 | 1761 | 99.0 | 143 | 2.1 |
| h7E6_SVG | 121000 | 96.7 | 2425 | 100.0 | 139 | 2.4 |
| h7E6_L | 110000 | 95.1 | 2469 | 100.0 | 158 | 2.5 |
| h7E6_N | 149000 | 98.6 | 2698 | 100.0 | 151 | 2.3 |
| h7E6_SVGL | 107000 | 93.1 | 2425 | 100.0 | 135 | 2.6 |
| h7E6_SVGN | 128000 | 98.1 | 2734 | 100.0 | 140 | 2.5 | b) 6G11

Similar to Example 7a), binding of chimeric mouse and humanized anti-Trop-2 6G11 antibodies (expressed in human IgG1 subtype) were assessed on Trop-2 expressing (A431 and Colo205) and non-expressing (SW620) cells by flow cytometry. 300,000 cells were used with 1 ug of primary antibody, followed by AlexaFluor 647 anti-human (Fab')2-specific secondary antibody. Table 11 shows at least about 99% binding on Trop-2 positive tumor cells by mouse 6G11 and humanized 6G11 antibodies.

TABLE 11

| Antibody | A431 (Trop-2+++) | | Colo205 (Trop-2+) | | SW620 (Trop-2−) | |
|---|---|---|---|---|---|---|
| | MFI | % positive | MFI | % positive | MFI | % positive |
| 2nd Ab only | 718 | 4.9 | 183 | 3.9 | 154 | 2.0 |
| mouse 6G11 | 16204 | 99.9 | 1667 | 100.0 | 134 | 2.5 |
| h6G11_WT | 19573 | 99.9 | 1716 | 99.0 | 154 | 3.9 |
| h6G11_FKG_SF | 20254 | 99.9 | 2064 | 100.0 | 157 | 2.5 |

Example 8

ADCC Activity of Chimeric and Humanized Anti-Trop-2 7E6 hIgG1 Antibodies on A431 Cells The ADCC (antibody-dependent cytotoxicity) activity of chimeric mouse (h7E6-WT) and humanized anti-Trop-2 7E6 human IgG1 antibodies (h7E6_SVG (VH region), h7E6_L (VL region), and h7E6-SVGL (both VH and VL regions)) were determined with the cytoTox 96 non-radioactive cytotoxicity assay kit (Promega, Madison Wis.). Target expressing A431 cells were seeded at 10,000 cells/well the day before the assay. Donor PBMCs (Cryopreserved Peripheral Blood Mononuclear Cells) were isolated through Ficoll gradient and cultured overnight at 37° C. in X-VIVO medium (Lonza, Wakersville, Mo.). The antibodies were added to the wells the following day at concentrations indicated in FIG. 3, followed by the addition of 500,000 PBMC cells (E:T=50:1) in RPMI+5% FBS (Fetal Bovine Serum). Anti-EGFR (Epidermal Growth Factor Receptor) antibody (ERBITUX®, Imclone, Bridgewater, N.J.) was used as a positive control for the assay. The plates were then incubated at 37° C. for 4 hours. At 3 and half hours time point, 20 uL of the lysis solution was added to the target cells alone wells. After spinning the plate at 8000 rpm for 3 minutes, 50 uL of supernatants were transferred to another plate. 50 ul of substrate was then added to each well and the plate was incubated at room temperature for 30 minutes in the dark. The reaction was stopped by adding 50 uL of stop solution from Promega (Madison, Wis.) to each well. The plates were then read at 490 nm with a spectrophotometer (Molecular Devices, Sunnyvale, Calif.). Percentages (%) of specific lysis were calculated with the following formula:

% specific lysis=(treatment LDH(Lactate Dehydrogenase)release−target cell spontaneous LDH release−effector cell spontaneous LDH release)/ (target cell maximum LDH release−target cell spontaneous LDH release)×100

FIG. 3 shows that both chimeric mouse and humanized anti-Trop-2 7E6 IgG1 antibodies induced ADCC killing in A431 cells.

Example 9

Cytotoxicity of Anti-Trop-2-ADCs in Trop-2 Positive Cells

Chimeric mouse (6G11 and 7E6) and humanized anti-Trop-2 (h7E6-SVG, h7E6-SVGL, and h7E6-SVGN) antibodies were expressed as human IgG1 subtypes engineered with glutamine-containing transglutaminase ("Q") tags (e.g., TG1, LCQ03, and TG6 correspond to SEQ ID NOs:75, (LLQGG); 78 (GGLLQGA), and 79 (LLQGA), respectively) and conjugated with AcLys-vcMMAD (Acetyl-Lysine-Valine-Citrulline-MMAD), aminocaproyl-vc-PABC-MMAD (aminocaproyl-Valine-Citrulline-p-aminobenzyloxycarbonyl-MMAD), or AcLys-vc-PABC-MMAD (Acetyl-Lysine-Valine-Citrulline-p-aminobenzyloxycarbonyl-MMAD) as indicated in Table 12. In one instance, the transglutaminase tags can be engineered at the light chain or heavy chain C-terminus of the antibody; in other instance, the transglutaminase tag (e.g., Q) is engineered at another site of the antibody, such as at position 297 of the human IgG (Kabat numbering scheme). For example, the wild-type amino acid asparagine (N) is substituted with glutamine at position 297 of the Trop-2 antibody (N297Q). Anti-Trop-2 antibody conjugation to MMAD was then achieved via microbial transglutaminase-catalyzed transamidation reaction between the anti-Trop-2 antibody carrying a glutamine-containing tag at the specific site (e.g., carboxyl terminus or amino terminus of the heavy chain or light chain, position 297, or at another site of the antibody) and an amine-containing derivative of the payload (e.g., MMAD). In some instances, the wild-type amino acid lysine at the carboxyl terminus (position 447 in accordance with Kabat numbering scheme) was deleted and replaced with the Q-tag. In other instances, the wild-type amino acid lysine at position 222, 340, or 370 (in accordance with Kabat numbering scheme) was replaced with amino acid arginine ("K222R", "K340R", or "K370R"). For example, the K222R substitution was found to have the surprising effect of resulting in more homogenous antibody and payload conjugate, better intermolecular crosslinking between the antibody and the payload, and/or significant decrease in inter-chain crosslinking with the glutamine tag on the C terminus of the antibody light chain. In the transamidation reaction, the glutamine on the antibody acted as an acyl donor, and the amine-containing compound acted as an acyl acceptor (amine donor). Purified anti-Trop-2 antibody in the concentration of 1.67-4.04 µM was incubated with a 20-100 M excess acyl acceptor, ranging between 167-404 µM, in the presence of 0.225-0.545% (w/v) Streptoverticillium mobaraense transglutaminase (ACTIVA™, Ajinomoto, Japan) in 150-900 mM NaCl, and 25 mM MES, HEPES [4-(2-hydroxyethyl)-1-piperazineethanesulfonic acid] or Tris HCl buffer at pH range 6.2-8.8. The reaction conditions were adjusted for individual acyl acceptor derivatives, and the optimal efficiency and specificity were typically observed for 2.87 µM antibody, 287 µM derivative, and 0.378% (w/v) transglutaminase in 150 mM NaCl, 25 mM Tris HCl, pH 8.8. Following incubation at room temperature for 2.5 hours, the antibody was purified on MabSelect resin (GE Healthcare, Waukesha, Wis.) using standard affinity chromatography methods known to persons skilled in the art, such as commercial affinity chromatography from GE Healthcare.

Target expressing (A431, BxPC3, CAPAN-2 and Colo205) or non-expressing (SW620) cells were seeded on white walled clear bottom plates at 2000 cells/well for 24 hours before treatment. Cells were treated with 4 fold serially diluted antibody-drug conjugates in triplicates. Cell viability was determined by CellTiter-Glo® Luminescent Cell Viability Assay 96 (Promega, Madison Wis.) 96 hours after treatment. Relative cell viability was determined as percentage of untreated control. IC50 was calculated by Prism software. Table 12 shows that chimeric mouse and humanized anti-Trop-2 7E6 antibodies conjugated to MMAD through transglutaminase tag exert potent cell killing activity in Trop-2 expressing cells.

TABLE 12

| Name | conjugate | Loading | A431(Trop-2+++) Ab-IC50 ug/mL | A431(Trop-2+++) Ab-IC50 (nM) | BxPC3(Trop-2++) Ab-IC50 ug/mL | BxPC3(Trop-2++) Ab-IC50 (nM) |
|---|---|---|---|---|---|---|
| 6G11-TG1-vcMMAD | AcLys-vcMMAD | 1.86 | 0.030 | 0.197 | | |
| 7E6-TG1-vcMMAD | AcLys-vcMMAD | 1.87 | 0.016 | 0.109 | 0.027 | 0.179 |
| h7E6-WT-TG1-vcMMAD | AcLys-vcMMAD | 1.79 | 0.022 | 0.144 | 0.025 | 0.169 |
| h7E6-L-TG1-vcMMAD | AcLys-vcMMAD | 1.85 | 0.020 | 0.132 | 0.035 | 0.232 |
| h7E6-N-TG1-vcMMAD | AcLys-vcMMAD | 1.87 | 0.024 | 0.163 | | |
| h7E6-SVG-TG1-vcMMAD | AcLys-vcMMAD | 1.88 | 0.016 | 0.105 | 0.031 | 0.206 |
| h7E6-SVGL-TG1-vcMMAD | AcLys-vcMMAD | 1.85 | 0.018 | 0.120 | | |
| h7E6-SVGN-TG1-vcMMAD | AcLys-vcMMAD | 1.87 | 0.023 | 0.153 | 0.051 | 0.337 |
| NNC-TG1-vcMMAD | Aminocapryl-vcMMAD | 1.83 | | | 7.260 | 48.400 |
| 7E6-TG1-vcMMAD | Aminocapryl-vcMMAD | 1.87 | | | 0.030 | 0.197 |

TABLE 12-continued

| Name | Linker | | | | | |
|---|---|---|---|---|---|---|
| h7E6-SVG-TG1-vcMMAD | Aminocapryl-vcMMAD | 1.91 | | | 0.034 | 0.229 |
| 7E6-TG6-AcLys-vc-PABC-MMAD | AcLys-vc-PABC-MMAD | 1.87 | | | 0.008 | 0.053 |
| 7E6-K222R-LCQ3-AcLys-vc-PABC-MMAD | AcLys-vc-PABC-MMAD | 0.74 | | | 0.008 | 0.054 |
| h7E6SVG-TG6-AcLys-vc-PABC-MMAD | AcLys-vc-PABC-MMAD | 1.93 | 0.011 | 0.072 | 0.032 | 0.214 |
| h7E6SVG-K222R-LCQ3-AcLys-vc-PABC-MMAD | AcLys-vc-PABC-MMAD | 1.90 | 0.01 | 0.07 | 0.014 | 0.092 |

| | CAPAN-2 (Trop-2+/++) | | Colo205 (Trop-2+) | | SW620 (Trop-2-) | |
|---|---|---|---|---|---|---|
| Name | Ab-IC50 ug/mL | Ab-IC50 (nM) | Ab-IC50 (ug/mL) | Ab-IC50 (nM) | Ab-IC50 ug/mL | Ab-IC50 (nM) |
| 6G11-TG1-vcMMAD | | | 0.379 | 2.525 | | |
| 7E6-TG1-vcMMAD | 2.320 | 15.467 | 0.152 | 1.011 | 14.180 | 94.533 |
| h7E6-WT-TG1-vcMMAD | 1.956 | 13.040 | 0.445 | 2.969 | 10.330 | 68.867 |
| h7E6-L-TG1-vcMMAD | 2.027 | 13.513 | 0.082 | 0.549 | 8.535 | 56.900 |
| h7E6-N-TG1-vcMMAD | 2.021 | 13.473 | 0.100 | 0.668 | 11.150 | 74.333 |
| h7E6-SVG-TG1-vcMMAD | 1.659 | 11.060 | 0.118 | 0.787 | 10.680 | 71.200 |
| h7E6-SVGL-TG1-vcMMAD | 2.440 | 16.267 | 0.052 | 0.345 | 10.800 | 72.000 |
| h7E6-SVGN-TG1-vcMMAD | 2.009 | 13.393 | 0.083 | 0.552 | 10.410 | 69.400 |
| NNC-TG1-vcMMAD | | | 22.790 | 151.933 | 22.990 | 153.267 |
| 7E6-TG1-vcMMAD | | | | | 24.180 | 161.200 |
| h7E6-SVG-TG1-vcMMAD | | | | | 25.310 | 168.733 |
| 7E6-TG6-AcLys-vc-PABC-MMAD | | | | | | |
| 7E6-K222R-LCQ3-AcLys-vc-PABC-MMAD | | | | | | |
| h7E6SVG-TG6-AcLys-vc-PABC-MMAD | | | 0.209 | 1.393 | | |
| h7E6SVG-K222R-LCQ3-AcLys-vc-PABC-MMAD | | | 2.681 | 17.873 | | |

Example 10

Anti-Trop-2 7E6 Auristatin Conjugate Induced Long Term Tumor Regression in BxPC3 Xenograft Model In vivo efficacy studies of control antibody hIgG1-TG1-vcMMAD ("NNCTG1-vcMMAD") and chimeric anti-Trop-2 antibody 7E6 conjugated with 1) LCQ03-AcLys-vc-PABC-MMAD K222R variant or 2) TG6-AcLys-vc-PABC-MMAD via transglutaminase were performed with target-expressing BxPC3 xenograft model. For h7E6-K222R-LCQ03-AcLys-vc-PABC-MMAD variant conjugate, the wild-type amino acid lysine in the anti-Trop-2 antibody is substituted with amino acid arginine (i.e., K222R) at position 222 in accordance with Kabat numbering scheme. LCQ03 corresponds to SEQ ID NO:78 (GGLLQGG), and TG6 corresponds to SEQ ID NO:79 (LLQGA). General method of conjugating Trop-2 antibodies using transglutaminase tags LCQ03 and TG6 is described in Example 9. Two million BxPC3 cancer cells were implanted subcutaneously into 5-8 weeks old CB17 SCID mice until the tumor sizes reached around 250 mm$^3$. Animals were randomized by tumor sizes, and dosing was done through bolus tail vein injection. 3 mg/kg of control hIgG1, chimeric h7E6-K222R-LCQ03-AcLys-vc-PABC-MMAD variant, or chimeric 7E6-TG6-AcLys-vc-PABC-MMAD were administered through bolus tail vein injection once for total of 1 dose. Tumor volume was measured once a week by a Caliper device and calculated with the following formula: Tumor volume=(length×width2)/2. Studies were terminated before their tumor volumes reached 2000 mm$^3$. Single dose of the chimeric anti-Trop-2 antibody 7E6 conjugated with AcLys-vc-PABC-MMAD resulted in long term tumor regression. See FIG. 8.

Example 11

Cytotoxicity of Anti-Trop-2-ADCs in Trop-2 Positive Cells

Negative control (NNC) and humanized anti-Trop-2 (h7E6SVG) antibodies were expressed as human IgG1 subtypes engineered with glutamine-containing transglutaminase tags at the C-terminus of heavy chain (TG6 (SEQ ID NO: 79)), light chain (LCQ03 (SEQ ID NO: 78) and LCQ04 (SEQ ID NO: 79)) or with N297Q/K222R mutations in the CH2/Hinge domains of heavy chain and conjugated with AcLys-vc-PABC-0101 ("vc0101" or Acetyl-lysine-valine-citrulline-p-aminobenzyloxycarbonyl-(2-methylalanyl-N-[(3R,4S,5S)-3-methoxy-1-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-5-methyl-1-oxoheptan-4-yl]-N-methyl-L-valinamide)) or aminocaproyl-PEG6 (Propylene Glycol)$_6$-propionyl)-MMAD as indicated. 2-methylalanyl-N-[(3R,4S,5S)-3-methoxy-1-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-5-methyl-1-oxoheptan-4-yl]-N-methyl-L-valinamide is a novel auristatin, as described in U.S. Application Nos: 61/561,255 and 61/676,423. Method of conjugating Trop-2 antibodies using transglutaminase tags is described in Example 9. Target expressing or non-expressing (SW620) cells were seeded on white walled clear bottom plates at 2000 (A431, BxPC3, NCI-H292, NCI-H1650, MDA-MB-468 and SW620), 2500 (Calu-3) or 3000 (OVCAR3 and SKBR3) cells per well for 24 hours before treatment. Cells were treated with 4 fold serially diluted antibody-drug conjugates in triplicates. Cell viability was determined by CellTiter-Glo® Luminescent Cell Viability Assay 96 (Promega, Madison, Wis.) 96 hours after treatment. Relative cell viability was determined as percentage of untreated control. IC50 was calculated by GraphPad Prism 5 software and expressed as concentration (nM) of total Ab. Table 13 shows that humanized anti-Trop-2 7E6 antibodies conjugated to vc0101 or PEG6-MMAD through transglutaminase tag exert potent cell killing activity in Trop-2 expressing cells.

Example 12

Anti-Trop-2 7E6 Auristatin Conjugate Induced Tumor Regression in Pancreatic Tumor BxPC3 Xenograft Model In vivo efficacy studies of Trop-2 ADCs were performed with target-expressing BxPC3 xenograft model. Two million BxPC3 pancreatic cancer cells were implanted subcutaneously into 5-8 weeks old CB17/SCID mice until the tumor sizes reached between 300-400 mm³. Animals were randomized by tumor sizes, and single dose of humanized anti-Trop2 antibody conjugated with 1) TG6-AcLys-vc-PABC-0101 (equivalent to TG6-AcLys-vc-0101 as depicted in FIG. 9A); 2) N297Q/K222R-PEG6-MMAD ((Propylene Glycol)-6-propionyl-MMAD); and 3) LCQ04-K222R-vc-PABC0101 (equivalent to LCQ04/K222R-vc0101 as depicted in FIG. 9C); LCQ04 corresponds to SEQ ID NO: 79 (LLQGA)) and control conjugates were administered through bolus tail vein injection. Tumor volume was measured once a week by a Caliper device and calculated with the following formula: Tumor volume=(length×width²)/2. Studies were terminated before their tumor volumes reached 2000 mm³. FIGS. 9A-9C show that a single dose of the humanized anti-Trop2 antibody conjugated with 1) TG6-AcLys-vc-PABC-0101; 2) N297Q/K222R-PEG6-MMAD; and 3) LCQ04-K222R-vc-PABC0101 resulted in tumor regression in pancreatic tumor BxPC3 xenograft model.

Example 13

Anti-Trop-2 7E6 Auristatin Conjugate Induced Tumor Regression in Colorectal Tumor Colo205 Xenograft Model In vivo efficacy study of Trop-2 ADCs was performed with target-expressing colo205 xenograft model. Three millions of colo205 colon cancer cells were implanted subcutaneously

TABLE 13

| Cell name | Cell type | Trop2 expression | h7E6SVG-TG6-vc0101 Ab IC50 (nM) | h7E6SVG-N297Q/K222R-PEG6MMAD Ab IC50 (nM) | h7E6SVG-LCQ03/K222R-vc0101 Ab IC50 (nM) | h7E6SVG-LCQ04/K222R-vc0101 Ab IC50 (nM) | NNC-TG6-vc0101 Ab IC50 (nM) | NNC-N297Q/K222R-PEG6MMAD Ab IC50 (nM) |
|---|---|---|---|---|---|---|---|---|
| A431 | Epidermoid carcinoma | +++ | 0.12 | 0.07 | 0.03 | | | >267 |
| BxPCS | Pancreas adenocarcinoma | ++ | 0.32 | 0.03 | 0.13 | 0.11 | | |
| NCI-H292 | Mucoepidermoid pulmonary carcinoma | ++ | 0.63 | 0.03 | | 1.84 | | |
| Calu-3 | Lung adenocarcinoma | ++ | 0.53 | 0.50 | | 1.51 | | |
| NCI-H1650 | Lung bronchoalveolar carcinoma | ++ | 1.92 | 0.38 | | | >267 | >267 |
| OVCAR3 | Ovary adenocarcinoma | +++ | 0.56 | 0.98 | | | 168.5 | >267 |
| MDA-MB-468 | Mammary adenocarcinoma | ++ | 0.77 | 0.19 | | | >267 | >267 |
| SKBR3 | Mammary adenocarcinoma | +/++ | 0.42 | 0.08 | | | 200.5 | >267 |
| Colo205 | Colorectal adenocarcinoma | + | 32.89 | 21.15 | 174.50 | | | |
| SW620 | Colorectal adenocarcinoma | | 156.20 | >267 | >267 | >267 | >267 | >267 | into 5-8 weeks old nu/nu mice until the tumor sizes reached ~300 mm³. Animals were randomized by tumor sizes, and single dose of 6 mg/kg humanized anti-Trop2 antibody conjugated with 1) TG6-AcLys-vc-PABC-0101 (equivalent to TG6-vc-0101 as depicted in FIG. 10); and 2) LCQ03-vc-PABC-0101 having K222R substitution in the hinge/CH2 domains of heavy chain (equivalent to LCQ03/K222R-vc0101 as depicted in FIG. 10; LCQ03 corresponds to SEQ ID NO: 78 (GGLLQGG)); and control conjugate (IgG-vc-PABC-0101) were administered through bolus tail vein injection. Tumor volume is measured once a week by a Caliper device and calculated with the following formula: Tumor volume=(length×width²)/2. Studies were terminated before their tumor volumes reached 2000 mm³. FIG. 10 shows that a single dose of the humanized anti-Trop2 antibody conjugated with 1) TG6-AcLys-vc-PABC-0101; and 2) LCQ03-vc-PABC-0101 having K222R substitution in the hinge/CH2 domains of heavy chain resulted in tumor regression in colorectal tumor Colo205 xenograft model.

Example 14

Anti-Trop-2 7E6 Auristatin Conjugate Induced Tumor Regression in Ovarian PDX Ova196756 Xenograft Model In vivo efficacy study of Trop-2 ADC using humanized anti-Trop2 antibody (h7E6SVG) conjugated with TG6-vc-0101 was performed with target-expressing ovarian cancer patient derived xenograft model (PDX Ova196756). This tumor sample was derived from surgical specimen and propagated in NSG mice (Jackson Laboratories, Bar Harbor, Me.). For efficacy studies, approximately 1-2 mm³ of tumor fragments were implanted subcutaneously into the lateral flanks of CB17/SCID mice. Animals were randomized by tumor sizes once they reached ~400 mm³, and a single dose of h7E6SVG-TG6-AcLys-vc-PABC-0101 (0.75 mg/kg and 1.5 mg/kg; equivalent to TG6-vc0101 as depicted in FIG. 11) and control conjugate (1.5 mg/kg; IgG-vc-PABC-0101 or IgG-vc0101 as depicted in FIG. 11) were administered through bolus tail vein injection. Tumor volume was measured once a week by a caliper device and calculated with the following formula: Tumor volume=(length×width²)/2. Studies were terminated before their tumor volumes reached 2000 mm³. FIG. 11 shows that a single dose of the humanized anti-Trop2 antibody conjugated with TG6-AcLys-vc-PABC-0101 resulted in tumor regression in ovarian PDX Ova196756 xenograft model.

Example 15

Anti-Trop-2 7E6 Auristatin Conjugate Shows Superior Efficacy Than Gemcitabine to Induce Tumor Regression in Pan0146 Pancreatic PDX Model In vivo efficacy studies of Trop-2 ADC using humanized anti-Trop-2 antibody (h7E6SVG) conjugated with TG6-vc0101 were performed with target-expressing pancreatic cancer patient derived xenograft model (PDX Pan0146) from Jackson Laboratories (Bar Harbor, Me.). For efficacy studies, 1-2 mm³ of tumor fragments were implanted subcutaneously into the lateral flanks of the animals. Animals were randomized by tumor sizes once they reached ~300 mm³, and h7E6SVG-TG6-AcLys-vc-PABC-0101 and the control conjugate were administered through bolus tail vein injection. FIG. 12A: Single dose of h7E6SVG-TG6-AcLys-vc-PABC-0101 (shown as h7E6SVG-TG6-vc0101 in the Figure) and control conjugate were given at doses indicated. Gemcitabine was given at 75 mg/kg twice weekly for a total of 6 doses. FIG. 12B: h7E6SVG-TG6-AcLys-vc-PABC-0101 was given at 0.75 mg/kg weekly for 4 doses, 1.5 mg/kg bi-weekly for two doses or 3.0 mg/kg single dose. Gemcitabine was given once weekly at 75 mg/kg for 4 doses. Tumor volume was measured once a week by a Caliper device and calculated with the following formula: Tumor volume=(length×width²)/2. Studies were terminated before their tumor volumes reached 2000 mm³. The data show that the humanized anti-Trop2 antibody conjugated with TG6-AcLys-vc-PABC-0101 has superior efficacy to gemcitabine to induce tumor regression in Pan0146 pancreatic PDX model and that continuous dosing of h7E6SVG-TG6-AcLys-vc-PABC-0101 resulted in sustained tumor regression in pancreatic PDX Pan0146 xenograft model.

Example 16

Anti-Trop-2 7E6 Auristatin Conjugate Induces Tumor Regression in Pancreatic Pan144607 PDX Model In vivo efficacy study of Trop-2 ADC using humanized anti-Trop-2 antibody (h7E6SVG) conjugated with vc0101 or PEG6MMAD was performed with target-expressing pancreatic cancer patient derived xenograft model (PDX Pan144607). This tumor sample was derived from surgical specimen and propagated in NSG mice (Jackson Laboratories, Bar Harbor, Me.). For efficacy studies, approximately 1-2 mm³ of tumor fragments were implanted subcutaneously into the lateral flanks of CB17/SCID mice. Animals were randomized by tumor sizes once they reached ~300 mm³, and single dose of 1.5, 3.0 and 6.0 mg/kg h7E6SVG-N297Q/K222R-PEG6MMAD and the control conjugate were administered through bolus tail vein injection. Tumor volume was measured once a week by a Caliper device and calculated with the following formula: Tumor volume=(length×width²)/2. Studies were terminated before their tumor volumes reach 2000 mm³. FIG. 13 shows that a single dose of the humanized anti-Trop2 antibody conjugated with PEG6-MMAD resulted in tumor regression in pancreatic Pan144607 PDX model.

Example 17

Anti-Trop-2 7E6 Auristatin Conjugate Induces Tumor Regression in Pancreatic Pan0135 PDX Model In vivo efficacy study of Trop-2 ADC using humanized anti-Trop-2 antibody (h7E6SVG) conjugated with PEG6MMAD was performed with target-expressing pancreatic cancer patient derived xenograft model (PDX Pan0135) from Jackson Laboratories. For efficacy studies, approximately 1-2 mm³ of tumor fragments were implanted subcutaneously into the lateral flanks of the animals. Animals were randomized by tumor sizes once they reached ~300 mm³ and 6 mg/kg of h7E6SVG-N297Q/K222R-PEG6MMAD and the control conjugate were administered through bolus tail vein injection with single dose. Tumor volume was measured once a week by a Caliper device and calculated with the following formula: Tumor volume=(length×width²)/2. Studies were terminated before their tumor volumes reached 2000 mm³. FIG. 14 shows that a single dose of the humanized anti-Trop2 antibody conjugated with PEG6-MMAD resulted in tumor regression in pancreatic Pan0135 PDX model.

Example 18

Antibody Binding Affinity Determination for Humanized Anti-Trop-2 Antibodies Analysis of Fab/human Trop2-ECD (Extracellular Domain) interactions was performed using a Bio-Rad Proteon XPR36Surface Plasmon Resonance (SPR) biosensor (Bio-Rad, Hercules, Calif.) equipped with a GLC sensor chip. The assay temperature was 25° C., and the assay buffer was 10 mM Sodium Phosphate, 150 mM NaCl, 0.05% Tween-20, pH 7.4. An array of amine-coupled Fabs was prepared using the methodology described in Abdiche et al. (Anal. Biochem., 411: 139-151 (2011)). In each analysis cycle, monovalent human Trop2-ECD antigen was flowed at 30 µL/min over the immobilized Fabs for 3 minutes followed by a buffer wash for 15 minutes to monitor dissociation of the Fab/Trop2 complex. The sensor surface was regenerated between analysis cycles, using three 18-second injections of a 2:1 mixture (by volume) of Pierce IgG Elution buffer:4 M NaCl (Pierce, Rockford, Ill.). Binding and regeneration cycles were repeated at human Trop2-ECD concentrations of 6, 30 and 150 nM. The resulting data were fit to a 1:1 Langmuir binding model using the Proteon evaluation software. The results appear in the table below.

TABLE 14

| Sequence | $k_a$ (1/Ms) | $k_d$ (1/s) | $t_{1/2}$ (min) | $K_D$ (nM) |
| --- | --- | --- | --- | --- |
| DG (h7E6_SVG) | 1.7E+05 | 6.9E−04 | 17 | 4.1 |
| DK (h7E6_SVG20) | <1.7E+05 | 1.3E−02 | 0.88 | >75 |
| DA (h7E6_SVG22) | <1.8E+05 | 1.3E−02 | 0.86 | >75 |

TABLE 14-continued

| Sequence | $k_a$ (1/Ms) | $k_d$ (1/s) | $t_{1/2}$ (min) | $K_D$ (nM) |
| --- | --- | --- | --- | --- |
| DL (h7E6_SVG28) | <2.1E+05 | 1.6E−02 | 0.72 | >75 |
| DE (h7E6_SVG30) | <8.5E+05 | 6.4E−02 | 0.18 | >75 |
| DS (h7E6_SVG19) | <6.0E+05 | 4.5E−02 | 0.26 | >75 |

Although the disclosed teachings have been described with reference to various applications, methods, kits, and compositions, it will be appreciated that various changes and modifications can be made without departing from the teachings herein and the claimed invention below. The foregoing examples are provided to better illustrate the disclosed teachings and are not intended to limit the scope of the teachings presented herein. While the present teachings have been described in terms of these exemplary embodiments, the skilled artisan will readily understand that numerous variations and modifications of these exemplary embodiments are possible without undue experimentation. All such variations and modifications are within the scope of the current teachings.

All references cited herein, including patents, patent applications, papers, text books, and the like, and the references cited therein, to the extent that they are not already, are hereby incorporated by reference in their entirety. In the event that one or more of the incorporated literature and similar materials differs from or contradicts this application, including but not limited to defined terms, term usage, described techniques, or the like, this application controls.

The foregoing description and Examples detail certain specific embodiments of the invention and describes the best mode contemplated by the inventors. It will be appreciated, however, that no matter how detailed the foregoing may appear in text, the invention may be practiced in many ways and the invention should be construed in accordance with the appended claims and any equivalents thereof.

It is claimed:

1. An isolated antibody, or an antigen binding fragment thereof, which specifically binds to trophoblast cell-surface antigen-2 (Trop-2), wherein the antibody comprises
(a) a heavy chain variable (VH) region comprising (i) a VH complementary determining region one (CDR1) comprising the sequence SYGVH (SEQ ID NO: 30), GGSISSY (SEQ ID NO: 36), or GGSISSYGVH (SEQ ID NO: 37); (ii) a VH CDR2 comprising the sequence VIWTX$_1$GX$_2$TDYNSALMX$_3$, wherein X$_1$ is G or S; X$_2$ is S or V; X$_3$ is S or G (SEQ ID NO: 49), or WTX$_1$GX$_2$, wherein X$_1$ is G or S, X$_2$ is S or V (SEQ ID NO: 50); and iii) a VH CDR3 comprising the sequence DGDYDRYT-MDY (SEQ ID NO: 35); and (b) a light chain variable region (VL) comprising (i) a VL CDR1 comprising the sequence RASKSVSTSX$_1$YSYMH, wherein X$_1$ is G, L, or N (SEQ ID NO: 63); (ii) a VL CDR2 comprising the sequence LASNLES (SEQ ID NO: 55); and (iii) a VL CDR3 comprising the sequence QHSRELPYT (SEQ ID NO: 56).

2. An isolated antibody, or an antigen binding fragment thereof, which specifically binds to Trop-2, wherein the antibody comprises:
a VH region comprising VH CDR1, VH CDR2, and VH CDR3 of the VH sequence shown in SEQ ID NO: 4 or 5; and
a VL region comprising VL CDR1, VL CDR2, and VL CDR3 of the VL sequence shown in SEQ ID NO:3, 6, or 7.

3. The antibody or the antigen binding fragment of claim 2, wherein the VH region comprises (i) a VH CDR1 comprising the sequence SYGVH (SEQ ID NO: 30), GGSISSY (SEQ ID NO: 36), or GGSISSYGVH (SEQ ID NO: 37); (ii) a VH CDR2 comprising the sequence VIWTSGVTDYNSALMG (SEQ ID NO: 38) or WTSGV (SEQ ID NO: 39); and (iii) a VH CDR3 comprising the sequence DGDYDRYTMDY (SEQ ID NO: 35), and wherein the VL region comprises (i) a VL CDR1 comprising the sequence RASKSVSTS-GYSYMH (SEQ ID NO: 54); (ii) a VL CDR2 comprising the sequence LASNLES (SEQ ID NO: 55); and (iii) a VL CDR3 comprising the sequence QHSRELPYT (SEQ ID NO: 56).

4. The antibody or the antigen binding fragment of claim 3, wherein the VH region comprises the sequence shown in SEQ ID NO: 5 or a variant with one or several conservative amino acid substitutions in residues that are not within a CDR and the VL region comprises the amino acid sequence shown in SEQ ID NO: 3 or a variant thereof with one or several amino acid substitutions in amino acids that are not within a CDR.

5. The antibody or the antigen binding fragment of claim 4, wherein the antibody comprises a light chain comprising the sequence shown in SEQ ID NO: 66 and a heavy chain comprising the sequence shown in SEQ ID NO: 65.

6. The antibody or the antigen binding fragment of claim 3, wherein the antibody comprises a VH region produced by the expression vector with ATCC Accession No. PTA-12872.

7. The antibody or the antigen binding fragment of claim 3, wherein the antibody comprises a VL region produced by the expression vector with ATCC Accession No. PTA-12871.

8. The antibody of claim 1, wherein the antibody comprises an acyl donor glutamine-containing tag engineered at a specific site.

9. The antibody of claim 8, wherein the tag comprises an amino acid sequence GGLLQGG (SEQ ID NO: 78), LLQGA (SEQ ID NO:79), or LLQ.

10. The antibody of claim 9, wherein the antibody further comprises an amino acid modification at position K222, K340, or K370.

11. The antibody of claim 10, wherein the amino acid modification is a substitution from lysine to arginine.

12. A conjugate of the antibody or the antigen binding fragment of claim 1, wherein the antibody or the antigen binding fragment is conjugated to an agent, wherein the agent is selected from the group consisting of a cytotoxic agent, an immunomodulating agent, an imaging agent, a therapeutic protein, a biopolymer, and an oligonucleotide.

13. The conjugate of claim 12, wherein the agent is a cytotoxic agent.

14. The conjugate of claim 13, wherein the cytotoxic agent is MMAD (Monomethyl Auristatin D) or 0101 (2-methylalanyl-N-[(3R,4S,5S)-3-methoxy-1-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-5-methyl-1-oxoheptan-4-yl]-N-methyl-L-valinamide).

15. The conjugate of claim 14, wherein the conjugate comprises the formula: antibody-(acyl donor glutamine-containing tag)-(linker)-(cytotoxic agent).

16. The conjugate of claim 15, wherein the acyl donor glutamine-containing tag comprises an amino acid sequence GGLLQGG (SEQ ID NO: 78), LLQGA (SEQ NO: 79), LLQ, or LLQX$_1$X$_2$X$_3$X$_4$X$_5$, wherein X$_1$ is G or P, wherein X$_2$ is A, G, P, or absent, wherein X$_3$ is A, G, K, P, or absent, wherein X$_4$ is G, K, or absent, and wherein X$_5$ is K or absent (SEQ ID NO: 88), and wherein the linker comprises acetyl-lysine-valine-citrulline-p-aminobenzyloxycarbonyl or amino-PEG6-propionyl.

17. The conjugate of claim 16, wherein the conjugate is selected from the group consisting of 1) antibody-LLQGA (SEQ ID NO: 79)-(acetyl-lysine-valine-citrulline-p-aminobenzyloxycarbonyl (AcLys-VC-PABC))-0101; 2) antibody-LLQGA (SEQ ID NO: 79)-(AcLys-VC-PABC)-MMAD; 3) antibody-LLQX$_1$X$_2$X$_3$X$_4$X$_5$ (SEQ ID NO: 88)-(AcLys-VC-PABC)-0101; 4) antibody-LLQX$_1$X$_2$X$_3$X$_4$X$_5$ (SEQ ID NO: 88)-(AcLys-VC-PABC)-MMAD; 5) antibody-GGLLQGG (SEQ ID NO: 78)-(AcLys-VC-PABC)-0101; and 6) antibody-GGLLQGG (SEQ ID NO: 78)-(AcLys-VC-PABC)-MMAD.

18. The conjugate of claim 17, wherein the conjugate 1) antibody-GGLLQGG (SEQ ID NO: 78)-(AcLys-VC-PABC)-0101; 2) antibody-GGLLQGG (SEQ ID NO: 78)-(AcLys-VC-PABC)-MMAD; 3) antibody-LLQX$_1$X$_2$X$_3$X$_4$X$_5$ (SEQ ID NO: 88)-(AcLys-VC-PABC)-0101; 4) antibody-LLQX$_1$X$_2$X$_3$X$_4$X$_5$ (SEQ ID NO: 88)-(AcLys-VC-PABC)-MMAD; 5) antibody-LLQGA (SEQ ID NO: 79)-(AcLys-VC-PABC)-0101; or 6) antibody-LLQGA (SEQ ID NO: 79)-AcLys-VC-PABC-MMAD comprises an amino acid substitution from lysine to arginine at position 222 of the antibody.

19. The conjugate of claim 17, wherein the conjugate is 1) antibody-LLQGA (SEQ ID NO: 79)-(AcLys-VC-PABC)-0101; 2) antibody-LLQGA (SEQ ID NO: 79)-AcLys-VC-PABC-MMAD; 3) antibody-LLQX$_1$X$_2$X$_3$X$_4$X$_5$ (SEQ ID NO: 88)-(AcLys-VC-PABC)-0101; or 4) antibody-LLQX$_1$X$_2$X$_3$X$_4$X$_5$ (SEQ ID NO: 88)-(AcLys-VC-PABC)-MMAD; and wherein the amino acid lysine at the C-terminus of heavy chain of the antibody is deleted.

20. The conjugate of claim 14, wherein the conjugate comprises amino acid substitutions at position N297Q and K222R of the antibody, a linker comprising amino-PEG6-propionyl, and a cytotoxic agent comprising MMAD.

21. A pharmaceutical composition comprising a therapeutically effective amount of the antibody of claim 1 or the conjugate of claim 12 and a pharmaceutically acceptable carrier.

22. A method of treating a cancer expressing Trop-2 in a subject comprising administering to a subject in need thereof an effective amount of the pharmaceutical composition of claim 21.

23. The method of claim 22, wherein the cancer is selected from the group consisting of bladder, breast, cervical, choriocarcinoma, colon, esophageal, gastric, glioblastoma, head and neck, kidney, lung, oral, ovarian, pancreatic, prostate, and skin cancer.

24. A method of inhibiting tumor growth or progression in a subject who has a Trop-2 expressing tumor, comprising administering to the subject in need thereof an effective amount of the pharmaceutical composition of claim 21 to the subject.

25. A method of inhibiting metastasis of Trop-2 expressing cancer cells in a subject, comprising administering to the subject in need thereof an effective amount of the pharmaceutical composition of claim 21 to the subject.

26. A method of inducing tumor regression in a subject who has a Trop-2 expressing tumor, comprising administering to the subject in need thereof an effective amount of the pharmaceutical composition of claim 21 to the subject.

* * * * *

```
                         SEQUENCE LISTING

<160> NUMBER OF SEQ ID NOS: 130

<210> SEQ ID NO 1
<211> LENGTH: 111
<212> TYPE: PRT
<213> ORGANISM: Artificial Sequence
<220> FEATURE:
<223> OTHER INFORMATION: Synthetic Construct

<400> SEQUENCE: 1

Asp Ile Val Leu Thr Gln Ser Pro Ala Ser Leu Ala Val Ser Leu Gly
1               5                   10                  15

Gln Arg Ala Thr Ile Ser Cys Arg Ala Ser Lys Ser Val Ser Thr Ser
            20                  25                  30

Gly Tyr Ser Tyr Met His Trp Tyr Gln Gln Lys Pro Gly Gln Pro Pro
        35                  40                  45

Lys Leu Leu Ile Tyr Leu Ala Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln His Ser Arg
                85                  90                  95

Glu Leu Pro Tyr Thr Phe Gly Gly Gly Thr Lys Leu Glu Ile Lys
            100                 105                 110
```

```
<210> SEQ ID NO 2
<211> LENGTH: 119
<212> TYPE: PRT
<213> ORGANISM: Artificial Sequence
<220> FEATURE:
<223> OTHER INFORMATION: synthetic construct

<400> SEQUENCE: 2

Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Thr Ser Tyr
            20                  25                  30

Gly Val His Trp Val Arg Gln Pro Pro Gly Lys Gly Leu Glu Trp Leu
        35                  40                  45

Gly Val Ile Trp Thr Gly Gly Ser Thr Asp Tyr Asn Ser Ala Leu Met
    50                  55                  60

Ser Arg Leu Ser Ile Asn Lys Asp Asn Ser Lys Ser Gln Val Phe Leu
65                  70                  75                  80

Lys Met Asn Ser Leu Gln Thr Asp Asp Thr Ala Met Tyr Tyr Cys Ala
                85                  90                  95

Arg Asp Gly Asp Tyr Asp Arg Tyr Thr Met Asp Tyr Trp Gly Gln Gly
            100                 105                 110

Thr Ser Val Thr Val Ser Ser
        115

<210> SEQ ID NO 3
<211> LENGTH: 111
<212> TYPE: PRT
<213> ORGANISM: Artificial Sequence
<220> FEATURE:
<223> OTHER INFORMATION: Synthetic construct

<400> SEQUENCE: 3

Asp Ile Val Met Thr Gln Ser Pro Asp Ser Leu Ala Val Ser Leu Gly
1               5                   10                  15

Glu Arg Ala Thr Ile Asn Cys Arg Ala Ser Lys Ser Val Ser Thr Ser
            20                  25                  30

Gly Tyr Ser Tyr Met His Trp Tyr Gln Gln Lys Pro Gly Gln Pro Pro
        35                  40                  45

Lys Leu Leu Ile Tyr Leu Ala Ser Asn Leu Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln His Ser Arg
                85                  90                  95

Glu Leu Pro Tyr Thr Phe Gly Gln Gly Thr Lys Leu Glu Ile Lys
            100                 105                 110

<210> SEQ ID NO 4
<211> LENGTH: 119
<212> TYPE: PRT
<213> ORGANISM: Artificial Sequence
<220> FEATURE:
<223> OTHER INFORMATION: Synthetic construct

<400> SEQUENCE: 4

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
```

```
                20                  25                  30
Gly Val His Trp Ile Arg Gln Pro Pro Gly Lys Gly Leu Glu Trp Ile
            35                  40                  45

Gly Val Ile Trp Thr Gly Gly Ser Thr Asp Tyr Asn Ser Ala Leu Met
        50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Asp Gly Asp Tyr Asp Arg Tyr Thr Met Asp Tyr Trp Gly Gln Gly
                100                 105                 110

Thr Leu Val Thr Val Ser Ser
            115

<210> SEQ ID NO 5
<211> LENGTH: 119
<212> TYPE: PRT
<213> ORGANISM: Artificial Sequence
<220> FEATURE:
<223> OTHER INFORMATION: Synthetic construct

<400> SEQUENCE: 5

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
                20                  25                  30

Gly Val His Trp Ile Arg Gln Pro Pro Gly Lys Gly Leu Glu Trp Ile
            35                  40                  45

Gly Val Ile Trp Thr Ser Gly Val Thr Asp Tyr Asn Ser Ala Leu Met
        50                  55                  60

Gly Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Asp Gly Asp Tyr Asp Arg Tyr Thr Met Asp Tyr Trp Gly Gln Gly
                100                 105                 110

Thr Leu Val Thr Val Ser Ser
            115

<210> SEQ ID NO 6
<211> LENGTH: 111
<212> TYPE: PRT
<213> ORGANISM: Artificial Sequence
<220> FEATURE:
<223> OTHER INFORMATION: Synthetic construct

<400> SEQUENCE: 6

Asp Ile Val Met Thr Gln Ser Pro Asp Ser Leu Ala Val Ser Leu Gly
1               5                   10                  15

Glu Arg Ala Thr Ile Asn Cys Arg Ala Ser Lys Ser Val Ser Thr Ser
                20                  25                  30

Leu Tyr Ser Tyr Met His Trp Tyr Gln Gln Lys Pro Gly Gln Pro Pro
            35                  40                  45

Lys Leu Leu Ile Tyr Leu Ala Ser Asn Leu Glu Ser Gly Val Pro Asp
        50                  55                  60

Arg Phe Ser Gly Ser Gly Ser Gly Thr Asp Phe Thr Leu Thr Ile Ser
65                  70                  75                  80
```

```
Ser Leu Gln Ala Glu Asp Val Ala Val Tyr Tyr Cys Gln His Ser Arg
                85                  90                  95

Glu Leu Pro Tyr Thr Phe Gly Gln Gly Thr Lys Leu Glu Ile Lys
            100                 105                 110

<210> SEQ ID NO 7
<211> LENGTH: 111
<212> TYPE: PRT
<213> ORGANISM: Artificial Sequence
<220> FEATURE:
<223> OTHER INFORMATION: Synthetic construct

<400> SEQUENCE: 7

Asp Ile Val Met Thr Gln Ser Pro Asp Ser Leu Ala Val Ser Leu Gly
1               5                   10                  15

Glu Arg Ala Thr Ile Asn Cys Arg Ala Ser Lys Ser Val Ser Thr Ser
            20                  25                  30

Asn Tyr Ser Tyr Met His Trp Tyr Gln Gln Lys Pro Gly Gln Pro Pro
        35                  40                  45

Lys Leu Leu Ile Tyr Leu Ala Ser Asn Leu Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln His Ser Arg
                85                  90                  95

Glu Leu Pro Tyr Thr Phe Gly Gln Gly Thr Lys Leu Glu Ile Lys
            100                 105                 110

<210> SEQ ID NO 8
<211> LENGTH: 107
<212> TYPE: PRT
<213> ORGANISM: Artificial Sequence
<220> FEATURE:
<223> OTHER INFORMATION: Synthetic construct

<400> SEQUENCE: 8

Asp Ile Leu Leu Thr Gln Ser Pro Ala Ile Leu Ser Val Ser Pro Gly
1               5                   10                  15

Glu Arg Val Ser Phe Ser Cys Arg Ala Ser Gln Thr Ile Gly Thr Ser
            20                  25                  30

Ile His Trp Tyr Gln Gln Arg Thr Asn Gly Ser Pro Arg Leu Leu Ile
        35                  40                  45

Lys Tyr Ala Ser Glu Ser Ile Ser Gly Ile Pro Ser Arg Phe Ser Gly
    50                  55                  60

Ser Gly Ser Gly Thr Asp Phe Thr Leu Ser Ile Asn Ser Val Glu Ser
65                  70                  75                  80

Glu Asp Ile Ala Asp Tyr Tyr Cys Gln Gln Ser Asn Ser Trp Pro Phe
                85                  90                  95

Thr Phe Gly Ser Gly Thr Lys Leu Glu Ile Lys
            100                 105

<210> SEQ ID NO 9
<211> LENGTH: 115
<212> TYPE: PRT
<213> ORGANISM: Artificial Sequence
<220> FEATURE:
<223> OTHER INFORMATION: Synthetic construct

<400> SEQUENCE: 9

Gln Val Gln Leu Gln Gln Pro Gly Ala Glu Leu Val Arg Pro Gly Ala
```

```
  1               5                  10                 15
Ser Val Lys Leu Ser Cys Lys Ala Ser Gly Tyr Thr Phe Thr Ser Tyr
                20                  25                 30

Trp Ile Asn Trp Val Lys Gln Arg Pro Gly His Gly Leu Glu Trp Ile
                35                  40                 45

Gly Asn Ile Tyr Pro Ser Asp Ser Tyr Ser Asn Tyr Asn Gln Lys Phe
                50                  55                 60

Lys Asp Lys Ala Thr Leu Thr Val Asp Lys Ser Ser Ser Thr Ala Tyr
65                  70                  75                 80

Met Gln Val Ser Ser Pro Thr Ser Glu Asp Ser Ala Val Tyr Tyr Cys
                85                  90                 95

Thr Tyr Gly Ser Ser Phe Asp Tyr Trp Gly Gln Gly Thr Thr Val Thr
                100                 105                110

Val Ser Ser
        115
```

<210> SEQ ID NO 10
<211> LENGTH: 107
<212> TYPE: PRT
<213> ORGANISM: Artificial Sequence
<220> FEATURE:
<223> OTHER INFORMATION: Synthetic construct

<400> SEQUENCE: 10

```
Glu Ile Val Leu Thr Gln Ser Pro Ala Thr Leu Ser Leu Ser Pro Gly
1               5                  10                 15

Glu Arg Ala Thr Leu Ser Cys Arg Ala Ser Gln Thr Ile Gly Thr Ser
                20                  25                 30

Ile His Trp Tyr Gln Gln Lys Pro Gly Gln Ala Pro Arg Leu Leu Ile
                35                  40                 45

Tyr Tyr Ala Ser Glu Ser Ile Ser Gly Ile Pro Ala Arg Phe Ser Gly
                50                  55                 60

Ser Gly Ser Gly Thr Asp Phe Thr Leu Thr Ile Ser Ser Leu Glu Pro
65                  70                  75                 80

Glu Asp Phe Ala Val Tyr Tyr Cys Gln Gln Ser Asn Ser Trp Pro Phe
                85                  90                 95

Thr Phe Gly Gln Gly Thr Lys Leu Glu Ile Lys
                100                 105
```

<210> SEQ ID NO 11
<211> LENGTH: 115
<212> TYPE: PRT
<213> ORGANISM: Artificial Sequence
<220> FEATURE:
<223> OTHER INFORMATION: Synthetic construct

<400> SEQUENCE: 11

```
Gln Val Gln Leu Val Gln Ser Gly Ala Glu Val Lys Lys Pro Gly Ala
1               5                  10                 15

Ser Val Lys Val Ser Cys Lys Ala Ser Gly Tyr Thr Phe Thr Ser Tyr
                20                  25                 30

Trp Ile Asn Trp Val Arg Gln Ala Pro Gly Gln Gly Leu Glu Trp Met
                35                  40                 45

Gly Asn Ile Tyr Pro Ser Asp Ser Tyr Ser Asn Tyr Asn Gln Lys Phe
                50                  55                 60

Lys Asp Arg Val Thr Met Thr Arg Asp Thr Ser Thr Ser Thr Val Tyr
65                  70                  75                 80
```

```
Met Glu Leu Ser Ser Leu Arg Ser Glu Asp Thr Ala Val Tyr Tyr Cys
                85                  90                  95

Ala Arg Gly Ser Ser Phe Asp Tyr Trp Gly Gln Gly Thr Leu Val Thr
            100                 105                 110

Val Ser Ser
        115

<210> SEQ ID NO 12
<211> LENGTH: 107
<212> TYPE: PRT
<213> ORGANISM: Artificial Sequence
<220> FEATURE:
<223> OTHER INFORMATION: Synthetic construct

<400> SEQUENCE: 12

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Thr Ile Gly Thr Ser
            20                  25                  30

Ile His Trp Tyr Gln Gln Lys Pro Gly Gln Ala Pro Arg Leu Leu Ile
        35                  40                  45

Tyr Tyr Ala Ser Glu Ser Ile Ser Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Ser Gln Ser Phe Ser Trp Pro Phe
                85                  90                  95

Thr Phe Gly Gln Gly Thr Lys Leu Glu Ile Lys
            100                 105

<210> SEQ ID NO 13
<211> LENGTH: 115
<212> TYPE: PRT
<213> ORGANISM: Artificial Sequence
<220> FEATURE:
<223> OTHER INFORMATION: Synthetic construct

<400> SEQUENCE: 13

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Ile Asn Trp Val Arg Gln Ala Pro Gly Gln Gly Leu Glu Trp Met
        35                  40                  45

Gly Asn Ile Phe Pro Ser Asp Ser Tyr Ser Asn Tyr Asn Lys Lys Phe
    50                  55                  60

Lys Asp Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Ser Gly Phe Asp Tyr Trp Gly Gln Gly Thr Leu Val Thr
            100                 105                 110

Val Ser Ser
        115

<210> SEQ ID NO 14
<211> LENGTH: 333
<212> TYPE: DNA
<213> ORGANISM: Artificial Sequence
```

<220> FEATURE:
<223> OTHER INFORMATION: Synthetic construct

<400> SEQUENCE: 14

```
gacattgtgc tgacacagtc tcctgcttcc ttagctgtat ctctggggca gagggccacc    60
atctcatgca gggccagcaa aagtgtcagt acatctggct atagttatat gcactggtac   120
caacagaaac caggacagcc acccaaactc ctcatctatc ttgcatccaa cctagaatct   180
ggggtccctg ccaggttcag tggcagtggg tctgggacag acttcaccct caacatccat   240
cctgtggagg aggaggatgc tgcaacctat tactgtcagc acagtaggga gcttccgtac   300
acgttcggag gggggaccaa gctggagatc aaa                                333
```

<210> SEQ ID NO 15
<211> LENGTH: 357
<212> TYPE: DNA
<213> ORGANISM: Artificial Sequence
<220> FEATURE:
<223> OTHER INFORMATION: Synthetic construct

<400> SEQUENCE: 15

```
caggtccaac tgcaggaatc aggtccaggc ctggtgaaac cgtctgaaac cctgagcctg    60
acatgcaccg tgagcggtgg tagtattagc tcttacggcg tccattggat ccgtcaaccg   120
cctggtaaag gtctggaatg gattggcgtg atctggaccg gtggtagcac cgactataac   180
agcgcactga tgagccgcgt gaccatctcg gtagacacgt cgaaaaacca gttcagcctg   240
aaactgagca gcgtgaccgc cgcggatacc gctgtttatt actgcgcacg cgacggggat   300
tatgatcgct acaccatgga ttattgggc cagggtaccc tggtcaccgt ctcctca      357
```

<210> SEQ ID NO 16
<211> LENGTH: 333
<212> TYPE: DNA
<213> ORGANISM: Artificial Sequence
<220> FEATURE:
<223> OTHER INFORMATION: Synthetic construct

<400> SEQUENCE: 16

```
gatatcgtaa tgacccaatc tccggattcg ctggcggtat cactgggcga acgtgccacg    60
attaactgcc gtgcaagcaa atcagtgtcg acctccggct acagctatat gcactggtat   120
caacagaaac cgggccagcc gccgaaactg ctgatctatc tggctagcaa cctggagagc   180
ggtgtgcctg atcgctttag tggctccggt agcggtaccg atttcacgct gaccatcagc   240
tccctgcagg cagaagacgt ggccgtgtat tattgtcagc acagccgtga gctgccgtat   300
acttttggcc aggggacaaa actggaaatc aaa                                333
```

<210> SEQ ID NO 17
<211> LENGTH: 357
<212> TYPE: DNA
<213> ORGANISM: Artificial Sequence
<220> FEATURE:
<223> OTHER INFORMATION: Synthetic construct

<400> SEQUENCE: 17

```
caggtccaac tgcaggaatc aggtccaggc ctggtgaaac cgtctgaaac cctgagcctg    60
acatgcaccg tgagcggtgg tagtattagc tcttacggcg tccattggat ccgtcaaccg   120
cctggtaaag gtctggaatg gattggcgtg atctggaccg gtggtagcac cgactataac   180
agcgcactga tgagccgcgt gaccatctcg gtagacacgt cgaaaaacca gttcagcctg   240
```

```
aaactgagca gcgtgaccgc cgcggatacc gctgtttatt actgcgcacg cgacggggat    300
tatgatcgct acaccatgga ttattggggc cagggtaccc tggtcaccgt ctcctca       357
```

<210> SEQ ID NO 18
<211> LENGTH: 357
<212> TYPE: DNA
<213> ORGANISM: Artificial Sequence
<220> FEATURE:
<223> OTHER INFORMATION: Synthetic construct

<400> SEQUENCE: 18

```
caggtccaac tgcaggaatc aggtccaggc ctggtgaaac cgtctgaaac cctgagcctg    60
acatgcaccg tgagcggtgg tagtattagc tcttacggcg tccattggat ccgtcaaccg   120
cctggtaaag gtctggaatg gattggcgtg atctggacca gtggtgtgac cgactataac   180
agcgcactga tgggccgcgt gaccatctcg gtagacacgt cgaaaaacca gttcagcctg   240
aaactgagca gcgtgaccgc cgcggatacc gctgtttatt actgcgcacg cgacggggat   300
tatgatcgct acaccatgga ttattggggc cagggtaccc tggtcaccgt ctcctca      357
```

<210> SEQ ID NO 19
<211> LENGTH: 333
<212> TYPE: DNA
<213> ORGANISM: Artificial Sequence
<220> FEATURE:
<223> OTHER INFORMATION: Synthetic construct

<400> SEQUENCE: 19

```
gatatcgtaa tgacccaatc tccggattcg ctggcggtat cactgggcga acgtgccacg    60
attaactgcc gtgcaagcaa atcagtgtcg acctccttgt acagctatat gcactggtat   120
caacagaaac cgggccagcc gccgaaactg ctgatctatc tggctagcaa cctggagagc   180
ggtgtgcctg atcgctttag tggctccggt agcggtaccg atttcacgct gaccatcagc   240
tccctgcagg cagaagacgt ggccgtgtat tattgtcagc acagccgtga gctgccgtat   300
acttttggcc aggggacaaa actggaaatc aaa                                333
```

<210> SEQ ID NO 20
<211> LENGTH: 333
<212> TYPE: DNA
<213> ORGANISM: Artificial Sequence
<220> FEATURE:
<223> OTHER INFORMATION: Synthetic construct

<400> SEQUENCE: 20

```
gatatcgtaa tgacccaatc tccggattcg ctggcggtat cactgggcga acgtgccacg    60
attaactgcc gtgcaagcaa atcagtgtcg acctccaatt acagctatat gcactggtat   120
caacagaaac cgggccagcc gccgaaactg ctgatctatc tggctagcaa cctggagagc   180
ggtgtgcctg atcgctttag tggctccggt agcggtaccg atttcacgct gaccatcagc   240
tccctgcagg cagaagacgt ggccgtgtat tattgtcagc acagccgtga gctgccgtat   300
acttttggcc aggggacaaa actggaaatc aaa                                333
```

<210> SEQ ID NO 21
<211> LENGTH: 321
<212> TYPE: DNA
<213> ORGANISM: Artificial Sequence
<220> FEATURE:
<223> OTHER INFORMATION: Synthetic construct

<400> SEQUENCE: 21

```
gacatcttgc tgactcagtc tccagccatc ctgtctgtga gtccaggaga aagagtcagt      60
ttctcctgca gggccagtca gaccattggc acaagcatac actggtatca gcaaagaaca     120
aatggttctc caaggcttct cataaagtat gcttctgagt ctatctctgg gatcccttcc     180
aggtttagtg gcagtggatc aggacagat tttactctta gcatcaacag tgtggagtct     240
gaagatattg cagattatta ctgtcaacaa agtaatagct ggccattcac gttcggctcg     300
gggaccaagc tggaaataaa a                                               321
```

<210> SEQ ID NO 22
<211> LENGTH: 345
<212> TYPE: DNA
<213> ORGANISM: Artificial Sequence
<220> FEATURE:
<223> OTHER INFORMATION: Synthetic construct

<400> SEQUENCE: 22

```
caggtccaac tgcagcagcc tggggctgag ctggtgaggc ctggggcttc agtgaagctg      60
tcctgcaagg cttctggcta caccttcacc agctactgga taaactgggt gaagcagagg     120
cctggacatg gccttgagtg gatcggaaat atttatcctt ctgatagtta ttctaactac     180
aatcaaaagt tcaaggacaa ggccacattg actgtagaca atcctccag cacagcctac     240 atgcaggtca gcagcccgac atctgaggac tctgcggtct attactgtac gtacggtagt     300
agctttgact actggggcca aggcaccacg gtcaccgtct cctca                     345
```

<210> SEQ ID NO 23
<211> LENGTH: 321
<212> TYPE: DNA
<213> ORGANISM: Artificial Sequence
<220> FEATURE:
<223> OTHER INFORMATION: Synthetic construct

<400> SEQUENCE: 23

```
gagatcgtgc tgacccaaag tccagccacc ctttccctgt ctccaggcga acgcgcaacc      60
ctgagctgcc gcgcttctca gaccattggt acctccattc attggtatca gcagaagccc     120
ggccaagccc cgcgtctgct gatctattac gcctcagaaa gtatttcagg catccccgct     180
cgcttctccg gctccggcag cggaaccgac ttcacactta caatctctag tttggagcca     240
gaagacttcg ccgtttacta ctgtcagcag tctaacagct ggccatttac ctttggccag     300
ggcacgaagc tggaaatcaa g                                               321
```

<210> SEQ ID NO 24
<211> LENGTH: 345
<212> TYPE: DNA
<213> ORGANISM: Artificial Sequence
<220> FEATURE:
<223> OTHER INFORMATION: Synthetic construct

<400> SEQUENCE: 24

```
caggtgcagt tggttcagag cggcgcggaa gtcaagaaac ccggcgcctc cgtgaaagtg      60
agctgcaaag cgagcggcta caccttcacc agttattgga ttaactgggt gcgccaggcc     120
ccaggccagg gctgagtg atgggaaac atctacccat ctgactctta cagcaactat     180
aatcagaaat ttaaggatcg cgtaacaatg acccgtgaca ccagcaccag cactgtttac     240
atggagctga gttctctgcg ttctgaagat accgccgtgt actactgcgc acgcggttcc     300
agtttcgatt actggggcca ggggaccctg gtcaccgtct cctca                     345
```

<210> SEQ ID NO 25
<211> LENGTH: 345
<212> TYPE: DNA
<213> ORGANISM: Artificial Sequence
<220> FEATURE:
<223> OTHER INFORMATION: Synthetic construct

<400> SEQUENCE: 25

```
caggtgcagt tggttcagag cggcgcggaa gtcaagaaac ccggcgcctc cgtgaaagtg      60
agctgcaaag cgagcggcta caccttcacc agttattgga ttaactgggt gcgccaggcc     120
ccaggccagg gctggagtg atgggaaac atcttcccat ctgactctta cagcaactat       180
aataagaaat ttaaggatcg cgtaacaatg acccgtgaca ccagcaccag cactgtttac     240
atggagctga gttctctgcg ttctgaagat accgccgtgt actactgcgc acgcggttcc     300
gggttcgatt actggggcca ggggaccctg gtcaccgtct cctca                    345
```

<210> SEQ ID NO 26
<211> LENGTH: 321
<212> TYPE: DNA
<213> ORGANISM: Artificial Sequence
<220> FEATURE:
<223> OTHER INFORMATION: Synthetic construct

<400> SEQUENCE: 26

```
gagatcgtgc tgacccaaag tccagccacc ctttccctgt ctccaggcga acgcgcaacc      60
ctgagctgcc gcgcttctca gaccattggt acctccattc attggtatca gcagaagccc     120
ggccaagccc cgcgtctgct gatctattac gcctcagaaa gtatttcagg catcccggct     180
cgcttctccg gctccggcag cggaaccgac ttcacactta caatctctag tttggagcca    240
gaagacttcg ccgtttacta ctgttcgcag tcttttagct ggccatttac ctttggccag     300
ggcacgaagc tggaaatcaa g                                               321
```

<210> SEQ ID NO 27
<211> LENGTH: 323
<212> TYPE: PRT
<213> ORGANISM: Homo sapiens

<400> SEQUENCE: 27

```
Met Ala Arg Gly Pro Gly Leu Ala Pro Pro Leu Arg Leu Pro Leu
1               5                   10                  15

Leu Leu Leu Val Leu Ala Ala Val Thr Gly His Thr Ala Ala Gln Asp
            20                  25                  30

Asn Cys Thr Cys Pro Thr Asn Lys Met Thr Val Cys Ser Pro Asp Gly
        35                  40                  45

Pro Gly Gly Arg Cys Gln Cys Arg Ala Leu Gly Ser Gly Met Ala Val
    50                  55                  60

Asp Cys Ser Thr Leu Thr Ser Lys Cys Leu Leu Leu Lys Ala Arg Met
65                  70                  75                  80

Ser Ala Pro Lys Asn Ala Arg Thr Leu Val Arg Pro Ser Glu His Ala
                85                  90                  95

Leu Val Asp Asn Asp Gly Leu Tyr Asp Pro Asp Cys Asp Pro Glu Gly
            100                 105                 110

Arg Phe Lys Ala Arg Gln Cys Asn Gln Thr Ser Val Cys Trp Cys Val
        115                 120                 125

Asn Ser Val Gly Val Arg Arg Thr Asp Lys Gly Asp Leu Ser Leu Arg
    130                 135                 140
```

```
Cys Asp Glu Leu Val Arg Thr His His Ile Leu Ile Asp Leu Arg His
145                 150                 155                 160

Arg Pro Thr Ala Gly Ala Phe Asn His Ser Asp Leu Asp Ala Glu Leu
                165                 170                 175

Arg Arg Leu Phe Arg Glu Arg Tyr Arg Leu His Pro Lys Phe Val Ala
            180                 185                 190

Ala Val His Tyr Glu Gln Pro Thr Ile Gln Ile Glu Leu Arg Gln Asn
        195                 200                 205

Thr Ser Gln Lys Ala Ala Gly Asp Val Asp Ile Gly Asp Ala Ala Tyr
    210                 215                 220

Tyr Phe Glu Arg Asp Ile Lys Gly Glu Ser Leu Phe Gln Gly Arg Gly
225                 230                 235                 240

Gly Leu Asp Leu Arg Val Arg Gly Glu Pro Leu Gln Val Glu Arg Thr
                245                 250                 255

Leu Ile Tyr Tyr Leu Asp Glu Ile Pro Pro Lys Phe Ser Met Lys Arg
            260                 265                 270

Leu Thr Ala Gly Leu Ile Ala Val Ile Val Val Val Val Ala Leu
        275                 280                 285

Val Ala Gly Met Ala Val Leu Val Ile Thr Asn Arg Arg Lys Ser Gly
290                 295                 300

Lys Tyr Lys Lys Val Glu Ile Lys Glu Leu Gly Glu Leu Arg Lys Glu
305                 310                 315                 320

Pro Ser Leu

<210> SEQ ID NO 28
<211> LENGTH: 317
<212> TYPE: PRT
<213> ORGANISM: Mus musculus

<400> SEQUENCE: 28

Met Ala Arg Gly Leu Asp Leu Ala Pro Leu Leu Leu Leu Leu Leu Ala
1               5                   10                  15

Met Ala Thr Arg Phe Cys Thr Ala Gln Ser Asn Cys Thr Cys Pro Thr
                20                  25                  30

Asn Lys Met Thr Val Cys Asp Thr Asn Gly Pro Gly Gly Val Cys Gln
            35                  40                  45

Cys Arg Ala Met Gly Ser Gln Val Leu Val Asp Cys Ser Thr Leu Thr
50                  55                  60

Ser Lys Cys Leu Leu Leu Lys Ala Arg Met Ser Ala Arg Lys Ser Gly
65                  70                  75                  80

Arg Ser Leu Val Met Pro Ser Glu His Ala Ile Leu Asp Asn Asp Gly
                85                  90                  95

Leu Tyr Asp Pro Glu Cys Asp Asp Lys Gly Arg Phe Lys Ala Arg Gln
            100                 105                 110

Cys Asn Gln Thr Ser Val Cys Trp Cys Val Asn Ser Val Gly Val Arg
        115                 120                 125

Arg Thr Asp Lys Gly Asp Gln Ser Leu Arg Cys Asp Glu Val Val Arg
    130                 135                 140

Thr His His Ile Leu Ile Glu Leu Arg His Arg Pro Thr Asp Arg Ala
145                 150                 155                 160

Phe Asn His Ser Asp Leu Asp Ser Glu Leu Arg Arg Leu Phe Gln Glu
                165                 170                 175

Arg Tyr Lys Leu His Pro Ser Phe Leu Ser Ala Val His Tyr Glu Glu
            180                 185                 190
```

```
Pro Thr Ile Gln Ile Glu Leu Arg Gln Asn Ala Ser Gln Lys Gly Leu
            195                 200                 205

Arg Asp Val Asp Ile Ala Asp Ala Ala Tyr Tyr Phe Glu Arg Asp Ile
210                 215                 220

Lys Gly Glu Ser Leu Phe Met Gly Arg Arg Gly Leu Asp Val Gln Val
225                 230                 235                 240

Arg Gly Glu Pro Leu His Val Glu Arg Thr Leu Ile Tyr Tyr Leu Asp
            245                 250                 255

Glu Lys Pro Pro Gln Phe Ser Met Lys Arg Leu Thr Ala Gly Val Ile
            260                 265                 270

Ala Val Ile Ala Val Val Ser Val Ala Val Val Ala Gly Val Val Val
            275                 280                 285

Leu Val Val Thr Lys Arg Arg Lys Ser Gly Lys Tyr Lys Lys Val Glu
290                 295                 300

Leu Lys Glu Leu Gly Glu Met Arg Ser Glu Pro Ser Leu
305                 310                 315

<210> SEQ ID NO 29
<211> LENGTH: 314
<212> TYPE: PRT
<213> ORGANISM: Homo sapiens

<400> SEQUENCE: 29

Met Ala Pro Pro Gln Val Leu Ala Phe Gly Leu Leu Leu Ala Ala Ala
1               5                   10                  15

Thr Ala Thr Phe Ala Ala Ala Gln Glu Glu Cys Val Cys Glu Asn Tyr
            20                  25                  30

Lys Leu Ala Val Asn Cys Phe Val Asn Asn Asn Arg Gln Cys Gln Cys
            35                  40                  45

Thr Ser Val Gly Ala Gln Asn Thr Val Ile Cys Ser Lys Leu Ala Ala
        50                  55                  60

Lys Cys Leu Val Met Lys Ala Glu Met Asn Gly Ser Lys Leu Gly Arg
65                  70                  75                  80

Arg Ala Lys Pro Glu Gly Ala Leu Gln Asn Asn Asp Gly Leu Tyr Asp
                85                  90                  95

Pro Asp Cys Asp Glu Ser Gly Leu Phe Lys Ala Lys Gln Cys Asn Gly
            100                 105                 110

Thr Ser Thr Cys Trp Cys Val Asn Thr Ala Gly Val Arg Arg Thr Asp
            115                 120                 125

Lys Asp Thr Glu Ile Thr Cys Ser Glu Arg Val Arg Thr Tyr Trp Ile
130                 135                 140

Ile Ile Glu Leu Lys His Lys Ala Arg Glu Lys Pro Tyr Asp Ser Lys
145                 150                 155                 160

Ser Leu Arg Thr Ala Leu Gln Lys Glu Ile Thr Thr Arg Tyr Gln Leu
                165                 170                 175

Asp Pro Lys Phe Ile Thr Ser Ile Leu Tyr Glu Asn Asn Val Ile Thr
            180                 185                 190

Ile Asp Leu Val Gln Asn Ser Ser Gln Lys Thr Gln Asn Asp Val Asp
            195                 200                 205

Ile Ala Asp Val Ala Tyr Tyr Phe Glu Lys Asp Val Lys Gly Glu Ser
        210                 215                 220

Leu Phe His Ser Lys Lys Met Asp Leu Thr Val Asn Gly Glu Gln Leu
225                 230                 235                 240

Asp Leu Asp Pro Gly Gln Thr Leu Ile Tyr Tyr Val Asp Glu Lys Ala
                245                 250                 255
```

Pro Glu Phe Ser Met Gln Gly Leu Lys Ala Gly Val Ile Ala Val Ile
            260                 265                 270

Val Val Val Val Ile Ala Val Val Ala Gly Ile Val Val Leu Val Ile
        275                 280                 285

Ser Arg Lys Lys Arg Met Ala Lys Tyr Glu Lys Ala Glu Ile Lys Glu
    290                 295                 300

Met Gly Glu Met His Arg Glu Leu Asn Ala
305                 310

<210> SEQ ID NO 30
<211> LENGTH: 5
<212> TYPE: PRT
<213> ORGANISM: Artificial Sequence
<220> FEATURE:
<223> OTHER INFORMATION: Synthetic construct

<400> SEQUENCE: 30

Ser Tyr Gly Val His
1               5

<210> SEQ ID NO 31
<211> LENGTH: 7
<212> TYPE: PRT
<213> ORGANISM: Artificial Sequence
<220> FEATURE:
<223> OTHER INFORMATION: Synthetic construct

<400> SEQUENCE: 31

Gly Phe Ser Leu Thr Ser Tyr
1               5

<210> SEQ ID NO 32
<211> LENGTH: 10
<212> TYPE: PRT
<213> ORGANISM: Artificial Sequence
<220> FEATURE:
<223> OTHER INFORMATION: Synthetic construct

<400> SEQUENCE: 32

Gly Phe Ser Leu Thr Ser Tyr Gly Val His
1               5                   10

<210> SEQ ID NO 33
<211> LENGTH: 16
<212> TYPE: PRT
<213> ORGANISM: Artificial Sequence
<220> FEATURE:
<223> OTHER INFORMATION: Synthetic construct

<400> SEQUENCE: 33

Val Ile Trp Thr Gly Gly Ser Thr Asp Tyr Asn Ser Ala Leu Met Ser
1               5                   10                  15

<210> SEQ ID NO 34
<211> LENGTH: 5
<212> TYPE: PRT
<213> ORGANISM: Artificial Sequence
<220> FEATURE:
<223> OTHER INFORMATION: Synthetic construct

<400> SEQUENCE: 34

Trp Thr Gly Gly Ser
1               5

```
<210> SEQ ID NO 35
<211> LENGTH: 11
<212> TYPE: PRT
<213> ORGANISM: Artificial Sequence
<220> FEATURE:
<223> OTHER INFORMATION: Synthetic construct

<400> SEQUENCE: 35

Asp Gly Asp Tyr Asp Arg Tyr Thr Met Asp Tyr
1               5                   10

<210> SEQ ID NO 36
<211> LENGTH: 7
<212> TYPE: PRT
<213> ORGANISM: Artificial Sequence
<220> FEATURE:
<223> OTHER INFORMATION: Synthetic construct

<400> SEQUENCE: 36

Gly Gly Ser Ile Ser Ser Tyr
1               5

<210> SEQ ID NO 37
<211> LENGTH: 10
<212> TYPE: PRT
<213> ORGANISM: Artificial Sequence
<220> FEATURE:
<223> OTHER INFORMATION: Synthetic construct

<400> SEQUENCE: 37

Gly Gly Ser Ile Ser Ser Tyr Gly Val His
1               5                   10

<210> SEQ ID NO 38
<211> LENGTH: 16
<212> TYPE: PRT
<213> ORGANISM: Artificial Sequence
<220> FEATURE:
<223> OTHER INFORMATION: Synthetic construct

<400> SEQUENCE: 38

Val Ile Trp Thr Ser Gly Val Thr Asp Tyr Asn Ser Ala Leu Met Gly
1               5                   10                  15

<210> SEQ ID NO 39
<211> LENGTH: 5
<212> TYPE: PRT
<213> ORGANISM: Artificial Sequence
<220> FEATURE:
<223> OTHER INFORMATION: Synthetic construct

<400> SEQUENCE: 39

Trp Thr Ser Gly Val
1               5

<210> SEQ ID NO 40
<211> LENGTH: 5
<212> TYPE: PRT
<213> ORGANISM: Artificial Sequence
<220> FEATURE:
<223> OTHER INFORMATION: Synthetic cosntruct

<400> SEQUENCE: 40

Ser Tyr Trp Ile Asn
1               5

<210> SEQ ID NO 41
```

<211> LENGTH: 7
<212> TYPE: PRT
<213> ORGANISM: Artificial Sequence
<220> FEATURE:
<223> OTHER INFORMATION: Synthetic construct

<400> SEQUENCE: 41

Gly Tyr Thr Phe Thr Ser Tyr
1               5

<210> SEQ ID NO 42
<211> LENGTH: 10
<212> TYPE: PRT
<213> ORGANISM: Artificial Sequence
<220> FEATURE:
<223> OTHER INFORMATION: Synthetic construct

<400> SEQUENCE: 42

Gly Tyr Thr Phe Thr Ser Tyr Trp Ile Asn
1               5                   10

<210> SEQ ID NO 43
<211> LENGTH: 17
<212> TYPE: PRT
<213> ORGANISM: Artificial Sequence
<220> FEATURE:
<223> OTHER INFORMATION: Synthetic construct

<400> SEQUENCE: 43

Asn Ile Tyr Pro Ser Asp Ser Tyr Ser Asn Tyr Asn Gln Lys Phe Lys
1               5                   10                  15

Asp

<210> SEQ ID NO 44
<211> LENGTH: 6
<212> TYPE: PRT
<213> ORGANISM: Artificial Sequence
<220> FEATURE:
<223> OTHER INFORMATION: Synthetic construct

<400> SEQUENCE: 44

Tyr Pro Ser Asp Ser Tyr
1               5

<210> SEQ ID NO 45
<211> LENGTH: 6
<212> TYPE: PRT
<213> ORGANISM: Artificial Sequence
<220> FEATURE:
<223> OTHER INFORMATION: Synthetic cosntruct

<400> SEQUENCE: 45

Gly Ser Ser Phe Asp Tyr
1               5

<210> SEQ ID NO 46
<211> LENGTH: 17
<212> TYPE: PRT
<213> ORGANISM: Artificial Sequence
<220> FEATURE:
<223> OTHER INFORMATION: Synthetic construct

<400> SEQUENCE: 46

Asn Ile Phe Pro Ser Asp Ser Tyr Ser Asn Tyr Asn Lys Lys Phe Lys
1               5                   10                  15

Asp

```
<210> SEQ ID NO 47
<211> LENGTH: 6
<212> TYPE: PRT
<213> ORGANISM: Artificial Sequence
<220> FEATURE:
<223> OTHER INFORMATION: Synthetic construct

<400> SEQUENCE: 47

Phe Pro Ser Asp Ser Tyr
1               5

<210> SEQ ID NO 48
<211> LENGTH: 6
<212> TYPE: PRT
<213> ORGANISM: Artificial Sequence
<220> FEATURE:
<223> OTHER INFORMATION: Synthetic construct

<400> SEQUENCE: 48

Gly Ser Gly Phe Asp Tyr
1               5

<210> SEQ ID NO 49
<211> LENGTH: 16
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (5)..(5)
<223> OTHER INFORMATION: Xaa can be G or S
<220> FEATURE:
<221> NAME/KEY: MISC_FEATURE
<222> LOCATION: (7)..(7)
<223> OTHER INFORMATION: Xaa can be S or V
<220> FEATURE:
<221> NAME/KEY: MISC_FEATURE
<222> LOCATION: (16)..(16)
<223> OTHER INFORMATION: Xaa can be G or S

<400> SEQUENCE: 49

Val Ile Trp Thr Xaa Gly Xaa Thr Asp Tyr Asn Ser Ala Leu Met Xaa
1               5                   10                  15

<210> SEQ ID NO 50
<211> LENGTH: 5
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (3)..(3)
<220> FEATURE:
<221> NAME/KEY: MISC_FEATURE
<222> LOCATION: (3)..(3)
<223> OTHER INFORMATION: Xaa can be G or S
<220> FEATURE:
<221> NAME/KEY: MISC_FEATURE
<222> LOCATION: (5)..(5)
<223> OTHER INFORMATION: Xaa can be S or V

<400> SEQUENCE: 50

Trp Thr Xaa Gly Xaa
1               5

<210> SEQ ID NO 51
<211> LENGTH: 17
```

```
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (3)..(3)
<223> OTHER INFORMATION: Xaa can be Y or F
<220> FEATURE:
<221> NAME/KEY: MISC_FEATURE
<222> LOCATION: (13)..(13)
<223> OTHER INFORMATION: Xaa can be Q or K

<400> SEQUENCE: 51

Asn Ile Xaa Pro Ser Asp Ser Tyr Ser Asn Tyr Asn Xaa Lys Phe Lys
1               5                   10                  15

Asp

<210> SEQ ID NO 52
<211> LENGTH: 6
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Xaa can be Y or F

<400> SEQUENCE: 52

Xaa Pro Ser Asp Ser Tyr
1               5

<210> SEQ ID NO 53
<211> LENGTH: 6
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (3)..(3)
<223> OTHER INFORMATION: Xaa can be G or S

<400> SEQUENCE: 53

Gly Ser Xaa Phe Asp Tyr
1               5

<210> SEQ ID NO 54
<211> LENGTH: 15
<212> TYPE: PRT
<213> ORGANISM: Artificial Sequence
<220> FEATURE:
<223> OTHER INFORMATION: Synthetic construct

<400> SEQUENCE: 54

Arg Ala Ser Lys Ser Val Ser Thr Ser Gly Tyr Ser Tyr Met His
1               5                   10                  15

<210> SEQ ID NO 55
<211> LENGTH: 7
<212> TYPE: PRT
<213> ORGANISM: Artificial Sequence
<220> FEATURE:
<223> OTHER INFORMATION: Synthetic construct

<400> SEQUENCE: 55

Leu Ala Ser Asn Leu Glu Ser
1               5
```

<210> SEQ ID NO 56
<211> LENGTH: 9
<212> TYPE: PRT
<213> ORGANISM: Artificial Sequence
<220> FEATURE:
<223> OTHER INFORMATION: Synthetic construct

<400> SEQUENCE: 56

Gln His Ser Arg Glu Leu Pro Tyr Thr
1               5

<210> SEQ ID NO 57
<211> LENGTH: 15
<212> TYPE: PRT
<213> ORGANISM: Artificial Sequence
<220> FEATURE:
<223> OTHER INFORMATION: Synthetic construct

<400> SEQUENCE: 57

Arg Ala Ser Lys Ser Val Ser Thr Ser Leu Tyr Ser Tyr Met His
1               5                   10                  15

<210> SEQ ID NO 58
<211> LENGTH: 15
<212> TYPE: PRT
<213> ORGANISM: Artificial Sequence
<220> FEATURE:
<223> OTHER INFORMATION: Synthetic construct

<400> SEQUENCE: 58

Arg Ala Ser Lys Ser Val Ser Thr Ser Asn Tyr Ser Tyr Met His
1               5                   10                  15

<210> SEQ ID NO 59
<211> LENGTH: 11
<212> TYPE: PRT
<213> ORGANISM: Artificial Sequence
<220> FEATURE:
<223> OTHER INFORMATION: Synthetic construct

<400> SEQUENCE: 59

Arg Ala Ser Gln Thr Ile Gly Thr Ser Ile His
1               5                   10

<210> SEQ ID NO 60
<211> LENGTH: 7
<212> TYPE: PRT
<213> ORGANISM: Artificial Sequence
<220> FEATURE:
<223> OTHER INFORMATION: Synthetic construct

<400> SEQUENCE: 60

Tyr Ala Ser Glu Ser Ile Ser
1               5

<210> SEQ ID NO 61
<211> LENGTH: 9
<212> TYPE: PRT
<213> ORGANISM: Artificial Sequence
<220> FEATURE:
<223> OTHER INFORMATION: Synthetic construct

<400> SEQUENCE: 61

Gln Gln Ser Asn Ser Trp Pro Phe Thr
1               5

<210> SEQ ID NO 62
<211> LENGTH: 9
<212> TYPE: PRT
<213> ORGANISM: Artificial Sequence
<220> FEATURE:
<223> OTHER INFORMATION: Synthetic construct

<400> SEQUENCE: 62

Ser Gln Ser Phe Ser Trp Pro Phe Thr
1               5

<210> SEQ ID NO 63
<211> LENGTH: 15
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (10)..(10)
<223> OTHER INFORMATION: Xaa can be G, L, or N

<400> SEQUENCE: 63

Arg Ala Ser Lys Ser Val Ser Thr Ser Xaa Tyr Ser Tyr Met His
1               5                   10                  15

<210> SEQ ID NO 64
<211> LENGTH: 9
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Xaa can be Q or S
<220> FEATURE:
<221> NAME/KEY: MISC_FEATURE
<222> LOCATION: (4)..(4)
<223> OTHER INFORMATION: Xaa can be N or F

<400> SEQUENCE: 64

Xaa Gln Ser Xaa Ser Trp Pro Phe Thr
1               5

<210> SEQ ID NO 65
<211> LENGTH: 449
<212> TYPE: PRT
<213> ORGANISM: Artificial Sequence
<220> FEATURE:
<223> OTHER INFORMATION: Synthetic construct

<400> SEQUENCE: 65

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Gly Val His Trp Ile Arg Gln Pro Pro Gly Lys Gly Leu Glu Trp Ile
        35                  40                  45

Gly Val Ile Trp Thr Ser Gly Val Thr Asp Tyr Asn Ser Ala Leu Met
    50                  55                  60

Gly Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Asp Gly Asp Tyr Asp Arg Tyr Thr Met Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 66
<211> LENGTH: 218
<212> TYPE: PRT
<213> ORGANISM: Artificial Sequence
<220> FEATURE:
<223> OTHER INFORMATION: Synthetic construct

<400> SEQUENCE: 66

Asp Ile Val Met Thr Gln Ser Pro Asp Ser Leu Ala Val Ser Leu Gly

```
                1               5                  10                 15
            Glu Arg Ala Thr Ile Asn Cys Arg Ala Ser Lys Ser Val Ser Thr Ser
                            20                  25                 30

Gly Tyr Ser Tyr Met His Trp Tyr Gln Gln Lys Pro Gly Gln Pro Pro
                            35                  40                 45

Lys Leu Leu Ile Tyr Leu Ala Ser Asn Leu Glu Ser Gly Val Pro Asp
                50                      55                  60

Arg Phe Ser Gly Ser Gly Ser Gly Thr Asp Phe Thr Leu Thr Ile Ser
             65                     70                  75                 80

Ser Leu Gln Ala Glu Asp Val Ala Val Tyr Tyr Cys Gln His Ser Arg
                            85                  90                 95

Glu Leu Pro Tyr Thr Phe Gly Gln Gly Thr Lys Leu Glu Ile Lys Arg
                           100                 105                110

Thr Val Ala Ala Pro Ser Val Phe Ile Phe Pro Pro Ser Asp Glu Gln
                           115                 120                125

Leu Lys Ser Gly Thr Ala Ser Val Val Cys Leu Leu Asn Asn Phe Tyr
                130                    135                 140

Pro Arg Glu Ala Lys Val Gln Trp Lys Val Asp Asn Ala Leu Gln Ser
            145                    150                 155                160

Gly Asn Ser Gln Glu Ser Val Thr Glu Gln Asp Ser Lys Asp Ser Thr
                           165                 170                175

Tyr Ser Leu Ser Ser Thr Leu Thr Leu Ser Lys Ala Asp Tyr Glu Lys
                180                    185                 190

His Lys Val Tyr Ala Cys Glu Val Thr His Gln Gly Leu Ser Ser Pro
                           195                 200                205

Val Thr Lys Ser Phe Asn Arg Gly Glu Cys
                210                    215

<210> SEQ ID NO 67
            <211> LENGTH: 445
            <212> TYPE: PRT
            <213> ORGANISM: Artificial Sequence
            <220> FEATURE:
            <223> OTHER INFORMATION: Synthetic construct

<400> SEQUENCE: 67

Gln Val Gln Leu Val Gln Ser Gly Ala Glu Val Lys Lys Pro Gly Ala
            1               5                  10                 15

Ser Val Lys Val Ser Cys Lys Ala Ser Gly Tyr Thr Phe Thr Ser Tyr
                            20                  25                 30

Trp Ile Asn Trp Val Arg Gln Ala Pro Gly Gln Gly Leu Glu Trp Met
                            35                  40                 45

Gly Asn Ile Phe Pro Ser Asp Ser Tyr Ser Asn Tyr Asn Lys Lys Phe
                50                      55                  60

Lys Asp Arg Val Thr Met Thr Arg Asp Thr Ser Thr Ser Thr Val Tyr
            65                     70                  75                 80

Met Glu Leu Ser Ser Leu Arg Ser Glu Asp Thr Ala Val Tyr Tyr Cys
                            85                  90                 95

Ala Arg Gly Ser Gly Phe Asp Tyr Trp Gly Gln Gly Thr Leu Val Thr
                           100                 105                110

Val Ser Ser Ala Ser Thr Lys Gly Pro Ser Val Phe Pro Leu Ala Pro
                           115                 120                125

Ser Ser Lys Ser Thr Ser Gly Gly Thr Ala Ala Leu Gly Cys Leu Val
                130                    135                 140

Lys Asp Tyr Phe Pro Glu Pro Val Thr Val Ser Trp Asn Ser Gly Ala
```

```
            145                 150                 155                 160
Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
    210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
        435                 440                 445

<210> SEQ ID NO 68
<211> LENGTH: 214
<212> TYPE: PRT
<213> ORGANISM: Artificial Sequence
<220> FEATURE:
<223> OTHER INFORMATION: Synthetic construct

<400> SEQUENCE: 68

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Thr Ile Gly Thr Ser
            20                  25                  30

Ile His Trp Tyr Gln Gln Lys Pro Gly Gln Ala Pro Arg Leu Leu Ile
        35                  40                  45

Tyr Tyr Ala Ser Glu Ser Ile Ser Gly Ile Pro Ala Arg Phe Ser Gly
    50                  55                  60

Ser Gly Ser Gly Thr Asp Phe Thr Leu Thr Ile Ser Ser Leu Glu Pro
```

```
                65                  70                  75                  80
Glu Asp Phe Ala Val Tyr Tyr Cys Ser Gln Ser Phe Ser Trp Pro Phe
                    85                  90                  95

Thr Phe Gly Gln Gly Thr Lys Leu Glu Ile Lys Arg Thr Val Ala Ala
                100                 105                 110

Pro Ser Val Phe Ile Phe Pro Pro Ser Asp Glu Gln Leu Lys Ser Gly
                115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
            195                 200                 205

Phe Asn Arg Gly Glu Cys
    210
```

```
<210> SEQ ID NO 69
<211> LENGTH: 316
<212> TYPE: PRT
<213> ORGANISM: Homo sapiens
<220> FEATURE:
<221> NAME/KEY: MISC_FEATURE
<222> LOCATION: (3)..(3)
<223> OTHER INFORMATION: Xaa can be Q or L
<220> FEATURE:
<221> NAME/KEY: MISC_FEATURE
<222> LOCATION: (4)..(4)
<223> OTHER INFORMATION: Xaa can be V or R
<220> FEATURE:
<221> NAME/KEY: MISC_FEATURE
<222> LOCATION: (6)..(6)
<223> OTHER INFORMATION: Xaa can be A or P
<220> FEATURE:
<221> NAME/KEY: MISC_FEATURE
<222> LOCATION: (7)..(7)
<223> OTHER INFORMATION: Xaa can be F or L
<220> FEATURE:
<221> NAME/KEY: MISC_FEATURE
<222> LOCATION: (8)..(8)
<223> OTHER INFORMATION: Xaa can be G or L
<220> FEATURE:
<221> NAME/KEY: MISC_FEATURE
<222> LOCATION: (12)..(12)
<223> OTHER INFORMATION: Xaa can be A or L
<220> FEATURE:
<221> NAME/KEY: MISC_FEATURE
<222> LOCATION: (15)..(15)
<223> OTHER INFORMATION: Xaa can be T or V
<220> FEATURE:
<221> NAME/KEY: MISC_FEATURE
<222> LOCATION: (16)..(16)
<223> OTHER INFORMATION: Xaa can be A or T
<220> FEATURE:
<221> NAME/KEY: MISC_FEATURE
<222> LOCATION: (17)..(17)
<223> OTHER INFORMATION: Xaa can be T or G
<220> FEATURE:
<221> NAME/KEY: MISC_FEATURE
<222> LOCATION: (18)..(18)
<223> OTHER INFORMATION: Xaa can be F or H
<220> FEATURE:
<221> NAME/KEY: MISC_FEATURE
<222> LOCATION: (19)..(19)
<223> OTHER INFORMATION: Xaa can be A or T
<220> FEATURE:
```

```
<221> NAME/KEY: MISC_FEATURE
<222> LOCATION: (24)..(24)
<223> OTHER INFORMATION: Xaa can be E or N
<220> FEATURE:
<221> NAME/KEY: MISC_FEATURE
<222> LOCATION: (26)..(26)
<223> OTHER INFORMATION: Xaa can be V or T
<220> FEATURE:
<221> NAME/KEY: MISC_FEATURE
<222> LOCATION: (28)..(28)
<223> OTHER INFORMATION: Xaa can be E or P
<220> FEATURE:
<221> NAME/KEY: MISC_FEATURE
<222> LOCATION: (29)..(29)
<223> OTHER INFORMATION: Xaa can be N or T
<220> FEATURE:
<221> NAME/KEY: MISC_FEATURE
<222> LOCATION: (30)..(30)
<223> OTHER INFORMATION: Xaa can be Y or N
<220> FEATURE:
<221> NAME/KEY: MISC_FEATURE
<222> LOCATION: (33)..(33)
<223> OTHER INFORMATION: Xaa can be A or T
<220> FEATURE:
<221> NAME/KEY: MISC_FEATURE
<222> LOCATION: (35)..(35)
<223> OTHER INFORMATION: Xaa can be N or C
<220> FEATURE:
<221> NAME/KEY: MISC_FEATURE
<222> LOCATION: (36)..(36)
<223> OTHER INFORMATION: Xaa can be C or S
<220> FEATURE:
<221> NAME/KEY: MISC_FEATURE
<222> LOCATION: (37)..(37)
<223> OTHER INFORMATION: Xaa can be F or P
<220> FEATURE:
<221> NAME/KEY: MISC_FEATURE
<222> LOCATION: (38)..(38)
<223> OTHER INFORMATION: Xaa can be V or D
<220> FEATURE:
<221> NAME/KEY: MISC_FEATURE
<222> LOCATION: (39)..(39)
<223> OTHER INFORMATION: Xaa can be N or G
<220> FEATURE:
<221> NAME/KEY: MISC_FEATURE
<222> LOCATION: (40)..(40)
<223> OTHER INFORMATION: Xaa can be N or P
<220> FEATURE:
<221> NAME/KEY: MISC_FEATURE
<222> LOCATION: (41)..(41)
<223> OTHER INFORMATION: Xaa can be N or G
<220> FEATURE:
<221> NAME/KEY: MISC_FEATURE
<222> LOCATION: (42)..(42)
<223> OTHER INFORMATION: Xaa can be R or G
<220> FEATURE:
<221> NAME/KEY: MISC_FEATURE
<222> LOCATION: (43)..(43)
<223> OTHER INFORMATION: Xaa can be Q or R
<220> FEATURE:
<221> NAME/KEY: MISC_FEATURE
<222> LOCATION: (47)..(47)
<223> OTHER INFORMATION: Xaa can be T or R
<220> FEATURE:
<221> NAME/KEY: MISC_FEATURE
<222> LOCATION: (52)..(52)
<223> OTHER INFORMATION: Xaa can be Q or G
<220> FEATURE:
<221> NAME/KEY: MISC_FEATURE
<222> LOCATION: (53)..(53)
<223> OTHER INFORMATION: Xaa can be N or M
<220> FEATURE:
<221> NAME/KEY: MISC_FEATURE
<222> LOCATION: (54)..(54)
<223> OTHER INFORMATION: Xaa can be T or A
<220> FEATURE:
<221> NAME/KEY: MISC_FEATURE
<222> LOCATION: (56)..(56)
<223> OTHER INFORMATION: Xaa can be I or D
```

-continued

```
<220> FEATURE:
<221> NAME/KEY: MISC_FEATURE
<222> LOCATION: (59)..(59)
<223> OTHER INFORMATION: Xaa can be K or T
<220> FEATURE:
<221> NAME/KEY: MISC_FEATURE
<222> LOCATION: (61)..(61)
<223> OTHER INFORMATION: Xaa can be A or T
<220> FEATURE:
<221> NAME/KEY: MISC_FEATURE
<222> LOCATION: (70)..(70)
<223> OTHER INFORMATION: Xaa can be E or R
<220> FEATURE:
<221> NAME/KEY: MISC_FEATURE
<222> LOCATION: (72)..(72)
<223> OTHER INFORMATION: Xaa can be N or S
<220> FEATURE:
<221> NAME/KEY: MISC_FEATURE
<222> LOCATION: (74)..(74)
<223> OTHER INFORMATION: Xaa can be S or P
<220> FEATURE:
<221> NAME/KEY: MISC_FEATURE
<222> LOCATION: (76)..(76)
<223> OTHER INFORMATION: Xaa can be L or N
<220> FEATURE:
<221> NAME/KEY: MISC_FEATURE
<222> LOCATION: (79)..(79)
<223> OTHER INFORMATION: Xaa can be R or T
<220> FEATURE:
<221> NAME/KEY: MISC_FEATURE
<222> LOCATION: (80)..(80)
<223> OTHER INFORMATION: Xaa can be A or L
<220> FEATURE:
<221> NAME/KEY: MISC_FEATURE
<222> LOCATION: (81)..(81)
<223> OTHER INFORMATION: Xaa can be K or V
<220> FEATURE:
<221> NAME/KEY: MISC_FEATURE
<222> LOCATION: (82)..(82)
<223> OTHER INFORMATION: Xaa can be R
<220> FEATURE:
<221> NAME/KEY: MISC_FEATURE
<222> LOCATION: (84)..(84)
<223> OTHER INFORMATION: Xaa can be S
<220> FEATURE:
<221> NAME/KEY: MISC_FEATURE
<222> LOCATION: (86)..(86)
<223> OTHER INFORMATION: Xaa can be G or H
<220> FEATURE:
<221> NAME/KEY: MISC_FEATURE
<222> LOCATION: (89)..(89)
<223> OTHER INFORMATION: Xaa can be Q or V
<220> FEATURE:
<221> NAME/KEY: MISC_FEATURE
<222> LOCATION: (90)..(90)
<223> OTHER INFORMATION: Xaa can be N or D
<220> FEATURE:
<221> NAME/KEY: MISC_FEATURE
<222> LOCATION: (101)..(101)
<223> OTHER INFORMATION: Xaa can be E or P
<220> FEATURE:
<221> NAME/KEY: MISC_FEATURE
<222> LOCATION: (102)..(102)
<223> OTHER INFORMATION: Xaa can be S or E
<220> FEATURE:
<221> NAME/KEY: MISC_FEATURE
<222> LOCATION: (104)..(104)
<223> OTHER INFORMATION: Xaa can be L or R
<220> FEATURE:
<221> NAME/KEY: MISC_FEATURE
<222> LOCATION: (112)..(112)
<223> OTHER INFORMATION: Xaa can be G or Q
<220> FEATURE:
<221> NAME/KEY: MISC_FEATURE
<222> LOCATION: (115)..(115)
<223> OTHER INFORMATION: Xaa can be T or V
<220> FEATURE:
<221> NAME/KEY: MISC_FEATURE
<222> LOCATION: (122)..(122)
```

```
<223> OTHER INFORMATION: Xaa can be A or V
<220> FEATURE:
<221> NAME/KEY: MISC_FEATURE
<222> LOCATION: (130)..(130)
<223> OTHER INFORMATION: Xaa can be G
<220> FEATURE:
<221> NAME/KEY: MISC_FEATURE
<222> LOCATION: (132)..(132)
<223> OTHER INFORMATION: Xaa can be T or L
<220> FEATURE:
<221> NAME/KEY: MISC_FEATURE
<222> LOCATION: (133)..(133)
<223> OTHER INFORMATION: Xaa can be E or S
<220> FEATURE:
<221> NAME/KEY: MISC_FEATURE
<222> LOCATION: (135)..(135)
<223> OTHER INFORMATION: Xaa can be T or R
<220> FEATURE:
<221> NAME/KEY: MISC_FEATURE
<222> LOCATION: (137)..(137)
<223> OTHER INFORMATION: Xaa can be S or D
<220> FEATURE:
<221> NAME/KEY: MISC_FEATURE
<222> LOCATION: (139)..(139)
<223> OTHER INFORMATION: Xaa can be R or L
<220> FEATURE:
<221> NAME/KEY: MISC_FEATURE
<222> LOCATION: (144)..(144)
<223> OTHER INFORMATION: Xaa can be W or H
<220> FEATURE:
<221> NAME/KEY: MISC_FEATURE
<222> LOCATION: (153)..(153)
<223> OTHER INFORMATION: Xaa can be A or P
<220> FEATURE:
<221> NAME/KEY: MISC_FEATURE
<222> LOCATION: (154)..(154)
<223> OTHER INFORMATION: Xaa can be R or T
<220> FEATURE:
<221> NAME/KEY: MISC_FEATURE
<222> LOCATION: (155)..(155)
<223> OTHER INFORMATION: Xaa can be E or A
<220> FEATURE:
<221> NAME/KEY: MISC_FEATURE
<222> LOCATION: (156)..(156)
<223> OTHER INFORMATION: Xaa can be K or G
<220> FEATURE:
<221> NAME/KEY: MISC_FEATURE
<222> LOCATION: (157)..(157)
<223> OTHER INFORMATION: Xaa can be P or A
<220> FEATURE:
<221> NAME/KEY: MISC_FEATURE
<222> LOCATION: (159)..(159)
<223> OTHER INFORMATION: Xaa can be D or N
<220> FEATURE:
<221> NAME/KEY: MISC_FEATURE
<222> LOCATION: (160)..(160)
<223> OTHER INFORMATION: Xaa can be S or H
<220> FEATURE:
<221> NAME/KEY: MISC_FEATURE
<222> LOCATION: (161)..(161)
<223> OTHER INFORMATION: Xaa can be K or S
<220> FEATURE:
<221> NAME/KEY: MISC_FEATURE
<222> LOCATION: (162)..(162)
<223> OTHER INFORMATION: Xaa can be S or D
<220> FEATURE:
<221> NAME/KEY: MISC_FEATURE
<222> LOCATION: (164)..(164)
<223> OTHER INFORMATION: Xaa can be R or D
<220> FEATURE:
<221> NAME/KEY: MISC_FEATURE
<222> LOCATION: (165)..(165)
<223> OTHER INFORMATION: Xaa can be T or A
<220> FEATURE:
<221> NAME/KEY: MISC_FEATURE
<222> LOCATION: (166)..(166)
<223> OTHER INFORMATION: Xaa can be A or E
<220> FEATURE:
<221> NAME/KEY: MISC_FEATURE
```

```
<222> LOCATION: (168)..(168)
<223> OTHER INFORMATION: Xaa can be Q or R
<220> FEATURE:
<221> NAME/KEY: MISC_FEATURE
<222> LOCATION: (170)..(170)
<223> OTHER INFORMATION: Xaa can be E or L
<220> FEATURE:
<221> NAME/KEY: MISC_FEATURE
<222> LOCATION: (171)..(171)
<223> OTHER INFORMATION: Xaa can be I or F
<220> FEATURE:
<221> NAME/KEY: MISC_FEATURE
<222> LOCATION: (172)..(172)
<223> OTHER INFORMATION: Xaa can be T or R
<220> FEATURE:
<221> NAME/KEY: MISC_FEATURE
<222> LOCATION: (173)..(173)
<223> OTHER INFORMATION: Xaa can be T or E
<220> FEATURE:
<221> NAME/KEY: MISC_FEATURE
<222> LOCATION: (176)..(176)
<223> OTHER INFORMATION: Xaa can be Q or R
<220> FEATURE:
<221> NAME/KEY: MISC_FEATURE
<222> LOCATION: (178)..(178)
<223> OTHER INFORMATION: Xaa can be D or H
<220> FEATURE:
<221> NAME/KEY: MISC_FEATURE
<222> LOCATION: (183)..(183)
<223> OTHER INFORMATION: Xaa can be T or A
<220> FEATURE:
<221> NAME/KEY: MISC_FEATURE
<222> LOCATION: (186)..(186)
<223> OTHER INFORMATION: Xaa can be L or H
<220> FEATURE:
<221> NAME/KEY: MISC_FEATURE
<222> LOCATION: (190)..(190)
<223> OTHER INFORMATION: Xaa can be N or P
<220> FEATURE:
<221> NAME/KEY: MISC_FEATURE
<222> LOCATION: (191)..(191)
<223> OTHER INFORMATION: Xaa can be V or T
<220> FEATURE:
<221> NAME/KEY: MISC_FEATURE
<222> LOCATION: (193)..(193)
<223> OTHER INFORMATION: Xaa can be T or Q
<220> FEATURE:
<221> NAME/KEY: MISC_FEATURE
<222> LOCATION: (197)..(197)
<223> OTHER INFORMATION: Xaa can be V or R
<220> FEATURE:
<221> NAME/KEY: MISC_FEATURE
<222> LOCATION: (204)..(204)
<223> OTHER INFORMATION: Xaa can be T or A
<220> FEATURE:
<221> NAME/KEY: MISC_FEATURE
<222> LOCATION: (205)..(205)
<223> OTHER INFORMATION: Xaa can be Q or A
<220> FEATURE:
<221> NAME/KEY: MISC_FEATURE
<222> LOCATION: (206)..(206)
<223> OTHER INFORMATION: Xaa can be N or G
<220> FEATURE:
<221> NAME/KEY: MISC_FEATURE
<222> LOCATION: (213)..(213)
<223> OTHER INFORMATION: Xaa can be V or A
<220> FEATURE:
<221> NAME/KEY: MISC_FEATURE
<222> LOCATION: (228)..(228)
<223> OTHER INFORMATION: Xaa can be H or Q
<220> FEATURE:
<221> NAME/KEY: MISC_FEATURE
<222> LOCATION: (229)..(229)
<223> OTHER INFORMATION: Xaa can be S or G
<220> FEATURE:
<221> NAME/KEY: MISC_FEATURE
<222> LOCATION: (231)..(231)
<223> OTHER INFORMATION: Xaa can be K or G
<220> FEATURE:
```

```
<221> NAME/KEY: MISC_FEATURE
<222> LOCATION: (232)..(232)
<223> OTHER INFORMATION: Xaa can be G
<220> FEATURE:
<221> NAME/KEY: MISC_FEATURE
<222> LOCATION: (236)..(236)
<223> OTHER INFORMATION: Xaa can be T or R
<220> FEATURE:
<221> NAME/KEY: MISC_FEATURE
<222> LOCATION: (238)..(238)
<223> OTHER INFORMATION: Xaa can be N or R
<220> FEATURE:
<221> NAME/KEY: MISC_FEATURE
<222> LOCATION: (241)..(241)
<223> OTHER INFORMATION: Xaa can be Q
<220> FEATURE:
<221> NAME/KEY: MISC_FEATURE
<222> LOCATION: (242)..(242)
<223> OTHER INFORMATION: Xaa can be L
<220> FEATURE:
<221> NAME/KEY: MISC_FEATURE
<222> LOCATION: (243)..(243)
<223> OTHER INFORMATION: Xaa can be D or P
<220> FEATURE:
<221> NAME/KEY: MISC_FEATURE
<222> LOCATION: (245)..(245)
<223> OTHER INFORMATION: Xaa can be D or Q
<220> FEATURE:
<221> NAME/KEY: MISC_FEATURE
<222> LOCATION: (246)..(246)
<223> OTHER INFORMATION: Xaa can be P or V
<220> FEATURE:
<221> NAME/KEY: MISC_FEATURE
<222> LOCATION: (247)..(247)
<223> OTHER INFORMATION: Xaa can be G or E
<220> FEATURE:
<221> NAME/KEY: MISC_FEATURE
<222> LOCATION: (248)..(248)
<223> OTHER INFORMATION: Xaa can be Q or R
<220> FEATURE:
<221> NAME/KEY: MISC_FEATURE
<222> LOCATION: (257)..(257)
<223> OTHER INFORMATION: Xaa can be K or I
<220> FEATURE:
<221> NAME/KEY: MISC_FEATURE
<222> LOCATION: (258)..(258)
<223> OTHER INFORMATION: Xaa can be A or P
<220> FEATURE:
<221> NAME/KEY: MISC_FEATURE
<222> LOCATION: (260)..(260)
<223> OTHER INFORMATION: Xaa can be E or K
<220> FEATURE:
<221> NAME/KEY: MISC_FEATURE
<222> LOCATION: (264)..(264)
<223> OTHER INFORMATION: Xaa can be Q or K
<220> FEATURE:
<221> NAME/KEY: MISC_FEATURE
<222> LOCATION: (265)..(265)
<223> OTHER INFORMATION: Xaa can be G or R
<220> FEATURE:
<221> NAME/KEY: MISC_FEATURE
<222> LOCATION: (267)..(267)
<223> OTHER INFORMATION: Xaa can be K or T
<220> FEATURE:
<221> NAME/KEY: MISC_FEATURE
<222> LOCATION: (286)..(267)
<223> OTHER INFORMATION: Xaa can be K or T
<220> FEATURE:
<221> NAME/KEY: MISC_FEATURE
<222> LOCATION: (286)..(286)
<223> OTHER INFORMATION: Xaa can be V or A
<220> FEATURE:
<221> NAME/KEY: MISC_FEATURE
<222> LOCATION: (292)..(292)
<223> OTHER INFORMATION: Xaa can be R or N
<220> FEATURE:
<221> NAME/KEY: MISC_FEATURE
<222> LOCATION: (296)..(296)
<223> OTHER INFORMATION: Xaa can be M or S
```

-continued

```
<220> FEATURE:
<221> NAME/KEY: MISC_FEATURE
<222> LOCATION: (300)..(300)
<223> OTHER INFORMATION: Xaa can be E or K
<220> FEATURE:
<221> NAME/KEY: MISC_FEATURE
<222> LOCATION: (302)..(302)
<223> OTHER INFORMATION: Xaa can be A or V
<220> FEATURE:
<221> NAME/KEY: MISC_FEATURE
<222> LOCATION: (311)..(311)
<223> OTHER INFORMATION: Xaa can be H or R
<220> FEATURE:
<221> NAME/KEY: MISC_FEATURE
<222> LOCATION: (314)..(314)
<223> OTHER INFORMATION: Xaa can be L or P
<220> FEATURE:
<221> NAME/KEY: MISC_FEATURE
<222> LOCATION: (315)..(315)
<223> OTHER INFORMATION: Xaa can be N or S
<220> FEATURE:
<221> NAME/KEY: MISC_FEATURE
<222> LOCATION: (316)..(316)
<223> OTHER INFORMATION: Xaa can be A or L

<400> SEQUENCE: 69

Pro Pro Xaa Xaa Leu Xaa Xaa Xaa Leu Leu Leu Xaa Ala Ala Xaa Xaa
1               5                   10                  15

Xaa Xaa Xaa Ala Ala Gln Asp Xaa Cys Xaa Cys Xaa Xaa Xaa Lys Leu
            20                  25                  30

Xaa Val Xaa Xaa Xaa Xaa Xaa Xaa Xaa Xaa Cys Gln Cys Xaa Ala
        35                  40                  45

Leu Gly Ala Xaa Xaa Xaa Val Xaa Cys Ser Xaa Leu Xaa Ala Lys Cys
50                  55                  60

Leu Leu Leu Lys Ala Xaa Met Xaa Ala Xaa Lys Xaa Ala Arg Xaa Xaa
65                  70                  75                  80

Xaa Xaa Pro Xaa Glu Xaa Ala Leu Xaa Xaa Asn Asp Gly Leu Tyr Asp
            85                  90                  95

Pro Asp Cys Asp Xaa Xaa Gly Xaa Phe Lys Ala Lys Gln Cys Asn Xaa
            100                 105                 110

Thr Ser Xaa Cys Trp Cys Val Asn Ser Xaa Gly Val Arg Arg Thr Asp
        115                 120                 125

Lys Xaa Asp Xaa Xaa Ile Xaa Cys Xaa Glu Xaa Val Arg Thr His Xaa
    130                 135                 140

Ile Ile Ile Asp Leu Lys His Lys Xaa Xaa Xaa Xaa Xaa Phe Xaa Xaa
145                 150                 155                 160

Xaa Xaa Leu Xaa Xaa Xaa Leu Xaa Lys Xaa Xaa Xaa Xaa Arg Tyr Xaa
            165                 170                 175

Leu Xaa Pro Lys Phe Ile Xaa Ala Ile Xaa Tyr Glu Asn Xaa Xaa Ile
        180                 185                 190

Xaa Ile Asp Leu Xaa Gln Asn Ser Ser Gln Lys Xaa Xaa Xaa Asp Val
    195                 200                 205

Asp Ile Ala Asp Xaa Ala Tyr Tyr Phe Glu Lys Asp Ile Lys Gly Glu
        210                 215                 220

Ser Leu Phe Xaa Xaa Lys Xaa Xaa Leu Asp Leu Xaa Val Xaa Gly Glu
225                 230                 235                 240

Xaa Xaa Xaa Leu Xaa Xaa Xaa Xaa Thr Leu Ile Tyr Tyr Leu Asp Glu
            245                 250                 255

Xaa Xaa Pro Xaa Phe Ser Met Xaa Xaa Leu Xaa Ala Gly Leu Ile Ala
        260                 265                 270

Val Ile Val Val Val Val Ile Ala Leu Val Ala Gly Ile Xaa Val Leu
```

```
                    275                 280                 285
Val Ile Ser Xaa Lys Lys Lys Xaa Ala Lys Tyr Xaa Lys Xaa Glu Ile
            290                 295                 300
Lys Glu Leu Gly Glu Leu Xaa Lys Glu Xaa Xaa Xaa
305                 310                 315

<210> SEQ ID NO 70
<211> LENGTH: 323
<212> TYPE: PRT
<213> ORGANISM: Homo sapiens
<220> FEATURE:
<221> NAME/KEY: MISC_FEATURE
<222> LOCATION: (5)..(5)
<223> OTHER INFORMATION: Xaa can be P or L
<220> FEATURE:
<221> NAME/KEY: MISC_FEATURE
<222> LOCATION: (6)..(6)
<223> OTHER INFORMATION: Xaa can be G or D
<220> FEATURE:
<221> NAME/KEY: MISC_FEATURE
<222> LOCATION: (10)..(10)
<223> OTHER INFORMATION: Xaa can be P
<220> FEATURE:
<221> NAME/KEY: MISC_FEATURE
<222> LOCATION: (11)..(11)
<223> OTHER INFORMATION: Xaa can be P
<220> FEATURE:
<221> NAME/KEY: MISC_FEATURE
<222> LOCATION: (12)..(12)
<223> OTHER INFORMATION: Xaa can be L
<220> FEATURE:
<221> NAME/KEY: MISC_FEATURE
<222> LOCATION: (13)..(13)
<223> OTHER INFORMATION: Xaa can be R
<220> FEATURE:
<221> NAME/KEY: MISC_FEATURE
<222> LOCATION: (14)..(14)
<223> OTHER INFORMATION: Xaa can be L
<220> FEATURE:
<221> NAME/KEY: MISC_FEATURE
<222> LOCATION: (15)..(15)
<223> OTHER INFORMATION: Xaa can be P
<220> FEATURE:
<221> NAME/KEY: MISC_FEATURE
<222> LOCATION: (23)..(23)
<223> OTHER INFORMATION: Xaa can be A or M
<220> FEATURE:
<221> NAME/KEY: MISC_FEATURE
<222> LOCATION: (24)..(24)
<223> OTHER INFORMATION: Xaa can be V or A
<220> FEATURE:
<221> NAME/KEY: MISC_FEATURE
<222> LOCATION: (26)..(26)
<223> OTHER INFORMATION: Xaa can be G or R
<220> FEATURE:
<221> NAME/KEY: MISC_FEATURE
<222> LOCATION: (27)..(27)
<223> OTHER INFORMATION: Xaa can be H or F
<220> FEATURE:
<221> NAME/KEY: MISC_FEATURE
<222> LOCATION: (28)..(28)
<223> OTHER INFORMATION: Xaa can be T or C
<220> FEATURE:
<221> NAME/KEY: MISC_FEATURE
<222> LOCATION: (29)..(29)
<223> OTHER INFORMATION: Xaa can be A or T
<220> FEATURE:
<221> NAME/KEY: MISC_FEATURE
<222> LOCATION: (32)..(32)
<223> OTHER INFORMATION: Xaa can be D or S
<220> FEATURE:
<221> NAME/KEY: MISC_FEATURE
<222> LOCATION: (45)..(45)
<223> OTHER INFORMATION: Xaa can be S or D
<220> FEATURE:
<221> NAME/KEY: MISC_FEATURE
```

```
<222> LOCATION: (46)..(46)
<223> OTHER INFORMATION: Xaa can be P or T
<220> FEATURE:
<221> NAME/KEY: MISC_FEATURE
<222> LOCATION: (47)..(47)
<223> OTHER INFORMATION: Xaa can be D or N
<220> FEATURE:
<221> NAME/KEY: MISC_FEATURE
<222> LOCATION: (52)..(52)
<223> OTHER INFORMATION: Xaa can be R or V
<220> FEATURE:
<221> NAME/KEY: MISC_FEATURE
<222> LOCATION: (61)..(61)
<223> OTHER INFORMATION: Xaa can be G or Q
<220> FEATURE:
<221> NAME/KEY: MISC_FEATURE
<222> LOCATION: (63)..(63)
<223> OTHER INFORMATION: Xaa can be A or L
<220> FEATURE:
<221> NAME/KEY: MISC_FEATURE
<222> LOCATION: (83)..(83)
<223> OTHER INFORMATION: Xaa can be P or R
<220> FEATURE:
<221> NAME/KEY: MISC_FEATURE
<222> LOCATION: (85)..(85)
<223> OTHER INFORMATION: Xaa can be N or S
<220> FEATURE:
<221> NAME/KEY: MISC_FEATURE
<222> LOCATION: (91)..(91)
<223> OTHER INFORMATION: Xaa can be R or M
<220> FEATURE:
<221> NAME/KEY: MISC_FEATURE
<222> LOCATION: (110)..(110)
<223> OTHER INFORMATION: Xaa can be P or D
<220> FEATURE:
<221> NAME/KEY: MISC_FEATURE
<222> LOCATION: (111)..(111)
<223> OTHER INFORMATION: Xaa can be E or K
<220> FEATURE:
<221> NAME/KEY: MISC_FEATURE
<222> LOCATION: (141)..(141)
<223> OTHER INFORMATION: Xaa can be L or Q
<220> FEATURE:
<221> NAME/KEY: MISC_FEATURE
<222> LOCATION: (164)..(164)
<223> OTHER INFORMATION: Xaa can be A or D
<220> FEATURE:
<221> NAME/KEY: MISC_FEATURE
<222> LOCATION: (165)..(165)
<223> OTHER INFORMATION: Xaa can be G or R
<220> FEATURE:
<221> NAME/KEY: MISC_FEATURE
<222> LOCATION: (181)..(181)
<223> OTHER INFORMATION: Xaa can be R or Q
<220> FEATURE:
<221> NAME/KEY: MISC_FEATURE
<222> LOCATION: (189)..(189)
<223> OTHER INFORMATION: Xaa can be K or S
<220> FEATURE:
<221> NAME/KEY: MISC_FEATURE
<222> LOCATION: (198)..(198)
<223> OTHER INFORMATION: Xaa can be Q or E
<220> FEATURE:
<221> NAME/KEY: MISC_FEATURE
<222> LOCATION: (209)..(209)
<223> OTHER INFORMATION: Xaa can be T or A
<220> FEATURE:
<221> NAME/KEY: MISC_FEATURE
<222> LOCATION: (214)..(214)
<223> OTHER INFORMATION: Xaa can be A or D
<220> FEATURE:
<221> NAME/KEY: MISC_FEATURE
<222> LOCATION: (214)..(214)
<223> OTHER INFORMATION: Xaa can be A or L
<220> FEATURE:
<221> NAME/KEY: MISC_FEATURE
<222> LOCATION: (215)..(215)
<223> OTHER INFORMATION: Xaa can be G or R
<220> FEATURE:
```

<221> NAME/KEY: MISC_FEATURE
<222> LOCATION: (237)..(237)
<223> OTHER INFORMATION: Xaa can be Q or M
<220> FEATURE:
<221> NAME/KEY: MISC_FEATURE
<222> LOCATION: (240)..(240)
<223> OTHER INFORMATION: Xaa can be G or R
<220> FEATURE:
<221> NAME/KEY: MISC_FEATURE
<222> LOCATION: (245)..(245)
<223> OTHER INFORMATION: Xaa can be R or Q
<220> FEATURE:
<221> NAME/KEY: MISC_FEATURE
<222> LOCATION: (252)..(252)
<223> OTHER INFORMATION: Xaa can be Q or H
<220> FEATURE:
<221> NAME/KEY: MISC_FEATURE
<222> LOCATION: (264)..(264)
<223> OTHER INFORMATION: Xaa can be I or K
<220> FEATURE:
<221> NAME/KEY: MISC_FEATURE
<222> LOCATION: (267)..(267)
<223> OTHER INFORMATION: Xaa can be K or Q
<220> FEATURE:
<221> NAME/KEY: MISC_FEATURE
<222> LOCATION: (282)..(282)
<223> OTHER INFORMATION: Xaa can be V or A
<220> FEATURE:
<221> NAME/KEY: MISC_FEATURE
<222> LOCATION: (285)..(285)
<223> OTHER INFORMATION: Xaa can be V or S
<220> FEATURE:
<221> NAME/KEY: MISC_FEATURE
<222> LOCATION: (293)..(293)
<223> OTHER INFORMATION: Xaa can be A or V
<220> FEATURE:
<221> NAME/KEY: MISC_FEATURE
<222> LOCATION: (299)..(299)
<223> OTHER INFORMATION: Xaa can be N or K
<220> FEATURE:
<221> NAME/KEY: MISC_FEATURE
<222> LOCATION: (319)..(319)
<223> OTHER INFORMATION: Xaa can be K or S

<400> SEQUENCE: 70

```
Met Ala Arg Gly Xaa Xaa Leu Ala Pro Xaa Xaa Xaa Xaa Xaa Xaa Leu
1               5                   10                  15

Leu Leu Leu Leu Ala Xaa Xaa Thr Xaa Xaa Xaa Xaa Ala Gln Xaa
            20                  25                  30

Asn Cys Thr Cys Pro Thr Asn Lys Met Thr Val Cys Xaa Xaa Xaa Gly
        35                  40                  45

Pro Gly Gly Xaa Cys Gln Cys Arg Ala Leu Gly Ser Xaa Met Xaa Val
    50                  55                  60

Asp Cys Ser Thr Leu Thr Ser Lys Cys Leu Leu Lys Ala Arg Met
65                  70                  75                  80

Ser Ala Xaa Lys Xaa Ala Arg Ser Leu Val Xaa Pro Ser Glu His Ala
                85                  90                  95

Ile Leu Asp Asn Asp Gly Leu Tyr Asp Pro Asp Cys Asp Xaa Xaa Gly
            100                 105                 110

Arg Phe Lys Ala Arg Gln Cys Asn Gln Thr Ser Val Cys Trp Cys Val
        115                 120                 125

Asn Ser Val Gly Val Arg Arg Thr Asp Lys Gly Asp Xaa Ser Leu Arg
    130                 135                 140

Cys Asp Glu Leu Val Arg Thr His His Ile Leu Ile Asp Leu Arg His
145                 150                 155                 160

Arg Pro Thr Xaa Xaa Ala Phe Asn His Ser Asp Leu Asp Ala Glu Leu
                165                 170                 175
```

```
Arg Arg Leu Phe Xaa Glu Arg Tyr Lys Leu His Pro Xaa Phe Leu Ala
            180                 185                 190

Ala Val His Tyr Glu Xaa Pro Thr Ile Gln Ile Glu Leu Arg Gln Asn
        195                 200                 205

Xaa Ser Gln Lys Ala Xaa Xaa Asp Val Asp Ile Ala Asp Ala Ala Tyr
    210                 215                 220

Tyr Phe Glu Arg Asp Ile Lys Gly Glu Ser Leu Phe Xaa Gly Arg Xaa
225                 230                 235                 240

Gly Leu Asp Leu Xaa Val Arg Gly Glu Pro Leu Xaa Val Glu Arg Thr
                245                 250                 255

Leu Ile Tyr Tyr Leu Asp Glu Xaa Pro Pro Xaa Phe Ser Met Lys Arg
            260                 265                 270

Leu Thr Ala Gly Leu Ile Ala Val Ile Xaa Val Val Xaa Val Ala Leu
        275                 280                 285

Val Ala Gly Met Xaa Val Leu Val Ile Thr Xaa Arg Arg Lys Ser Gly
        290                 295                 300

Lys Tyr Lys Lys Val Glu Ile Lys Glu Leu Gly Glu Leu Arg Xaa Glu
305                 310                 315                 320

Pro Ser Leu

<210> SEQ ID NO 71
<211> LENGTH: 119
<212> TYPE: PRT
<213> ORGANISM: Artificial Sequence
<220> FEATURE:
<223> OTHER INFORMATION: Synthetic construct

<400> SEQUENCE: 71

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Gly Val His Trp Ile Arg Gln Pro Pro Gly Lys Gly Leu Glu Trp Ile
        35                  40                  45

Gly Val Ile Trp Thr Gly Gly Ser Thr Asp Tyr Asn Ser Ala Leu Met
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Asp Gly Asp Tyr Arg Asp Tyr Thr Met Asp Tyr Trp Gly Gln Gly
            100                 105                 110

Thr Leu Val Thr Val Ser Ser
        115

<210> SEQ ID NO 72
<211> LENGTH: 111
<212> TYPE: PRT
<213> ORGANISM: Artificial Sequence
<220> FEATURE:
<223> OTHER INFORMATION: Synthetic construct

<400> SEQUENCE: 72

Asp Ile Val Met Thr Gln Ser Pro Asp Ser Leu Ala Val Ser Leu Gly
1               5                   10                  15

Glu Arg Ala Thr Ile Asn Cys Arg Ala Ser Lys Ser Val Ser Thr Ser
            20                  25                  30
```

-continued

Gly Tyr Ser Tyr Met His Trp Tyr Gln Gln Lys Pro Gly Gln Pro Pro
                35                  40                  45

Lys Leu Leu Ile Tyr Leu Ala Ser Asn Leu Glu Ser Gly Val Pro Asp
 50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln His Ser Arg
                85                  90                  95

Glu Leu Pro Tyr Thr Phe Gly Gln Gly Thr Lys Leu Glu Ile Lys
            100                 105                 110

<210> SEQ ID NO 73
<211> LENGTH: 115
<212> TYPE: PRT
<213> ORGANISM: Artificial Sequence
<220> FEATURE:
<223> OTHER INFORMATION: Synthetic construct

<400> SEQUENCE: 73

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Trp Ile Asn Trp Val Arg Gln Ala Pro Gly Gln Gly Leu Glu Trp Met
            35                  40                  45

Gly Asn Ile Tyr Pro Ser Asp Ser Tyr Ser Asn Tyr Asn Gln Lys Phe
        50                  55                  60

Lys Asp Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Ser Ser Phe Asp Tyr Trp Gly Gln Gly Thr Leu Val Thr
            100                 105                 110

Val Ser Ser
        115

<210> SEQ ID NO 74
<211> LENGTH: 107
<212> TYPE: PRT
<213> ORGANISM: Artificial Sequence
<220> FEATURE:
<223> OTHER INFORMATION: Synthetic construct

<400> SEQUENCE: 74

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Thr Ile Gly Thr Ser
                20                  25                  30

Ile His Trp Tyr Gln Gln Lys Pro Gly Gln Ala Pro Arg Leu Leu Ile
            35                  40                  45

Tyr Tyr Ala Ser Glu Ser Ile Ser Gly Ile Pro Ala Arg Phe Ser Gly
        50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Asn Ser Trp Pro Phe
                85                  90                  95

Thr Phe Gly Gln Gly Thr Lys Leu Glu Ile Lys
            100                 105

```
<210> SEQ ID NO 75
<211> LENGTH: 5
<212> TYPE: PRT
<213> ORGANISM: Artificial Sequence
<220> FEATURE:
<223> OTHER INFORMATION: Synthetic Construct

<400> SEQUENCE: 75

Leu Leu Gln Gly Gly
1               5

<210> SEQ ID NO 76
<211> LENGTH: 7
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (2)..(2)
<223> OTHER INFORMATION: Xaa can be F or G
<220> FEATURE:
<221> NAME/KEY: MISC_FEATURE
<222> LOCATION: (4)..(4)
<223> OTHER INFORMATION: Xaa can be L or I
<220> FEATURE:
<221> NAME/KEY: MISC_FEATURE
<222> LOCATION: (5)..(5)
<223> OTHER INFORMATION: Xaa can be T or S

<400> SEQUENCE: 76

Gly Xaa Ser Xaa Xaa Ser Tyr
1               5

<210> SEQ ID NO 77
<211> LENGTH: 10
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (2)..(2)
<223> OTHER INFORMATION: Xaa can be L or I
<220> FEATURE:
<221> NAME/KEY: MISC_FEATURE
<222> LOCATION: (4)..(4)
<223> OTHER INFORMATION: Xaa can be L or I
<220> FEATURE:
<221> NAME/KEY: MISC_FEATURE
<222> LOCATION: (5)..(5)
<223> OTHER INFORMATION: Xaa can be T or S

<400> SEQUENCE: 77

Gly Xaa Ser Xaa Xaa Ser Tyr Gly Val His
1               5                   10

<210> SEQ ID NO 78
<211> LENGTH: 7
<212> TYPE: PRT
<213> ORGANISM: Artificial Sequence
<220> FEATURE:
<223> OTHER INFORMATION: Synthetic construct

<400> SEQUENCE: 78

Gly Gly Leu Leu Gln Gly Gly
1               5

<210> SEQ ID NO 79
```

```
<211> LENGTH: 5
<212> TYPE: PRT
<213> ORGANISM: Artificial Sequence
<220> FEATURE:
<223> OTHER INFORMATION: Synthetic construct

<400> SEQUENCE: 79

Leu Leu Gln Gly Ala
1               5

<210> SEQ ID NO 80
<211> LENGTH: 15
<212> TYPE: PRT
<213> ORGANISM: Artificial Sequence
<220> FEATURE:
<223> OTHER INFORMATION: Synthetic construct

<400> SEQUENCE: 80

Gly Gly Gly Gly Ser Gly Gly Gly Ser Gly Gly Gly Gly Ser
1               5                   10                  15

<210> SEQ ID NO 81
<211> LENGTH: 7
<212> TYPE: PRT
<213> ORGANISM: Artificial Sequence
<220> FEATURE:
<223> OTHER INFORMATION: Synthetic construct

<400> SEQUENCE: 81

Gly Gly Leu Leu Gln Gly Ala
1               5

<210> SEQ ID NO 82
<211> LENGTH: 9
<212> TYPE: PRT
<213> ORGANISM: Artificial Sequence
<220> FEATURE:
<223> OTHER INFORMATION: Synthetic construct
<220> FEATURE:
<221> NAME/KEY: Xaa
<222> LOCATION: (7)..(7)
<223> OTHER INFORMATION: Xaa can be M or E
<220> FEATURE:
<221> NAME/KEY: Xaa
<222> LOCATION: (7)..(7)
<223> OTHER INFORMATION: Xaa can be E or M
<220> FEATURE:
<221> NAME/KEY: MISC_FEATURE
<222> LOCATION: (7)..(7)
<223> OTHER INFORMATION: Xaa can be M or E

<400> SEQUENCE: 82

Asp Tyr Asp Arg Tyr Thr Xaa Asp Tyr
1               5

<210> SEQ ID NO 83
<211> LENGTH: 9
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (7)..(7)
<223> OTHER INFORMATION: Xaa can be any naturally occurring amino acid

<400> SEQUENCE: 83

Asp Tyr Asp Arg Tyr Thr Xaa Asp Tyr
1               5
```

```
<210> SEQ ID NO 84
<211> LENGTH: 119
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (98)..(98)
<223> OTHER INFORMATION: Xaa can be any naturally occurring amino acid
<220> FEATURE:
<221> NAME/KEY: MISC_FEATURE
<222> LOCATION: (99)..(99)
<223> OTHER INFORMATION: Xaa can be any naturally occurring amino acid
<220> FEATURE:
<221> NAME/KEY: MISC_FEATURE
<222> LOCATION: (106)..(106)
<223> OTHER INFORMATION: Xaa can be any naturally occurring amino acid

<400> SEQUENCE: 84

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Gly Val His Trp Ile Arg Gln Pro Pro Gly Lys Gly Leu Glu Trp Ile
        35                  40                  45

Gly Val Ile Trp Thr Ser Gly Val Thr Asp Tyr Asn Ser Ala Leu Met
    50                  55                  60

Gly Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Xaa Xaa Asp Tyr Asp Arg Tyr Thr Xaa Asp Tyr Trp Gly Gln Gly
            100                 105                 110

Thr Leu Val Thr Val Ser Ser
        115

<210> SEQ ID NO 85
<211> LENGTH: 119
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (98)..(98)
<223> OTHER INFORMATION: Xaa can be any naturally occurring amino acid
<220> FEATURE:
<221> NAME/KEY: MISC_FEATURE
<222> LOCATION: (99)..(99)
<223> OTHER INFORMATION: Xaa can be any naturally occurring amino acid
<220> FEATURE:
<221> NAME/KEY: MISC_FEATURE
<222> LOCATION: (106)..(106)
<223> OTHER INFORMATION: Xaa can be M or E
<220> FEATURE:
<221> NAME/KEY: MISC_FEATURE
<222> LOCATION: (106)..(106)
<223> OTHER INFORMATION: Xaa can be E or M

<400> SEQUENCE: 85

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Gly Val His Trp Ile Arg Gln Pro Pro Gly Lys Gly Leu Glu Trp Ile
```

```
                35                  40                  45
Gly Val Ile Trp Thr Ser Gly Val Thr Asp Tyr Asn Ser Ala Leu Met
    50                  55                  60

Gly Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Xaa Xaa Asp Tyr Asp Arg Tyr Thr Xaa Asp Tyr Trp Gly Gln Gly
            100                 105                 110

Thr Leu Val Thr Val Ser Ser
        115

<210> SEQ ID NO 86
<211> LENGTH: 11
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Xaa can be any naturally occurring amino acid
<220> FEATURE:
<221> NAME/KEY: MISC_FEATURE
<222> LOCATION: (2)..(2)
<223> OTHER INFORMATION: Xaa can be any naturally occurring amino acid
<220> FEATURE:
<221> NAME/KEY: MISC_FEATURE
<222> LOCATION: (9)..(9)
<223> OTHER INFORMATION: Xaa can be any naturally occurring amino acid

<400> SEQUENCE: 86

Xaa Xaa Asp Tyr Asp Arg Tyr Thr Xaa Asp Tyr
1               5                   10

<210> SEQ ID NO 87
<211> LENGTH: 11
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Xaa can be any naturally occurring amino acid
<220> FEATURE:
<221> NAME/KEY: MISC_FEATURE
<222> LOCATION: (2)..(2)
<223> OTHER INFORMATION: Xaa can be any naturally occurring amino acid
<220> FEATURE:
<221> NAME/KEY: MISC_FEATURE
<222> LOCATION: (9)..(9)
<223> OTHER INFORMATION: Xaa can be E or M

<400> SEQUENCE: 87

Xaa Xaa Asp Tyr Asp Arg Tyr Thr Xaa Asp Tyr
1               5                   10

<210> SEQ ID NO 88
<211> LENGTH: 8
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (4)..(4)
<223> OTHER INFORMATION: Xaa can be G or P
<220> FEATURE:
```

```
<221> NAME/KEY: MISC_FEATURE
<222> LOCATION: (5)..(5)
<223> OTHER INFORMATION: Xaa can be A, G, P, or absent
<220> FEATURE:
<221> NAME/KEY: MISC_FEATURE
<222> LOCATION: (6)..(6)
<223> OTHER INFORMATION: Xaa can be A, G, K, P, or absent
<220> FEATURE:
<221> NAME/KEY: MISC_FEATURE
<222> LOCATION: (7)..(7)
<223> OTHER INFORMATION: Xaa can be G, K, or absent
<220> FEATURE:
<221> NAME/KEY: MISC_FEATURE
<222> LOCATION: (8)..(8)
<223> OTHER INFORMATION: Xaa can be K or absent

<400> SEQUENCE: 88

Leu Leu Gln Xaa Xaa Xaa Xaa Xaa
1               5

<210> SEQ ID NO 89
<211> LENGTH: 8
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (4)..(4)
<223> OTHER INFORMATION: Xaa can be any naturally occurring amino acid
<220> FEATURE:
<221> NAME/KEY: MISC_FEATURE
<222> LOCATION: (5)..(5)
<223> OTHER INFORMATION: Xaa can be any naturally occurring amino acid
      or absent
<220> FEATURE:
<221> NAME/KEY: MISC_FEATURE
<222> LOCATION: (6)..(6)
<223> OTHER INFORMATION: Xaa can be any naturally occurring amino acid
      or absent
<220> FEATURE:
<221> NAME/KEY: MISC_FEATURE
<222> LOCATION: (7)..(7)
<223> OTHER INFORMATION: Xaa can be any naturally occurring amino acid
      or absent
<220> FEATURE:
<221> NAME/KEY: MISC_FEATURE
<222> LOCATION: (8)..(8)
<223> OTHER INFORMATION: Xaa can be any naturally occurring amino acid
      or absent

<400> SEQUENCE: 89

Leu Leu Gln Xaa Xaa Xaa Xaa Xaa
1               5

<210> SEQ ID NO 90
<211> LENGTH: 7
<212> TYPE: PRT
<213> ORGANISM: Artificial Sequence
<220> FEATURE:
<223> OTHER INFORMATION: Synthetic construct

<400> SEQUENCE: 90

Leu Leu Gln Gly Pro Gly Lys
1               5

<210> SEQ ID NO 91
<211> LENGTH: 6
<212> TYPE: PRT
<213> ORGANISM: Artificial Sequence
<220> FEATURE:
<223> OTHER INFORMATION: Synthetic construct
```

```
<400> SEQUENCE: 91

Leu Leu Gln Gly Pro Gly
1               5

<210> SEQ ID NO 92
<211> LENGTH: 6
<212> TYPE: PRT
<213> ORGANISM: Artificial Sequence
<220> FEATURE:
<223> OTHER INFORMATION: Synthetic construct

<400> SEQUENCE: 92

Leu Leu Gln Gly Pro Ala
1               5

<210> SEQ ID NO 93
<211> LENGTH: 5
<212> TYPE: PRT
<213> ORGANISM: Artificial Sequence
<220> FEATURE:
<223> OTHER INFORMATION: Synthetic construct

<400> SEQUENCE: 93

Leu Leu Gln Gly Pro
1               5

<210> SEQ ID NO 94
<211> LENGTH: 4
<212> TYPE: PRT
<213> ORGANISM: Artificial Sequence
<220> FEATURE:
<223> OTHER INFORMATION: Synthetic construct

<400> SEQUENCE: 94

Leu Leu Gln Pro
1

<210> SEQ ID NO 95
<211> LENGTH: 6
<212> TYPE: PRT
<213> ORGANISM: Artificial Sequence
<220> FEATURE:
<223> OTHER INFORMATION: Synthetic construct

<400> SEQUENCE: 95

Leu Leu Gln Pro Gly Lys
1               5

<210> SEQ ID NO 96
<211> LENGTH: 8
<212> TYPE: PRT
<213> ORGANISM: Artificial Sequence
<220> FEATURE:
<223> OTHER INFORMATION: Synthetic construct

<400> SEQUENCE: 96

Leu Leu Gln Gly Ala Pro Gly Lys
1               5

<210> SEQ ID NO 97
<211> LENGTH: 7
<212> TYPE: PRT
<213> ORGANISM: Artificial Sequence
<220> FEATURE:
<223> OTHER INFORMATION: Synthetic construct

<400> SEQUENCE: 97
```

Leu Leu Gln Gly Ala Pro Gly
1               5

<210> SEQ ID NO 98
<211> LENGTH: 6
<212> TYPE: PRT
<213> ORGANISM: Artificial Sequence
<220> FEATURE:
<223> OTHER INFORMATION: Synthetic construct

<400> SEQUENCE: 98

Leu Leu Gln Gly Ala Pro
1               5

<210> SEQ ID NO 99
<211> LENGTH: 9
<212> TYPE: PRT
<213> ORGANISM: Artificial Sequence
<220> FEATURE:
<223> OTHER INFORMATION: Synthetic construct

<400> SEQUENCE: 99

Asp Tyr Asp Arg Tyr Thr Met Asp Tyr
1               5

<210> SEQ ID NO 100
<211> LENGTH: 9
<212> TYPE: PRT
<213> ORGANISM: Artificial Sequence
<220> FEATURE:
<223> OTHER INFORMATION: Synthetic construct

<400> SEQUENCE: 100

Asp Tyr Asp Arg Tyr Thr Glu Asp Tyr
1               5

<210> SEQ ID NO 101
<211> LENGTH: 449
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (98)..(98)
<223> OTHER INFORMATION: Xaa can be any naturally occurring amino acid
<220> FEATURE:
<221> NAME/KEY: MISC_FEATURE
<222> LOCATION: (99)..(99)
<223> OTHER INFORMATION: Xaa can be any naturally occurring amino acid
<220> FEATURE:
<221> NAME/KEY: MISC_FEATURE
<222> LOCATION: (106)..(106)
<223> OTHER INFORMATION: Xaa can be any naturally occurring amino acid

<400> SEQUENCE: 101

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Gly Val His Trp Ile Arg Gln Pro Pro Gly Lys Gly Leu Glu Trp Ile
        35                  40                  45

Gly Val Ile Trp Thr Ser Gly Val Thr Asp Tyr Asn Ser Ala Leu Met
    50                  55                  60

Gly Arg Val Thr Ile Ser Val Asp Thr Ser Lys Asn Gln Phe Ser Leu
65                  70                  75                  80

```
Lys Leu Ser Ser Val Thr Ala Ala Asp Thr Ala Val Tyr Tyr Cys Ala
                85                  90                  95

Arg Xaa Xaa Asp Tyr Asp Arg Tyr Thr Xaa Asp Tyr Trp Gly Gln Gly
            100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
            355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Lys

<210> SEQ ID NO 102
<211> LENGTH: 449
<212> TYPE: PRT
<213> ORGANISM: Artificial Sequence
<220> FEATURE:
<223> OTHER INFORMATION: Synthetic construct
```

```
<220> FEATURE:
<221> NAME/KEY: MISC_FEATURE
<222> LOCATION: (98)..(98)
<223> OTHER INFORMATION: Xaa can be any naturally occurring amino acid
<220> FEATURE:
<221> NAME/KEY: MISC_FEATURE
<222> LOCATION: (99)..(99)
<223> OTHER INFORMATION: Xaa can be any naturally occurring amino acid
<220> FEATURE:
<221> NAME/KEY: MISC_FEATURE
<222> LOCATION: (106)..(106)
<223> OTHER INFORMATION: Xaa can be E or M

<400> SEQUENCE: 102
```

| | | | | | | | | | | | | | | |
|---|---|---|---|---|---|---|---|---|---|---|---|---|---|---|
| Gln | Val | Gln | Leu | Gln | Glu | Ser | Gly | Pro | Gly | Leu | Val | Lys | Pro | Ser | Glu |
| 1 | | | | 5 | | | | | 10 | | | | | 15 | |

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Gly Val His Trp Ile Arg Gln Pro Pro Gly Lys Gly Leu Glu Trp Ile
        35                  40                  45

Gly Val Ile Trp Thr Ser Gly Val Thr Asp Tyr Asn Ser Ala Leu Met
    50                  55                  60

Gly Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Xaa Xaa Asp Tyr Asp Arg Tyr Thr Xaa Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr

```
                    340                 345                 350
Leu Pro Pro Ser Arg Glu Glu Met Thr Lys Asn Gln Val Ser Leu Thr
            355                 360                 365

Cys Leu Val Lys Gly Phe Tyr Pro Ser Asp Ile Ala Val Glu Trp Glu
        370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 103
<211> LENGTH: 11
<212> TYPE: PRT
<213> ORGANISM: Artificial Sequence
<220> FEATURE:
<223> OTHER INFORMATION: Synthetic construct

<400> SEQUENCE: 103

Leu Gly Asp Tyr Asp Arg Tyr Thr Met Asp Tyr
1               5                   10

<210> SEQ ID NO 104
<211> LENGTH: 11
<212> TYPE: PRT
<213> ORGANISM: Artificial Sequence
<220> FEATURE:
<223> OTHER INFORMATION: Synthetic construct

<400> SEQUENCE: 104

Tyr Gly Asp Tyr Asp Arg Tyr Thr Met Asp Tyr
1               5                   10

<210> SEQ ID NO 105
<211> LENGTH: 11
<212> TYPE: PRT
<213> ORGANISM: Artificial Sequence
<220> FEATURE:
<223> OTHER INFORMATION: Synthetic construct

<400> SEQUENCE: 105

Phe Gly Asp Tyr Asp Arg Tyr Thr Met Asp Tyr
1               5                   10

<210> SEQ ID NO 106
<211> LENGTH: 11
<212> TYPE: PRT
<213> ORGANISM: Artificial Sequence
<220> FEATURE:
<223> OTHER INFORMATION: Synthetic construct

<400> SEQUENCE: 106

His Gly Asp Tyr Asp Arg Tyr Thr Met Asp Tyr
1               5                   10

<210> SEQ ID NO 107
<211> LENGTH: 11
<212> TYPE: PRT
<213> ORGANISM: Artificial Sequence
```

```
<220> FEATURE:
<223> OTHER INFORMATION: Synthetic construct

<400> SEQUENCE: 107

Ala Gly Asp Tyr Asp Arg Tyr Thr Met Asp Tyr
1               5                   10

<210> SEQ ID NO 108
<211> LENGTH: 11
<212> TYPE: PRT
<213> ORGANISM: Artificial Sequence
<220> FEATURE:
<223> OTHER INFORMATION: Synthetic construct

<400> SEQUENCE: 108

Thr Gly Asp Tyr Asp Arg Tyr Thr Met Asp Tyr
1               5                   10

<210> SEQ ID NO 109
<211> LENGTH: 11
<212> TYPE: PRT
<213> ORGANISM: Artificial Sequence
<220> FEATURE:
<223> OTHER INFORMATION: Synthetic construct

<400> SEQUENCE: 109

Ser Gly Asp Tyr Asp Arg Tyr Thr Met Asp Tyr
1               5                   10

<210> SEQ ID NO 110
<211> LENGTH: 11
<212> TYPE: PRT
<213> ORGANISM: Artificial Sequence
<220> FEATURE:
<223> OTHER INFORMATION: Synthetic construct

<400> SEQUENCE: 110

Ile Gly Asp Tyr Asp Arg Tyr Thr Met Asp Tyr
1               5                   10

<210> SEQ ID NO 111
<211> LENGTH: 11
<212> TYPE: PRT
<213> ORGANISM: Artificial Sequence
<220> FEATURE:
<223> OTHER INFORMATION: Synthetic construct

<400> SEQUENCE: 111

Arg Gly Asp Tyr Asp Arg Tyr Thr Met Asp Tyr
1               5                   10

<210> SEQ ID NO 112
<211> LENGTH: 11
<212> TYPE: PRT
<213> ORGANISM: Artificial Sequence
<220> FEATURE:
<223> OTHER INFORMATION: Synthetic construct

<400> SEQUENCE: 112

Val Gly Asp Tyr Asp Arg Tyr Thr Met Asp Tyr
1               5                   10

<210> SEQ ID NO 113
<211> LENGTH: 11
<212> TYPE: PRT
<213> ORGANISM: Artificial Sequence
<220> FEATURE:
```

<223> OTHER INFORMATION: Synthetic construct

<400> SEQUENCE: 113

Trp Gly Asp Tyr Asp Arg Tyr Thr Met Asp Tyr
1               5                   10

<210> SEQ ID NO 114
<211> LENGTH: 11
<212> TYPE: PRT
<213> ORGANISM: Artificial Sequence
<220> FEATURE:
<223> OTHER INFORMATION: Synthetic construct

<400> SEQUENCE: 114

Gln Gly Asp Tyr Asp Arg Tyr Thr Met Asp Tyr
1               5                   10

<210> SEQ ID NO 115
<211> LENGTH: 11
<212> TYPE: PRT
<213> ORGANISM: Artificial Sequence
<220> FEATURE:
<223> OTHER INFORMATION: Synthetic construct

<400> SEQUENCE: 115

Gly Gly Asp Tyr Asp Arg Tyr Thr Met Asp Tyr
1               5                   10

<210> SEQ ID NO 116
<211> LENGTH: 11
<212> TYPE: PRT
<213> ORGANISM: Artificial Sequence
<220> FEATURE:
<223> OTHER INFORMATION: Synthetic construct

<400> SEQUENCE: 116

Lys Gly Asp Tyr Asp Arg Tyr Thr Met Asp Tyr
1               5                   10

<210> SEQ ID NO 117
<211> LENGTH: 11
<212> TYPE: PRT
<213> ORGANISM: Artificial Sequence
<220> FEATURE:
<223> OTHER INFORMATION: Synthetic construct

<400> SEQUENCE: 117

Asp Ser Asp Tyr Asp Arg Tyr Thr Met Asp Tyr
1               5                   10

<210> SEQ ID NO 118
<211> LENGTH: 11
<212> TYPE: PRT
<213> ORGANISM: Artificial Sequence
<220> FEATURE:
<223> OTHER INFORMATION: Synthetic construct

<400> SEQUENCE: 118

Asp Lys Asp Tyr Asp Arg Tyr Thr Met Asp Tyr
1               5                   10

<210> SEQ ID NO 119
<211> LENGTH: 11
<212> TYPE: PRT
<213> ORGANISM: Artificial Sequence
<220> FEATURE:
<223> OTHER INFORMATION: Synthetic construct

<400> SEQUENCE: 119

Asp His Asp Tyr Asp Arg Tyr Thr Met Asp Tyr
1               5                   10

<210> SEQ ID NO 120
<211> LENGTH: 11
<212> TYPE: PRT
<213> ORGANISM: Artificial Sequence
<220> FEATURE:
<223> OTHER INFORMATION: Synthetic construct

<400> SEQUENCE: 120

Asp Ala Asp Tyr Asp Arg Tyr Thr Met Asp Tyr
1               5                   10

<210> SEQ ID NO 121
<211> LENGTH: 11
<212> TYPE: PRT
<213> ORGANISM: Artificial Sequence
<220> FEATURE:
<223> OTHER INFORMATION: Synthetic construct

<400> SEQUENCE: 121

Asp Phe Asp Tyr Asp Arg Tyr Thr Met Asp Tyr
1               5                   10

<210> SEQ ID NO 122
<211> LENGTH: 11
<212> TYPE: PRT
<213> ORGANISM: Artificial Sequence
<220> FEATURE:
<223> OTHER INFORMATION: Synthetic construct

<400> SEQUENCE: 122

Asp Thr Asp Tyr Asp Arg Tyr Thr Met Asp Tyr
1               5                   10

<210> SEQ ID NO 123
<211> LENGTH: 11
<212> TYPE: PRT
<213> ORGANISM: Artificial Sequence
<220> FEATURE:
<223> OTHER INFORMATION: Synthetic construct

<400> SEQUENCE: 123

Asp Arg Asp Tyr Asp Arg Tyr Thr Met Asp Tyr
1               5                   10

<210> SEQ ID NO 124
<211> LENGTH: 11
<212> TYPE: PRT
<213> ORGANISM: Artificial Sequence
<220> FEATURE:
<223> OTHER INFORMATION: Synthetic construct

<400> SEQUENCE: 124

Asp Val Asp Tyr Asp Arg Tyr Thr Met Asp Tyr
1               5                   10

<210> SEQ ID NO 125
<211> LENGTH: 11
<212> TYPE: PRT
<213> ORGANISM: Artificial Sequence
<220> FEATURE:
<223> OTHER INFORMATION: Synthetic construct

```
<400> SEQUENCE: 125

Asp Gln Asp Tyr Asp Arg Tyr Thr Met Asp Tyr
1               5                   10

<210> SEQ ID NO 126
<211> LENGTH: 11
<212> TYPE: PRT
<213> ORGANISM: Artificial Sequence
<220> FEATURE:
<223> OTHER INFORMATION: Synthetic construct

<400> SEQUENCE: 126

Asp Leu Asp Tyr Asp Arg Tyr Thr Met Asp Tyr
1               5                   10

<210> SEQ ID NO 127
<211> LENGTH: 11
<212> TYPE: PRT
<213> ORGANISM: Artificial Sequence
<220> FEATURE:
<223> OTHER INFORMATION: Synthetic construct

<400> SEQUENCE: 127

Asp Tyr Asp Tyr Asp Arg Tyr Thr Met Asp Tyr
1               5                   10

<210> SEQ ID NO 128
<211> LENGTH: 11
<212> TYPE: PRT
<213> ORGANISM: Artificial Sequence
<220> FEATURE:
<223> OTHER INFORMATION: Synthetic construct

<400> SEQUENCE: 128

Asp Glu Asp Tyr Asp Arg Tyr Thr Met Asp Tyr
1               5                   10

<210> SEQ ID NO 129
<211> LENGTH: 11
<212> TYPE: PRT
<213> ORGANISM: Artificial Sequence
<220> FEATURE:
<223> OTHER INFORMATION: Synthetic construct

<400> SEQUENCE: 129

Asp Asn Asp Tyr Asp Arg Tyr Thr Met Asp Tyr
1               5                   10

<210> SEQ ID NO 130
<211> LENGTH: 11
<212> TYPE: PRT
<213> ORGANISM: Artificial Sequence
<220> FEATURE:
<223> OTHER INFORMATION: Synthetic construct

<400> SEQUENCE: 130

Asp Trp Asp Tyr Asp Arg Tyr Thr Met Asp Tyr
1               5                   10
```